(12) United States Patent
Zepeda et al.

(10) Patent No.: US 12,150,840 B2
(45) Date of Patent: Nov. 26, 2024

(54) SKIN TREATMENT DEVICES

(71) Applicant: Neodyne Biosciences, Inc., Newark, CA (US)

(72) Inventors: John A. Zepeda, Los Altos, CA (US); Jasper Jackson, Newark, CA (US); William Beasley, Los Altos, CA (US); Darren Doud, Los Altos, CA (US); Brett Follmer, Santa Clara, CA (US)

(73) Assignee: Neodyne Biosciences, Inc., Newark, CA (US)

( * ) Notice: Subject to any disclaimer, the term of this patent is extended or adjusted under 35 U.S.C. 154(b) by 987 days.

(21) Appl. No.: 16/728,454

(22) Filed: Dec. 27, 2019

(65) Prior Publication Data

US 2021/0113384 A1 Apr. 22, 2021

Related U.S. Application Data

(63) Continuation of application No. 15/293,084, filed on Oct. 13, 2016, now Pat. No. 10,517,768, which is a
(Continued)

(51) Int. Cl.
*A61F 13/00* (2024.01)
*A61B 17/08* (2006.01)
(Continued)

(52) U.S. Cl.
CPC ........ *A61F 13/0236* (2013.01); *A61B 17/085* (2013.01); *A61B 90/02* (2016.02); *A61F 13/00076* (2013.01); *A61F 13/00085* (2013.01); *A61F 13/01038* (2024.01); *A61F 13/023* (2013.01); *A61F 13/0243* (2013.01);
(Continued)

(58) Field of Classification Search
None
See application file for complete search history.

(56) References Cited

U.S. PATENT DOCUMENTS

| 114,750 A | 5/1871 | Battersby |
| 363,538 A | 5/1887 | Penny |

(Continued)

FOREIGN PATENT DOCUMENTS

| CA | 2321491 A1 | 9/1999 |
| CA | 2621387 A1 | 3/2007 |

(Continued)

OTHER PUBLICATIONS

3M Healthcare (May 2004). "Tips for Trouble-Free Taping," 3M HealthCare: St. Paul, MN, four pages.
(Continued)

*Primary Examiner* — Kim M Lewis
(74) *Attorney, Agent, or Firm* — Dorsey & Whitney LLP

(57) ABSTRACT

Devices, kits and methods described herein may be for wound healing, including the treatment, amelioration, or prevention of scars and/or keloids by applying and/or maintaining a pre-determined strain in an elastic skin treatment device that is then affixed to the skin surface using skin adhesives to transfer a generally planar force from the bandage to the skin surface. Applicators are used to apply and/or maintain the strains, and some of the applicators are further configured to provide at least some mechanical advantage to the user when exerting loads onto the skin treatment device.

21 Claims, 140 Drawing Sheets

Related U.S. Application Data continuation of application No. 14/158,741, filed on Jan. 17, 2014, now Pat. No. 9,492,329, which is a continuation of application No. 13/089,129, filed on Apr. 18, 2011, now Pat. No. 8,674,164, which is a continuation of application No. 12/854,859, filed on Aug. 11, 2010, now Pat. No. 8,592,640.

(60) Provisional application No. 61/264,205, filed on Nov. 24, 2009, provisional application No. 61/243,020, filed on Sep. 16, 2009, provisional application No. 61/233,122, filed on Aug. 11, 2009.

(51) Int. Cl.
 A61B 90/00 (2016.01)
 A61F 13/01 (2024.01)
 A61F 13/02 (2006.01)
 A61F 13/0246 (2024.01)
 A61F 15/00 (2006.01)
 A61L 15/26 (2006.01)

(52) U.S. Cl.
 CPC ...... *A61F 13/0253* (2013.01); *A61F 13/0256* (2013.01); *A61F 13/0266* (2013.01); *A61F 15/001* (2013.01); *A61F 15/005* (2013.01); *A61L 15/26* (2013.01); *A61B 17/08* (2013.01); *A61F 13/0246* (2013.01); *A61F 13/0259* (2013.01)

(56) References Cited

U.S. PATENT DOCUMENTS

| | | |
|---|---|---|
| 633,050 A | 9/1899 | Spenard |
| 1,074,413 A | 9/1913 | Baun et al. |
| 1,774,489 A | 8/1930 | David |
| 1,969,188 A | 8/1934 | Spicer |
| 2,018,517 A | 10/1935 | Edward |
| 2,303,131 A | 11/1942 | Morgan |
| 2,371,978 A | 3/1945 | Perham |
| 2,421,193 A | 5/1947 | James |
| 2,472,009 A | 5/1949 | James |
| 2,714,382 A | 8/1955 | Solis |
| 2,722,220 A | 11/1955 | Mestrand |
| 2,762,371 A | 9/1956 | Guio |
| 3,103,218 A | 9/1963 | Ajemian |
| 3,402,716 A | 9/1968 | Baxter |
| 3,487,836 A | 1/1970 | Niebel et al. |
| 3,528,426 A | 9/1970 | Vukojevic |
| 3,575,782 A | 4/1971 | Hansen |
| 3,613,679 A | 10/1971 | Bijou |
| 3,645,835 A | 2/1972 | Hodgson |
| 3,698,395 A | 10/1972 | Hasson |
| 3,863,640 A | 2/1975 | Haverstock |
| 3,926,193 A | 12/1975 | Hasson |
| 3,933,158 A | 1/1976 | Haverstock |
| 3,983,878 A | 10/1976 | Kawchitch |
| 4,038,989 A | 8/1977 | Romero-sierra et al. |
| 4,073,298 A | 2/1978 | Le |
| 4,114,624 A | 9/1978 | Haverstock |
| 4,141,363 A | 2/1979 | James et al. |
| 4,173,131 A | 11/1979 | Melton et al. |
| 4,222,383 A | 9/1980 | Schossow |
| 4,282,005 A | 8/1981 | Sato et al. |
| 4,346,700 A | 8/1982 | Dunshee et al. |
| 4,370,981 A | 2/1983 | Sanderson |
| 4,413,621 A | 11/1983 | Mccracken et al. |
| 4,423,731 A | 1/1984 | Roomi |
| 4,425,176 A | 1/1984 | Shibano et al. |
| 4,447,482 A | 5/1984 | Heinzelman et al. |
| 4,496,535 A | 1/1985 | Gould et al. |
| 4,531,521 A | 7/1985 | Haverstock |
| 4,535,772 A | 8/1985 | Sheehan |
| 4,539,990 A | 9/1985 | Stivala |
| 4,549,653 A | 10/1985 | Lauritzen |
| 4,598,004 A | 7/1986 | Heinecke |
| 4,605,005 A | 8/1986 | Sheehan |
| 4,646,731 A | 3/1987 | Brower |
| 4,653,492 A | 3/1987 | Parsons |
| 4,696,301 A | 9/1987 | Barabe |
| 4,699,133 A | 10/1987 | Schaefer et al. |
| 4,702,251 A | 10/1987 | Sheehan |
| 4,706,661 A | 11/1987 | Barrett |
| 4,732,146 A | 3/1988 | Fasline et al. |
| 4,742,826 A | 5/1988 | Mclorg |
| 4,753,232 A | 6/1988 | Ward |
| 4,780,168 A | 10/1988 | Beisang et al. |
| 4,787,381 A | 11/1988 | Hubbard et al. |
| 4,807,613 A | 2/1989 | Koehnke et al. |
| 4,815,457 A | 3/1989 | Mazars et al. |
| 4,815,468 A | 3/1989 | Annand |
| 4,825,866 A | 5/1989 | Pierce |
| 4,881,546 A | 11/1989 | Kaessmann |
| 4,915,102 A | 4/1990 | Kwiatek et al. |
| 4,917,929 A | 4/1990 | Heinecke |
| 4,924,866 A | 5/1990 | Yoon |
| 4,950,282 A | 8/1990 | Beisang et al. |
| RE33,353 E | 9/1990 | Heinecke |
| 4,984,584 A | 1/1991 | Hansen et al. |
| 5,011,492 A | 4/1991 | Heimerl et al. |
| 5,026,389 A | 6/1991 | Thieler |
| 5,047,047 A | 9/1991 | Yoon |
| 5,058,579 A | 10/1991 | Terry et al. |
| 5,066,299 A | 11/1991 | Bellingham |
| 5,106,629 A | 4/1992 | Cartmell et al. |
| 5,127,412 A | 7/1992 | Cosmetto et al. |
| 5,176,703 A | 1/1993 | Peterson |
| 5,234,462 A | 8/1993 | Pavletic |
| 5,259,835 A | 11/1993 | Clark et al. |
| 5,263,970 A | 11/1993 | Preller |
| 5,333,753 A | 8/1994 | Etheredge |
| 5,383,900 A | 1/1995 | Krantz |
| 5,507,775 A | 4/1996 | Ger et al. |
| 5,520,762 A | 5/1996 | Rasmussen et al. |
| 5,522,879 A | 6/1996 | Scopelianos |
| 5,545,713 A | 8/1996 | Krejci et al. |
| 5,549,713 A | 8/1996 | Kim |
| 5,552,162 A | 9/1996 | Lee |
| 5,562,705 A | 10/1996 | Whiteford |
| 5,628,724 A | 5/1997 | Debusk et al. |
| 5,649,960 A | 7/1997 | Pavletic |
| 5,662,624 A | 9/1997 | Sundstroem et al. |
| 5,662,714 A | 9/1997 | Charvin et al. |
| 5,662,717 A | 9/1997 | Burns |
| 5,713,842 A | 2/1998 | Kay |
| 5,723,009 A | 3/1998 | Frechet et al. |
| 5,758,662 A | 6/1998 | Hall |
| 5,759,560 A | 6/1998 | Dillon |
| 5,779,659 A | 7/1998 | Allen |
| 5,885,254 A | 3/1999 | Matyas |
| 5,891,076 A | 4/1999 | Fabo |
| 5,919,476 A | 7/1999 | Fischer et al. |
| 5,931,800 A | 8/1999 | Rasmussen et al. |
| 5,947,998 A | 9/1999 | Cartmell et al. |
| 5,998,694 A | 12/1999 | Jensen et al. |
| 6,007,564 A | 12/1999 | Haverstock |
| 6,043,406 A | 3/2000 | Sessions et al. |
| 6,093,465 A | 7/2000 | Gilchrist et al. |
| 6,120,525 A | 9/2000 | Westcott |
| 6,255,552 B1 | 7/2001 | Cummings et al. |
| 6,264,976 B1 | 7/2001 | Heinecke et al. |
| 6,284,941 B1 | 9/2001 | Cox et al. |
| 6,297,420 B1 | 10/2001 | Heincke |
| 6,297,423 B1 | 10/2001 | Schoenfeldt et al. |
| 6,343,224 B1 | 1/2002 | Parker |
| 6,346,653 B1 | 2/2002 | Sessions et al. |
| 6,410,818 B1 | 6/2002 | Oyaski |
| 6,469,066 B1 | 10/2002 | Dosch et al. |
| 6,472,581 B1 | 10/2002 | Muramatsu et al. |
| 6,485,503 B2 | 11/2002 | Jacobs et al. |
| 6,495,230 B1 | 12/2002 | Do |
| 6,570,051 B1 | 5/2003 | Beaudry |
| 6,572,878 B1 | 6/2003 | Blaine |

(56) References Cited

U.S. PATENT DOCUMENTS

| | | |
|---|---|---|
| 6,573,419 B2 | 6/2003 | Naimer |
| 6,634,653 B2 | 10/2003 | Chatterjea |
| 6,726,696 B1 | 4/2004 | Houser et al. |
| 6,759,481 B2 | 7/2004 | Tong |
| 6,822,133 B2 | 11/2004 | Lebner |
| 6,831,205 B2 | 12/2004 | Lebner |
| 6,870,074 B2 | 3/2005 | Gilman |
| 6,986,855 B1 | 1/2006 | Hood et al. |
| 7,066,182 B1 | 6/2006 | Dunshee |
| 7,066,934 B2 | 6/2006 | Kirsch |
| 7,122,712 B2 | 10/2006 | Lutri et al. |
| 7,135,606 B1 | 11/2006 | Dozier et al. |
| 7,227,050 B2 | 6/2007 | Sigurjonsson et al. |
| 7,332,641 B2 | 2/2008 | Lebner et al. |
| 7,354,446 B2 | 4/2008 | Lebner |
| 7,414,168 B2 | 8/2008 | Lebner |
| 7,456,332 B2 | 11/2008 | Beaudry |
| 7,511,185 B2 | 3/2009 | Lebner |
| 7,563,941 B2 | 7/2009 | Lebner et al. |
| 7,683,234 B2 | 3/2010 | Gurtner et al. |
| 7,834,232 B2 | 11/2010 | Rastegar et al. |
| RE42,126 E | 2/2011 | Ye et al. |
| 8,063,263 B2 | 11/2011 | Gurtner et al. |
| 8,168,850 B2 | 5/2012 | Gurtner et al. |
| 8,183,428 B2 | 5/2012 | Gurtner et al. |
| 8,389,791 B2 | 3/2013 | Gurtner et al. |
| 8,395,011 B2 | 3/2013 | Zepeda et al. |
| 8,592,640 B2 | 11/2013 | Zepeda et al. |
| 8,674,164 B2 | 3/2014 | Zepeda et al. |
| 9,248,048 B2 | 2/2016 | Jackson et al. |
| 9,248,049 B2 | 2/2016 | Gurtner et al. |
| 9,248,051 B2 | 2/2016 | Gurtner et al. |
| 9,358,009 B2 | 6/2016 | Yock et al. |
| 9,492,329 B2 | 11/2016 | Zepeda et al. |
| 9,649,226 B2 | 5/2017 | Zepeda et al. |
| 9,844,470 B2 | 12/2017 | Jackson et al. |
| 10,420,557 B2 | 9/2019 | Yock et al. |
| 10,517,768 B2 | 12/2019 | Zepeda et al. |
| 11,013,638 B2 | 5/2021 | Jackson et al. |
| 2002/0013300 A1 | 1/2002 | Capelli-schellpfeffer |
| 2002/0193723 A1 | 12/2002 | Girardin et al. |
| 2003/0014053 A1 | 1/2003 | Nguyen et al. |
| 2003/0040687 A1 | 2/2003 | Boynton et al. |
| 2003/0092969 A1 | 5/2003 | Omalley et al. |
| 2003/0220700 A1 | 11/2003 | Hammer et al. |
| 2004/0059280 A1 | 3/2004 | Makower et al. |
| 2004/0236360 A1 | 11/2004 | Cohn et al. |
| 2005/0033215 A1 | 2/2005 | Lebner |
| 2005/0034731 A1 | 2/2005 | Rousseau et al. |
| 2005/0070956 A1 | 3/2005 | Rousseau |
| 2005/0080453 A1 | 4/2005 | Lebner et al. |
| 2005/0095275 A1 | 5/2005 | Zhu et al. |
| 2005/0095276 A1 | 5/2005 | Kartheus et al. |
| 2005/0125051 A1 | 6/2005 | Eidenschink et al. |
| 2005/0245966 A1 | 11/2005 | Hammerslag et al. |
| 2005/0274453 A1 | 12/2005 | Anvar |
| 2006/0009099 A1 | 1/2006 | Jonn et al. |
| 2006/0020235 A1 | 1/2006 | Siniaguine |
| 2006/0037091 A1 | 2/2006 | Gurtner et al. |
| 2006/0246802 A1 | 11/2006 | Hughes et al. |
| 2006/0282135 A1 | 12/2006 | Tankovich |
| 2007/0093161 A1 | 4/2007 | Eede et al. |
| 2007/0129776 A1 | 6/2007 | Robins et al. |
| 2007/0142761 A1 | 6/2007 | Aali |
| 2007/0191752 A1 | 8/2007 | Lebner |
| 2007/0282235 A1 | 12/2007 | Beaudry |
| 2007/0282374 A1 | 12/2007 | Sogard et al. |
| 2008/0033334 A1 | 2/2008 | Gurtner et al. |
| 2008/0051687 A1 | 2/2008 | Rogers |
| 2008/0208098 A1 | 8/2008 | Rennix |
| 2008/0228220 A1 | 9/2008 | Weiser |
| 2009/0163844 A1 | 6/2009 | Gurtner et al. |
| 2009/0177136 A1 | 7/2009 | Liedtke et al. |
| 2010/0056873 A1 | 3/2010 | Allen et al. |
| 2010/0191253 A1 | 7/2010 | Oostman et al. |
| 2010/0280428 A1 | 11/2010 | Widgerow et al. |
| 2011/0152738 A1 | 6/2011 | Zepeda et al. |
| 2011/0319798 A1 | 12/2011 | Digrazia |
| 2012/0035521 A1 | 2/2012 | Zepeda et al. |
| 2012/0046586 A1 | 2/2012 | Gurtner et al. |
| 2012/0046590 A1 | 2/2012 | Yock et al. |
| 2012/0046591 A1 | 2/2012 | Gurtner et al. |
| 2012/0203273 A1 | 8/2012 | Riskin et al. |
| 2012/0209377 A1 | 8/2012 | Machold et al. |
| 2012/0221044 A1 | 8/2012 | Archibald et al. |
| 2012/0226214 A1 | 9/2012 | Gurtner et al. |
| 2012/0226306 A1 | 9/2012 | Jackson et al. |
| 2013/0012858 A1 | 1/2013 | Jackson et al. |
| 2013/0184629 A1 | 7/2013 | Gurtner et al. |
| 2013/0190673 A1 | 7/2013 | Gurtner et al. |
| 2013/0281904 A1 | 10/2013 | Jackson et al. |
| 2014/0088481 A1 | 3/2014 | Jackson et al. |
| 2014/0135677 A1 | 5/2014 | Zepeda et al. |
| 2014/0135678 A1 | 5/2014 | Zepeda et al. |
| 2015/0141836 A1 | 5/2015 | Naumann et al. |
| 2016/0213522 A1 | 7/2016 | Gurtner et al. |
| 2017/0020522 A1 | 1/2017 | Yock et al. |
| 2017/0112673 A1 | 4/2017 | Jackson et al. |

FOREIGN PATENT DOCUMENTS

| | | |
|---|---|---|
| CN | 1414842 A | 4/2003 |
| CN | 1608604 A | 4/2005 |
| CN | 102665623 A | 9/2012 |
| EP | 2161011 A1 | 3/2010 |
| EP | 2464322 A2 | 6/2012 |
| JP | 2004515256 A | 5/2004 |
| JP | 2004223087 A | 8/2004 |
| JP | 2004536898 A | 12/2004 |
| JP | 2006513748 A | 4/2006 |
| JP | 2007537781 A | 12/2007 |
| JP | 2009545382 A | 12/2009 |
| JP | 2013501591 A | 1/2013 |
| RU | 2019138 C1 | 9/1994 |
| WO | 9717919 A1 | 5/1997 |
| WO | 9730700 A2 | 8/1997 |
| WO | 9730700 A3 | 10/1997 |
| WO | 0053139 A1 | 9/2000 |
| WO | 0139693 A2 | 6/2001 |
| WO | 0139693 A3 | 12/2001 |
| WO | 0215816 A2 | 2/2002 |
| WO | 0245698 A2 | 6/2002 |
| WO | 0245698 A3 | 7/2002 |
| WO | 02092783 A2 | 11/2002 |
| WO | 2002087645 A1 | 11/2002 |
| WO | 0215816 A3 | 10/2003 |
| WO | 2004060413 A1 | 7/2004 |
| WO | 02092783 A3 | 7/2005 |
| WO | 2005079674 A1 | 9/2005 |
| WO | 2005096981 A2 | 10/2005 |
| WO | 2005096981 A3 | 3/2006 |
| WO | 2006124671 A2 | 11/2006 |
| WO | 2006124671 A3 | 4/2007 |
| WO | 2008019051 A2 | 2/2008 |
| WO | 2008019051 A3 | 4/2008 |
| WO | 2011019859 A2 | 2/2011 |
| WO | 2011019859 A3 | 4/2011 |
| WO | 2012094648 A1 | 7/2012 |
| WO | 2012119131 A1 | 9/2012 |

OTHER PUBLICATIONS

3M Healthcare. (2001). "Reducing the Risk of Superficial Skin Damage Related to Adhesive Use," 3M HealthCare: St Paul, MN, two pages.

3M Healthcare. (2003). "Steri-Strip: Skin Closures," Product Insert, 3M HealthCare: St. Paul, MN, one page.

3M Healthcare. (2006). "3MTM Steri-StripTM S Surgical Skin Closure. The Simple, Non-Invase Alternative to Staples and Sutures from the Steri-Strip Family," HealthCare: St. Paul, MN, two pages.

3M Healthcare. (Date Unknown). "3M™ Steri-Strip™ S Surgical Skin Closure," 3M HealthCare: St. Paul, MN, one page.

(56) References Cited

OTHER PUBLICATIONS

3M Healthcare. (Date unknown). 3M™ Steri-Strip™ S Surgical Skin Closure. Poster of Available Sizes, 3M HealthCare: St Paul, MN, three pages.
3M Healthcare. (Jun. 27, 2002). "3M™ Steri-Strip™ Adhesive Skin Closures (reinforced): Commonly Asked Questions," 3M HealthCare: St Paul, MN, pp. 1-4.
3M Healthcare. (Oct. 19, 2006). "3M™ Steri-Strip™ S Surgical Skin Closure: Commonly Asked Questions," 3M Healthcare: St. Paul, MN, pp. 1-8.
3M Medical. (2006). "3MTM Steri-StripTM S Surgical Skin Closure. Patient Care Information," 3M HealthCare: St. Paul, MN, two pages.
3M Medical. (2007). "3MTM Steri-StripTM S Surgical Skin Closure. Application Examples, Comparisons and Results," 3M HealthCare: St. Paul, MN, four pages.
Anonymous (2003). "3MTM Steri-StripTM Adhesive Skin Closures," 3M HealthCare Brochure, twelve pages.
Anonymous. (2005). "3MTM TegadermTM Family of Transparent Dressings," 3M HealthCare Brochure, six pages.
Anonymous. (2006). "Avocet Polymer Technologies," located at <http://www.avocetcorp.com/index.html>, last visited on Nov. 5, 2007, one page.
Anonymous. (2006). "Avogel Scar Hydrogel," located at <http://www.avocetcorp.com/avogel_scar_hydrogel.html>, last visited on Nov. 5, 2007, two pages.
Anonymous. (2006). "Avosil Ointment," located at <http://www.avocetcorp.com/avosil.html>, last visited on Nov. 5, 2007, three pages.
Anonymous. (Date Unknown). "Mepiform Instructions of Use," Tendra Corporation Brochure, two pages.
Anonymous. (Date Unknown). "Silicone Scar Bandage: Standard Wound Healing Application," located at <http://www.thejamushop.com/silicon_sheet_for_keloids.htm>, last visited on Mar. 18, 2009, four pages.
Brace, "Definition of Brace", Merriam Webster, Available Online at <www.merriam-webster.com>, 2015, 4 pages.
Canica Design Inc. (Date Unknown). "ABRA® Abdominal Wall Closure Set," located at < http://www.canica.com/instructions/1D1544RA%20-%20ABRA%20CWK08%20IFU.pdf>, last visited on Sep. 10, 2009, pp. 1-11.
Canica Design Inc. (Date Unknown). "ABRA® Surgical Skin Closure Set," located at <http://www.canica.com/instructions/1D0830RH.pdf>, last visited on Sep. 10, 2009, pp. 1-4.
Corrected Notice of Allowability malled on Jan. 23, 2013, for U.S. Appl. No. 13/315,214, filed Dec. 8, 2011, 2 pages.
Decision for Grant received for Korean Patent Application No. 10-2009-7003220, mailed on May 14, 2014, 3 pages.
Decision for Grant received for Korean Patent Application No. 10-2014-7005383, mailed on Dec. 10, 2014, 3 pages.
Extended European Search Report (includes Supplementary European Search Report and Search Opinion) received for European Patent Application No. 12752239.9, mailed on Oct. 1, 2014, 7 pages.
Extended European Search Report mailed on Aug. 19, 2013 for European Patent Application No. 10 808 724.8, filed on Aug. 11, 2010, 8 pages.
Extended European Search Report mailed on Feb. 23, 2016, for European Patent Application No. 13 825 488.3, filed on Feb. 8, 2013, 6 pages.
Extended European Search Report mailed on Jun. 19, 2017 for European Patent Application No. 16205575.0, filed Aug. 11, 2010, 8 pages.
Extended European Search Report received for European Patent Application No. 12732236.0, mailed on Jun. 29, 2015, 6 pages.
International Preliminary Report on Patentability received for PCT Patent Application No. PCT/US2007/017320, issued on Feb. 3, 2009, 8 pages.
International Preliminary Report on Patentability received for PCT Patent Application No. PCT/US2010/045239, mailed on Feb. 23, 2012, 10 pages.
International Preliminary Report on Patentability received for PCT Patent Application No. PCT/US2012/025510, mailed on Aug. 29, 2013, 10 pages.
International Preliminary Report on Patentability received for PCT Patent Application No. PCT/US2012/027618, mailed on Sep. 12, 2013, 12 pages.
International Preliminary Report on Patentability received for PCT Patent Application No. PCT/US2013/025449, mailed on Feb. 5, 2015, 7 pages.
International Search Report and Written Opinion mailed May 1, 2012, for PCT Patent Application No. PCT/US2012/020561, filed Jan. 6, 2012, three pages.
International Search Report and Written Opinion mailed on Feb. 7, 2008, for PCT Application No. PCT/US2007/017320, filed on Aug. 3, 2007, 11 pages.
International Search Report and Written Opinion mailed on Feb. 8, 2011, for PCT Patent Application No. PCT/US2010/045239, filed on Aug. 11, 2010, one page.
International Search Report and Written Opinion received for PCT Patent Application No. PCT/US2013/025449, mailed on Feb. 5, 2015, 8 pages.
International Search Report mailed Jun. 28, 2012, for PCT Patent Application No. PCT/US2012/027618, filed Mar. 2, 2012, two pages.
International Search Report mailed May 29, 2012, for PCT Patent Application No. PCT/US2012/25510, filed Feb. 16, 2012, three pages.
Mask, "Definition of Mask", Merriam Webster, Available Online at <www.merriam-webster.com>, 2015, 4 pages.
Nahabedian, M.Y. (Dec. 2005). "Scar Wars: Optimizing Outcomes with Reduction Mammaplasty," Plastic and Reconstructive Surgery, 116(7):2026-2029.
NHSSB Wound Management Manual, Northern Health and Social Services Board, 2005, pp. 1-97.
Notice of Allowance received for Japanese Patent Application No. 2009-522879, mailed on Mar. 17, 2014, 6 pages.
Notice of Allowance received for Japanese Patent Application No. 2012-524855, mailed on Apr. 30, 2015, 3 pages.
Notice of Allowance received for Japanese Patent Application No. 2013-037053 mailed on Jan. 6, 2015, 3 pages.
Office Action Received for Australian Patent Application No. 2010282523, mailed on May 6, 2014, 4 pages.
Office Action received for Canadian Patent Application No. 2,659,772, mailed on Oct. 30, 2013, 3 pages.
Office Action received for Canadian Patent Application No. 2,659,772, mailed on Sep. 11, 2014, 2 pages.
Office Action received for Chinese Patent Application No. 201080045471.4, mailed on May 21, 2014, 6 pages.
Office Action received for Chinese Patent Application No. 201080045471.4, mailed on Sep. 29, 2013, 4 pages.
Office Action received for Chinese Patent Application No. 201280012003.6, mailed on Jun. 30, 2014, 9 pages.
Office Action received for Chinese Patent Application No. 201280021431.5, mailed on Sep. 22, 2014, 3 pages.
Office Action received for Chinese Patent Application No. 201310474149.9, mailed on Jan. 27, 2015, 10 pages.
Office Action received for European Patent Application No. 07836471.8, mailed on Jul. 13, 2010, 7 pages.
Office Action received for European Patent Application No. 10808724.8, mailed on Jan. 15, 2015, 4 pages.
Office Action received for Indian Patent Application No. 654/DELNP/2009, mailed on Jul. 31, 2014, 4 pages.
Office Action received for Israeli Patent Application No. 218020, issued on Dec. 1, 2013, 12 pages.
Office Action received for Japanese Patent Application No. 2012-524855, mailed on Apr. 14, 2014, 7 pages.
Office Action received for Japanese Patent Application No. 2012-524855, mailed on Oct. 24, 2014, 5 pages.
Office Action received for Japanese Patent Application No. 2013-037053, mailed on Mar. 17, 2014, 5 pages.

(56) References Cited

OTHER PUBLICATIONS

Office Action received for Korean Patent Application No. 10-2009-7003220, mailed on Oct. 28, 2013, 6 pages.
Office Action received for Korean Patent Application No. 10-2014-7005383, mailed on May 14, 2014, 6 pages.
Office Action received in EP Application No. 16205575.0, mailed Jan. 30, 2020.
Shanghai Dongyue Medical Health Product Co., Ltd. (2005). Silicon-gel Membrane—Scar Bandage, located at <http://www.shdongyue.com/cp/shaos/shaos02b.asp>, last visited on Nov. 6, 2008, two pages.
Smith & Nephew. (Date Unknown). "CICA-Care. Silicone Gel Sheeting," located at <http://wound.smith-nepehew.com/za/Product/asp?NodeId=569&Tab=5&hide=True>, last visited on Jun. 9, 2009, one page.
Wound Care Technologies. (2008). "DERMACloseTM RC: Continuous External Tissue Expander, Brochure No. PL-0020-F," located at < http://www.woundcaretech.com/sell-sheet.pdf>, last visited on Sep. 10, 2009, two pages.
Wound Care Technologies. (2008). "Instructions for Use. DERMACloseTM RC, Brochure No. DR-0079-A," located at < http://www.dermaclose.com/instructions.pdf>, last visited on Sep. 10, 2009, two pages.
Written Opinion of the International Searching Authority mailed Jun. 28, 2012, for PCT Application No. PCT/US2012/027618, filed Mar. 2, 2012, 10 pages.
Written Opinion of the International Searching Authority mailed May 29, 2012, for PCT Application No. PCT/US2012/25510, filed on Feb. 16, 2012, 8 pages.
Decision to Grant received for Chinese Patent Application No. 201280012003.6, mailed on Feb. 3, 2015, 2 pages., pp. all.
Intention to Grant received for European Patent Application No. 12752239.9 mailed on Sep. 24, 2015, 5 pages., pp. all.
Notice of Allowance received for Australian Patent Application No. 2010282523, mailed on Jul. 2, 2015, 2 pages., pp. all.
Notice of Allowance received for Israel Patent Application No. 218020, mailed on Dec. 11, 2014, 4 pages., pp. all.
Office Action for European Patent Application No. 07836471.8, mailed on Nov. 6, 2015, 7 pages., pp. all.
Office Action received for Australian Patent Application No. 2012204174, mailed on Aug. 4, 2015, 2 pages., pp. all.
Office Action received for Chinese Patent Application No. 201280021431.5 mailed on Jul. 17, 2015, 4 pages., pp. all.
Office Action received for Chinese Patent application No. 201310474149.9, mailed on Jul. 27, 2015, 10 pages., pp. all.
Office Action received for Japanese Patent Application No. 2013-548594, mailed on Jul. 7, 2015, 6 pages., pp. all.
Office Action received for Japanese Patent Application No. 2014-123100, mailed on May 18, 2015, 1 page., pp. all.
Office Action received for Japanese Patent Application No. 2014-143959 mailed on May 18, 2015, 1 page., pp. all.
Office Action received in EP Application No. 16205575.0 mailed Dec. 10, 2018, pp. all.
3M Medical, 3M Medical. (2006). "They Say Every Scar Tells a Story," 3M HealthCare: St. Paul, MN, one page.
Aarabi, et al., Aarabi, S. et al. (Oct. 2007). "Mechanical Load Initiates Hypertrophic Scar Formation Through Decreased Cellular Apoptosis," The FASEB Journal 21(12):3250-3261.
Al-Attar, et al., Al-Attar, A. et al. (Jan. 2006). "Keloid Pathogenesis and Treatment," Plastic and Reconstructive Surgery 117(1): 286-300.
Angelini, et al., Angelini, G.D. et al. (1984). "Comparative Study of Leg Wound Skin Closure in Coronary Artery Bypass Graft Operations," Thorax 39:942-945.
Atkinson, et al., (Nov. 2005). "A Randomized, Controlled Trial to Determine the Efficacy of Paper Tape in Preventing Hypertrophic Scar Formation in Surgical Incisions that Traverse Langer's Skin Tension Lines," Plastic and Reconstructive Surgery 116(6)., 1648-1656.

Bachert, et al., Bachert, B. et al. (2003). "Probing Elastic Modulus and Depth of a Two Layer Human Skin Model with Piezoelectric Cantilevers," Biomedical Engineering Senior Design Team, Drexel University, 27 pages.
Berman, et al., Berman, B. et al. (Mar. 3, 2005). "Keloid and Hypertrophic Scar," located at <http://www.emedicine.com/DERM/topic205.htm>, last visited on Nov. 19, 2007, 23 pages.
Bunker, , Bunker, T.D. (1983). "Problems with the Use of Op-Site Sutureless Skin Closures in Orthopaedic Procedures," Annals of the Royal College of Surgeons of England 65:260-262.
Burd, et al., Burd, A. et al. (Dec. 2005). "Hypertrophic Response and Keloid Diathesis: Two Very Different Forms of Scar," Plastic and Reconstructive Surgery 116(7):150-157.
Chen, et al., Chen, H-H. et al. (Jul. 2001). "Prospective Study Comparing Wounds Closed With Tape With Sutured Wounds in Colorectal Surgery," Arch. Surg. 136:801-803.
Davison, et al., Davison, S.P. et al. (Jan. 2006). "Ineffective Treatment of Keloids with Interferon Alpha-2b," Plastic and Reconstructive Surgery 117(1):247-252.
Escoffier, et al., Escoffier, C. et al. (Sep. 1989). "Age-Related Mechanical Properties of Human Skin: An In Vivo Study," J. Invest. Dermatol. 9(3)3:353-357.
Evans, et al., Evans, S.L. et al. (2009). "Measuring the Mechanical Properties of Human Skin in vivo Using Digital Correlation and Finite Element Modeling," J. Strain Analysis 44:337-345.
Fairclough, et al., Fairclough, J.A. et al. (1987). "The Use of Sterile Adhesive Tape in the Closure of Arthroscopic Puncture Wounds: A Comparison with a Single Layer Nylon Closure," Annals of the Royal College of Surgeons of England 69:140-141.
Gorney, , Gorney, M. (Mar. 2006). "Scar: The Trigger to the Claim," Plastic and Reconstructive Surgery 117(3):1036-1037.
Hof, et al., Hof, M. et al. (Jul. 2006). "Comparing Silicone Pressure-Sensitive Adhesives to Silicone Gels for Transdermal Drug Delivery," presented at 33 Annual Meeting and Exposition of the Controlled Release Society, Vienna, Austria, Jul. 22-26, 2006, seven pages.
Koval, et al., Koval, K.J. et al. (Oct. 2003). "Tape Blisters Following Hip Surgery. A Prospective Randomized Study of Two Types of Tape," The Journal of Bone and Joint Surgery, 85-5(10):1884-1887.
Kuo, et al., Kuo, F. et al. (May 2006). "Prospective Randomized, Blinded Study of a New Wound Closure Film Versus Cutaneous Suture for Surgical Wound Closure," Dermatological Surgery 32(5):676-681.
Mustoe, et al., Mustoe, T.A.,et al. (Nov. 2005). "A Randomized, Controlled Trial to Determine the Efficacy of Paper Tape in Preventing Hypertrophic Scar Formation in Surgical Incisions that Traverse Langer's Skin Tension Lines," Plastic and Reconstructive Surgery 116.6, 1657-1658.
O'Brien, et al., O'Brien, L. et al. (2009). "Silicon Gel Sheeting for Preventing and Treating Hypertrophic and Keloid Scars," The Cochrane Collaboration, pp. 1-47.
Pitcher, , Pitcher, D. (Feb. 1983). "Sutureless Skin Closure for Pacemaker Implantation: Comparison with Subcuticular Suture," Postgraduate Medical Journal 59:83-85.
Shirado, et al., "Realization of Human Skin-Like Texture by Emulating Surface Shape Pattern and Elastic Structure," presented at Symposium on Haptic Interfaces for Virtual Environment and Teleoperator Systems 2006, Mar. 25-26, 2006, Alexandria, VA, pp. 295-296.
Sullivan, et al., Sullivan, S.R. et al. (2007). "Acute Wound Care," Chapter 7 in ACS Surgery: Principles and Practice, 24 pages.
Teot, , Téot, L. (2005). "Scar Control" European Tissue Repair Society, located at <http://www.etrs.org/bulletin12_1/section11.php>, last visited on Nov. 30, 2007, 13 pages.
Vaughan, et al., Vaughan, P. et al. (2006). "Optimal Closure of Surgical Wounds in Forefoot Surgery: Are Adhesive Strips Beneficial? " Acta Orthop. Belg. 72(6):731-733.
Vowden, , Vowden, K. (Mar. 2003). "Wound Management. Policy and Resource Pack," Bradford Teaching Hospitals NHS Foundation Trust, pp. 1-70.
Watson, , Watson, G.M. (1983). "Op-Site Skin Closure: A Comparison with Subcuticular and Interrupted Sutures," Annals of the Royal College of Surgeons of England 65:83-84.

(56) References Cited

OTHER PUBLICATIONS

Webster, et al., Webster, D.J.T. et al. (Sep. 1975). "Closure of Abdominal Wounds by Adhesive Strips: A Clinical Trial," British Medical Journal 20:696-698.

Westaby, , Westaby, S. (1980). "Evaluation of a New Product for Sutureless Skin Closure," Annals of the Royal College of Surgeons of England 62:129-132.

English Translation of Office Action for BR Application No. 122020025483-1, mailed May 4, 2021.

English translation of Office Action for BR Application No. 1120120032437, dated Sep. 2, 2020.

English translation of Written Opinion for BR Application No. 1120120032437, dated Feb. 22, 2021.

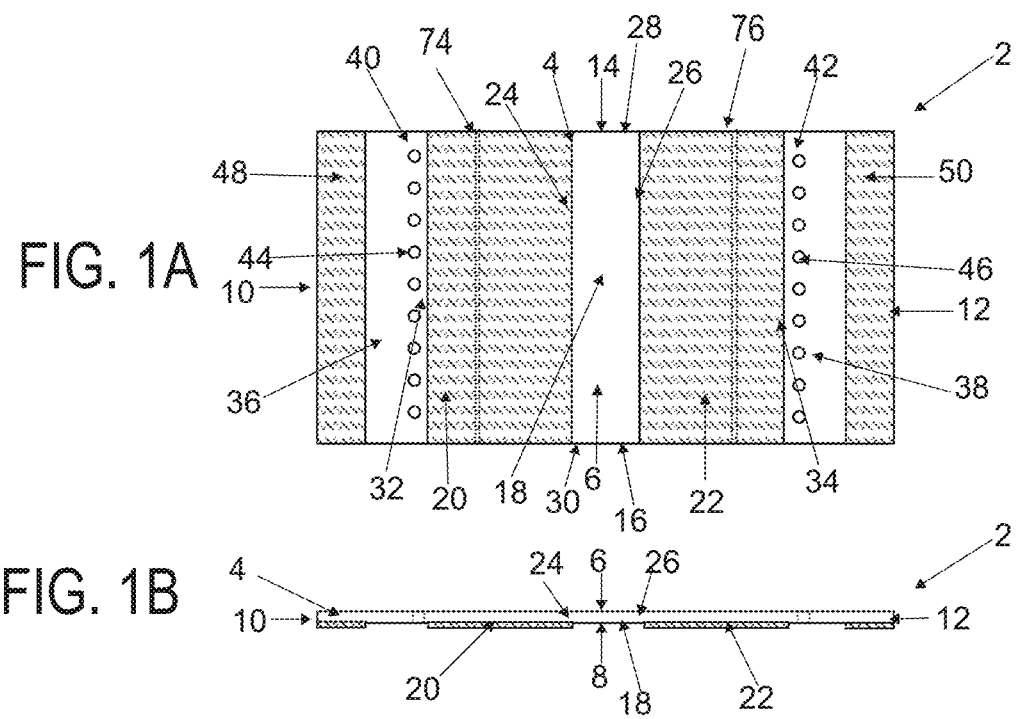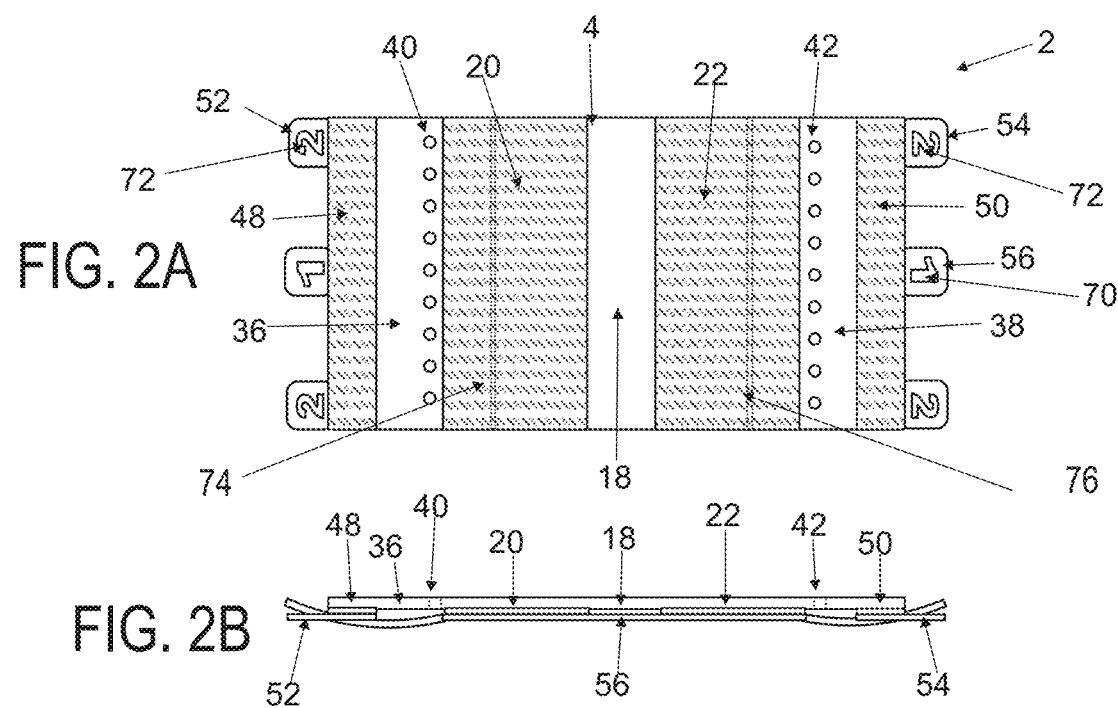

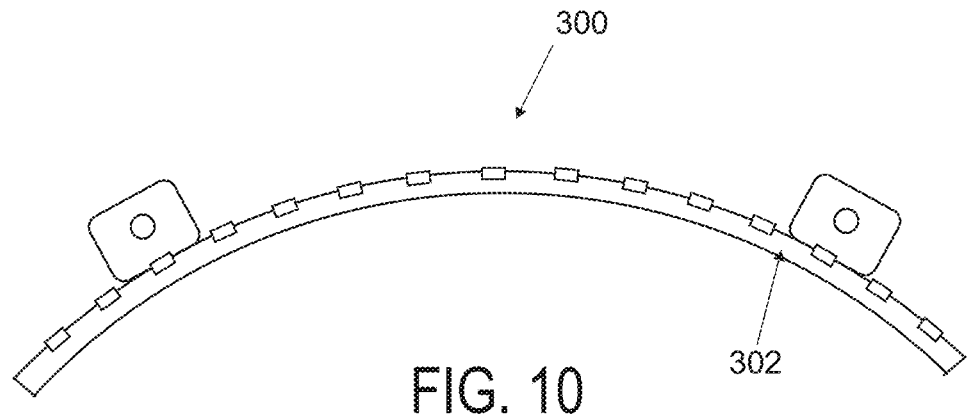
FIG. 10
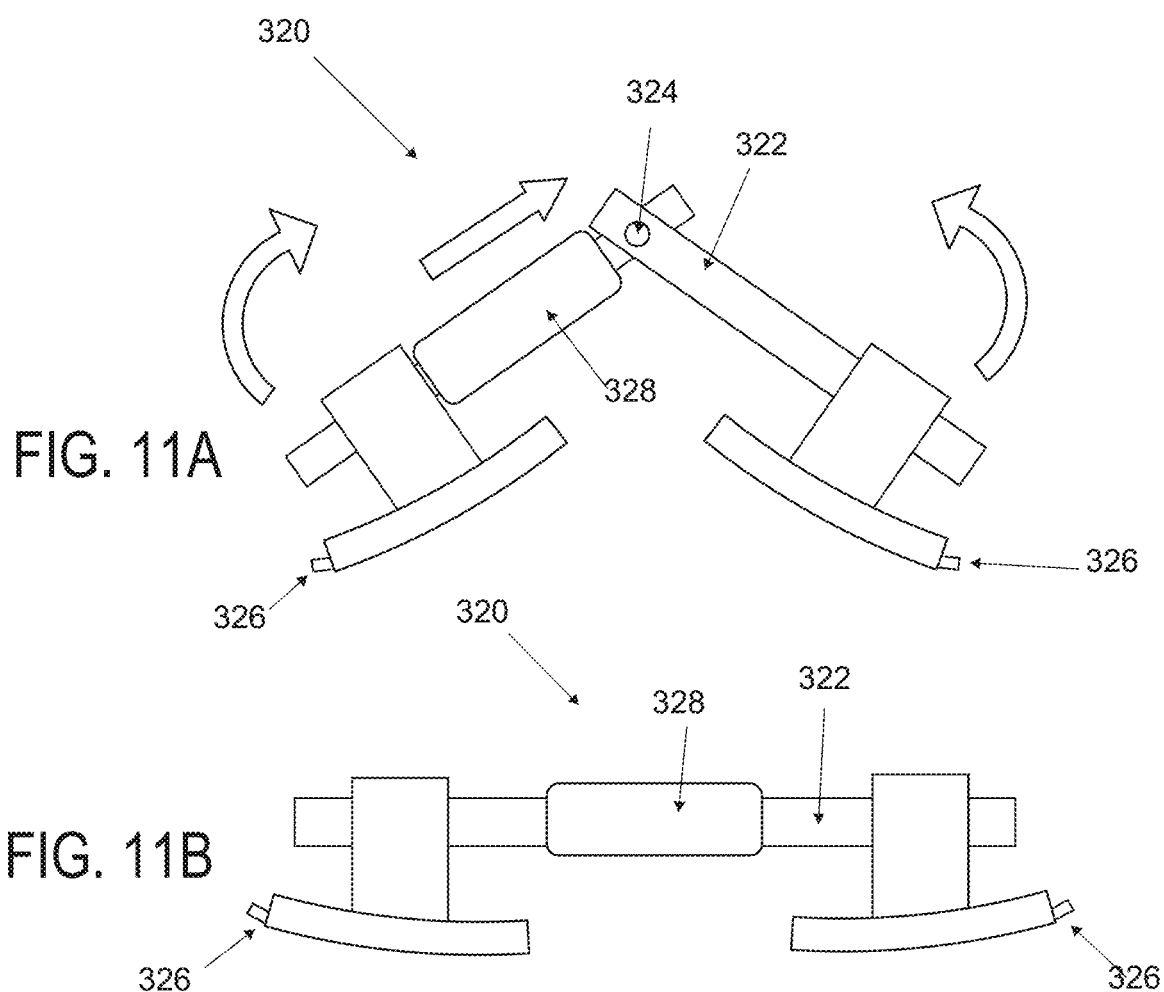
FIG. 11A
FIG. 11B

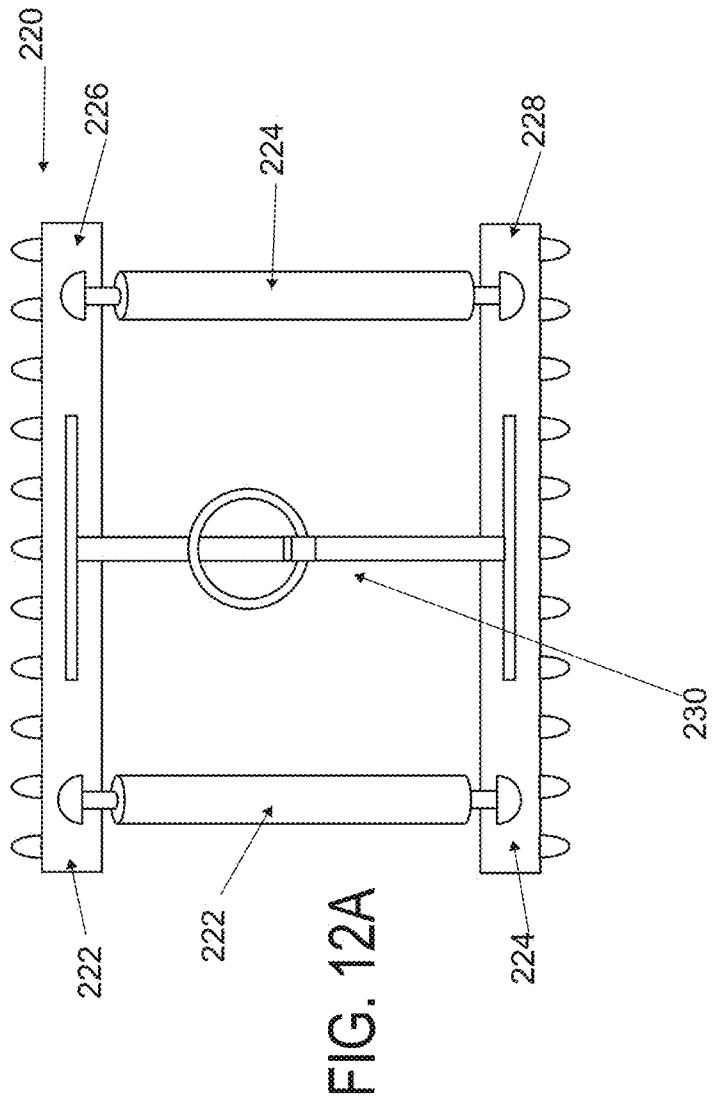
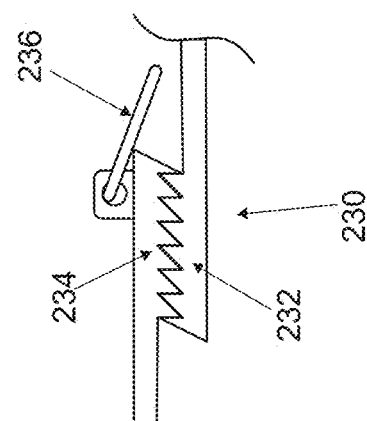
FIG. 12A
FIG. 12B

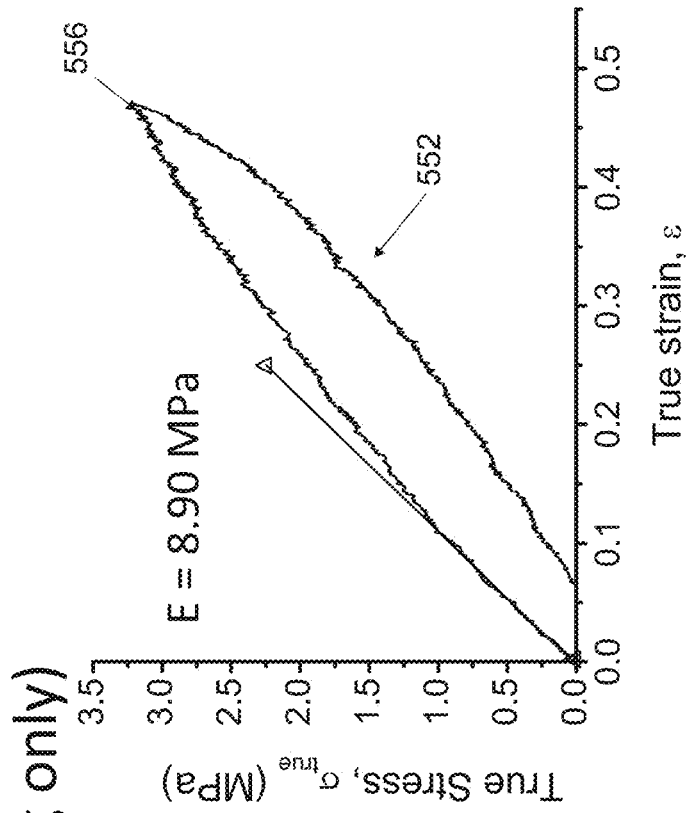
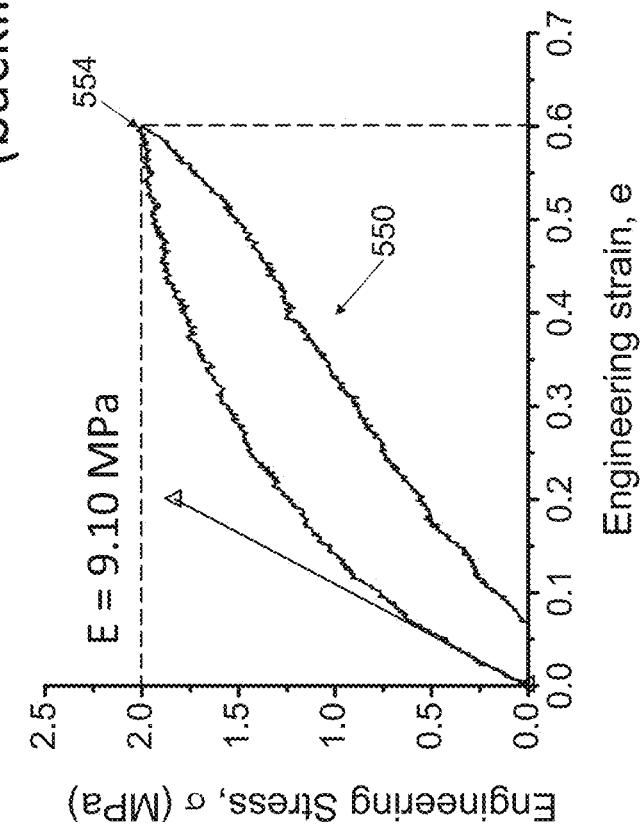
FIG. 19A
FIG. 19B

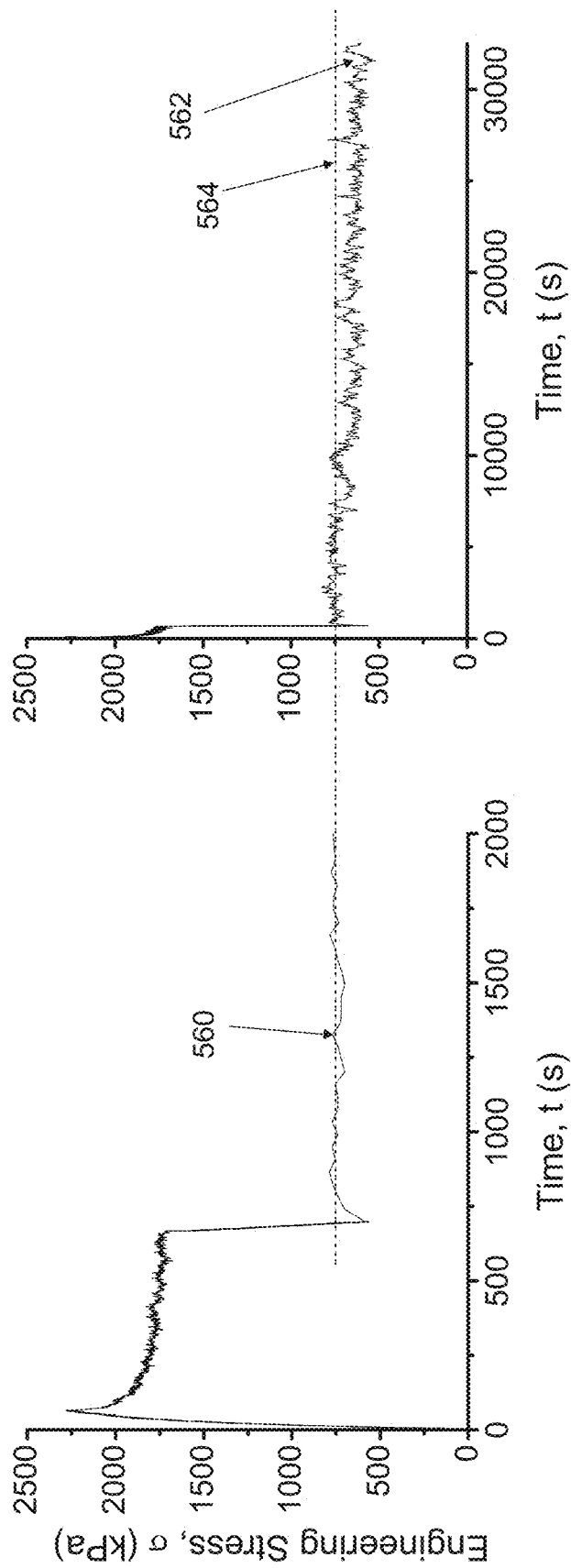

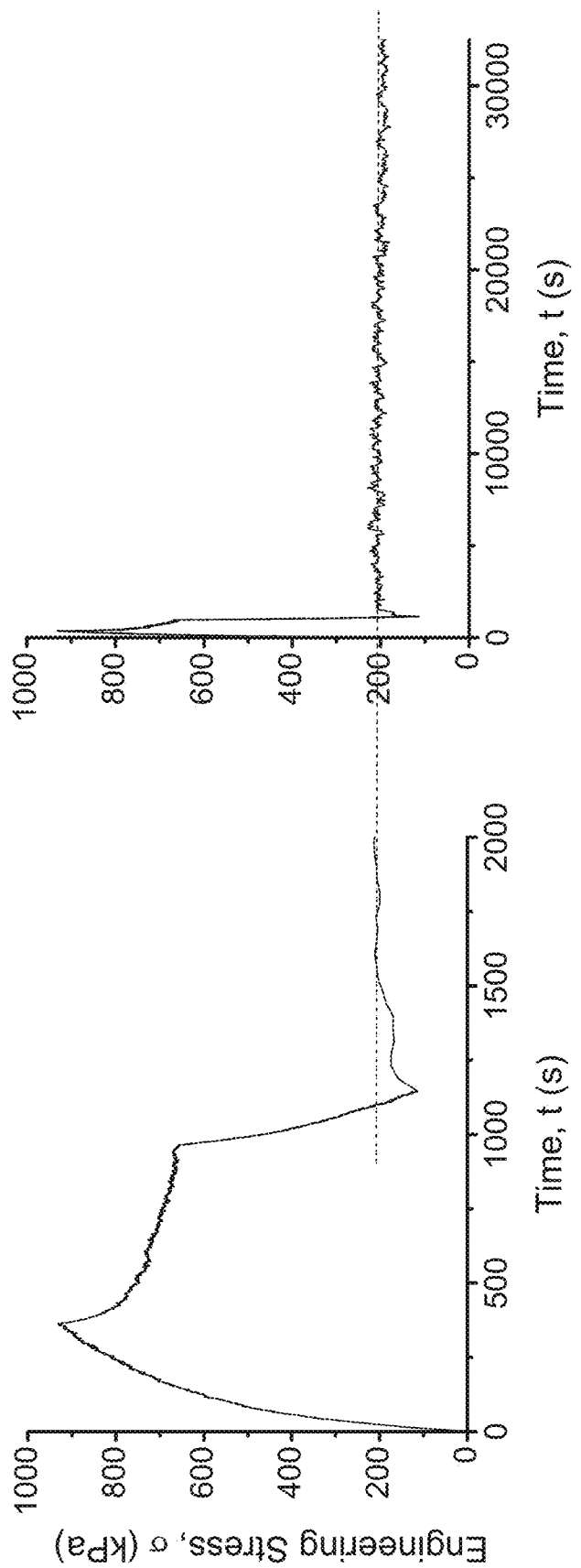

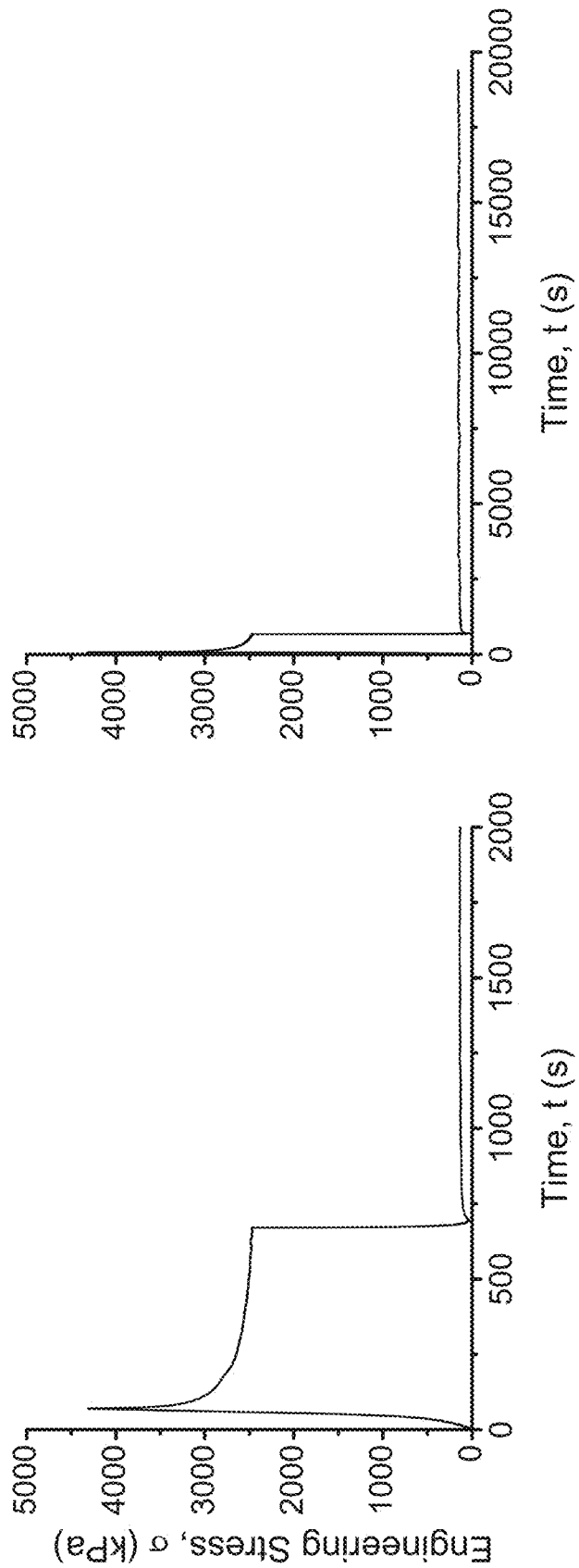

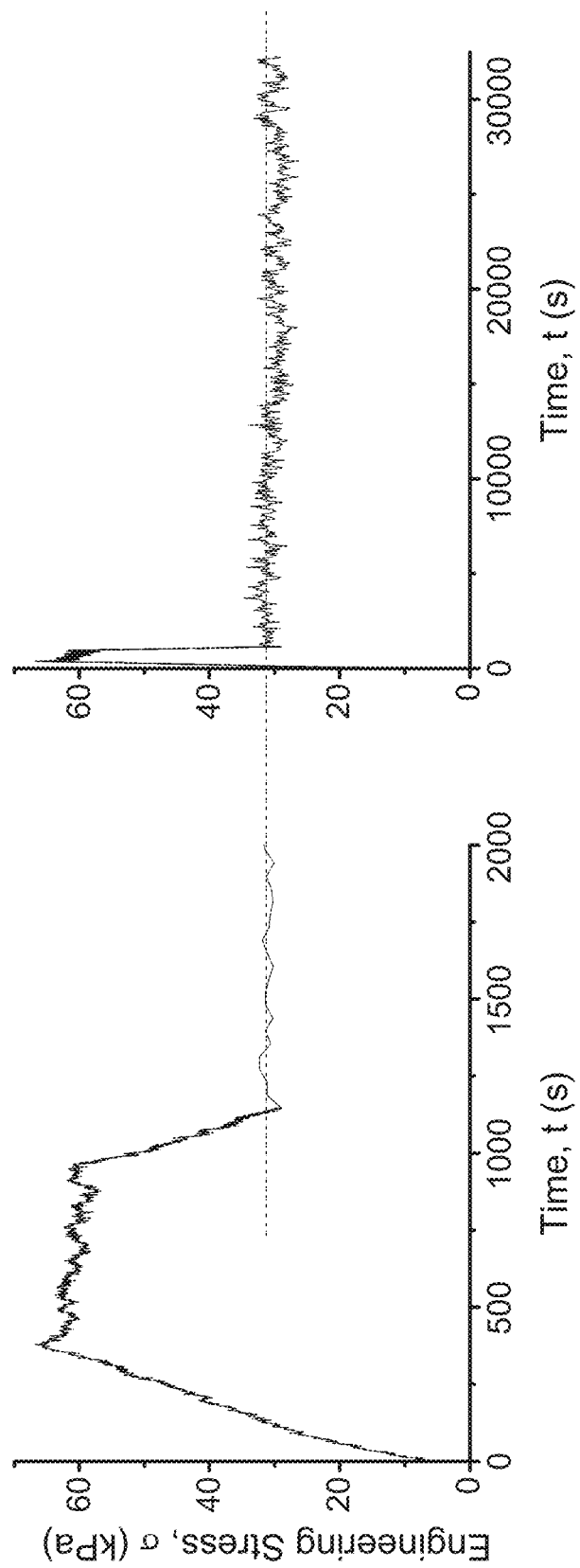

Smith & Nephew OpSite

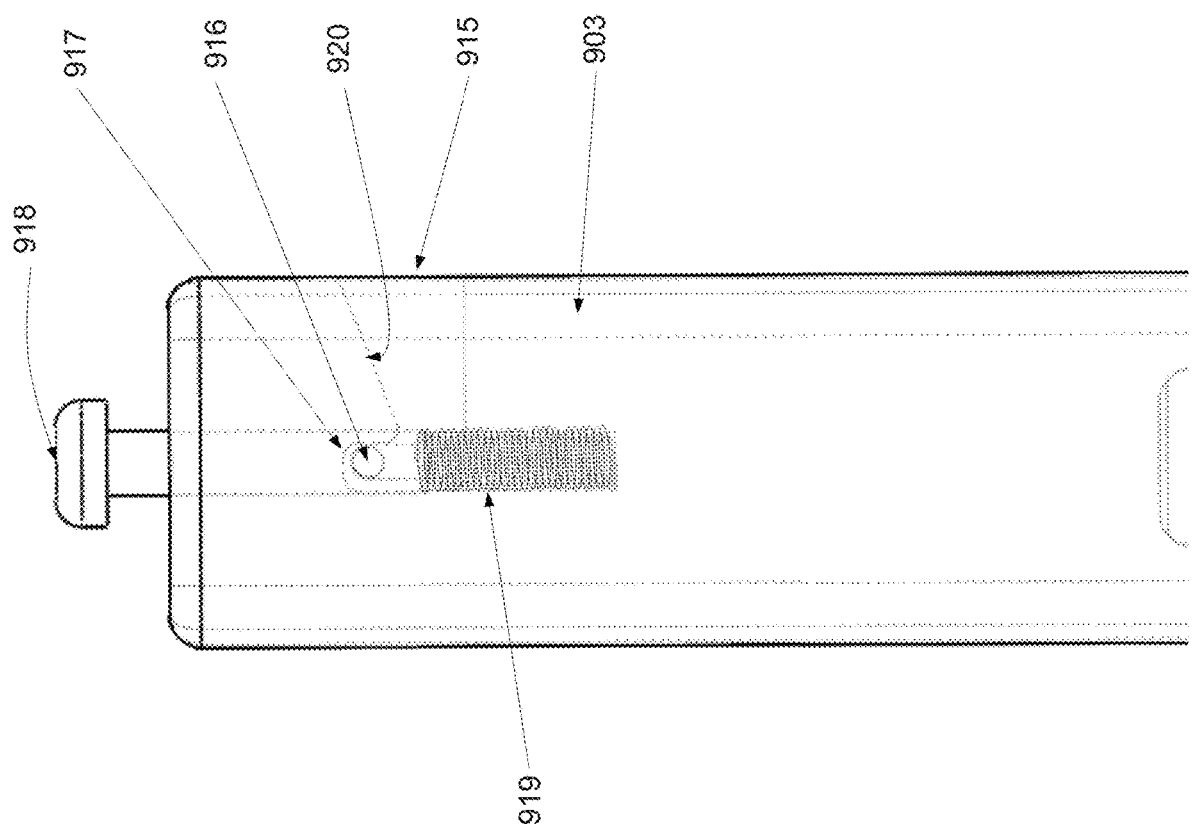

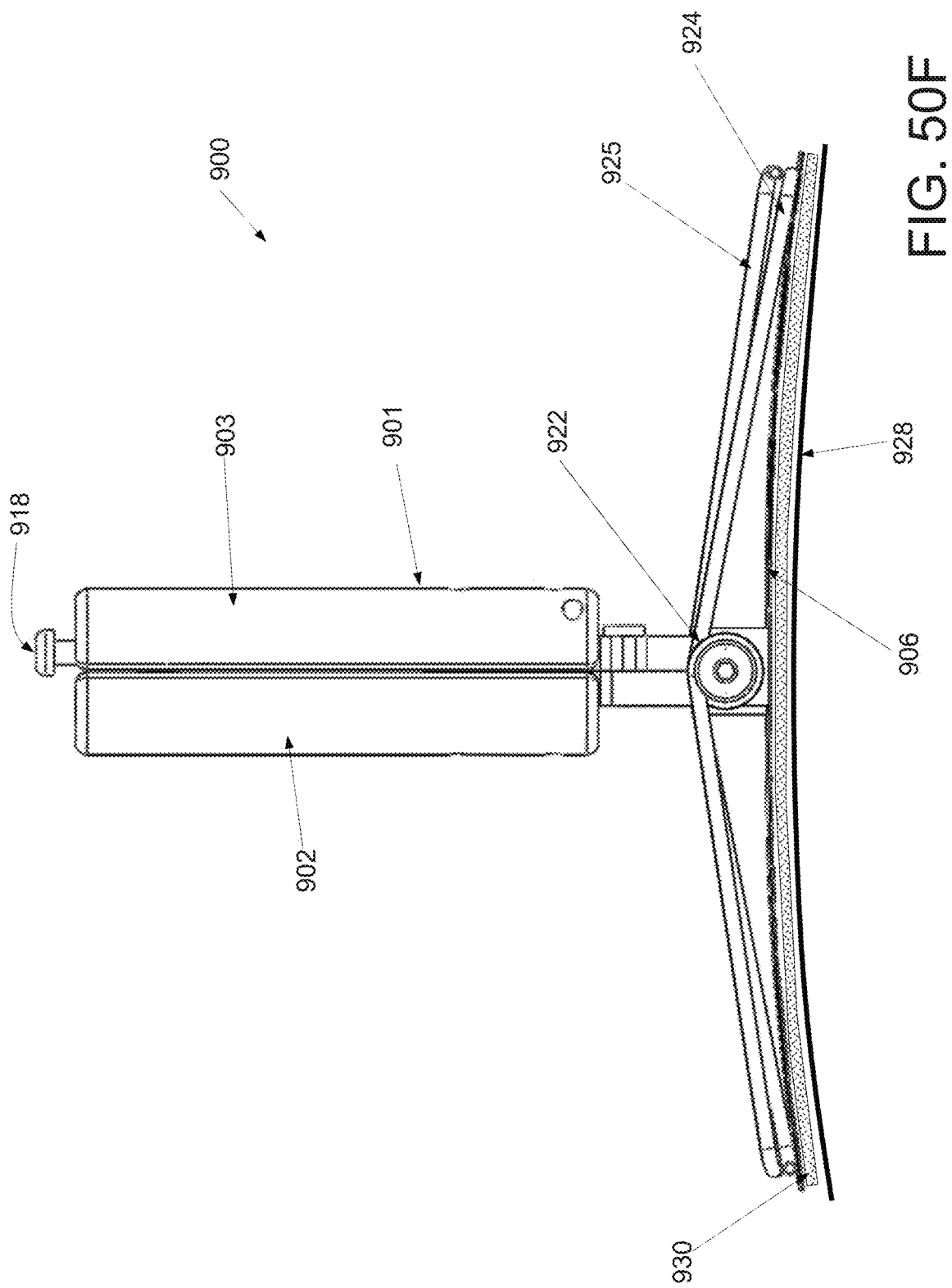

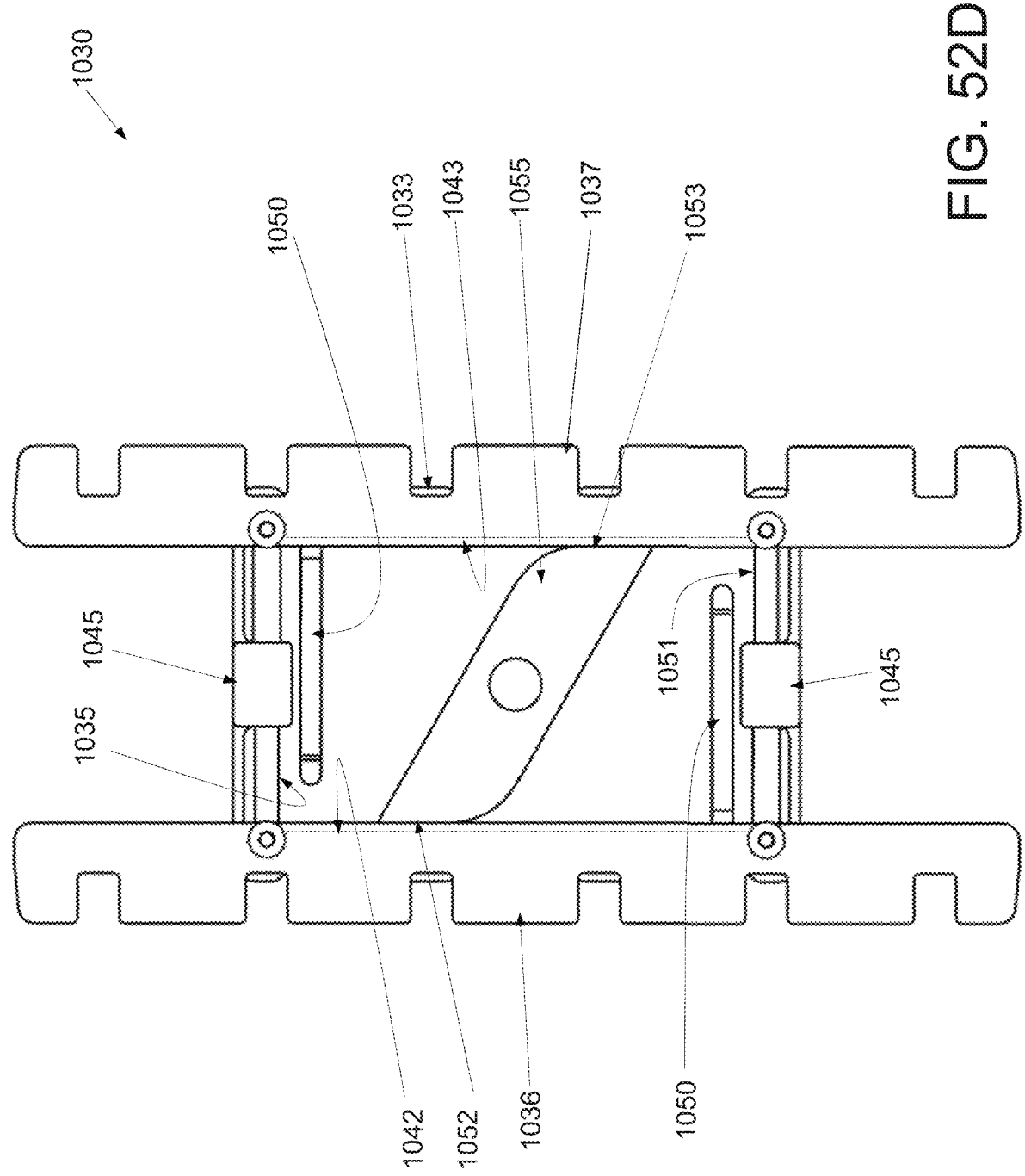

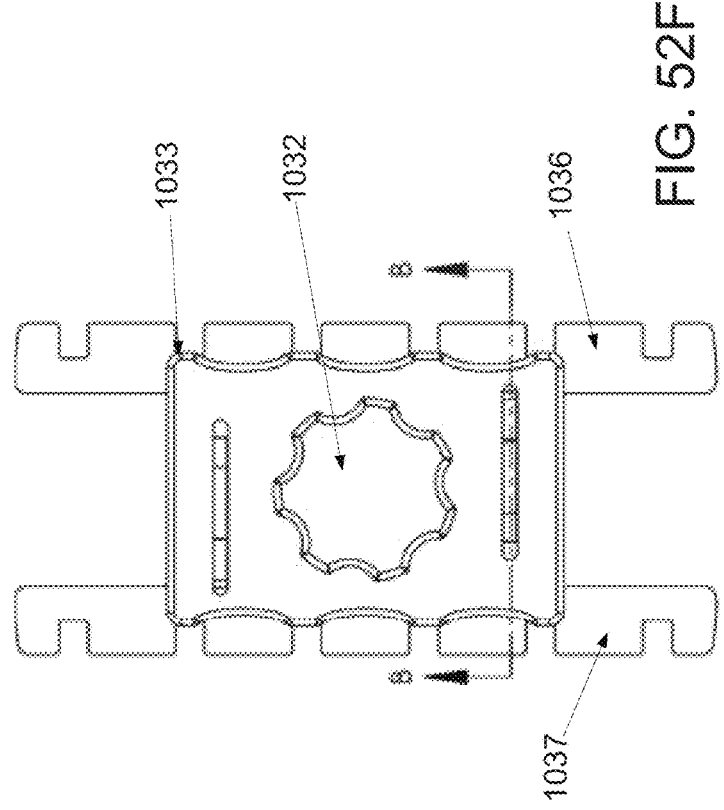
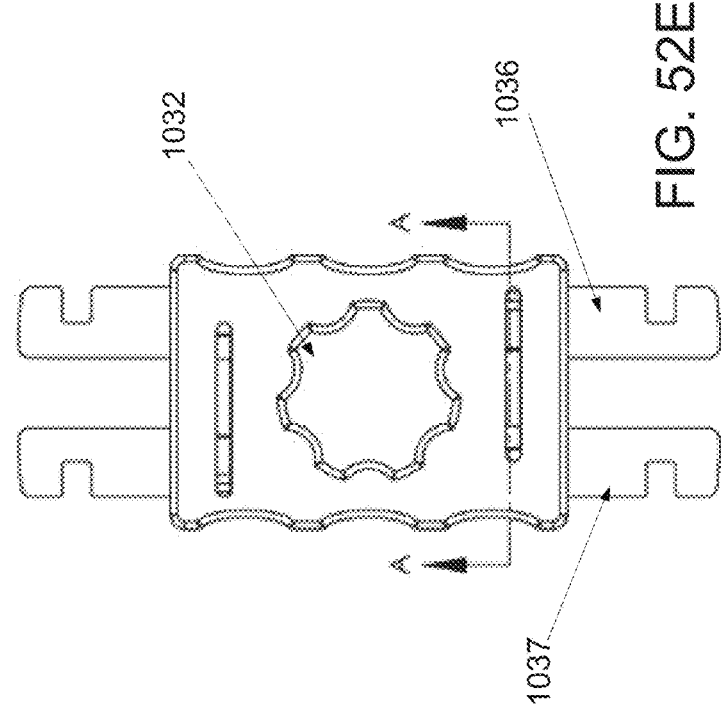
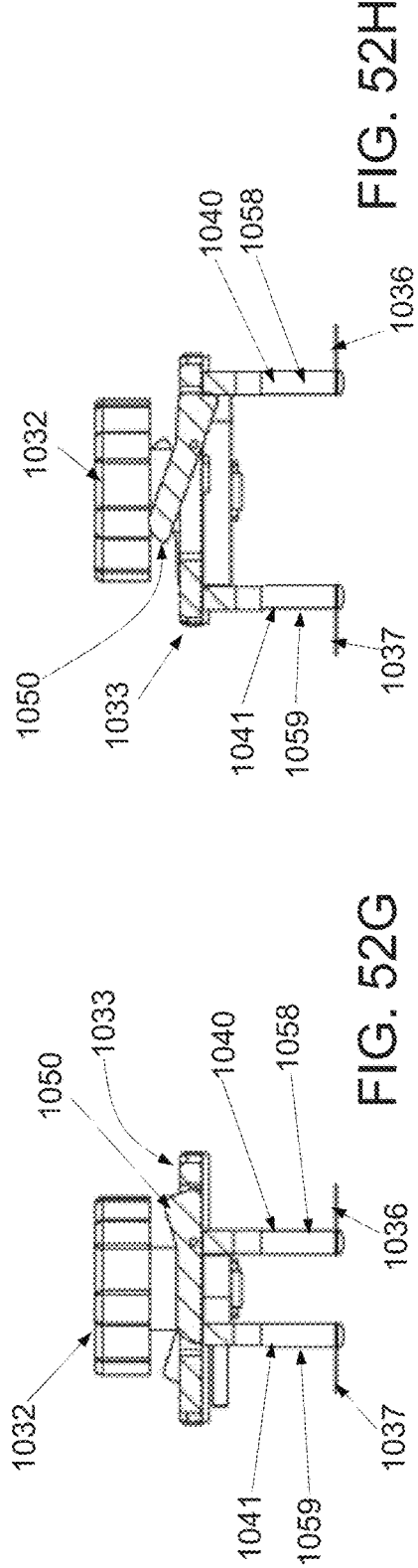

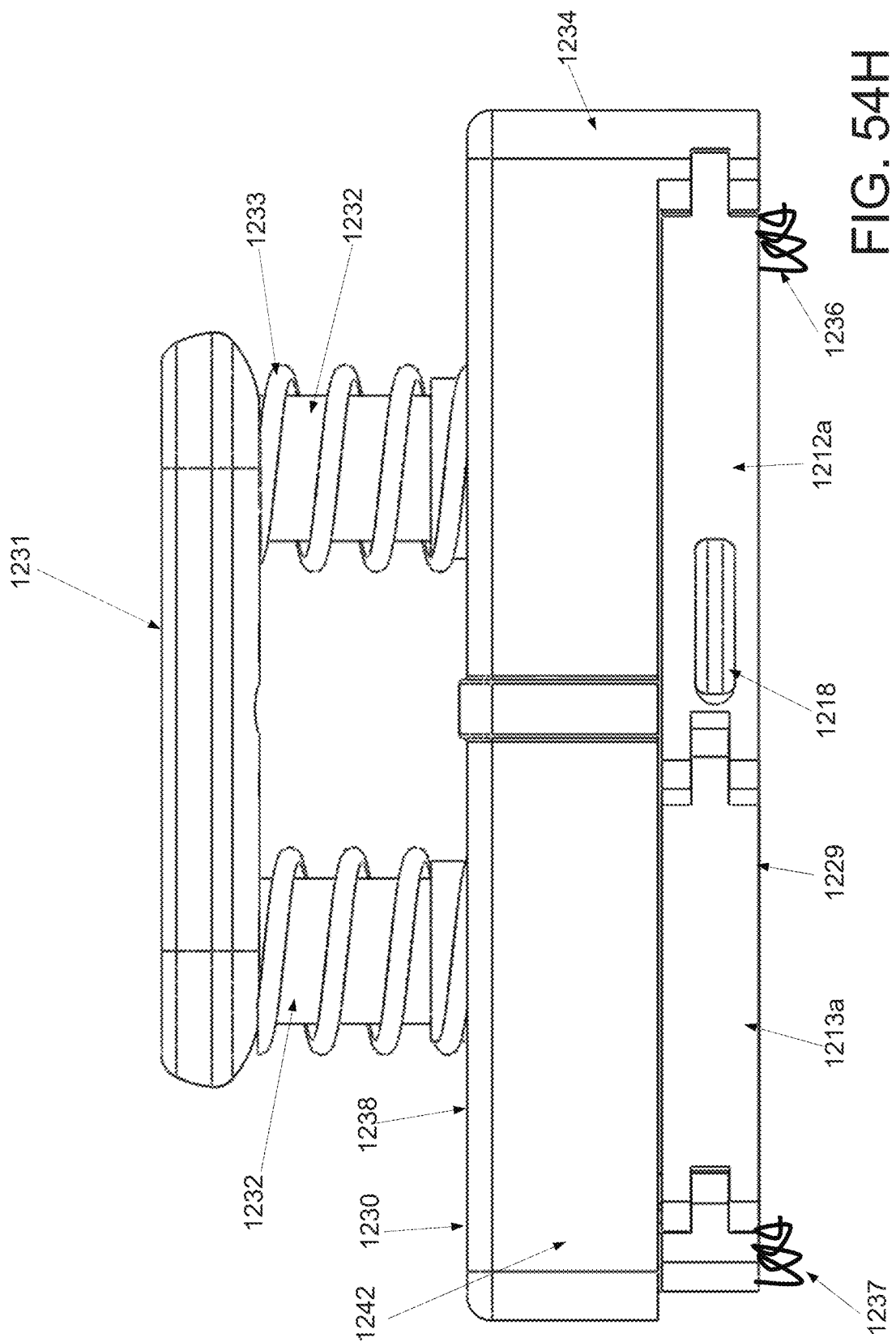

6.0cm Dressing

| Strain % | Deflection (in) | Angle (α) | Known Load ($F_y$) Lbf. | Unknown Load ($F_x$) |
|---|---|---|---|---|
| 0 | 0 | 45.58 | 0 | 0 |
| 10 | 0.236 | 51.79 | 0.87 | 0.684868397 |
| 20 | 0.472 | 59 | 1.475 | 0.886269413 |
| 30 | 0.708 | 68.21 | 2.09 | 0.83551726 |
| 40 | 0.944 | 89 | 3.055 | 0.053325223 |

6.0cm Dressing

| Strain % | Deflection (in) | Angle (α) | Known Load (F_x) Lbf. | Unknown Load (F_y) |
|---|---|---|---|---|
| 0 | 0 | 38.66 | 0.01 | 0.012490973 |
| 10 | 0.236 | 43.43 | 1.225 | 1.294043272 |
| 20 | 0.472 | 48.59 | 2.18 | 1.904966271 |
| 30 | 0.708 | 54.34 | 2.945 | 2.113081134 |
| 40 | 0.944 | 61.04 | 3.675 | 2.033733114 |
| 50 | 1.18 | 69.64 | 4.37 | 1.621716545 |
| 60 | 1.416 | 89.9 | 5.02 | 0.008761562 |

6.0cm Dressing

| Strain % | Deflection (in) | Angle (α) | Dressing Force (F_y) Lbf. | User Input Force (F_x) |
|---|---|---|---|---|
| 0 | 0 | 38.68 | 1 | 1.25 |
| 10 | 0.236 | 43.43 | 1 | 1.06 |
| 20 | 0.472 | 48.59 | 1 | 0.88 |
| 30 | 0.708 | 54.34 | 1 | 0.72 |
| 40 | 0.944 | 61.04 | 1 | 0.55 |
| 50 | 1.18 | 69.64 | 1 | 0.37 |
| 60 | 1.416 | 89.9 | 1 | 0.00 |

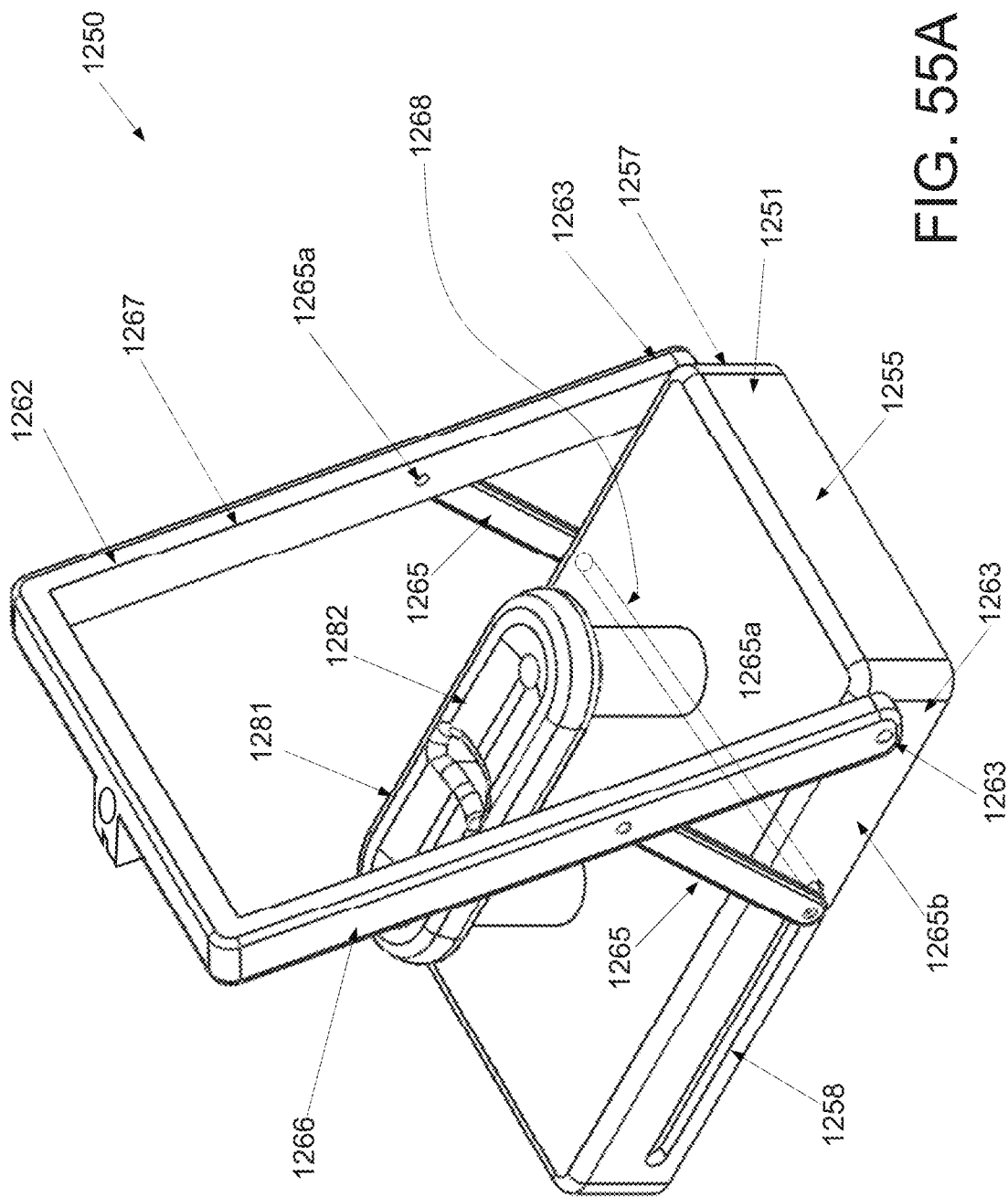

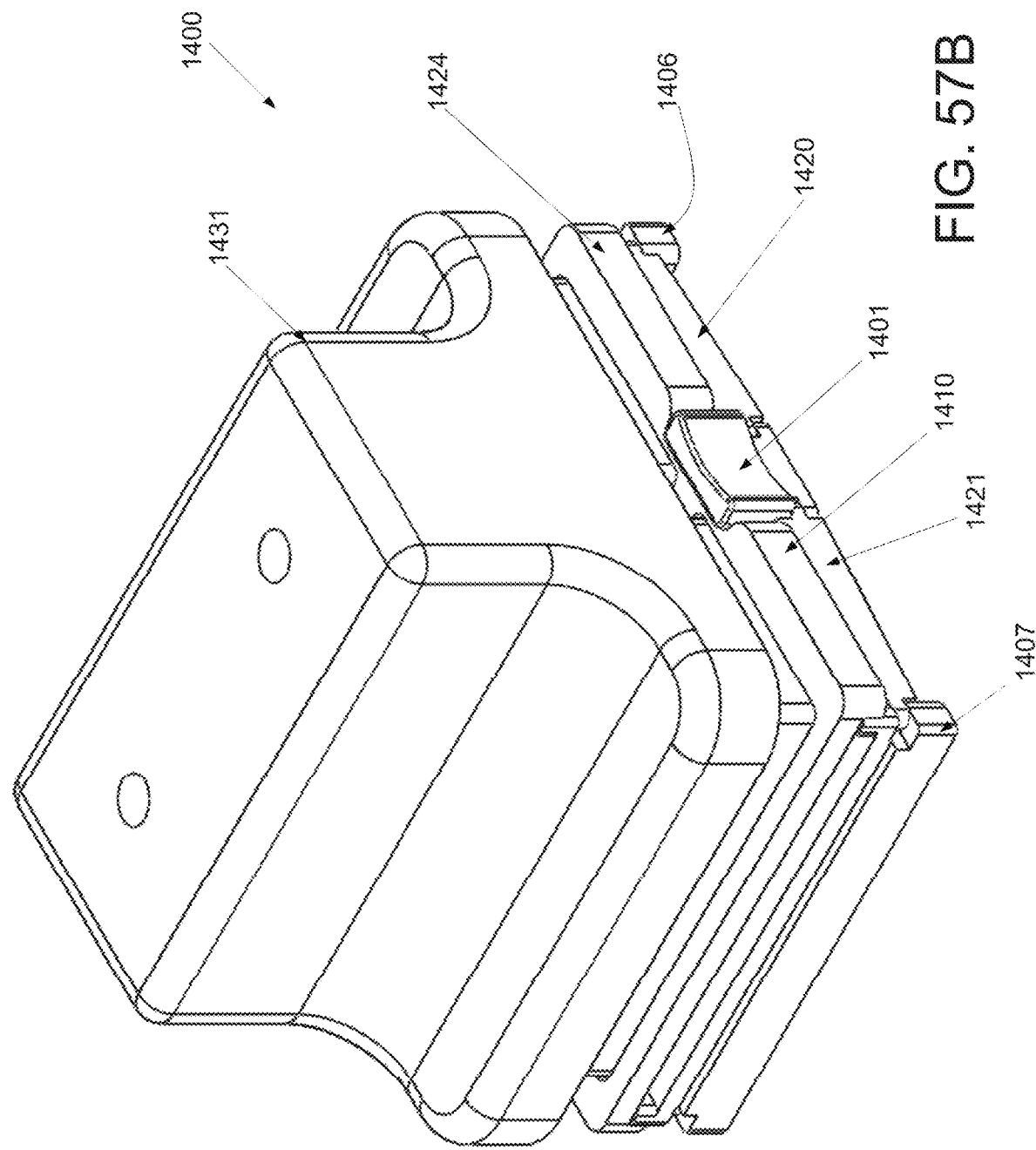

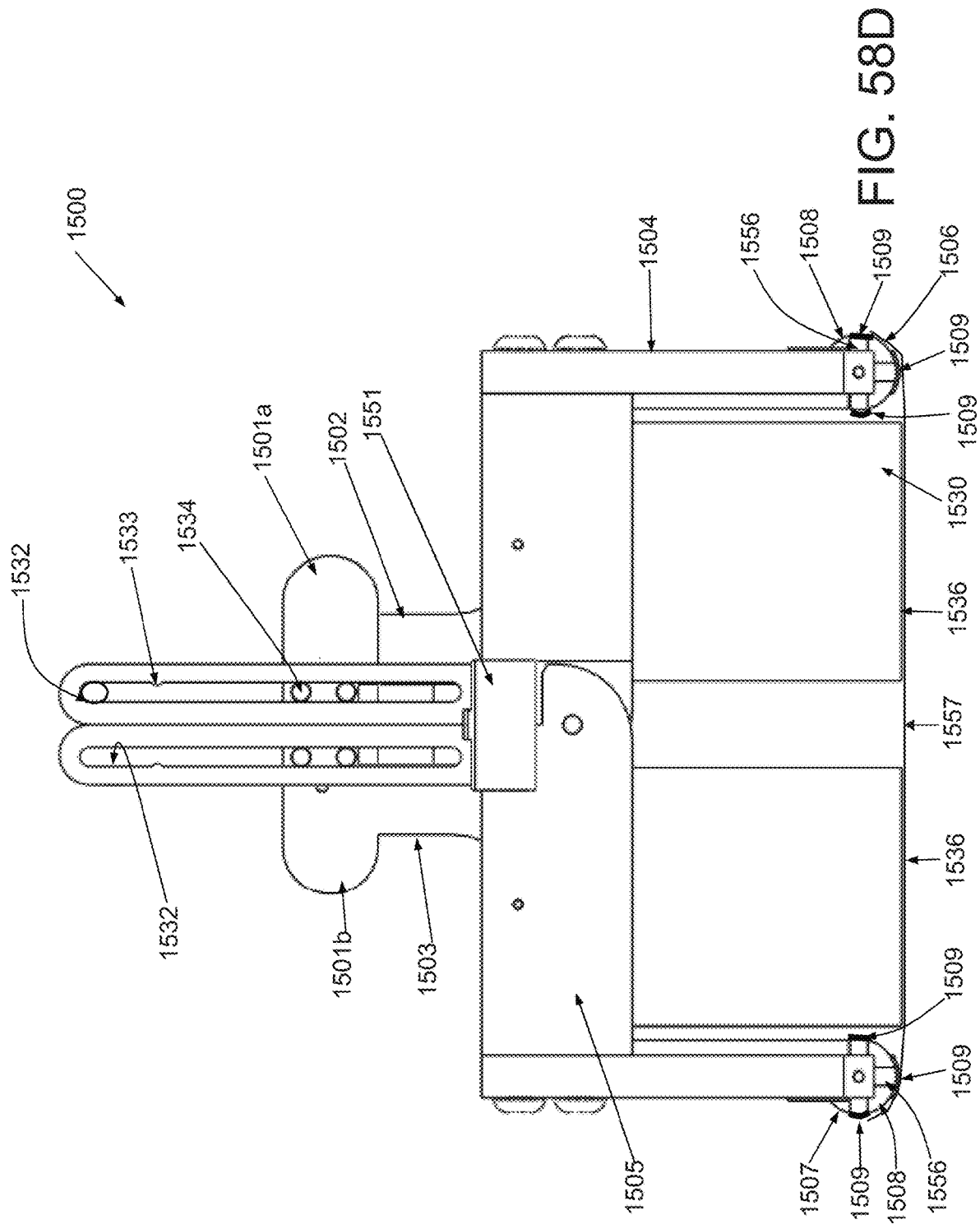

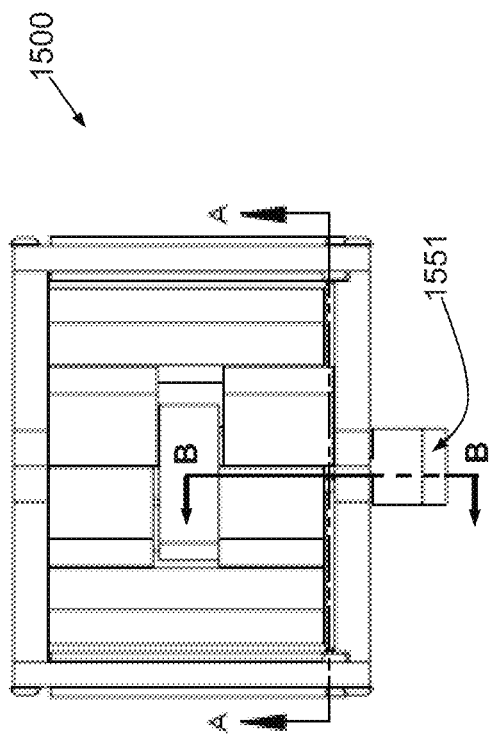

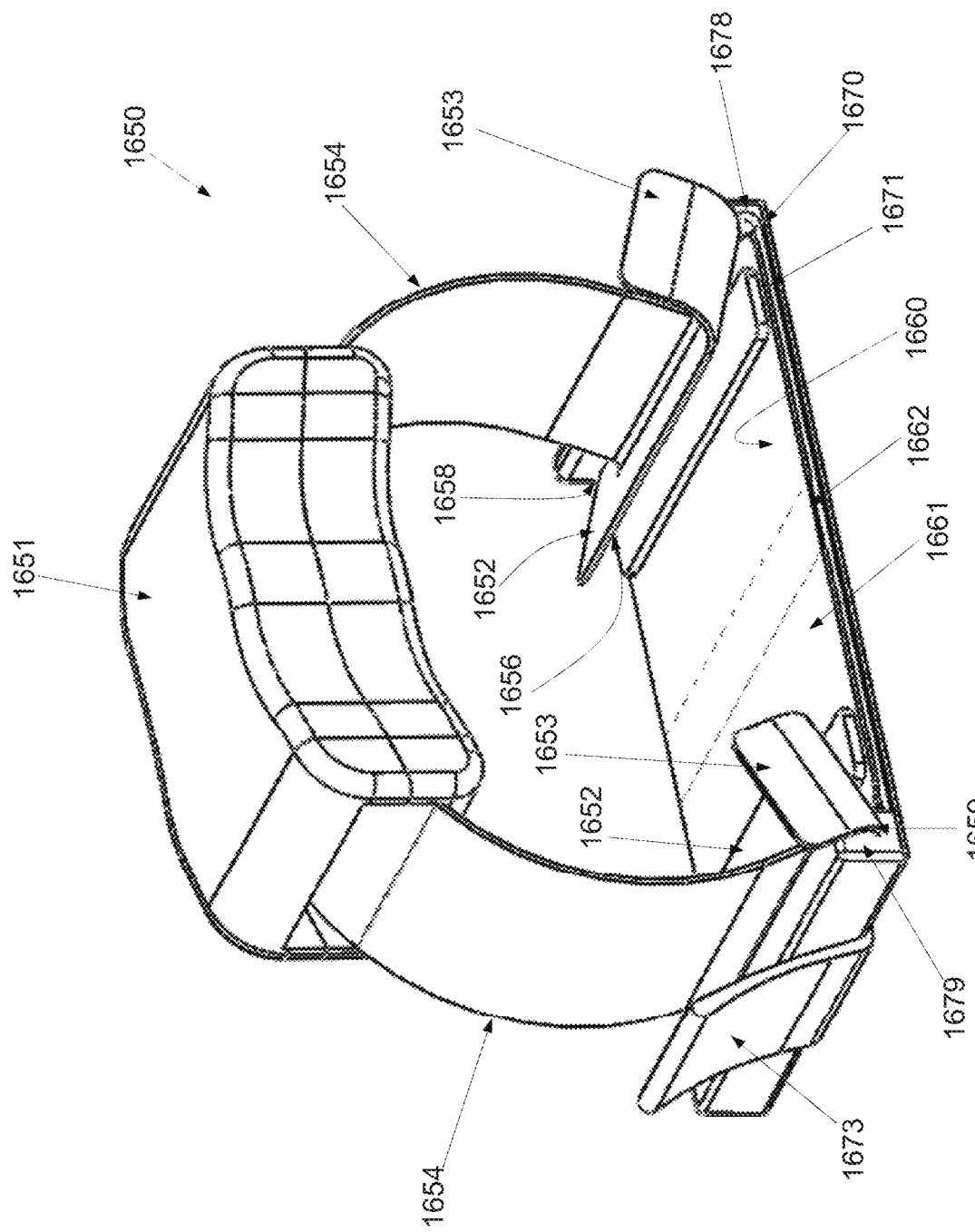

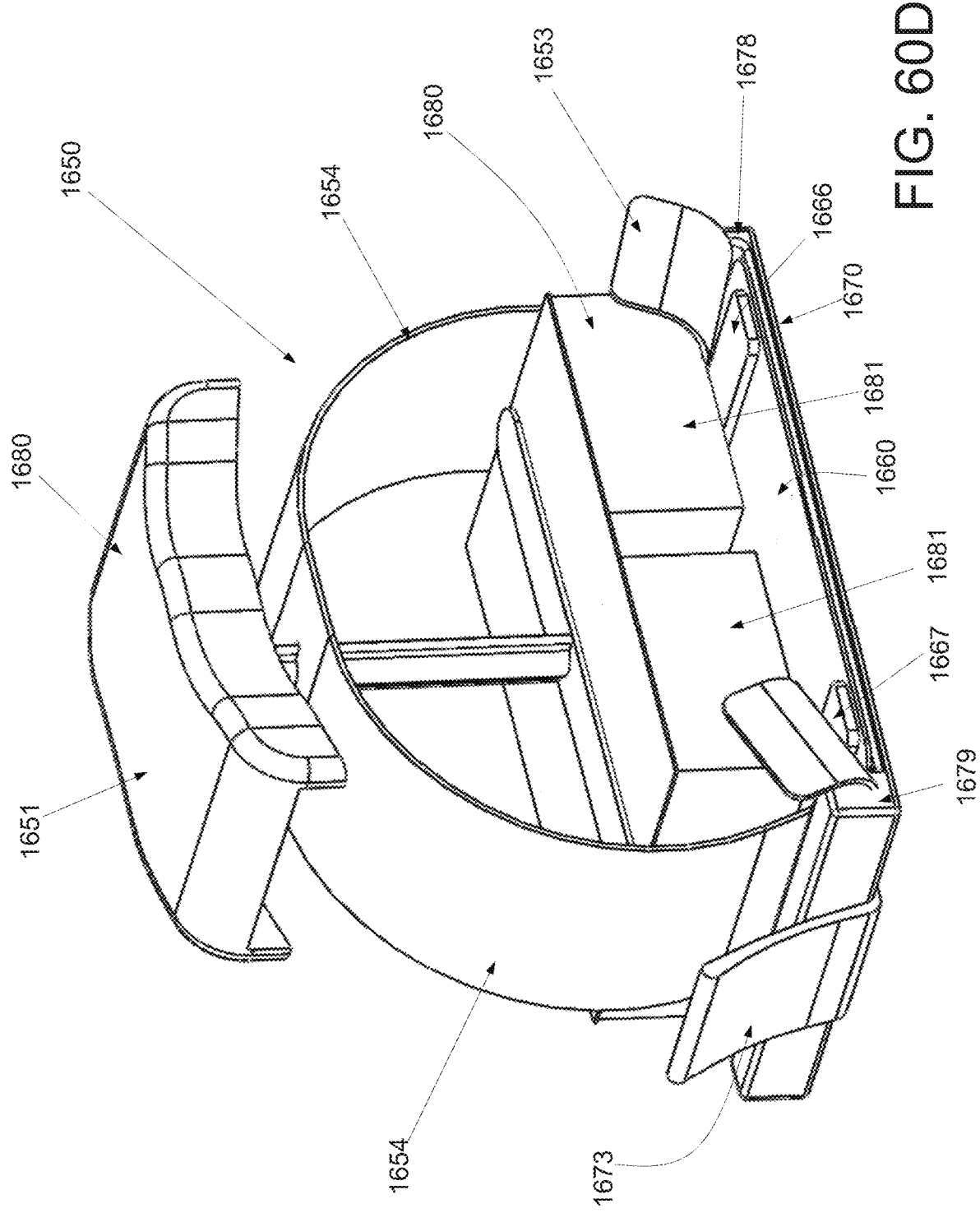

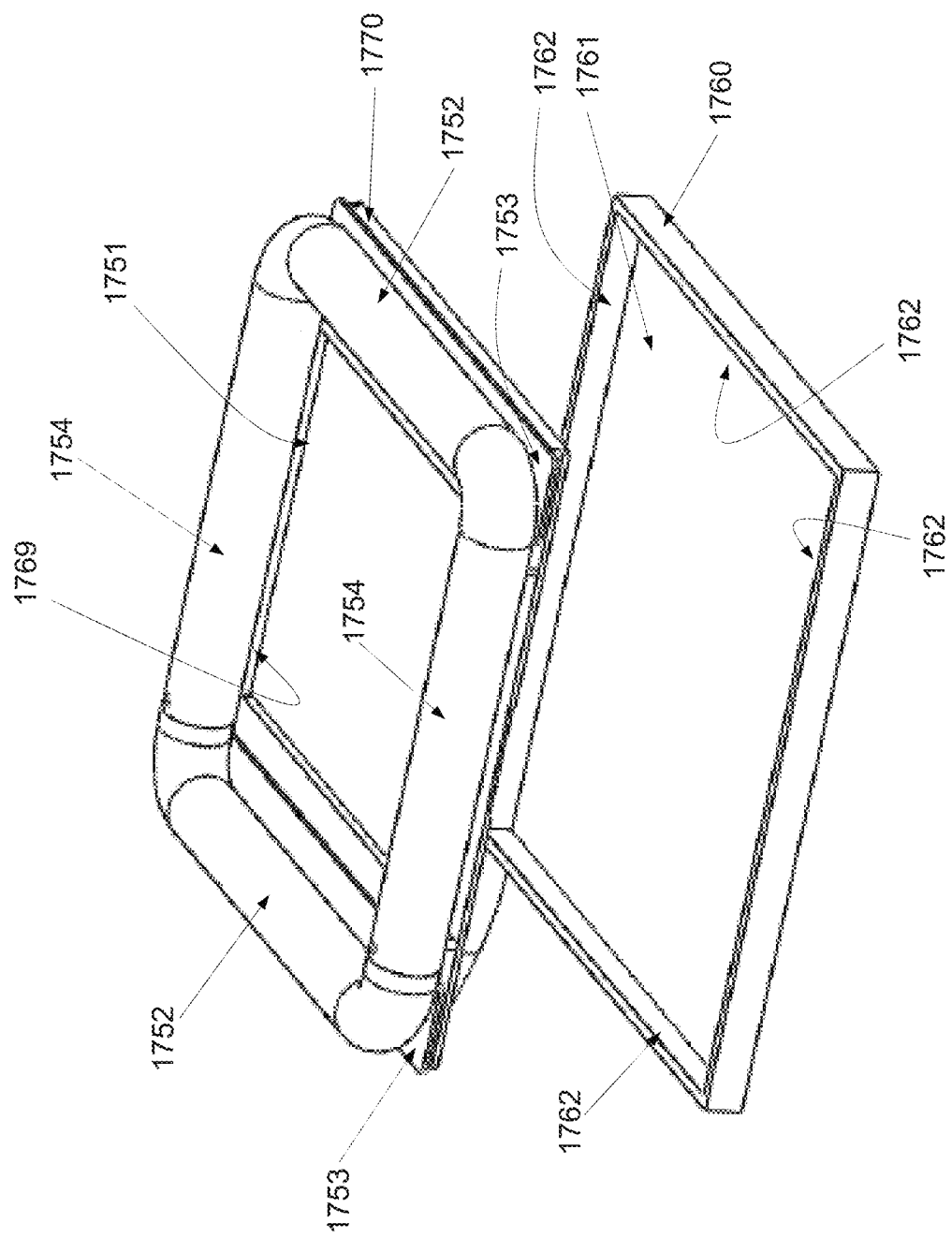

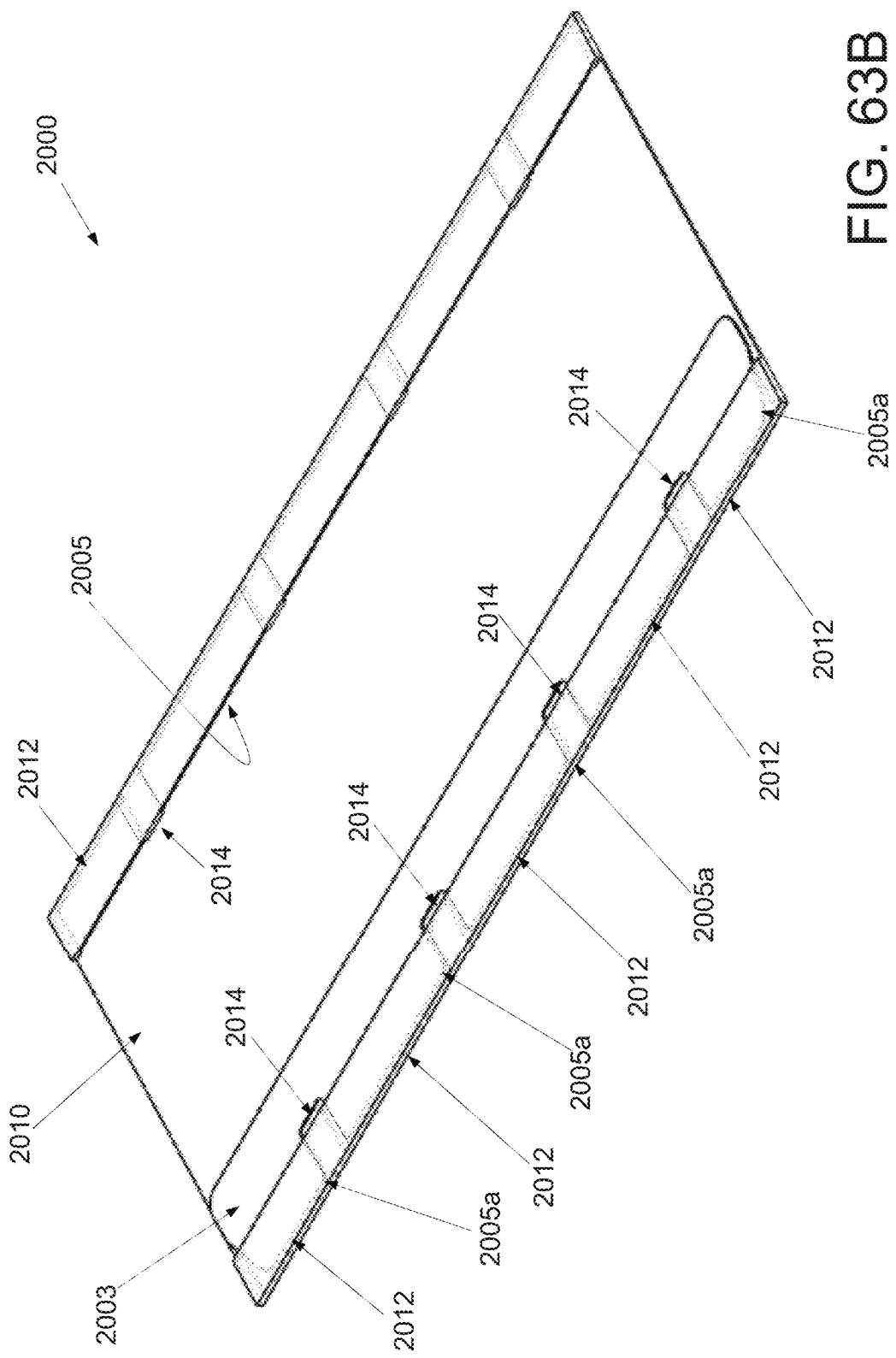

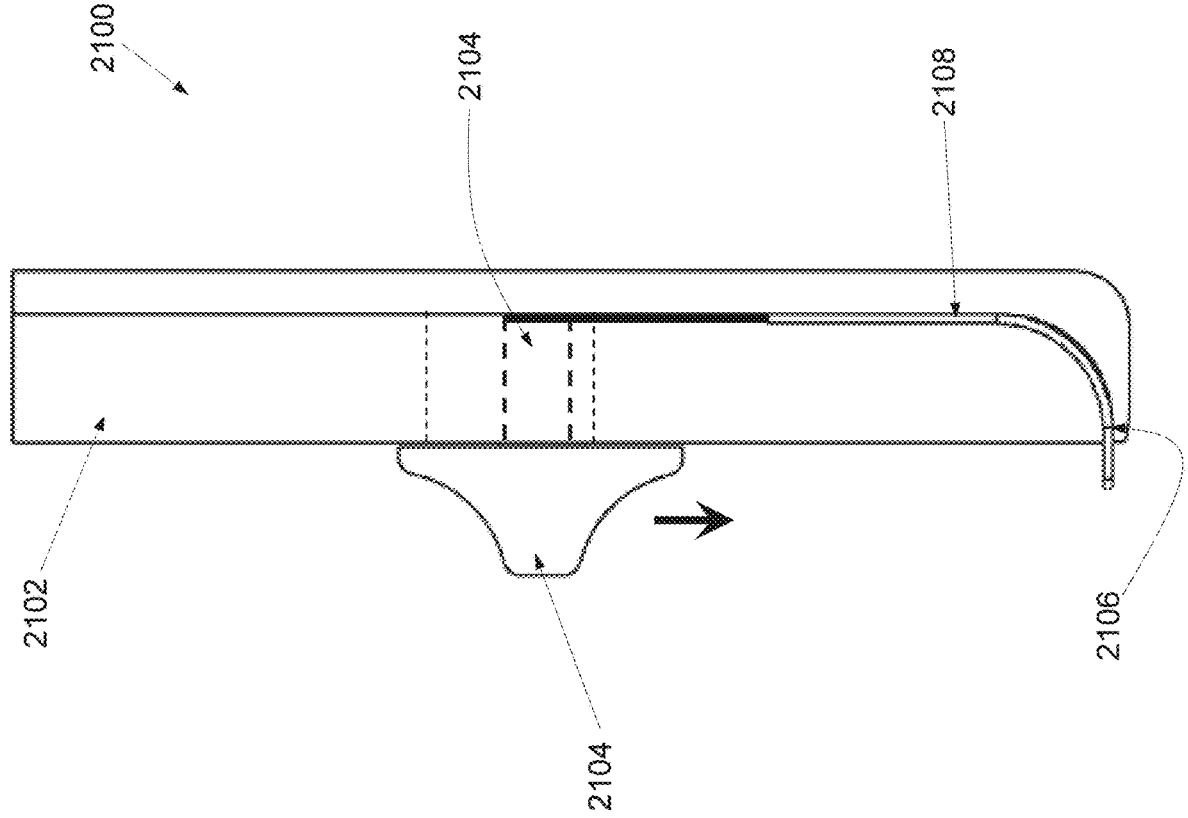

SKIN TREATMENT DEVICES

CROSS-REFERENCE TO RELATED APPLICATIONS

This application is continuation of U.S. application Ser. No. 15/293,084, filed Oct. 13, 2016, issued as U.S. Pat. No. 10,517,768 on Dec. 31, 2019, which is a continuation of U.S. application Ser. No. 14/158,741, filed Jan. 17, 2014, issued as U.S. Pat. No. 9,492,329 on Nov. 15, 2016, which is a continuation of U.S. application Ser. No. 13/089,129, filed Apr. 18, 2011, issued as U.S. Pat. No. 8,674,164 on Mar. 18, 2014, which is a continuation of U.S. application Ser. No. 12/854,859, tiled Aug. 11, 2010 issued as U.S. Pat. No. 8,592,640 on Nov. 26, 2013, which claims benefit under 35 U.S.C. § 119(e) to U.S. Provisional Application Ser. No. 61/233,122, filed Aug. 11, 2009, U.S. Provisional Application Ser. No. 61/243,020, filed Sep. 16, 2009, and U.S. Provisional Application Ser. No. 61/264,205, filed Nov. 24, 2009, all of which are hereby incorporated by reference in their entirety. This application is also related to U.S. application Ser. No. 11/888,978, filed Aug. 3, 2007 issued as U.S. Pat. No. 7,683,234 on Mar. 23, 2010, U.S. patent application Ser. No. 12/358,162, filed Jan. 22, 2009 issued as U.S. Pat. No. 8,168,850 on May 1, 2012, and U.S. patent application Ser. No. 12/358,164, filed Jan. 22, 2009 issued as U.S. Pat. No. 8,183,428 on May 22, 2012, which are hereby incorporated by reference in their entirety.

BACKGROUND

Scar formation in response to cutaneous injury is part of the natural wound healing process. Wound healing is a lengthy and continuous process, although it is typically recognized as occurring in stages. The process begins immediately after injury, with an inflammatory stage. During this stage, which typically lasts from two days to one week (depending on the wound), damaged tissues and foreign matter are removed from the wound. The proliferative stage occurs at a time after the inflammatory stage and is characterized by fibroblast proliferation and collagen and proteoglycan production. It is during the proliferative stage that the extracellular matrix is synthesized in order to provide structural integrity to the wound. The proliferative stage usually lasts about four days to several weeks, depending on the nature of the wound, and it is during this stage when hypertrophic scars usually form. The last stage is called the remodeling stage. During the remodeling stage the previously constructed and randomly organized matrix is remodeled into an organized structure that is highly cross-linked and aligned to increase mechanical strength.

While the histological features characterizing hypertrophic scars have been well documented, the underlying pathophysiology is not well known. Hypertrophic scars are a side effect of excessive wound healing, and generally result in the overproduction of cells, collagen, and proteoglycans. Typically, these scars are raised and are characterized by the random distribution of tissue bundles. The appearance (i.e., size, shape, and color) of these scars varies depending on the part of the body in which they form, and the underlying ethnicity of the person affected. Hypertrophic scars are very common, and may occur following any full thickness injury to the skin. Recently, it has been shown in U.S. Patent Application Publication 2006/0037091 (U.S. patent application Ser. No. 11/135,992 entitled "Method for Producing Hypertrophic Scarring Animal Model for Identification of Agents for Prevention and Treatment of Human Hypertrophic Scarring," filed May 24, 2005) which is hereby incorporated by reference in its entirety, that mechanical stress may increase hypertrophic scarring in a murine model.

Keloids are typically characterized as tumors consisting of highly hyperplastic masses that occur in the dermis and adjacent subcutaneous tissue in susceptible individuals, most commonly following trauma. Keloids are often more severe than hypertrophic scars, since they tend to invade normal adjacent tissue, while hypertrophic scars tend to remain confined within the original scar border.

Previous attempts to treat scars and keloids have included surgery, silicone dressings, steroids, x-ray irradiation, and cryotherapy. Each of these techniques has disadvantages. Perhaps the biggest disadvantage is that none of them effectively prevent or ameliorate the formation of scars or keloids in the first instance. That is, these techniques have primarily been used to treat scars after they are already well established.

BRIEF SUMMARY

Devices, kits and methods described herein may be for wound healing, including the treatment, amelioration, or prevention of scars and/or keloids by applying and/or maintaining a pre-determined strain in an elastic skin treatment device that is then affixed to the skin surface using skin adhesives to transfer a generally planar force from the bandage to the skin surface. Applicators are used to apply and/or maintain the strains, and some of the applicators are further configured to provide at least some mechanical advantage to the user when exerting loads onto the skin treatment device.

In one variation, a device for treating a skin surface is provided, comprising a first device attachment member comprising a first plurality of outwardly oriented projections, a second device attachment member comprising a second plurality of outwardly oriented projections, and a resilient member configured to exert a separation force between the first and second device attachment members. The device may further comprise a releasable locking mechanism configured to maintain the resilient member in a retracted configuration, and wherein the retracted configuration may be a strained configuration. The releasable locking mechanism may comprise a releasable latch, which may be configured to lock at a pre-determined strain and optionally resist further straining when locked at the pre-determined strain, or even a plurality of pre-determined strains. In some variations, the first device attachment member, the second device attachment member and the resilient member may be integrally formed.

In another variation, a wound dressing device is provided, comprising an applicator configured to maintain an attached dressing in a strained configuration, and wherein the applicator comprises a first attachment region, a second attachment region, and an access region between the first and second attachment regions configured to provide access to an attached dressing when the dressing is in a strained configuration.

In another variation, a wound dressing is provided, comprising a silicone sheet structure comprising an upper surface, a lower surface, a first edge and a second edge opposite the first edge, a first adhesive region, a second adhesive region spaced apart from the first adhesive region by a non-adhesive region, a first flap region located between the first edge and the first adhesive region, a second flap region located between the second edge and the second adhesive region, a first applicator attachment site located between the first flap region and the first adhesive region, and a second applicator attachment site located between the second flap region and the second adhesive region. The wound dressing may further comprise a first release liner releasably attached to the first adhesive region and the second adhesive region. In some further variations, the first and/or second flap regions may be adhesive flap regions, which may have a second and/or third release liner releasably attached to them, respectively. The first and second adhesive regions may comprise a pressure sensitive silicone adhesive with a release force of at least about 240 kg/m, about 270 kg/m, about 300 kg/m, or about 330 kg/m. The first applicator attachment site comprises a plurality of attachment openings or a pocket structure. The first release liner may have a lower surface and an upper surface with a different surface texture than the lower surface.

In still another variation, a dressing is provided, comprising an elastic layer comprising an upper surface, a lower surface, a first edge, a second edge, a first applicator attachment site, a flap region between the first edge and the first applicator attachment site, a second applicator attachment site spaced away from the second edge, and a first adhesive region located on the lower surface of the elastic layer.

In another variation, a method for treating a wound is provided, comprising straining an inner region of an elastic bandage between a first unstrained region and a second unstrained region, wherein each unstrained region is spaced away from two opposing edges of the bandage, and attaching the strained inner region of the bandage to a skin site. The straining of the inner region of the elastic bandage may be performed before attaching the strained inner region of the bandage to the skin site. In some further variations, attaching the strained inner region of the bandage to the skin site may be performed without attaching the two opposing edges of the bandage to the skin site. The method may also further comprise attaching the two opposing edges of the bandage to the skin site after attaching the inner region of the bandage to the skin site, reducing peak strain in the attached bandage while increasing peak strain at the skin site, and/or attaching the two opposing edges of the bandage to the skin site, which may include straining the unstrained regions of the bandage before attaching the two opposing edges of the bandage to the skin site. Straining the inner region of the unattached elastic bandage may comprise stretching the inner region of the unattached elastic bandage to a predetermined strain.

In one embodiment, a dressing is provided, comprising an elastic layer comprising an upper surface, a lower surface, a first edge, a second edge, a first applicator attachment site, a flap region between the first edge and the first applicator attachment site, a second applicator attachment site spaced away from the second edge, and a first adhesive region located on the lower surface of the elastic layer.

In another embodiment, a method for treating a wound is provide, comprising straining an inner region of an elastic bandage between a first unstained region and a second unstained region, wherein each unstrained region is spaced away from two opposing edges of the bandage, and attaching the strained inner region of the bandage to a skin site. Straining the inner region of the elastic bandage may be performed before attaching the strained inner region of the bandage to the skin site. Attaching the strained inner region of the bandage to the skin site may be performed without attaching the two opposing edges of the bandage to the skin site. The method may further comprise attaching the two opposing edges of the bandage to the skin site after attaching the inner region of the bandage to the skin site. The method may further comprise reducing peak strain in the attached bandage while increasing peak strain at the skin site. The method may further comprise attaching the two opposing edges of the bandage to the skin site. The method may further comprise straining the unstrained regions of the bandage before attaching the two opposing edges of the bandage to the skin site. Straining the inner region of the unattached elastic bandage may comprise stretching the inner region of the unattached elastic bandage to a predetermined strain.

In still another embodiment, an incision treatment system is provided, comprising an elastic member comprising at least two hook-and-loop regions and at least one skin adhesive region. The elastic member may be an elastic layer member. The at least one adhesive region may be located on an opposite surface of the elastic member than the at least two hook-and-loop regions. Each of the at least two hook-and-loop regions may be loop-type of hook-and-loop regions. The elastic member may comprise at least two skin adhesive regions. The incision treatment system may further comprise an applicator comprising at least two hook-and-loop regions complementary to the at least two hook-and-loop regions of the elastic member.

In one embodiment, a system for treating a skin surface is provided, comprising a tensioning member, comprising a first device attachment member, a second device attachment member, and a collapsible structure configured to movably separate the first and second device attachment members without requiring continuous application of external force onto the device to maintain separation of the first and second device attachment members. The system may further comprise an elastic member configured to attach to the first and second device attachment members of the tensioning member. The elastic member may be configured to releasably attach to the first and second device attachment members of the tensioning member. The elastic material may have a load per width of at least 0.35 Newtons per mm at an engineering strain of 60%. The elastic material may have a load per width of no greater than about 2 Newtons per mm at the engineering strain of 60%, about 1 Newtons per mm at the engineering strain of 60%, about 0.7 Newtons per mm at the engineering strain of 60%, or no greater than about 0.5 Newtons per mm at the engineering strain of 60%. The system elastic material may have a load per width that does not decrease from an engineering strain of 0% to 60%, a load per width plot that increases linearly from an engineering strain of 0% to 60%, or a load per width plot that is not convex from an engineering strain of 0% to 60%. The elastic material may comprise an adhesive configured to maintain a substantially constant stress in the range of 200 kPa to about 500 kPa for at least 8 hours when strained to an engineering strain of 30% and attached to a surface. The elastic material may comprise an adhesive configured to maintain a substantially constant stress in the range of 200 kPa to about 400 kPa for at least 8 hours when strained to an engineering strain of 30% and attached to a surface. The substantially constant stress may vary by less than 10% over at least 8 hours, or by less than 5% over at least 8 hours. The collapsible structure may comprise two collapsible supports and two rigid supports. Each of the two collapsible supports may articulate with both of the two rigid supports. The two collapsible supports may each comprise two pivotal* connected subsupports. The collapsible structure may comprise a collapsed state and an expanded state, and in the collapsed state, each of the pivotably connected subsupports form an angle of at least 30 degrees with a line that bisects the two collapsible supports. The system may further comprise a stamping structure configured to pass a user-exerted force through the collapsible structure. The stamping structure may comprise a stamping surface and a resilient member. The resilient member may be a spring. The two rigid supports may have a substantially parallel orientation and at least one of the two rigid supports is configured to translate along a movement axis perpendicular to the parallel orientation. The collapsible structure may be configured to provide a mechanical advantage when exerting the separation force. The mechanical advantage may be provided throughout a movement range of the collapsible structure, or may be provided partially through a movement range of the collapsible structure.

In one embodiment, a tensioning device configured to exert a separation force to cause a strain in a skin treatment device may be provided, the tensioning device comprising a tensioning member, and a first attachment portion configured to releasably attach to a skin treatment device and a second attachment portion configured to releasable attach to the skin treatment device, wherein the tensioning member may be configured to exert a separation force between the first attachment portion and the second attachment portion to cause a strain in a skin treatment device attached to the first and second attachment portions. The tensioning member may be configured to strain the skin treatment device to an engineering strain of 40% using a load of at least about 0.25 Newtons per mm width of the skin treatment device. The load to strain the skin treatment device to the engineering strain of 40% may be no greater than about 1 Newton per mm width of the skin treatment device, and may be no greater than about 0.5 Newton per mm width of the skin treatment device. In other embodiments, the tensioning member may be configured to strain the skin treatment device to an engineering strain of 60% using a load of at least about 0.35 Newtons per mm width of the skin treatment device. The load to strain the skin treatment device to the engineering strain of 60% may be no greater than about 1 Newton per mm width of the skin treatment device. The tensioning member may comprise a resilient member configured to exert the separation force. The tensioning device may further comprise a compressing member configured to retract the resilient member to a first configuration and then to release the resilient member to a strained configuration whereby a strain may be produced in a skin treatment device attached to the first and second attachment portions. The tensioning device may further comprise a releasable locking mechanism configured to releasably lock the resilient member in the first configuration. The locking mechanism may be configured to lock across a range of resilient member configurations corresponding to a range of predetermined strains in the skin treatment device. The locking mechanism may be configured to lock across a range of predetermined strains within a range from about 0% to about 60%, or a range from about 10% to about 50%. The tensioning member may comprise a mechanical force applicator configured to exert the separation force. The mechanical force applicator may provide a mechanical advantage to apply the force. The mechanical force applicator may be manually actuatable. At least one the first and second attachment portions may comprise a hook and loop mechanism. At least one of the first and second attachment portions may comprise an extension member configured to be received in an opening in a skin treatment device. At least one of the first and second attachment portions may comprise an opening for receiving an attachment member of a skin treatment device. At least one of the first attachment portion and the second attachment portion may be configured to move relative to the tensioning member to facilitate separation of the skin treatment device. At least one of the first attachment portion and the second attachment portion may be configured to pivot or rotate relative to the tensioning member. At least one of the first attachment portion and the second attachment portion may be configured to retract relative to the tensioning member. The tensioning device may be an applicator configured to permit a user to apply a skin treatment device to skin of a subject. The tensioning device may further comprise pressure pads configured to apply pressure to a skin treatment device being applied to skin of a subject. The pressure pads may be located between the first and second attachment portions. The tensioning member may have a curved configuration, which may also be a curved planar configuration. The tensioning member may be configured to automatically lock upon deformation to a predetermined locking configuration.

In another embodiment, a method of applying a treatment device to a surface is provided, comprising actuating the tensioning device to strain a treatment device to at least a predetermined strain threshold, maintaining a strain in the treatment device without requiring external application of force onto the tensioning device, applying the strained treatment device to a treatment site, and detaching the treatment device from the tensioning device. The method may further comprise attaching the treatment device to the tensioning device before actuating the tensioning device. Actuating the tensioning device may comprise squeezing the tensioning device. The method may further comprise relieving at least some of the strain in the treatment device. Relieving at least sonic of the strain in the treatment device may comprise collapsing the tensioning device. The method may further comprise locking the tensioning device to a predetermined configuration actuating the tensioning device. Locking the tensioning device may occur automatically after straining the treatment device to the predetermined strain threshold. Relieving the strain may comprise in the treatment device may comprise unlocking a locking mechanism of the tensioning device. Attaching the treatment device to the tensioning device may comprise attaching the treatment device to the tensioning device may occur at two separate locations using two attachment mechanisms located on the tensioning device. The method may further comprise pressing the treatment device against the treatment site. Pressing the treatment device may occur before detaching the treatment device from the tensioning device. Pressing the treatment device may comprise pushing down a resilient stamper mechanism located between the two attachment mechanisms of the tensioning device, or reaching into an access opening in the tensioning device to manually push on the treatment device.

BRIEF DESCRIPTION OF THE DRAWINGS

FIG. 1A is a schematic superior view of one variation of a wound treatment device; FIG. 1B is a schematic side elevational view of the wound treatment device in FIG. 1A;

FIGS. 2A and 2B are schematic superior and side elevational views of the wound treatment in FIGS. 1A and 1B, respectively, with release liners.

FIG. 10 is a schematic front elevational view of a curved attachment structure of an applicator;

FIGS. 11A and 11B are schematic side elevational views of an applicator with a hinged frame in an unlocked and locked configuration, respectively.

FIG. 12A is a schematic superior view of an applicator with pneumatic strut members; FIG. 12B is a schematic component view of the ratchet locking mechanism of the applicator in FIG. 12A.

FIGS. 19A and 19B illustrate engineering and true stress/strain plots, respectively, of NEXCARE™ TEGADERM™ backing material.

FIGS. 31A and 31B are engineering stress plots over time for the Nexcare™ Tegaderm™ under different loads using different X-axis scales, respectively.

FIGS. 33A and 33B are engineering stress plots over time for the elastic Steri-Strip™ under different loads using different X-axis scales, respectively.

FIGS. 35A and 35B are engineering stress plots over time for the Band-Aid® Flexible Fabric under different loads using different X-axis scales, respectively.

FIGS. 36A and 3B are engineering stress plots over time for CVS/Pharmacy® silicone scar sheeting under different loads using different X-axis scales, respectively.

FIGS. 39A and 39B are engineering stress plots over time for CVS/Pharmacy® elastic bandage under different loads using different X-axis scales, respectively.

FIG. 50D is a side elevational view of a handle and locking mechanism of the applicator of FIG. 50A in a strained configuration; FIG. 50F is a side elevational view of the applicator of FIG. 50A in a strained configuration.

FIG. 52D is an inferior view of the applicator of FIG. 52A in a strained configuration; FIG. 52E is a superior view of the applicator of FIG. 52A in an unstrained configuration; FIG. 52F is a superior view of the applicator of FIG. 52A in a strained configuration; FIG. 52G is a cross-sectional view of the applicator of FIG. 52E along the lines A-A in an unstrained configuration; and FIG. 52H is a cross-sectional view of an applicator of FIG. 52F along the lines B-B in a strained configuration.

FIG. 54H is a side view of the applicator of FIG. 54E in a strained configuration.

FIG. 55A is a perspective view of an applicator with an integrated foam stamper in an unstrained configuration.

FIG. 57B is a perspective view of the applicator of FIG. 57A in a strained configuration.

FIG. 58D is a side view of the applicator of FIG. 58A in a strained and stamped configuration; FIG. 58G is a superior view of the applicator of 58A in a strained, stamped and released configuration; FIG. 58H is a cross-sectional view of the applicator of FIG. 58G along the lines A-A.

FIG. 60A is a perspective view of an applicator and skin treatment device in an unstrained configuration; FIG. 60D is a perspective view of an applicator with an integrated foam stamper in an unstrained configuration.

FIG. 62B is a perspective view of the applicator and skin treatment device of FIG. 62A in a released configuration.

FIG. 63B is a perspective view of a variation of the attachment system of FIG. 63A in a loaded configuration.

FIG. 65B is a side view of the attachment structure system of FIG. 65A in the first position.

DETAILED DESCRIPTION

Figure 2C:
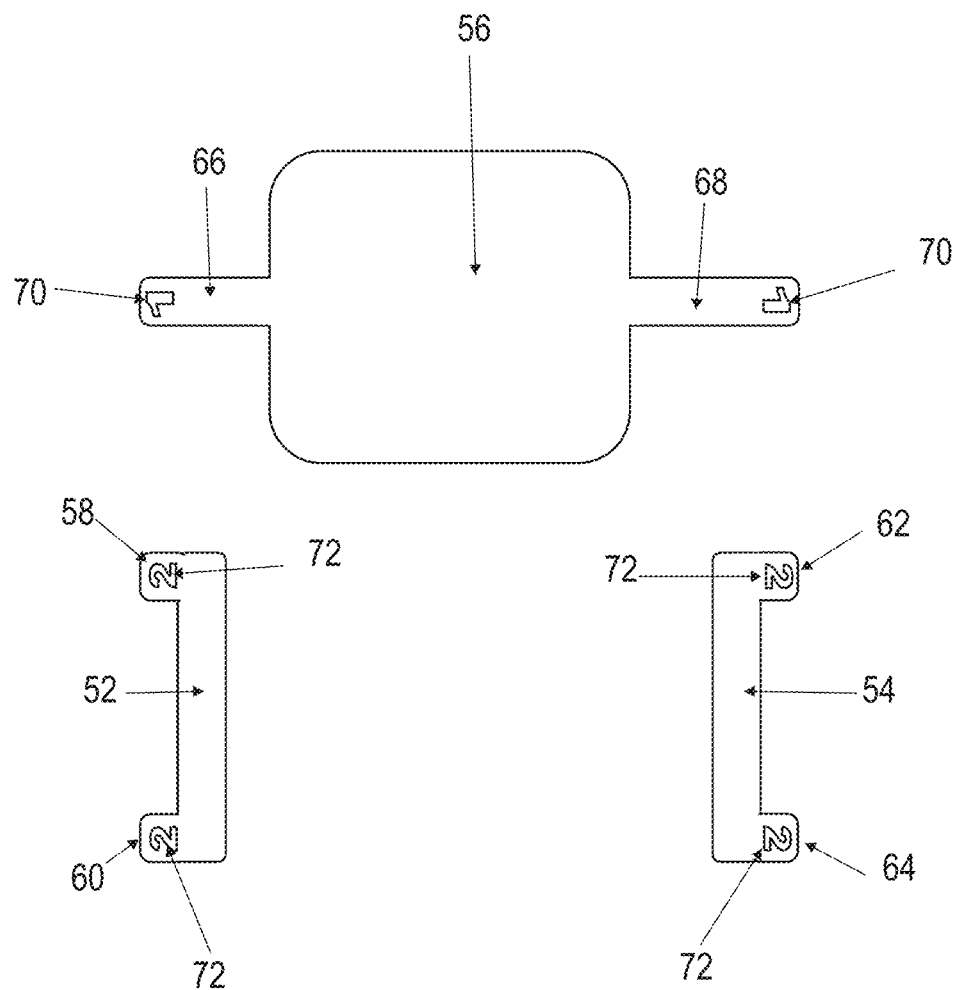
FIG. 2C is a superior component view of the release liners in FIGS. 2A and 2B.
Figure 3A:
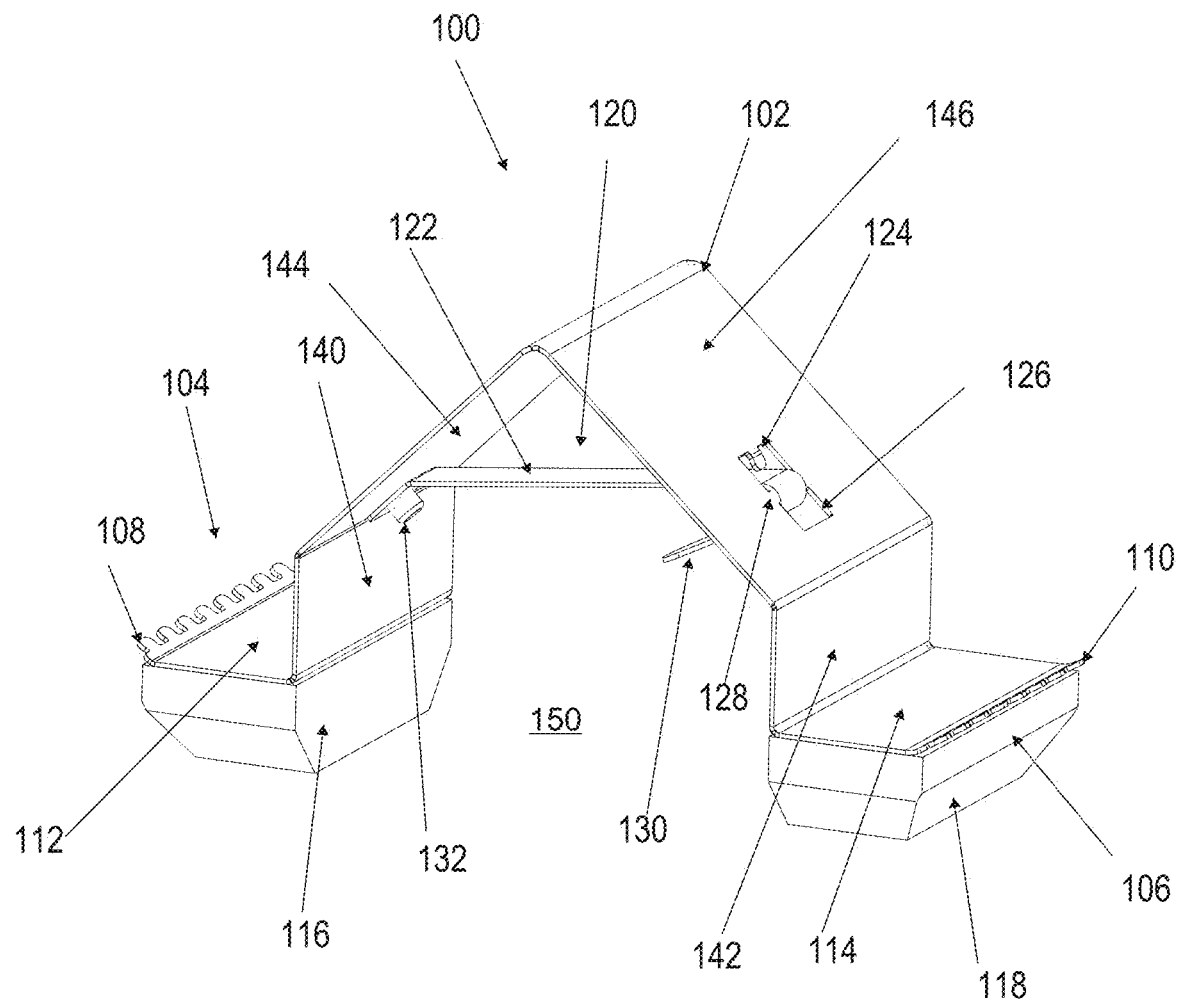
FIG. 3A is a perspective view of a wound treatment applicator in a base configuration.
Figure 3B:
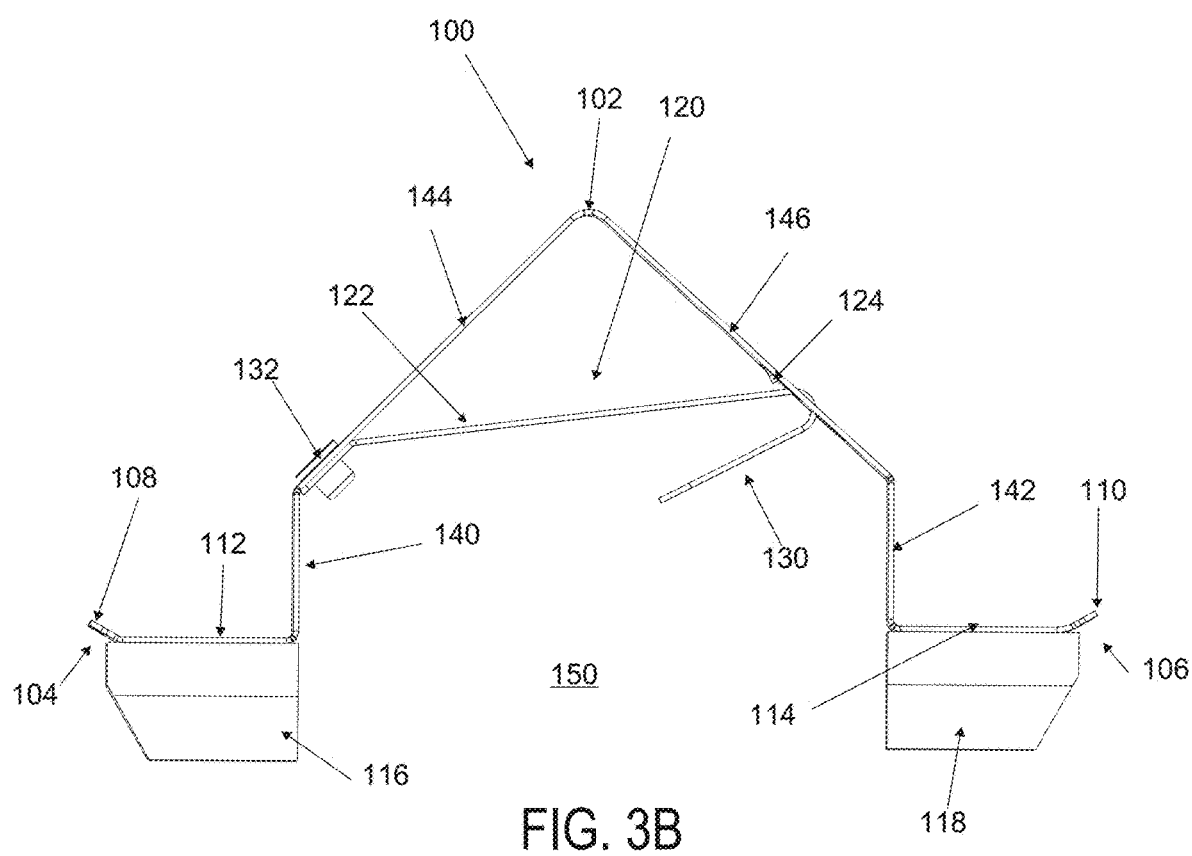
FIGS. 3B to 3D are side elevational, superior and inferior views of the applicator in FIG. 3A.
Figure 3C:
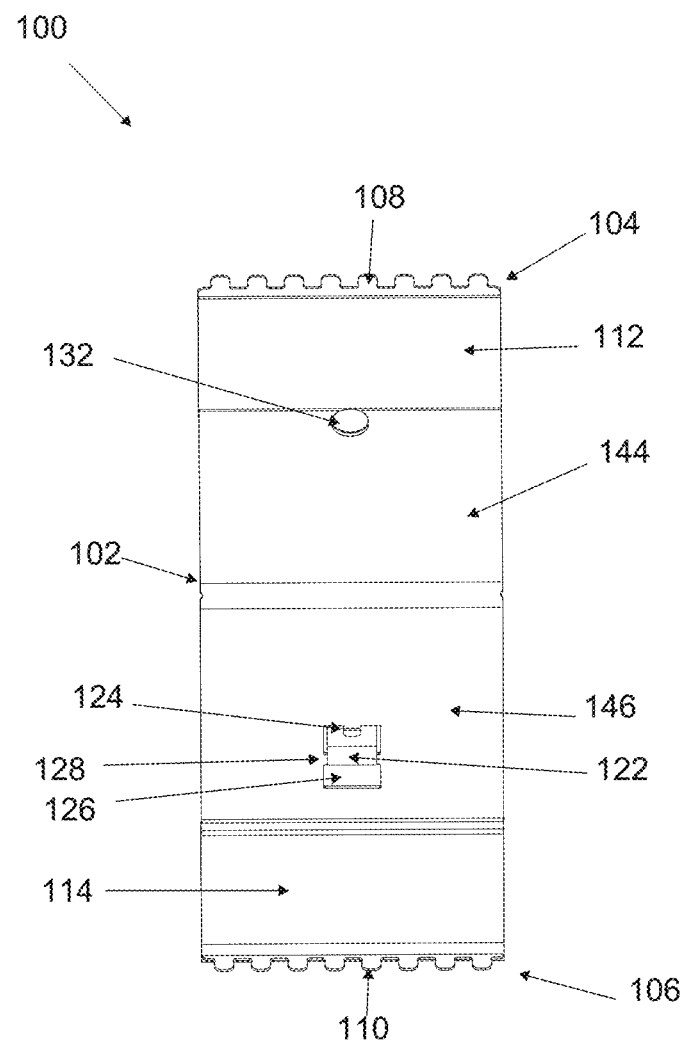
Figure 3D:
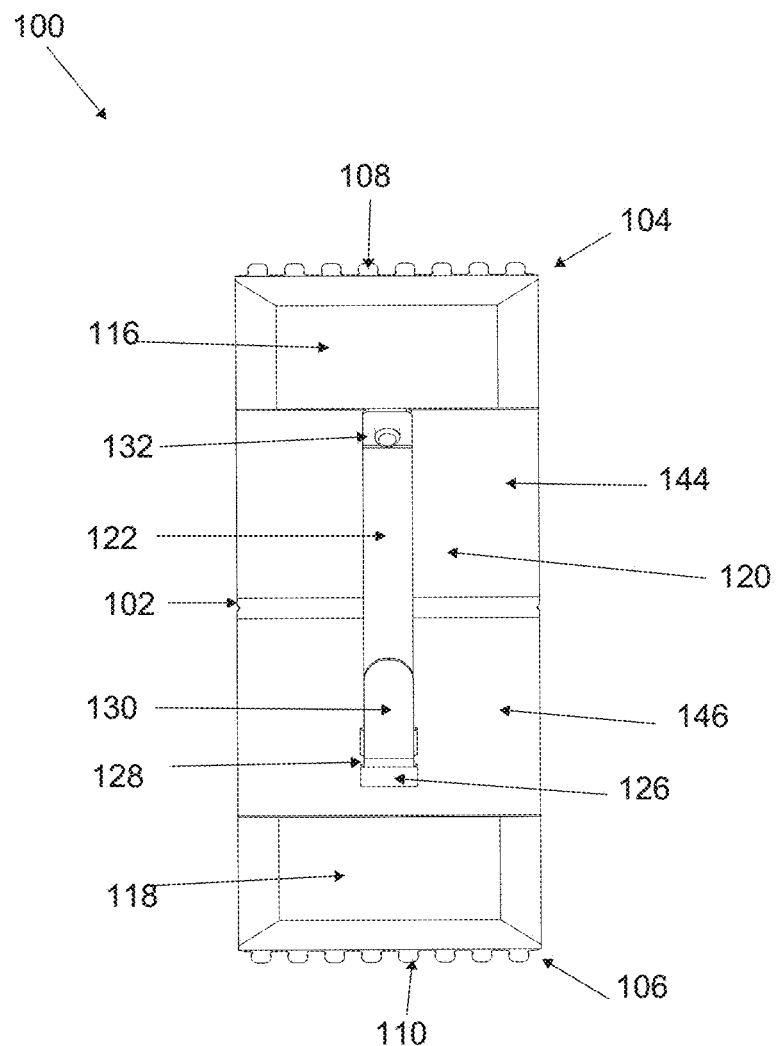
Figure 4A:
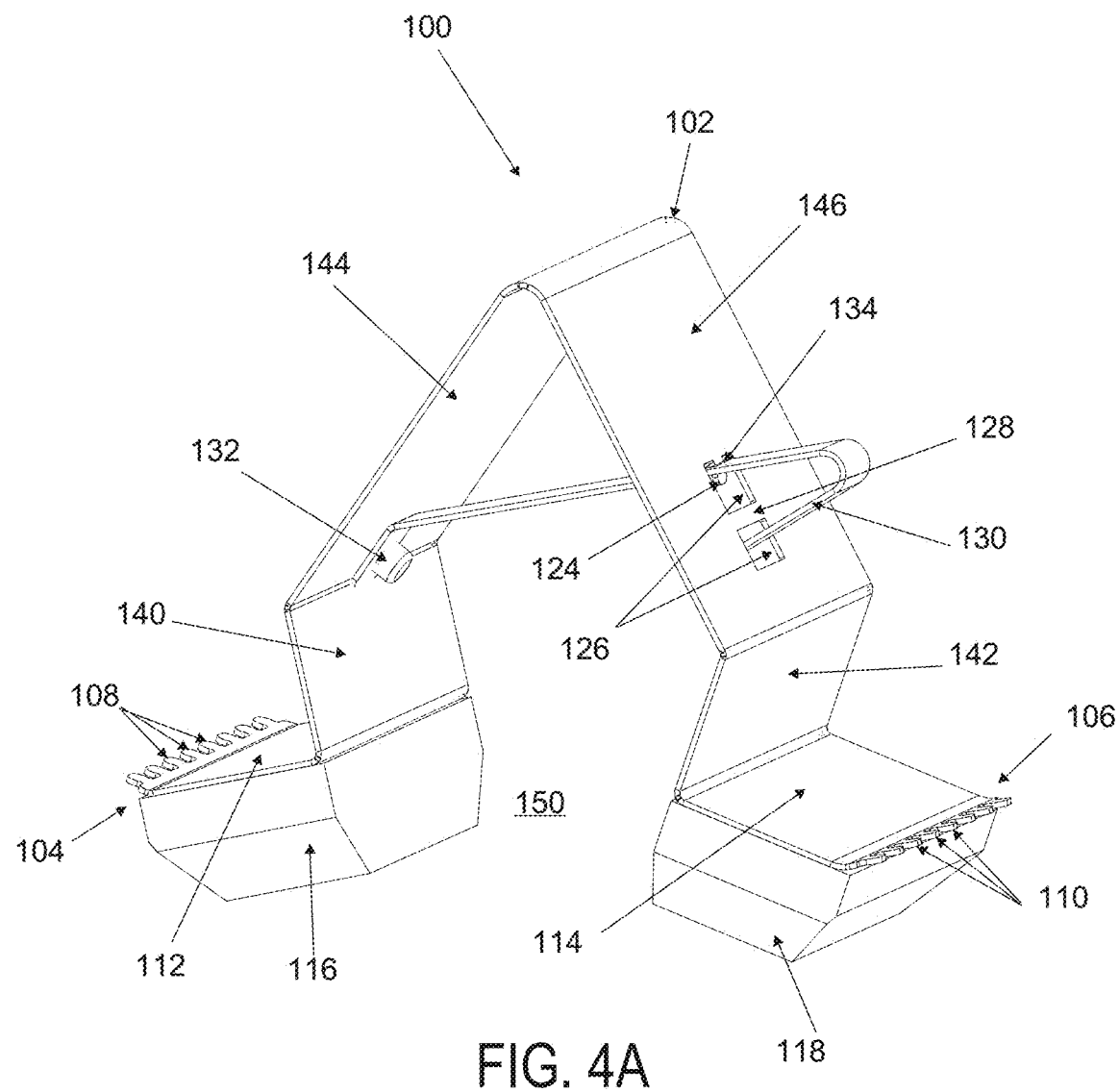
FIGS. 4A to 4D are perspective, side elevational, superior and inferior views of the applicator in FIGS. 3A to 3D in a locked configuration.
Figure 4B:
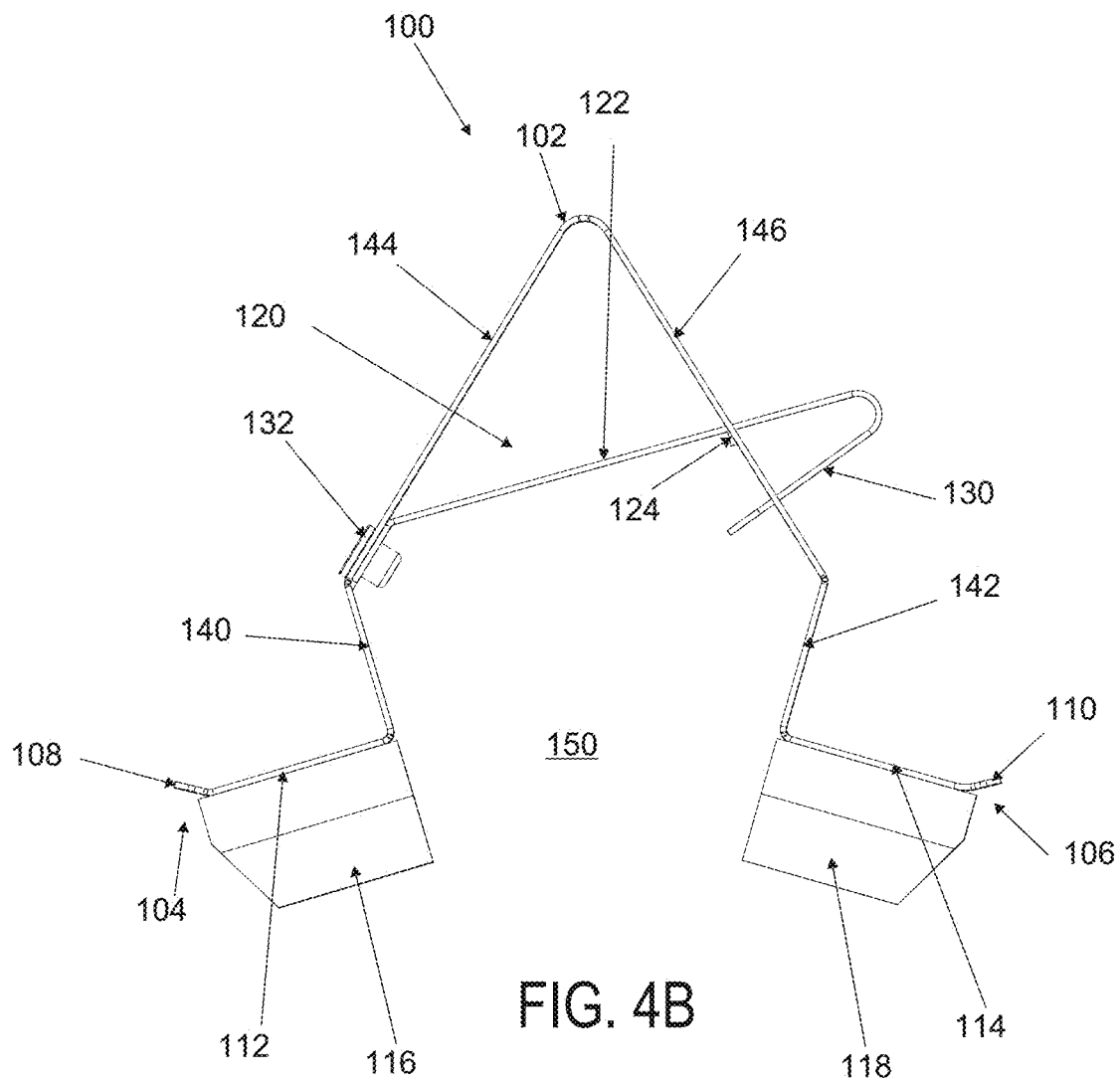
Figure 4C:
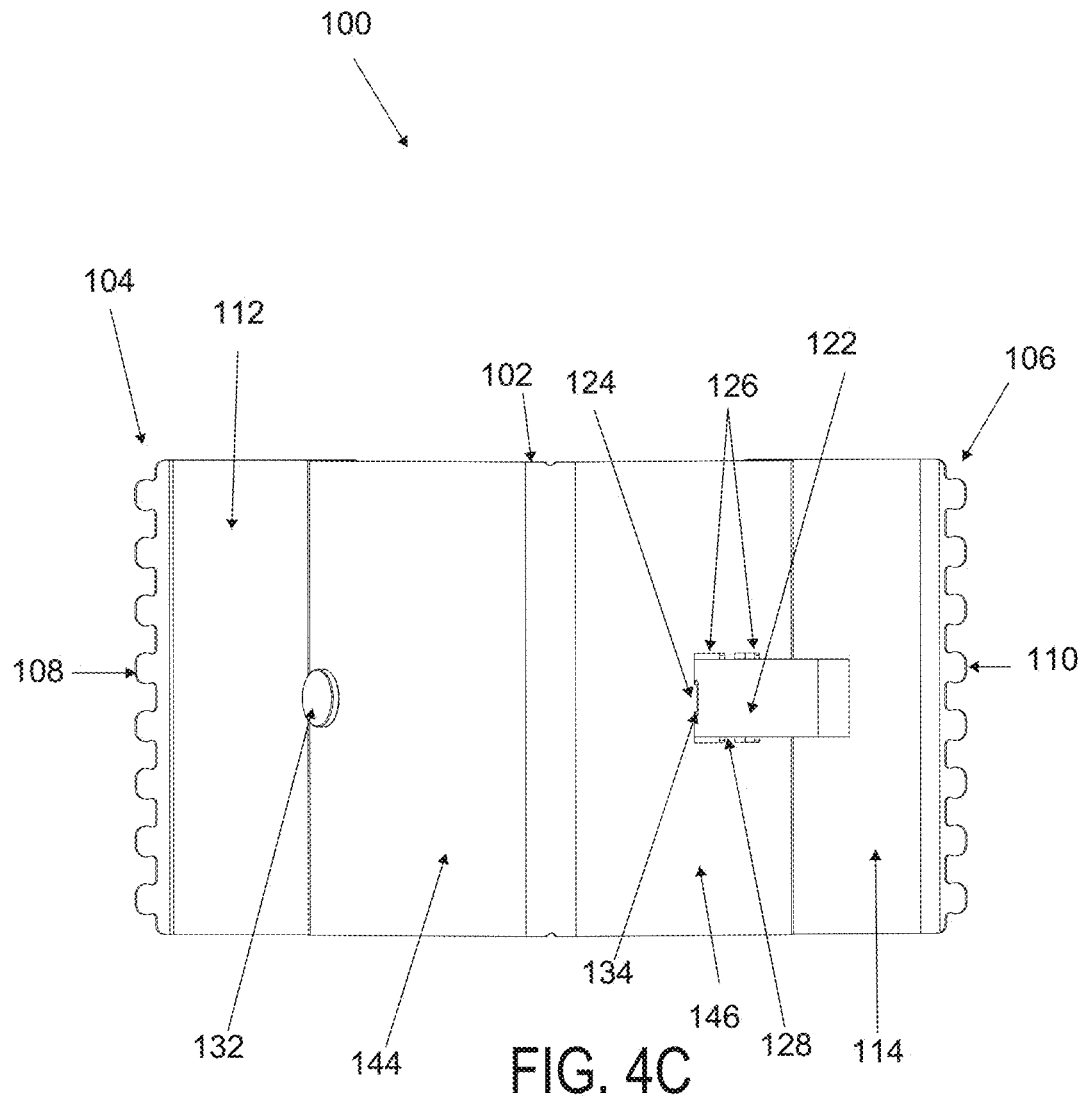
Figure 4D:
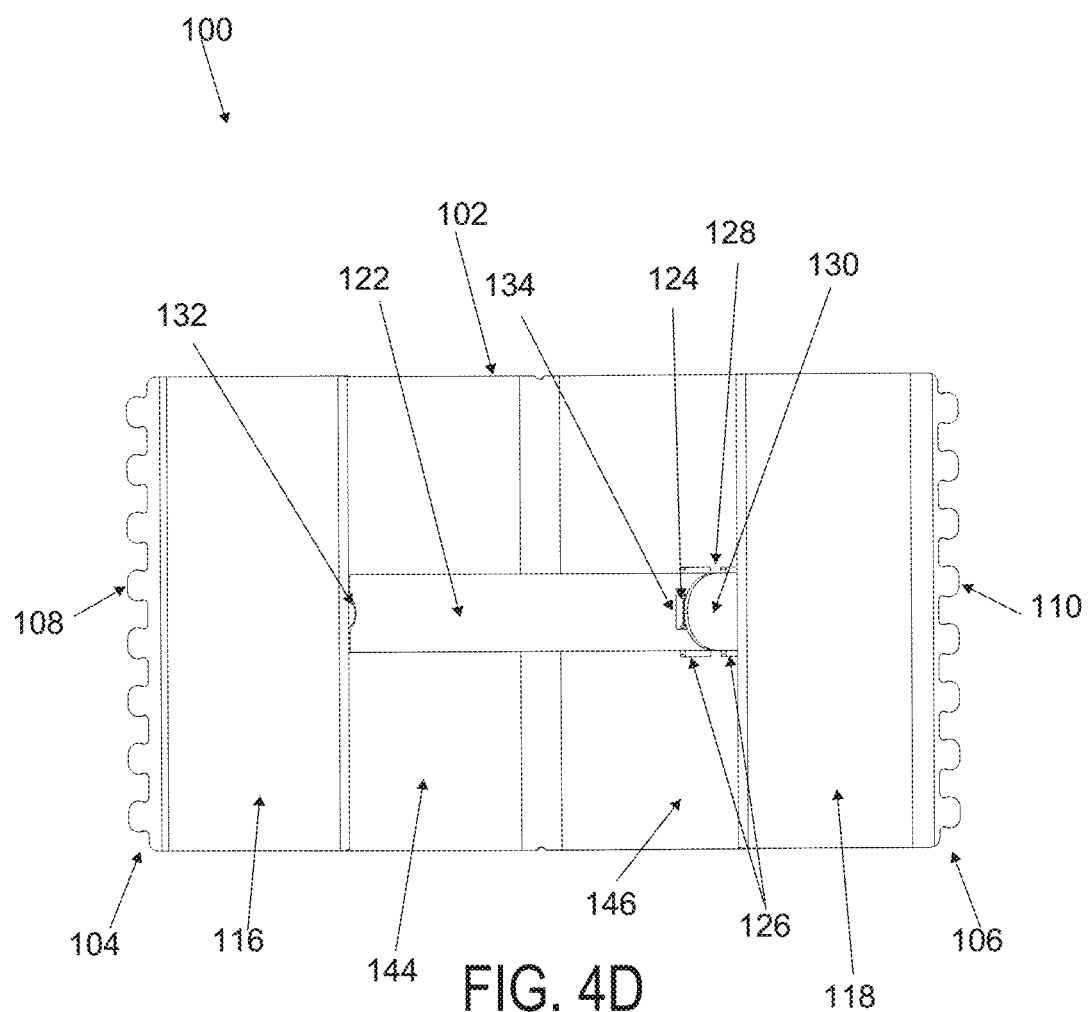

The mechanical environment of an injury may be an important factor in tissue response to that injury. The mechanical environment includes exogenous stress (i.e., physiological stress which includes stress transferred to the wound via muscle action or physical body movement) and endogenous stress (i.e., dermal stress originating from the physical properties of the skin itself, including stress induced at the wound site due to swelling or contraction of the skin). The devices, bandages, kits and methods described herein may control or regulate the mechanical environment of a wound to ameliorate scar and/or keloid formation. The mechanical environment of a wound includes stress, strain, and any combination of stress and strain. The control of a wound's mechanical environment may be active or passive, dynamic (e.g., by applying an oscillating stress) or static. The stresses and strains acting on the wound may involve the layers of the skin, such as the outer stratum corneum, the epidermis and dermis, as well as the underlying connective tissue layers, such as the subcutaneous fat. Devices and methods described here may shield a wound from its mechanical environment. The term "shield" is meant to encompass the unloading of stress experienced by the wound as well as providing a physical barrier against contact, contaminants, and the like. The devices and methods described here may shield a wound by unloading the wound and surrounding tissues from endogenous stress and/or exogenous stress. Thus, devices and methods described here may reduce the stress experienced by a wound and surrounding tissues to a lower level than that experienced by normal skin and tissue. Unloading of exogenous and/or endogenous stress in the vicinity of the wound may ameliorate the formation of scars, hypertrophic scars, or keloids.

A cell's external mechanical environment may trigger biological responses inside the cells and change cell behavior. Cells can sense and respond to changes in their mechanical environment using integrin, an integral membrane protein in the plasma membrane of cells, and intracellular pathways. The intracellular pathways are initiated by receptors attached to cell membranes and the cell membrane that can sense mechanical forces. For example, mechanical forces can induce secretion of cytokines, chemokines, growth factors, and other biologically active compounds that can increase or trigger the inflammatory response. Such secretions can act in the cells that secrete them (intracrine), on the cells that secrete them (autocrine), on cells surrounding the cells that secrete them (paracrine), or act at a distance from the point of secretion (endocrine). Intracrine interference can alter cell signaling, which can in turn alter cell behavior and biology including the recruitment of cells to the wound, proliferation of cells at the wound, and cell death in the wound. In addition, the extracellular matrix may be affected.

As noted above, the wound healing process may be characterized in three stages: early inflammatory phase, the proliferative phase, and remodeling. The inflammatory phase occurs immediately after injury and typically lasts about two days to one week. Blood clotting takes place to halt blood loss and factors are released to attract cells that can remove debris, bacteria and damaged tissue from the wound. In addition, factors are released to initiate the proliferative phase of wound healing. In the proliferative phase, which lasts about four days to several weeks, fibroblasts grow and build a new extracellular matrix by secreting collagen and proteoglycans. At the end of the proliferative phase, fibroblasts can act to contract the wound further. In the remodeling phase, randomly oriented collagen is organized and crosslinked along skin tension lines. Cells that are no longer needed can undergo apoptosis. The remodeling phase may continue for many weeks or months, or indefinitely after injury. Scars typically reach about 75-80% of normal skin breaking strength about 6-8 weeks after injury. In general, scars typically have a triangular cross-section. That is, a scar is usually smallest in volume near the skin surface (i.e., stratum corneum and epidermis) and increases in volume as it progresses into the deeper layers of the dermis.

There are three common possible outcomes to a wound healing process. First, a normal scar can result. Second, a pathologic increase in scar formation can result, such as formation of a hypertrophic scar or a keloid. Third, the wound may not heal completely and become a chronic wound or ulcer. The devices, kits and methods described herein can ameliorate the formation of any type of scar. In addition, the devices, kits and methods described here can be adapted for a variety of wound sizes, and for different thicknesses of skin, e.g., the devices may be configured for use in different areas of the body. In addition, the devices, kits and methods described here can be adapted to ameliorate scar formation in any type of skin, e.g., body location, age, race, or condition.

Without wishing to be bound by any particular theory, we believe that mechanical strain acting on a wound or incision early in the proliferative phase of the wound healing process may inhibit cellular apoptosis, leading to a significant accumulation of cells and matrix, and hence increased scarring or the production of hypertrophic scars. Given the underlying similarities between hypertrophic scars and keloids with respect to excessive matrix formation, we believe that the devices and methods described herein may also be useful in preventing and treating keloids by offloading or neutralizing at least some of the strain that may be acting on the wound or incision. This tensile strain may be exogenous and/or endogenous strain, and may include but is not limited to the strain from the intrinsic tensile forces found in normal intact skin tissue.

Devices are described here for ameliorating the formation of scars and/or keloids at a wound site. The scars may be any type of scar, e.g., a normal scar, a hypertrophic scar, etc. In general, the devices may be configured to be removably secured to a skin surface near a wound. The devices may shield the wound from endogenous stress and/or exogenous stress. In some variations, the devices may shield the wound from endogenous stress without affecting exogenous stress on the wound, e.g., devices that modify the elastic properties of the skin, etc. In other variations, the devices may shield the wound from exogenous stress without affecting endogenous stress on the wound. Such variations may include situations where the musculature and surrounding wound tissue has been paralyzed, e.g., through the use of botulinum toxin or the like. In still other variations, the devices shield the wound from both endogenous and exogenous stress.

The devices, dressings and bandages described herein may ameliorate the formation of scars at wound sites by controllably stressing or straining the epidermis and deeper layers of dermal tissue around the wound, thereby reducing tensile or compressive stress at the wound site itself. The stress at the wound site may be reduced to levels below that experienced by normal skin and tissue. The stress or strain may be applied to surrounding tissue in one, two, or three directions to reduce endogenous or exogenous stress at the wound in one, two or three directions.

The physical characteristics of the device and/or the method of applying the device may also be further configured to resist or reduce the rate of skin stripping or tension blistering from the application of strain to the incision site.

FIGS. 1A and 1B depict one variation of a wound treatment device 2, comprising an elastic layer of material 4 with an upper surface 6, a lower surface 8, and edges 10, 12, 14 and 16. The lower surface 8 of the elastic layer of material 4 may comprise a central non-adhesive region 18 flanked by two inner adhesive regions 20 and 22 along borders 24 and 26. In this particular variation, the central non-adhesive region 18 also has two borders 28 and 30 which are adhesive-free. This configuration may facilitate the treatment of longer incisional sites by serially placing the non-adhesive regions of multiple wound treatment devices along the incisional site, without the device edges directly adhering to the incisional site.

In some variations, the average width of the non-adhesive region, i.e. the distance between the adhesive regions along the axis of strain (or where the device is strained along multiple dimension, the largest dimension of the device 2 along one of its axes of strain), is in the range of about 3 mm to about 15 mm or more, in some variations about 5 mm to about 10 mm, and in other variations about 7 mm to about 8 mm. The width of the adhesive region may be the same or greater than the width of the non-adhesive regions, including but not limited to being 2×, 3×, or 4× or more in relative width. In some variations, the greater width of the adhesive regions relative to the non-adhesive region may lower focal concentrations of tissue stress, which may reduce tissue stripping and/or blistering. The widths of the non-adhesive region and/or the adhesive regions may be constant or may be variable, and the widths of the adhesive regions may be the same or different.

The inner adhesive regions 20 and 22 may comprise outer borders 32 and 34 which are opposite of the inner borders 24 and 26 shared with the central non-adhesive region 18 and shared with the outer non-adhesive regions 36 and 38. The non-adhesive regions 36 and 38 may further comprise applicator attachment regions or structures 40 and 42 that are configured to releasably attach to an applicator that may be used to apply the device 2 to a treatment site. In some further variations, the attachment structures may also facilitate stretching of the central adhesive region 18 and/or the adhesive regions 20 and 22. Various examples of applicators that may be used are described in greater detail below. In other variations, the applicator attachment structures 40 and 42 may be located in adhesive regions that may or may not be contiguous with more inner adhesive regions. In other variations, the elastic material about the attachment structures may comprise an adhesive. Examples of applicators are described in greater detail below.

The applicator attachment structures 40 and 42 may comprise a plurality of openings 44 and 46 located through the layer of elastic material 4. The openings 44 and 46 may be through-openings between the upper and lower surfaces. In other variations, the openings may be close-ended openings, e.g. a plurality of pockets or even a single pocket spanning the width or a portion of the width of the device.

In the variation depicted in FIGS. 1A and 1B, the openings 44 and 46 are configured to be fully penetrated by the applicator, but in other variations, the applicator and/or the openings may be configured for only partial insertion by the applicator. The openings 44 and 46 may be circular, ovoid, triangular, rectangular, square, polygonal or any other of a variety of shapes. Each of the openings may have the same or a different shape, size or configuration, and the shape, size or configuration may vary between the upper surface and the lower surface. The openings may be also be angled with respect to the upper surface or lower surface, and in some variations, one or more openings and/or a region about the openings may be partially or completely reinforced by wires, rings and/or frames and the like. In some variations, the applicator attachment structures may also comprise denser or thicker regions of the elastic material. In some variations, multiple sets of applicator attachment structures may be provided to permit use of different applicators or to strain the device to different degrees, for example.

Figure 42A:
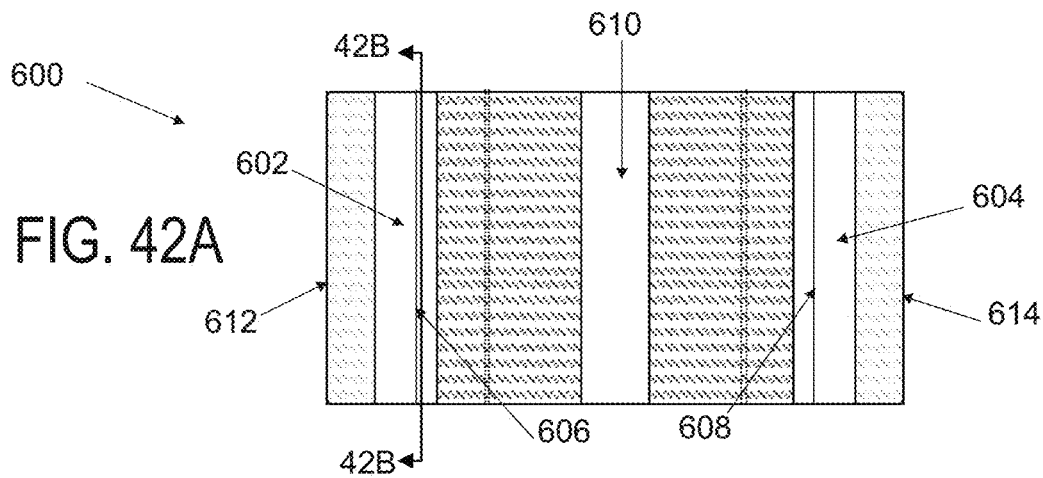
FIGS. 42A to 42C are superior cross sectional and side elevational views of a dressing comprising pockets.
Figure 42B:
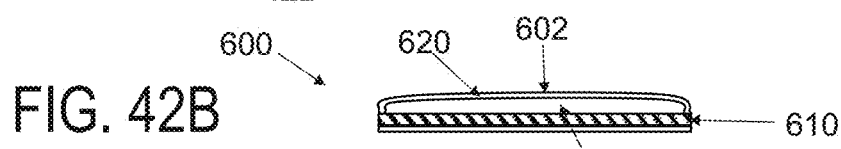
Figure 42C:
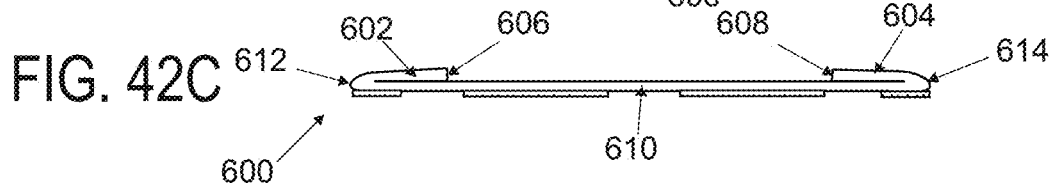
Figure 43A:
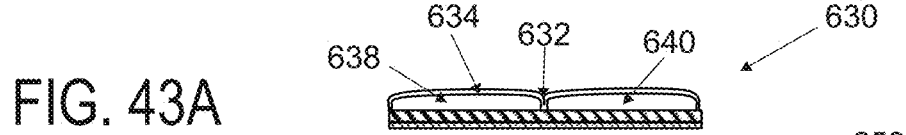
FIGS. 43A to 43C are cross sectional views of alternate embodiments of a dressing comprising pockets.
Figure 43B:
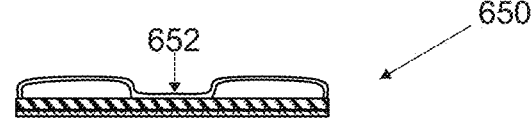
Figure 43C:
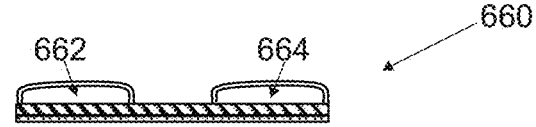
Figure 44A:
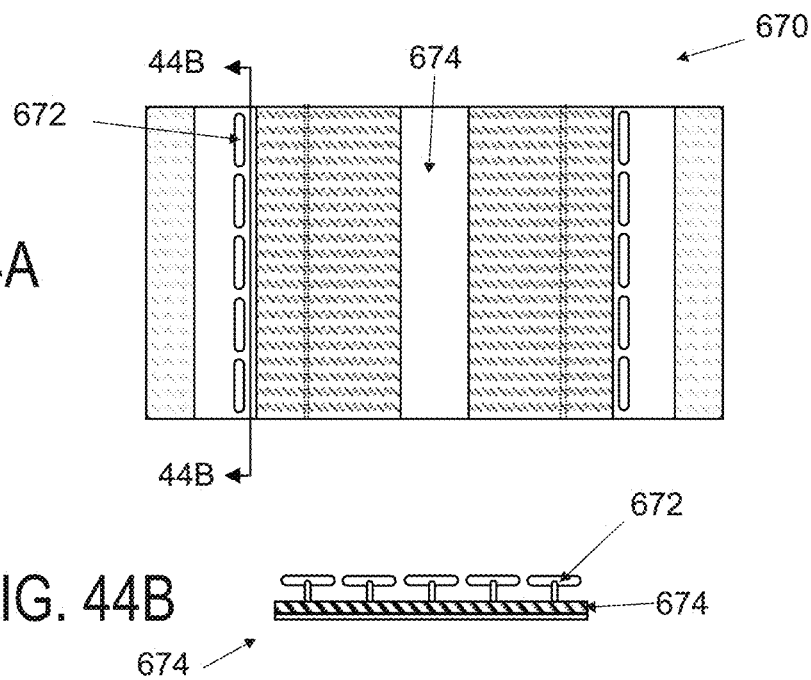
FIGS. 44A and 44B are superior and cross sectional views of another dressing comprising T-tag attachment structures.
Figure 44B:
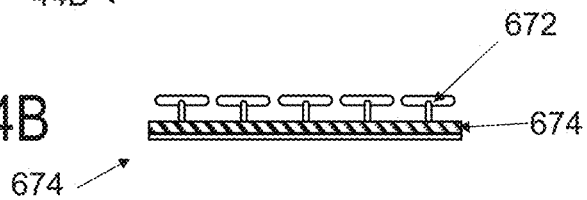
Figure 45A:
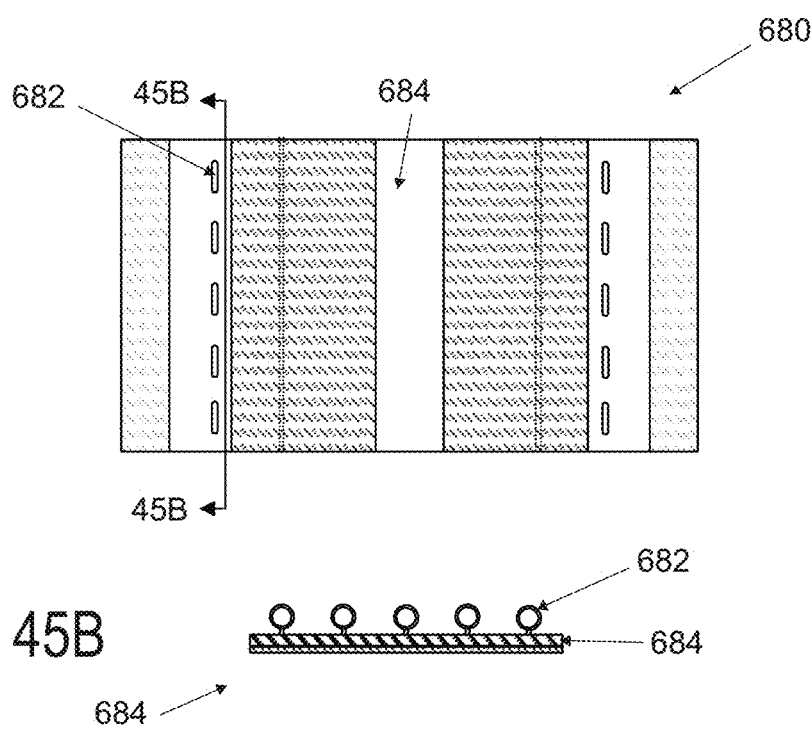
FIGS. 45A and 45B are superior and cross sectional views of another dressing comprising eyelet attachment structures.
Figure 45B:
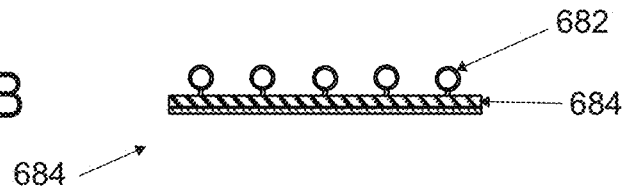

FIGS. 42A to 42C depict another variation of the dressing 600 comprising pockets 602 and 604 with inwardly facing pocket openings 606 and 608 configured to receive the attachment structures of a corresponding applicator. The pockets may comprise separate sheets of material that are attached to the elastic material and may comprise the same or a different material as the other portions of the dressing. The separate sheets of material may be adhered to the elastic material using adhesives, heat or plasma bonding, chemical bonding or mechanical attachment structures (e.g. staples and stitches). In the example depicted best in FIGS. 42B and 42C, the pockets 602 and 604 may be integrally formed structures of the base layer 610 that are folded over from the ends 612 and 614 of the dressing 600 and attached onto itself along the edges 616 and 618 without bonding the opening edge 620 to form the opening 606. In other variations, such as the dressing 630 depicted in FIG. 43A, the inner portions 632 of a pocket structure 634 or the distal edge 636 may also be adhered or fused to form multiple subpockets 638 and 640. Although FIG. 43A depicts a dressing with two subpockets 638 and 640, in other variations, three, four, five, six, seven, eight or more subpockets may be provided. The area or width of the fused inner portion(s) 652 may also vary, as shown in the dressing 650 in FIG. 43B. The width of the fused inner portion(s) may be in the range of about 0.5 mm to about 10 mm or more, sometimes about 1 mm to about 5 mm, and other times about 1 mm to about 2 mm. As shown in the dressing 660 of FIG. 43C, in other variations, the subpockets 662 and 664 may also be separately provided without an inner portion interconnecting them. In some further variations, the opening(s) of the pocket structures may be closed or sealed shut after application. Closure may result from using an adhesive, complementary sealable groove structures about the pocket openings (e.g. sandwich bag seal) or as a result of the cohesive properties of the elastic material when the pocket is pressed down. Closure of the pockets may reduce the risk of snagging the dressing following its application.

In other variations, the applicator attachment structures may comprise one or more projections or other structures protruding from the surface of the wound treatment device that form a mechanical or frictional interfit with the applicator. Referring to FIGS. 44A to 45B, examples of these alternate attachment structures include T-bar 672 or eyelet projections 682 of the dressings 670 and 680 that may be releasably engaged by an applicator. The t-bar 672 and eyelet projections 682 may be integrally formed with the base elastic layer 674 and 684 of the dressings 670 and 680, or may comprise a different material that is partially embedded in the elastic layer 674 and 684. In still other variations, the t-bar or eyelet projections may comprise individual or common base or pad structures that may be adhered to the surface of the elastic layer 674 and 684. The number of projecting attachment structures per side of the dressing may be in the range of about one to about twelve or more, sometimes about three to about eight, and other times about four to about five.

Figure 46A:
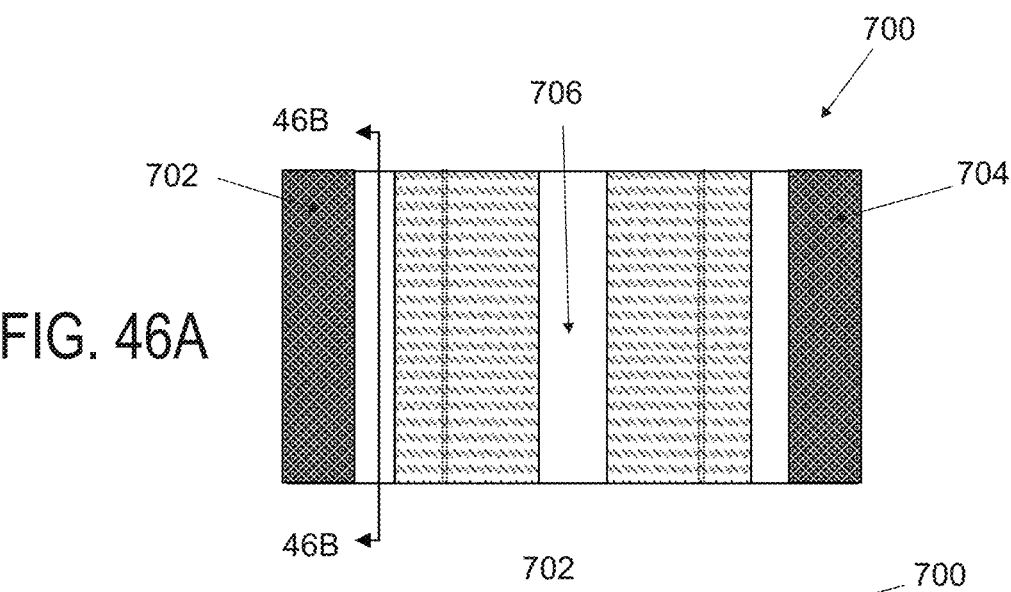
FIGS. 46A to 46C are superior, cross sectional and side elevational views of another dressing comprising a hook-and-loop type of attachment structure.
Figure 46B:
Figure 46C:
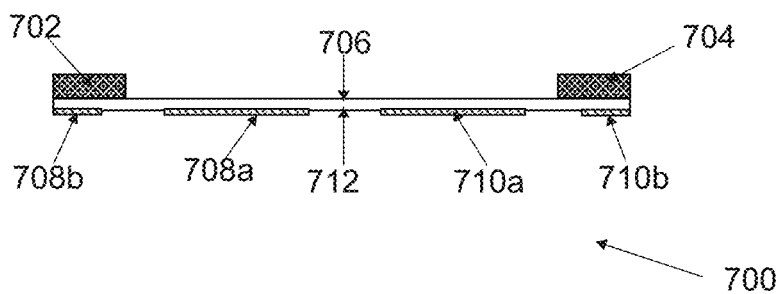
Figure 47:
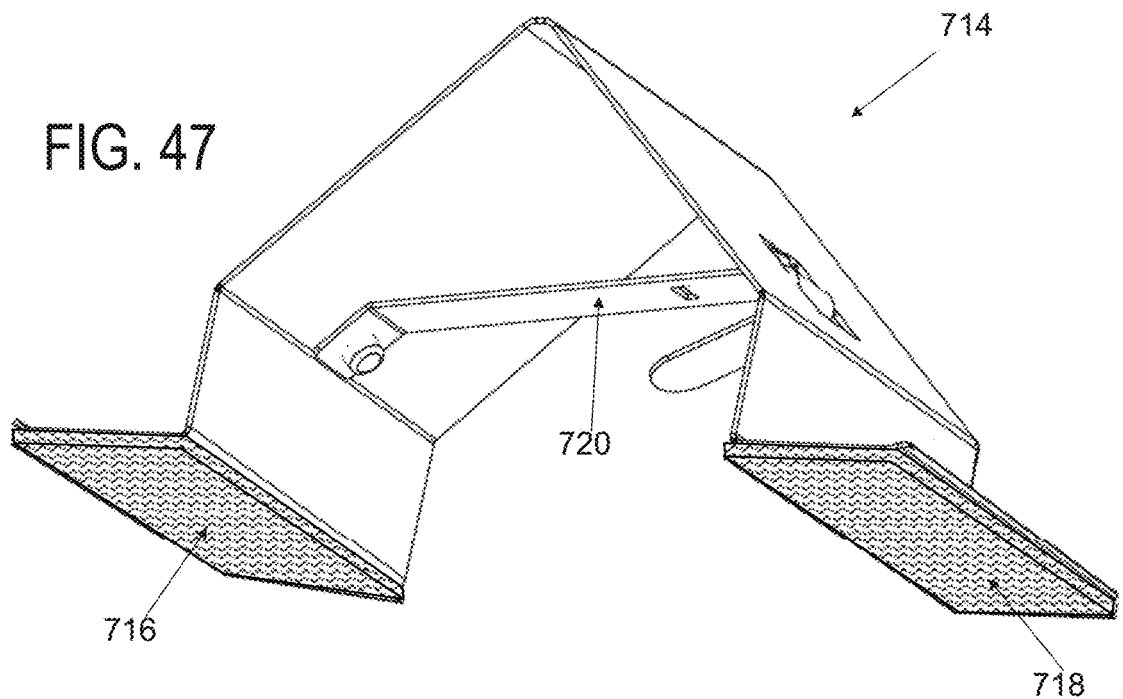
FIG. 47 depicts an applicator with corresponding hook-and-loop type of attachment structures configured for use with the dressing in FIGS. 46A to 46C.
Figure 48:
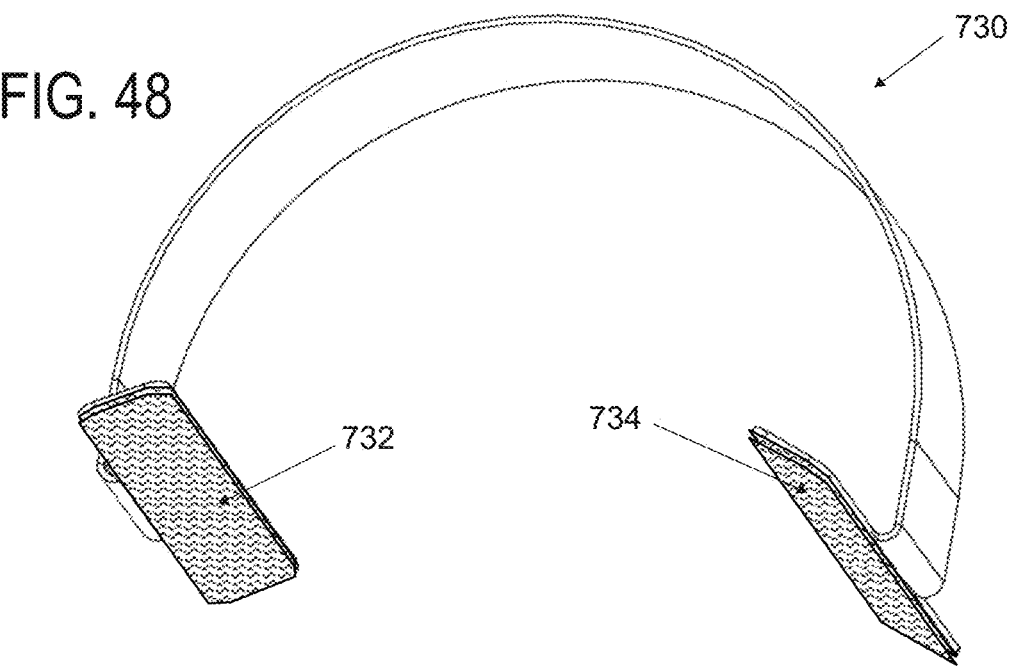
FIG. 48 depicts another applicator with corresponding hook-and-loop type of attachment structures configured for use with the dressing in FIGS. 46A to 46C.

In still another variation, the dressing may comprise complementary hook-and-loop attachment regions (e.g. VELCRO®) that may releasably attach to an applicator with a corresponding hook-and-loop attachment regions. In FIGS. 46A to 46C, for example, the bandage 700 comprises loop attachment regions 702 and 704 that are adhered to the upper surface 706 of the bandage 700, and with various adhesive regions 708a/b and 710a/b located on the lower surface 712. In use, a corresponding applicator, including but not limited to the exemplary applicator 714 depicted in FIG. 47, is squeezed or compressed to reduce the spacing between corresponding hook regions 716 and 718 to correspond to the spacing of the loop attachment regions 702 and 704 of the bandage 700 in its unstretched state. The hook regions 716 and 718 are aligned and then pressed against the loop attachment regions 702 and 704 to engage the bandage 700. In some examples, the applicator 714 may comprise a locking mechanism 720 to maintain the applicator 714 in a compressed state during engagement of the bandage 700, but in other examples, such as the applicator 730 in FIG. 48, the user will manually maintain the applicator 730 in a compressed state to align its hook regions 732 and 734 to the loop regions 702 and 704 to engage the bandage 700. A locking mechanism is not used. In some alternate application procedures, the applicator 714 (or 730) is not squeezed and instead, one of the loop regions 702 and 704 of the bandage 700 is first attached to a corresponding hook region 716 or 718, for example, and then the bandage 700 may be stretched and the remaining loop region 702 or 704 is attached to the applicator 714.

Figure 49A:
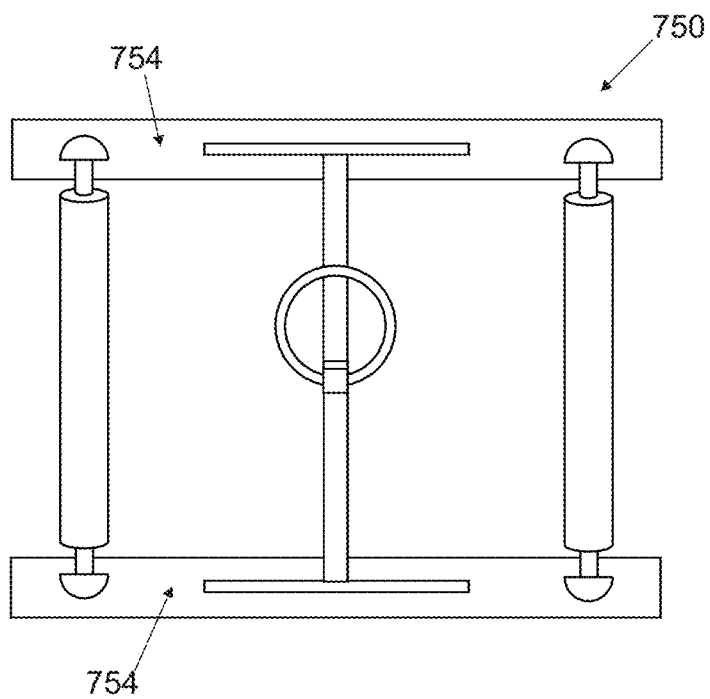
FIGS. 49A to 49B depicts another applicator with hook-and-loop type of attachment structures.
Figure 49B:
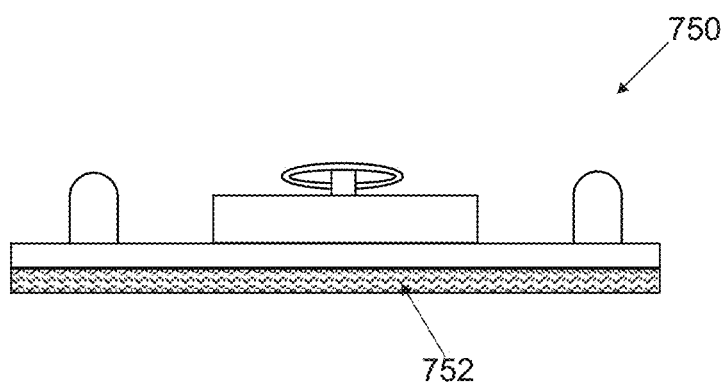

Although the examples in FIGS. 46A to 48 illustrate the loop regions 702 and 704 on the bandage 700 and the hook regions 716 and 718 located on the applicator 714, for example, in other variations, the relative relationships between the hook and the loop attachment regions may be reversed. The hook-and-loop attachment regions may be provided on any of the variety of dressing applicators the variety of applicators described herein. FIGS. 49A and 49B, for example, illustrate an applicator 750 that is a variation of the applicator 220 depicted in FIGS. 12A and 12B, but with hook and loop regions 752 on the force members 754 instead of the plurality of projections. Applicator 220 is described in greater detail below.

In some variations, one or more flap regions 48 and 50 may be provided adjacent to the outer non-adhesive regions 36 and 38, or the applicator attachment structures 40 and 42. Each of the flap regions 48 and 50 may be located directly between an edge 10 and 12 of the treatment device 2 and the outer non-adhesive regions 36 and 38 or applicator attachment structures 40 and 42. During use or preparation of the treatment device 2 for application to the skin, the flap regions 48 and 50 may remain unstretched relative to the central non-adhesive region 18 and inner adhesive regions 20 and 22. Once the adhesive regions 20 and 22 are adhered to the skin, the flap regions 48 and 50, which may optionally also comprise an adhesive on their skin contacting surface, may be adhered to the skin. The flap regions may be adhered to the skin in an unstrained state, or in a strained state that is less than, equal to, or greater than the strain in the central non-adhesive region 18 and adhesive regions 20 and 22. In still other variations, the flap regions may be cut or separated from the dressing after the dressing is applied. Perforations may be provided between the adhesive regions and the flap regions to facilitate separation.

The adhesive provided on the lower surface of the flap regions 48 and 50 may be the same or may be different than the adhesive of the inner adhesive regions 20 and 22, including but not limited to the composition, thickness and/or distribution of the adhesive material. In some variations, the adhesive of the flap regions 48 and 50 may have a reduced T-peel release force and/or blunt probe tack force relative to the adhesive provided for the inner regions 20 and 22. Various T-peel release force and/or blunt probe tack force ranges for the adhesive are provided below. In some variations, the unstrained or less-strained flap regions may redistribute at least some of the strains acting on tissue about the transition regions along the outer borders 32 and 34 of the inner adhesive regions 20 and 22. This may or may not reduce the risk of skin stripping or blistering compared to devices without flap regions or with flap regions of smaller width. In some variations, the actual width of a section of the flap region or the average width of the flap region or (or adhesive portion of the flap region) may be characterized relative to the corresponding width of the closest inner adhesive region and/or the width of the closest outer non-adhesive region. The width of the flap region may be in the range of about 1 mm to about 10 cm or more, sometimes about 5 mm to about 3 cm, and other times about 1 cm to about 2 cm. The size of the flap region may be also characterized relative to the size of the other regions of the dressing. For example, in some variations, the width of the flap region may be at least about 25%, about 33%, about 50%, about 75%, about 100%, or about 120% or higher than the corresponding width of the closest inner adhesive region. The width of the flap region relative to the closest outer non-adhesive region may be at least about 50%, about 75%, about 100%, about 120% or higher.

The stretching of the adhesive regions when applied to the skin surface may result in an increased tissue density under the adhesive region. This may be the result of generally planar, tangential or parallel compression of skin tissue that is directly attached to that adhesive region, resulting from the relaxation of the adhesive region. In some examples, this tissue compression may reduce the risk of tissue stripping and/or blistering of skin in direct contact with the adhesive, in contrast to bandage "strapping" where one end of a bandage is adhered to the skin and then tensioned or pulled across a wound before the other end is attached to the skin on the opposite side of the wound.

Furthermore, bandage "strapping", while generating tension in the bandage during the application, may simultaneously generate a relatively high tissue strain at the first adhesion site. This high tissue strain then decreases when the bandage is attached to the skin at a second adhesion site as the high peak stresses are redistributed along the skin under the bandage. In contrast, when a pre-strained bandage is applied to the skin, little if any strain may be transferred or generated in the skin as the adhesive regions are applied to the desired locations. When the pre-strained bandage is permitted to relax, however, the strain (or peak strain) in the skin may be increased. Thus, with a pre-strained bandage, temporary high tissue strain may be avoided or otherwise reduced during the application procedure. In other variations, however, the device 2 may also be applied to the skin by strapping, or by a combination of pre-straining and strapping.

Although the depicted wound treatment device 2 may have a generally rectangular configuration with a size of about 80 mm to about 40 mm, in other variations the device may have any of a variety of lengths and widths, and may comprise any of a variety of other shapes. Also, the corners of the device may be squared or rounded, for example. The lengths and/or widths of the device may be in the range of about 5 mm to about 1 meter or more, in some variations about 20 mm to about 500 mm, and in other variations about 30 mm to about 50 mm, and in still other variations about 50 mm to about 100 mm. In some variations, the ratio of the maximum dimension of the wound device (e.g. its length) to an orthogonal dimension to the maximum dimension (e.g. width), excluding the minimum dimension of the device(e.g. the thickness), may be in the range of about 1:1, about 2;1, about 3:1, about 4:1 about 5:1, about 6:1, about 7:1, about 8:1, about 9:1 or about 10:1 or greater. In some variations, the strain axis of the device in use may be oriented with respect to the maximum dimension or to the orthogonal dimension to the maximum dimension.

The elastic material of the device may comprise a single layer of material or multiple layers of the same or different materials. The material may have any of a variety of configurations, including a solid, foam, lattice, or woven configuration. The elastic material may be a biocompatible polymer, e.g., silicone. The thickness of polymer sheets, e.g., silicone polymer sheets or shape memory polymer sheets, may be selected to provide the devices or bandages with sufficient load carrying capacity to achieve desired recoverable strains, and to prevent undesired amounts of creep deformation of the bandages or devices over time. In some variations, the thickness across devices or bandages is not uniform, e.g., the thickness across the device may be varied to change the stiffness, the load carrying capacity, or recovery strains in selected orientations and/or locations. The elastic material may have a thickness in the range of about 50 microns to 1 mm or more, about 100 microns to about 500 microns, about 120 microns to about 300 microns, or in some variations about 200 microns to about 260 microns. In some examples, devices having an edge thickness of about 500 microns or less, 400 microns or less, or about 300 microns or less may exhibit less risk of skin separation from inadvertent lifting when inadvertently brushed against clothing or objects. In some variations, the devices or bandages are tapered near the edges to reduce thickness. A tapered edge may also ameliorate peak tensile forces acting on skin tissue adjacent to the adhesive edges of the wound treatment device. This may or may not reduce the risk of skin blistering or other tension-related skin trauma. In other variations, the edges of the devices or bandage may be thicker than the middle of the device or bandage. It is hypothesized that in some configurations, a thicker device or bandage edge may provide a relative inward shift of the location of the peak tensile forces acting near the device or bandage edge, compared to devices or bandages of uniform thickness.

The adhesive regions may comprise a pressure sensitive adhesive, e.g., polyacrylate-based, polyisobutylene-based, silicone-based pressure sensitive adhesives, and the like. The T-peel release force and blunt probe tack force of the adhesive may be measured by a standardized test method, such as ASTM D1876 and ASTMD2979 or other appropriate method. In some variations, the T-peel release force or blunt probe tack test value of the adhesive is configured to maintain loads of at least about 50 mPa/mm for at least about 24 hours, about 48 hours, about 72 hours, about 1 week, about 2 weeks, about 3 weeks, about 4 weeks or more. In other variations, the loads may be at least about 75 mPa/mm, about 100 mPa/mm, about 125 mPa/mm, or at least about 150 mPa/mm over the particular time period. The degree of adhesion (e.g. as measured by the T-peel release force or blunt probe tack test value) may vary depending upon the degree of strain placed onto the skin or incision site, and in some variations, these time periods may be based upon an average skin strain of about 10%, about 20%, about 30%, about 40%, or about 50% or more. In some variations, the adhesive may have a T-peel release force of at least about 150 kg/m, about 160 kg/m, about 170 kg/m, about 180 kg/m, about 190 kg/m, about 200 kg/m, about 210 kg/m, about 220 kg/m, about 230 kg/m, about 240 kg/m, about 250 kg/m, about 260 kg/m, about 270 kg/m, about 280 kg/m, about 290 kg/m, about 300 kg/m, about 310 kg/m, about 320 kg/m, about 330 kg/m, about 340 kg/m, about 350 kg/m, about 400 kg/m, about 450 kg/m, or at least about 500 kg/m or higher. In some further variations, the T-peel release force may be no greater than about 1000 kg/m, about 900 kg/m, about 800 kg/m, about 700 kg/m, about 600 kg/m, about 500 kg/m, about 400 kg/m or about 300 kg/m. The blunt probe tack test value of the adhesive may be at least about 0.50 kg, about 0.55 kg, about 0.60 kg, about 0.65 kg, about 0.70 kg or about 0.75 kg or higher, and may be no greater than about 1 kg, about 0.9 kg, about 0.8 kg, about 0.7 kg, or about 0.6 kg. The T-peel release force and blunt probe tack force may be measured by a standardized test method, such as ASTM D1876 and ASTMD2979 or other appropriate method. Other features or variations of the device are described in U.S. application Ser. No. 11/888,978, filed on Aug. 3, 2007, which was previously incorporated by reference.

In some variations, the final compressive stress and strain imposed onto the skin by the elastic material 4 may be the result of the dynamic equilibrium between the tensile stress in the skin and the elastic material 4 of the wound treatment device 2. Referring to FIGS. 13A to 13D, the skin at incision site 90 typically comprises an inherent tension 96a that stretches incision site 90, whether or not any tissue was excised from the incision site 90. The elastic material 4 and the adhesive region 18 may be configured to be applied to a skin location so that when the device 2 is stretched to a particular tension 94a and then adhered to the incision site 90, tensile stress in the device 2 is transferred to the incision site 90 to compress the tissue directly under the device 2 along a tangential axis 98 to the skin surface 99, the stress and strain imposed onto the skin location has a net or resultant orientation or axis is also generally tangential or planar to the elastic material 4 and/or the outer surface of the skin location, with a similar axis to the orientation or axis of the tensile stress in the device 2. The tension 94a in the device 2 will relax to a tension level 94b that maintains equilibrium with increased tension 96b in the skin adjacent to the device 2. The application of the device 2 to the skin location may involve the placement of the device 2 without overlapping or being wrapped onto itself, e.g. wherein only adjacent regions of the device 2 are interconnected and wherein non-adjacent regions of the device 2 are not interconnected. The actual amount of stress and strain imposed on the skin may vary, depending upon the particular person, skin location, the thickness or various mechanical characteristics of the skin layers (e.g. epidermis, dermis, or underlying connective tissues), and/or the degree of pre-existing scarring, for example. In some further variations, the wound treatment device 2 may be selected or configured for use at a specific body location, such as the scalp, forehead, cheek, neck, upper back, lower back, abdominal region, upper torso (including but not limited to the breast folds), shoulder, upper arm, lower arm, palm regions, the dorsum of the hand, finger, thigh, lower leg, the dorsum or plantar surface of the foot, and/or toe. Where applicable, some body regions may be further delineated into anterior, posterior, medial, lateral, proximal and/or distal regions, e.g. the arms and legs.

The wound treatment device 2 may be configured to impose a skin strain in the range of about 10% to about 60% or more, in other configurations about 15% to about 50%, and in still other configurations, about 20% to about 30% or about 40%. To achieve the desired degree of skin strain, the wound treatment device 2 may be configured to undergo elastic tensile strain in the range of about 20% to about 80% or more, sometimes about 30% to about 60%, and other times about 40% to about 50% or about 60%. The device 2 may comprise any of a variety of elastic materials, including but not limited to silicones, styrenic block copolymers, natural rubbers, fluoroelastomers, perfluoroelastomers, polyether block amides, thermoplastic elastomers, thermoplastic polyurethane, polyisoprene, polybutadiene, and the like. The material may have a Shore A durometer in the range of about 20 to about 90, about 30 to about 80, about 50 to about 80. One example of the elastic material 4 is MED 82-5010-05 by NUSIL TECHNOLOGY LLC (Carpinteria, CA). Other examples of suitable materials are described in U.S. application Ser. No. 11/888,978, which was previously incorporated by reference in its entirety.

When the strained device 2 is applied to a skin location and allowed to at least partially recover to its base configuration, the recovery level or equilibrium level of strain in the device may be in the range of about 10% to about 60% or more, in other configurations about 15% to about 50%, and in still other configurations, about 20% to about 30% or about 40%. The ratio between the initial engineering tensile strain placed onto the device 2 before recovery and the resulting engineering compressive strain in the skin may vary depending upon the skin type and location, but in some examples, may be about 2:1. In other examples, the ratio may be in the range of about 4:1 to about 5:4, about 3:1 to about 5:3, or about 5:2 to about 2:1. These skin strain characteristics may be determined with respect to a reference position of the body or body part, e.g. anatomical position, to facilitate reproducible measurements. The particular degree of strain may be characterized as either an engineering strain or a true strain, but may or may not be calculated based upon or converted from the other type of strain (e.g. the strain may be based upon a 60% engineering strain that is converted to a true strain).

Figures 21A, 21B:
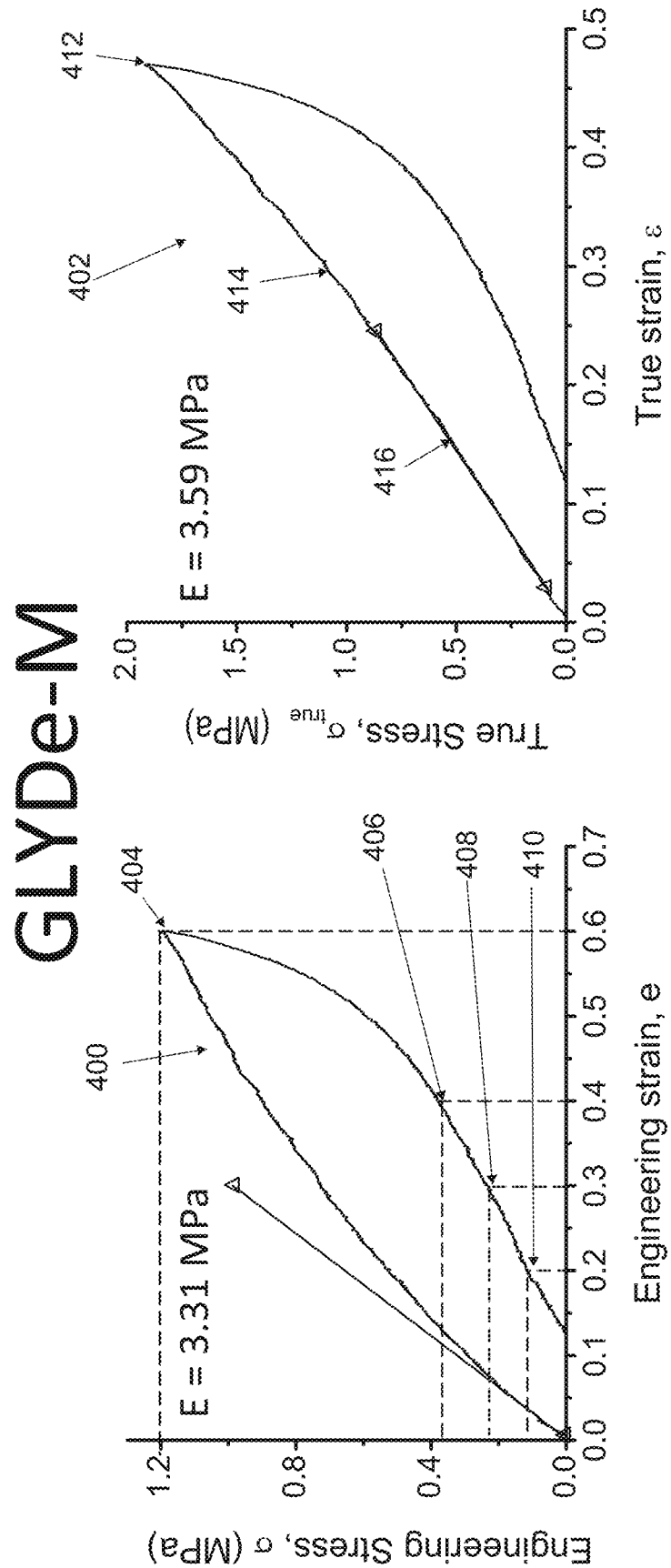
FIGS. 21A and 21B illustrate engineering and true stress/strain plots, respectively, of one embodiment of a backing material configured to impose a skin strain using a predetermined strain in the backing material.
Figure 22B:
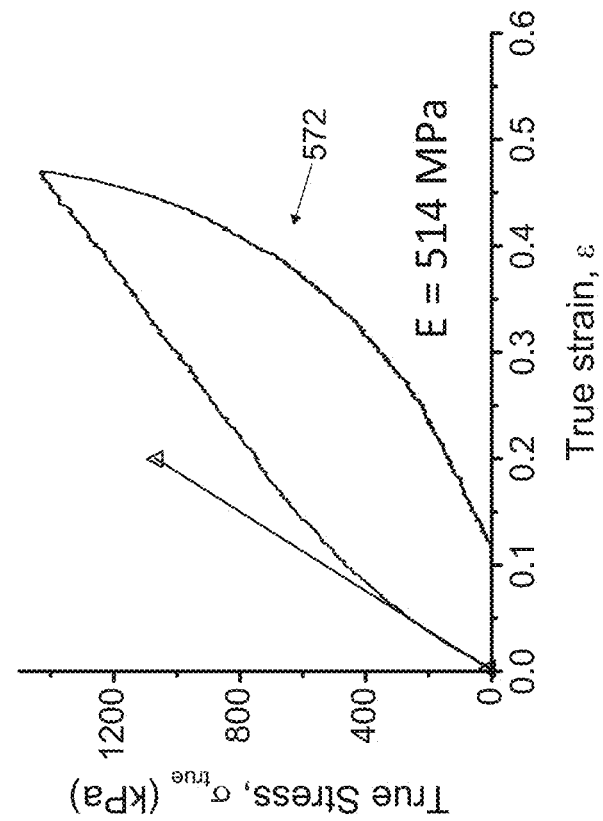
FIGS. 22A and 22B illustrate engineering and true stress/strain plots, respectively, of elastic Steri-Strip™ material.
Figure 22A:
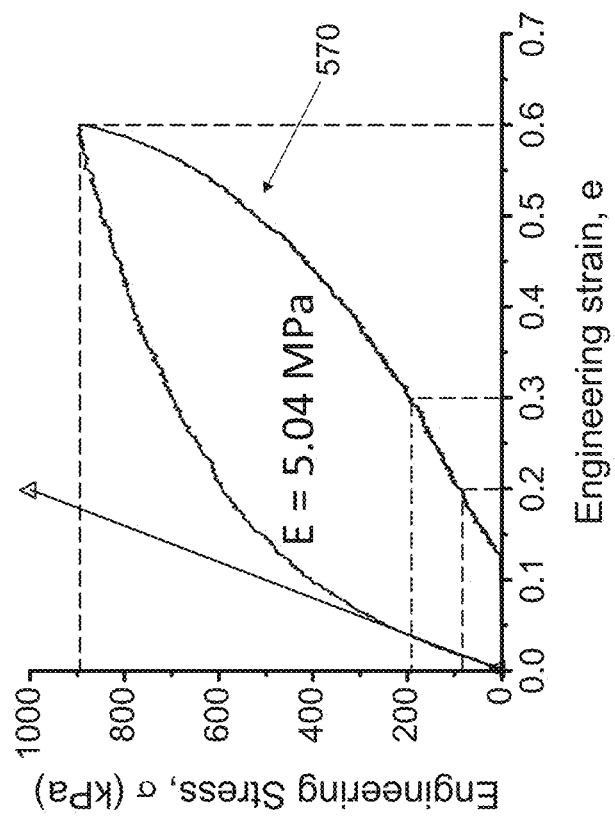
Figures 23A, 23B:
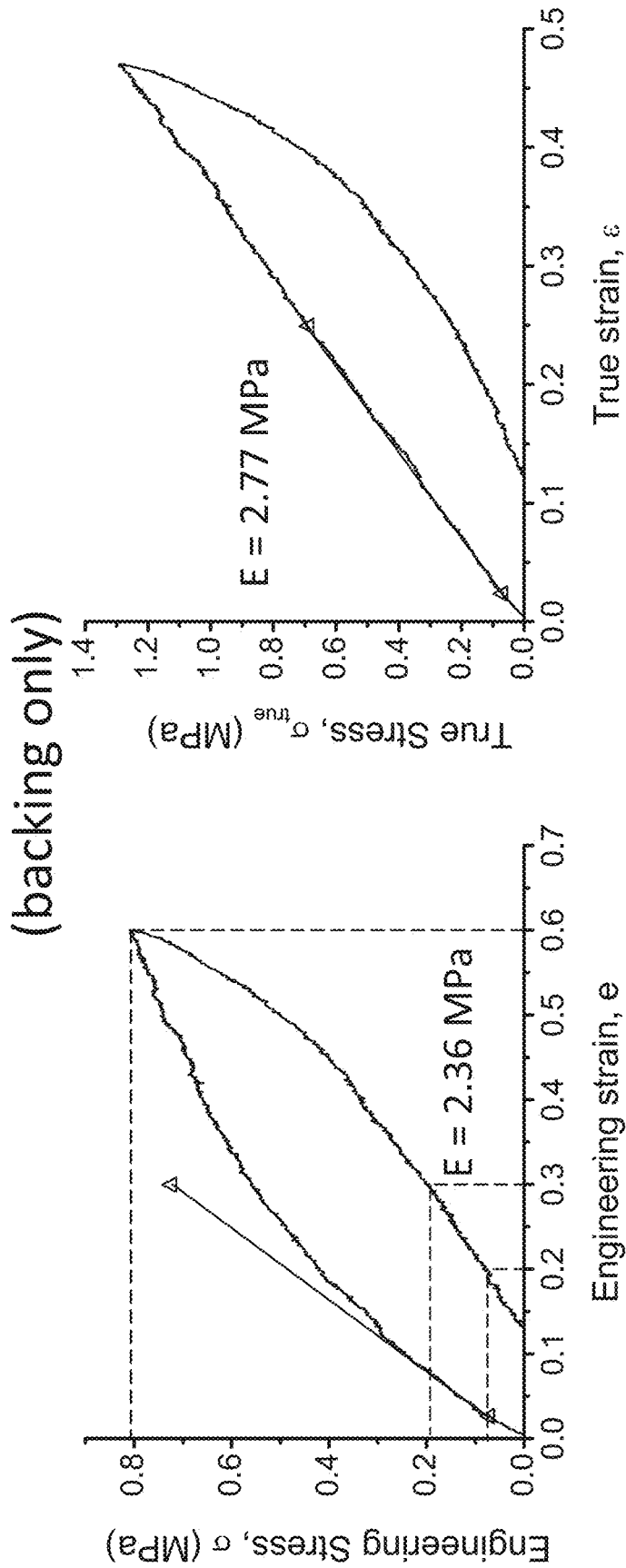
FIGS. 23A and 23B illustrate engineering and true stress/strain plots, respectively, of BAND-AID® ULTRA STRIP® backing material.
Figures 24A, 24B:
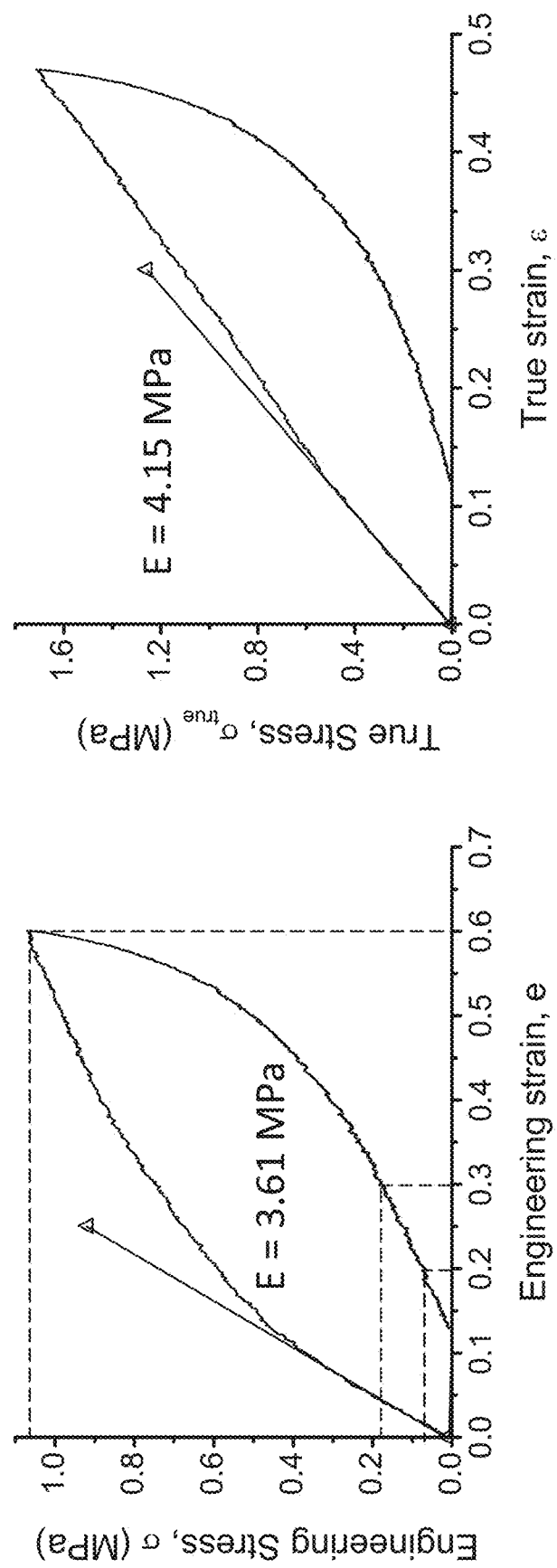
FIGS. 24A and 24B illustrate engineering and true stress/strain plots, respectively, of an intact BAND-AID® ULTRA. STRIP® bandage.
Figure 25B:
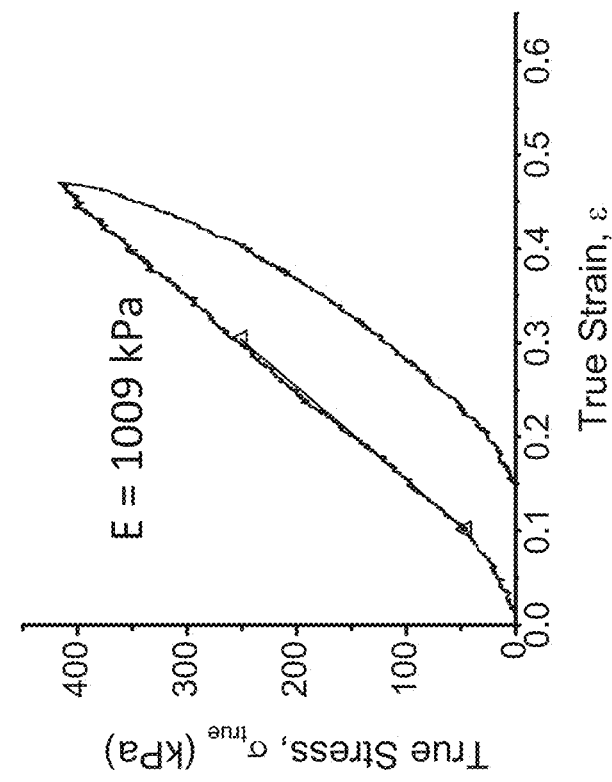
FIGS. 25A and 25B illustrate engineering and true stress/strain plots, respectively, of DuoDERM® Extra Thin material.
Figure 25A:
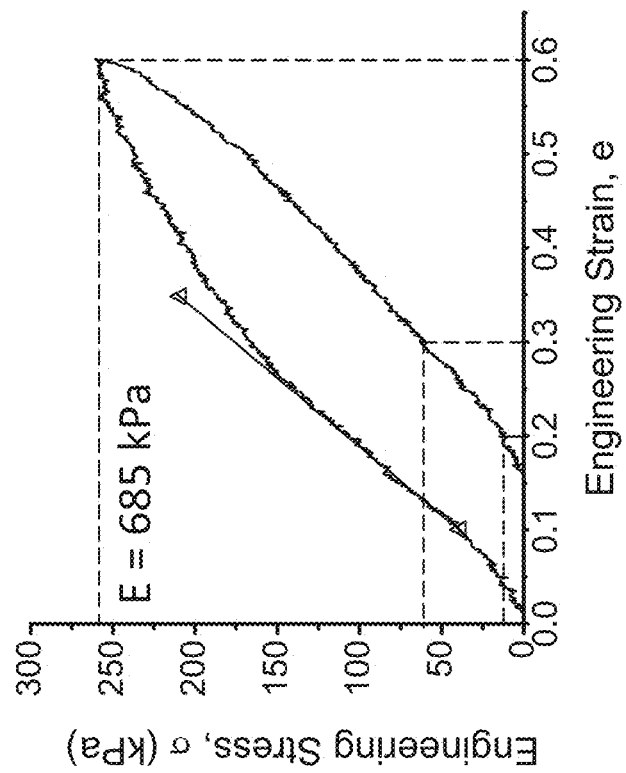
Figures 26A, 26B:
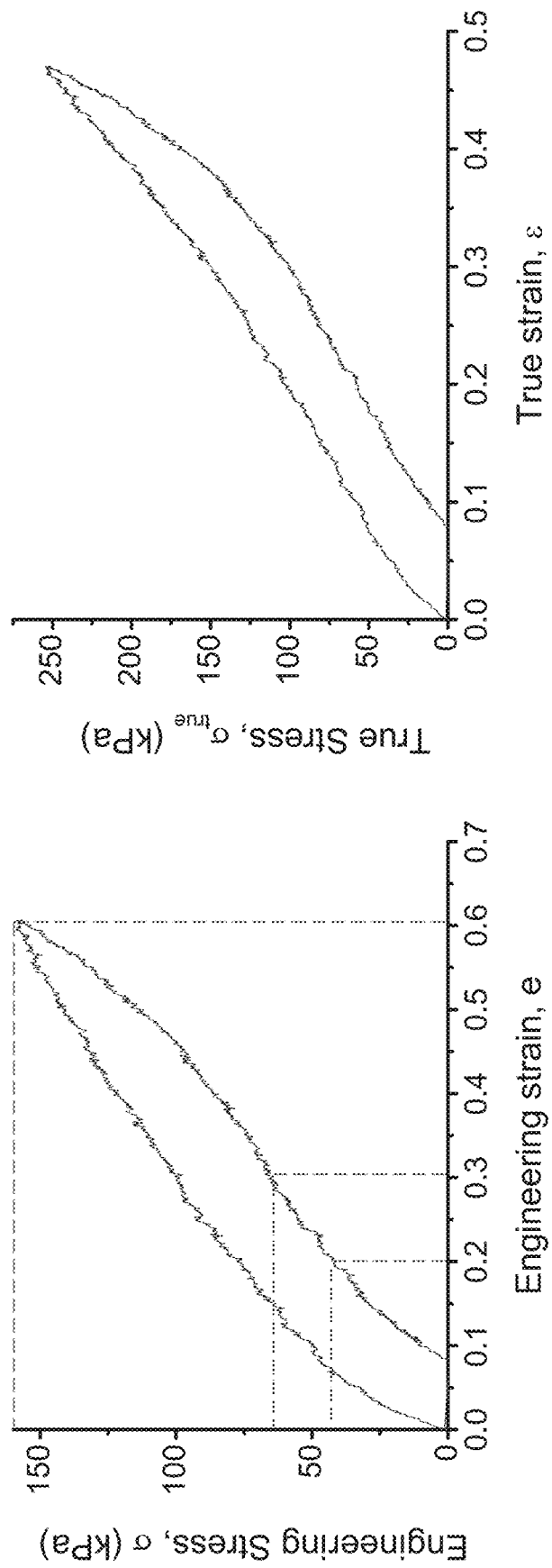
FIGS. 26A and 26B illustrate engineering and true stress/strain plots, respectively, of CVS/Pharmacy® silicone scar sheet backing material.
Figures 27A, 27B:
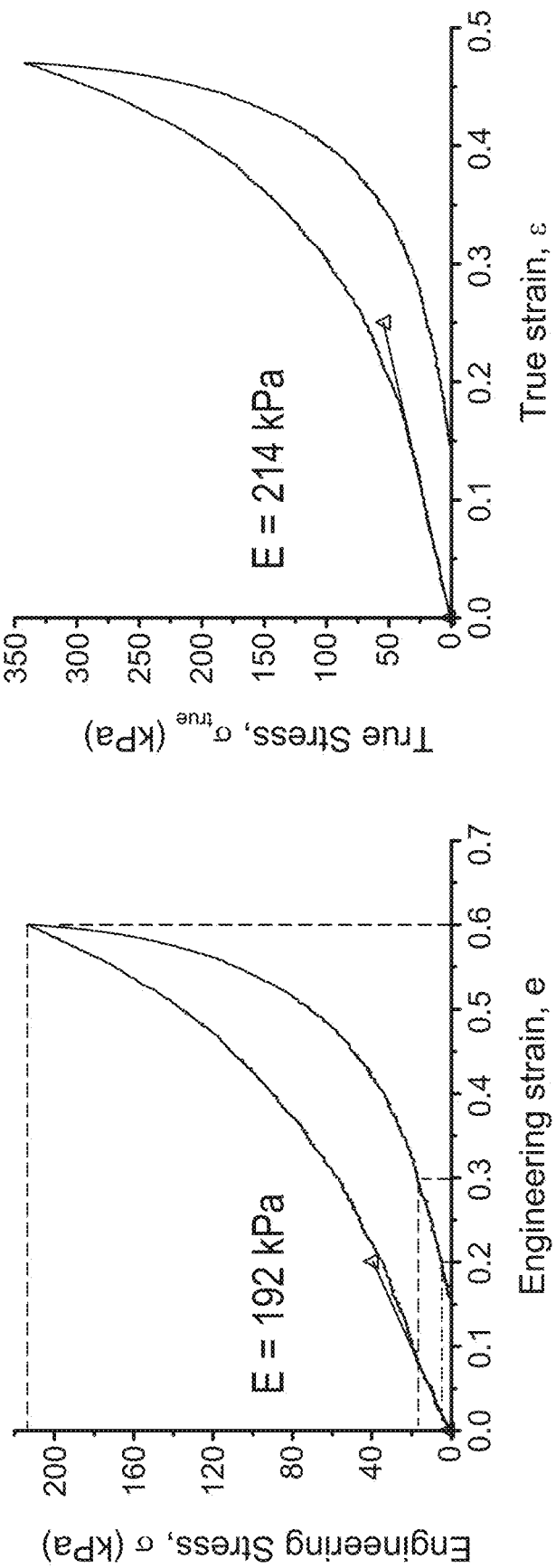
FIGS. 27A and 27B illustrate engineering and true stress/strain plots, respectively, of CVS/Pharmacy® self-adherent gentle wrap material.
Figures 28A, 28B:
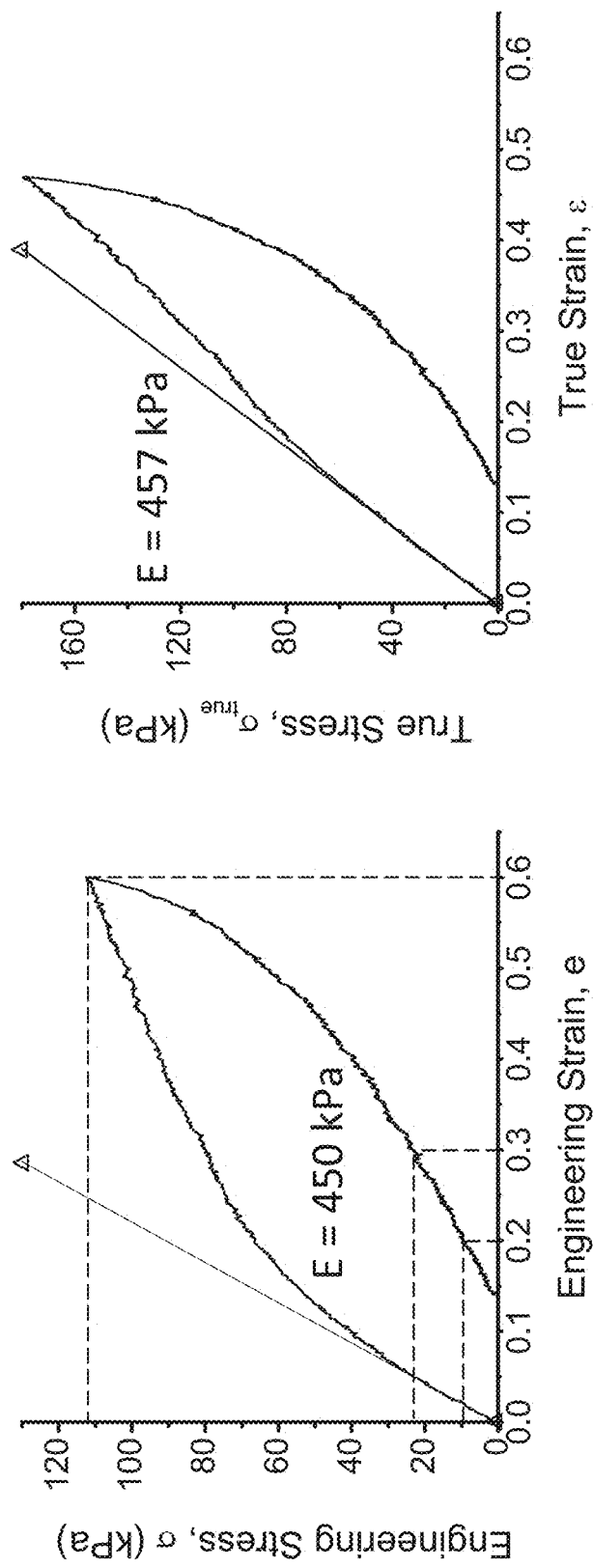
FIGS. 28A and 28B illustrate engineering and true stress/strain plots, respectively, of DuoDERM® CGF® material.
Figures 29A, 29B:
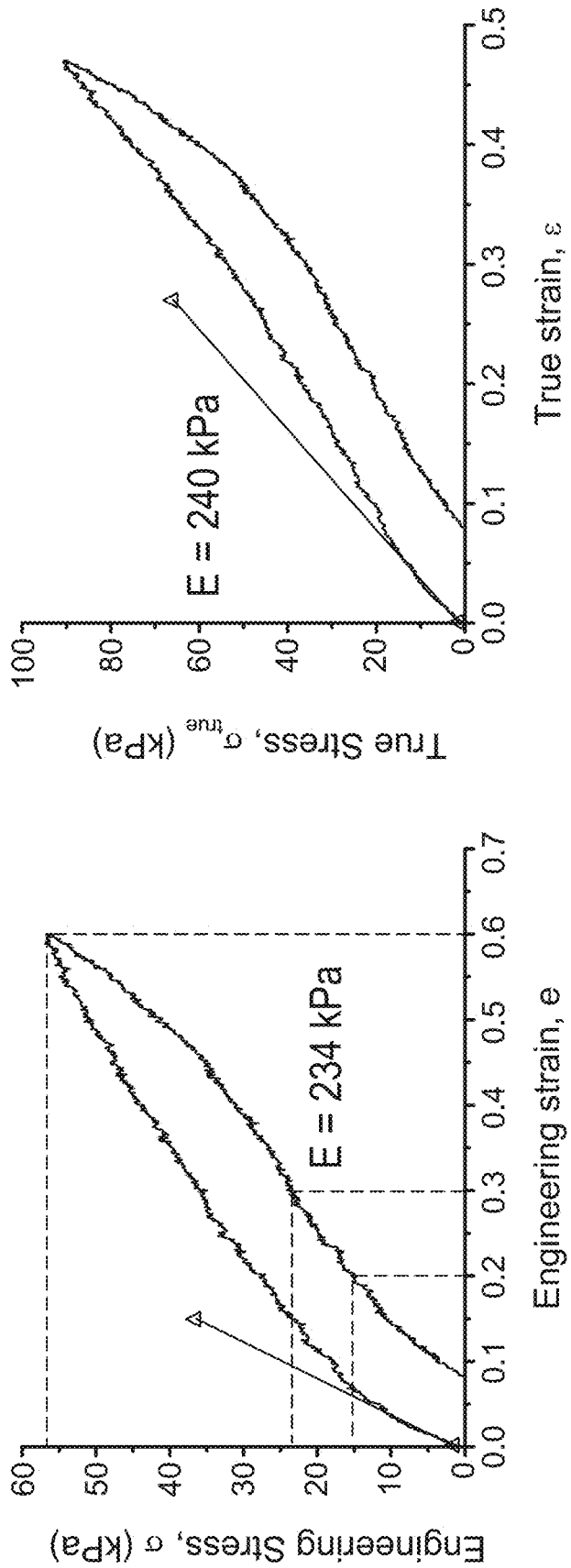
FIGS. 29A and 29B illustrate engineering and true stress/strain plots, respectively, of CVS/Pharmacy® elastic bandage material.

In some further variations, one or more characteristics of the elastic material 4 may correspond to various features on the stress/strain curve of the material 4. In FIGS. 21A and 21B, for example, the engineering and true stress/strain curves 400 and 402, respectively, for one specific example of the wound treatment device (GLYDe-M) is depicted. As illustrated in FIG. 21A, the device comprises a material that exhibits an engineering stress 404 of about 1.2 MPa at about 60% engineering strain, but in other examples, the engineering stress may be in the range of about 900 KPa to about 2.5 MPa, about 1.1 MPa to about 2.2 MPa, about 1 MPa to about 2 MPa, about 1.1 MPa to about 1.8 MPa, about 1.1 MPa to about 1.5 MPa, about 1.2 MPa to about 1.4 MPa. When unloading or relieving stress from the device 2, the material 4 may be configured with an engineering stress of about 380 KPa at about 40% engineering strain 406, but in other examples, the engineering stress during unloading of the material 4 to about a 40% strain may be in the range of about 300 KPa to about 700 KPa, about 325 KPa to about 600 KPa, about 350 KPa to about 500 KPa, or about 375 KPA to about 425 KPa. When unloading the material 4 to an engineering strain 408 of about 30%, the material exhibits an engineering stress of about 300 KPa, but in other examples, the engineering stress when unloading the material 4 to about 30% strain may be in the range of about 250 KPa to about 500 KPa, about 275 KPa to about 450 KPa, about 300 KPa to about 400 KPa, or about 325 KPA to about 375 KPa. When unloading to an engineering strain 410 of about 20%, the material may have an engineering stress of about 100 KPa, but in other examples, the unloading engineering stress at about 20% may be in the range of about 50 KPa to about 200 KPa, about 75 KPa to about 150 KPa, or about 100 KPa to about 125 KPa. In some examples, the material 4 may be configured to at least achieve a specific range or level of engineering stress at each of the specified engineering strain levels described above, but in other examples, the material 4 may be configured for lower levels of maximum engineering strain, e.g. up to about 30% or about 40%.

In some examples, certain portions of the stress/strain curve may have a particular morphology. For example, for a particular level of maximum strain the loading curve may be generally linear on the corresponding true stress/strain curve. As illustrated in FIG. 2113, up to a true strain 412 of about 45%, the loading curve 414 has a generally linear configuration. In other examples, the configuration may only be linear along a portion of the loading curve or may be curved along the entire loading curve. Where the loading curve is non-linear, the loading curve may be convex, concave or both. Also, in some examples, the tangent line 416 of the loading curve 414 (i.e. the line between the two triangles) may also be generally co-linear.

In some variations, the elastic material 4 comprises a material having an elastic modulus E of at least about 1 MPa, about 1.5 MPa, about 2 MPa, about 2.5 MPa, about 3 MPa, about 3.5 MPa, about 4 MPa, about 5 MPa, about 6 MPa, about 7 MPa, about 8 MPa, about 9 MPa or at least about 10 MPa or greater. The material elastic modulus E may be no greater than about 10 MPa, about 9 MPa, about 8 MPA, about 7 MPa, about 6 MPa, or about 5 MPa, or about 4 MPa.

In addition to the absolute stress levels at certain strain levels described above, the material may also be characterized with respect to the ratio between a) the stress to achieve a particular strain during loading, and b) the stress at the same strain during unloading. For example, the material may have a ratio of at least 4:1 to about 3:2 at each of the 20%, 30% and 40% strain levels, but in other examples, the material may exhibit these ratios only at 20%, at 30%, or at 40% strain levels, or at both 20% and 30% but not 40%, or at both 30% and 40% but not 20%. In other examples, the ratio at one, some or all of the strain levels may be in the range of about 3:1 to about 2:1, or about 5:2 to about 2:1.

Figures 32A, 32B:
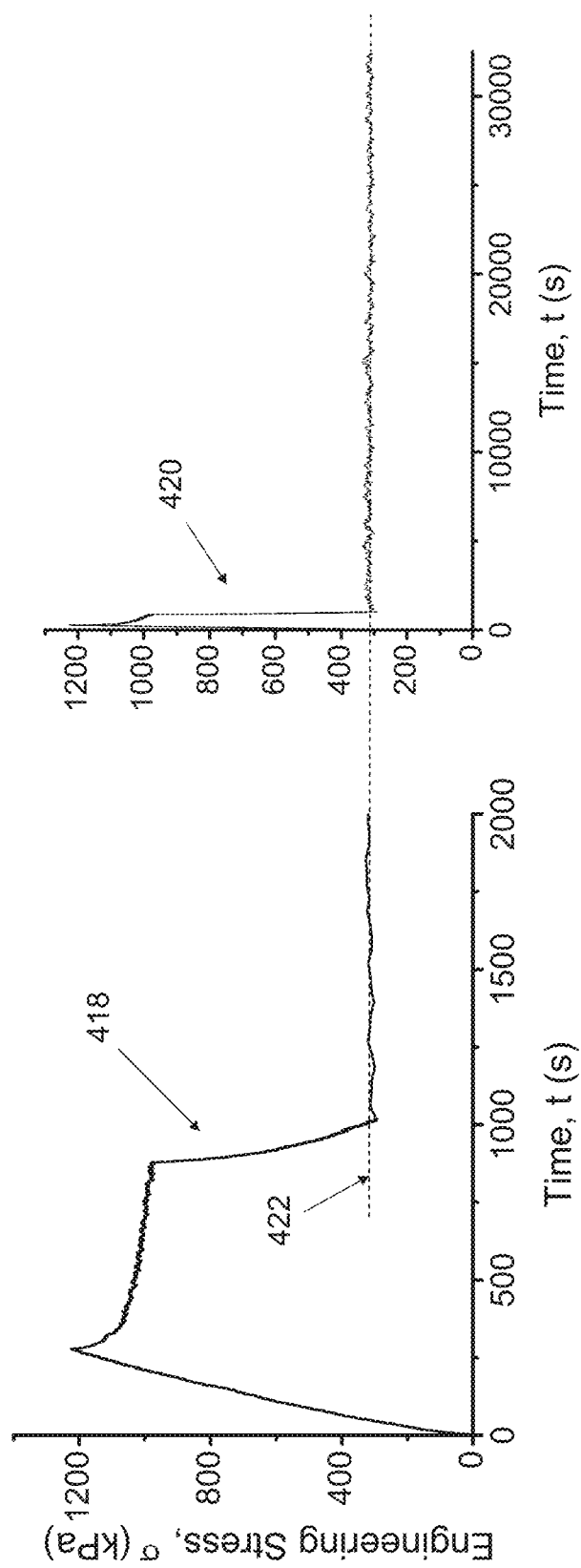
FIGS. 32A and 32B are engineering stress plots over time for the device under different loads using different X-axis scales, respectively.
Figures 34A, 34B:
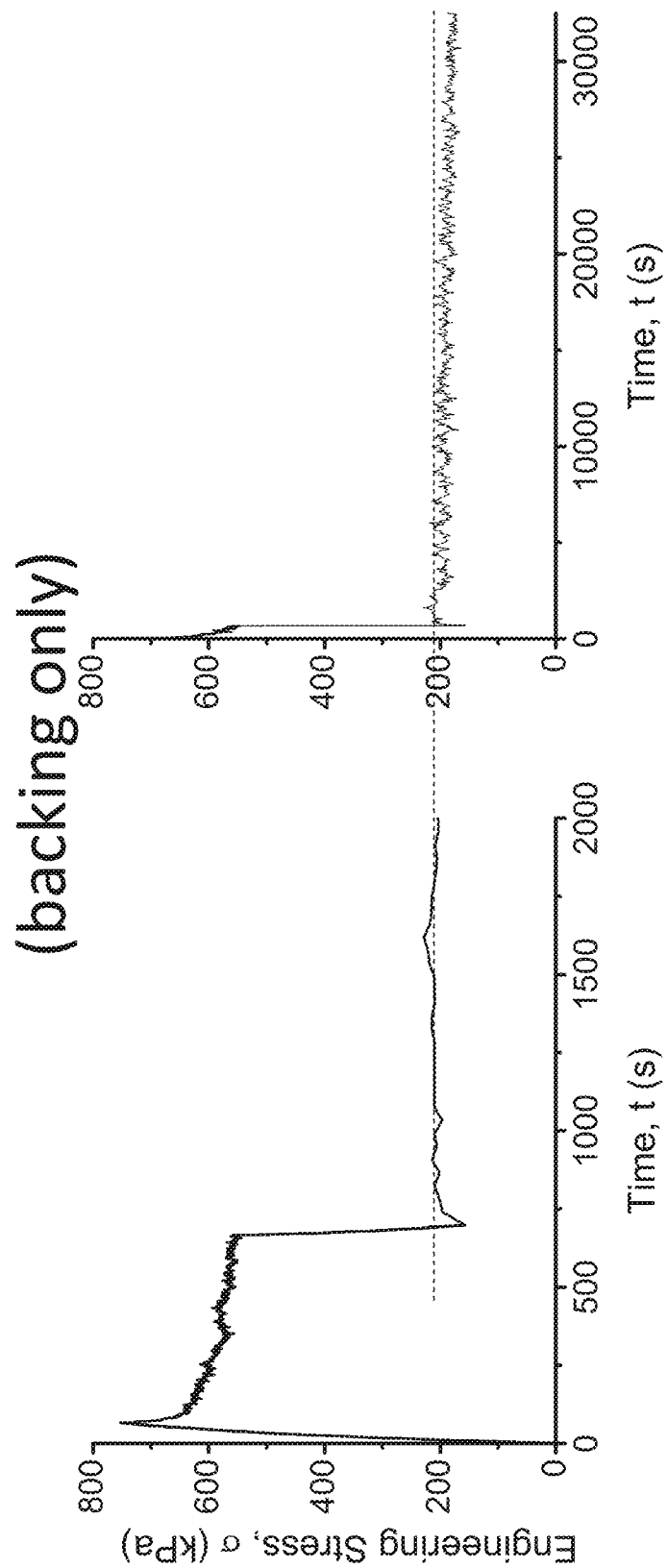
FIGS. 34A and 34B are engineering stress plots over time for Band-Aid® Ultra Strip® backing material under different loads using different X-axis scales, respectively.
Figures 36A, 36B:
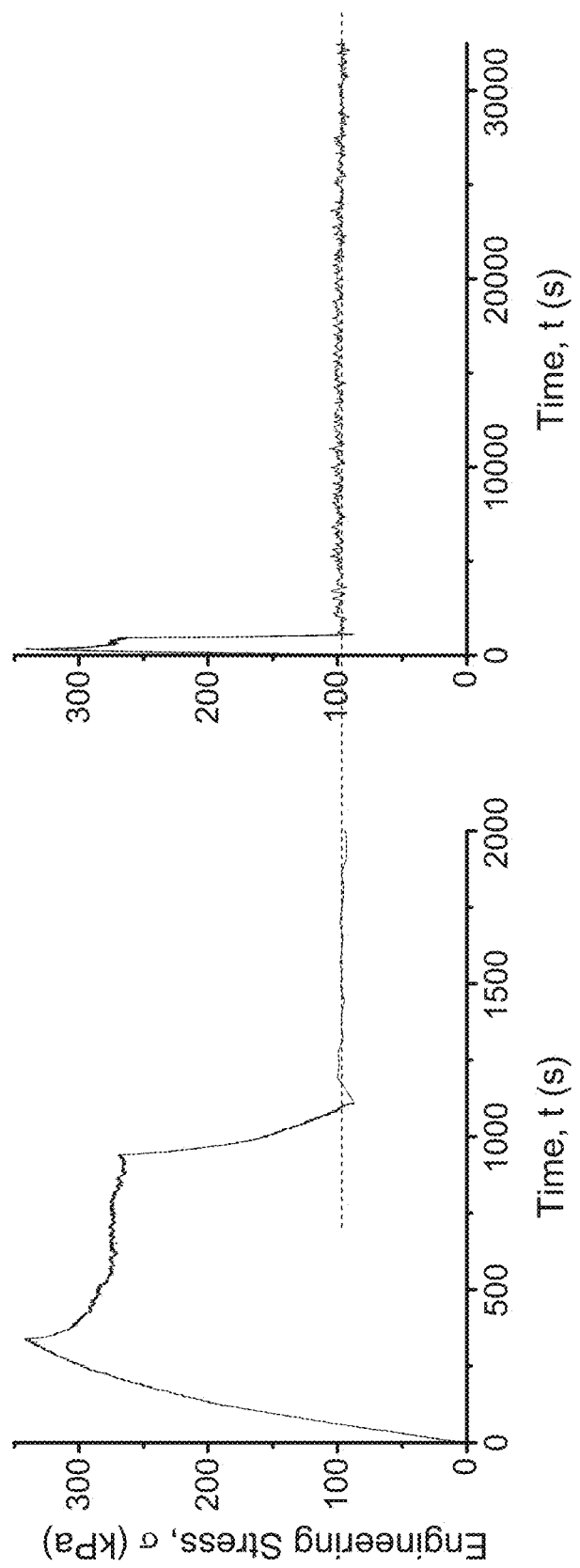

In some examples, the elastic material of the device 2 may be configured under testing conditions to achieve a stable level of stress at a constant strain, e.g. the material exhibits a limited amount of stress relaxation over a particular period of time and at a particular level of strain. The period of time may be at least about 8 hours, about 12 hours, about 18 hours, about 24 hours, about 36 hours, about 48 hours, about 72 hours, about 4 days, about 5 days, about 6 days, or about a week or more. The level of strain may be about 10%, about 20%, about 30%, about 40%, about 50%, about 60%, about 70%, or about 80% or more. FIGS. 32A and 32B illustrate the stress of the GLYDe-M device over various time curves 418 and 420, respectively. Specifically in FIG. 32B, the GLYDe-M device is configured to maintain an engineering stress of about 300 KPa at an engineering strain of about 30% without noticeable deviation over a period of about 1 hour, about 2 hours, about 3 hours, about 4 hours, about 5 hours, about 6 hours, about 7 hours, or about 8 hours or more. The stresses at 10% strain, 20% strain, and at 40% may be lower or higher. A comparator line 422 is provided to illustrate the strain level between the two curves 418 and 420.

In some variations, the elastic material or the device may be configured under testing conditions to maintain a particular minimum level of stress when held at a constant strain over a particular time period. To assess the ability of a backing material to maintain a stress and strain on skin over time, engineering strains were measured while each backing material was tensile strained to 60% at a rate of 100 microns per second and held for 10 minutes, and then dropped to a strain of 30% at a rate of 100 microns per second and held for 9 hours. In FIGS. 32A and 32B, for example, the GLYDe-M device is able to maintain an engineering stress level of about 350 KPa at an engineering strain of 30%. In some other examples, the minimum level of stress may be about 100 KPa, about 120 KPa, about 140 KPa, about 160 KPa, about 180 KPa, about 200 KPa, about 220 KPa, about 240 KPa, about 260 KPa, about 280 KPa, about 300 KPa, about 320 KPa, about 340 KPa, about 360 KPa, about 380 KPa, about 400 KPa, about 420 KPa, about 440 KPa, about 460 KPa, about 480 KPa, about 500 KPa, about 600 KPa, about 700 KPa, about 800 KPa, about 900 KPa or about 1000 KPa or greater. The level of constant strain may be different in other configuration, with a level of about 15%, about 20%, about 25%, about 30%, about 35%, about 40%, about 45%, about 50%, about 55%, about 60%, about 65%, about 70%, about 75%, or about 80%. The time period over which the device is able to maintain a stress level may be at least about 2000 seconds, about 3000 seconds, about 4000 seconds, about 5000 seconds, about 6000 seconds, about 7000 seconds, about 8000 seconds, about 9000 seconds, about 10000 seconds, about 20000 seconds, about 30000 seconds, about 40000 seconds, about 50000 seconds, about 60000 seconds, about 70000 seconds, about 24 hours, about 36 hours, about 48 hours, about 72 hours, about 4 days, about 5 days, about 6 days, about 7 days, about 10 days, about 2 weeks, about 1 month or more. In some variations, the device 2, the elastic material 4 and/or the adhesive material is configured to exhibit less than about a 15% change in stress or strain level over the particular period when applied to a skin surface or test surface. In other examples, the degree of change may be about 12%, about 10%, about 8%, about 6%, about 5%, about 4%, about 3%, or about 2% or less. The stress or strain may be an engineering stress or strain, and/or a true stress or strain.

Materials Testing

A variety of commercially available bandages were evaluated along with one specific example of a wound treatment device (GLYDe-M) to assess various force loading and recovery properties. Where the commercially available bandage comprised a backing material along with an absorbent pad, the bandage was tested both as an intact bandage, and also with the absorbent pad carefully removed to isolate the properties of the backing material. The following commercially available bandages were tested along with the GLYDe-M system:

TABLE 1

| Manufacturer | Product | Product Thickness (backing only)* |
|---|---|---|
| — | Wound treatment device (GLYDe-M) | 0.26 mm |
| 3M (St. Paul, MN) | Steri-Strip ™ (regular) | 0.15 mm |
| 3M (St. Paul, MN) | Steri-Strip ™ (elastic) | 0.27 mm |
| CVS/Pharmacy ® | Self-Adherent Wrap (generic) | 1 mm |
| J&J (New Brunswick, NJ) | BAND-AID ® Flexible Fabric | 0.32 mm |
| J&J (New Brunswick, NJ) | BAND-AID ® Tough Strip | 0.18 mm |
| J&J (New Brunswick, NJ) | BAND-AID ® Ultra Strip | 0.23 mm |
| 3M Nexcare ™ (St. Paul, MN) | Tegaderm ™ | 0.05 mm |
| ConvaTec (Skillman, NJ) | DuoDERM ® Extra Thin | 0.49 mm |
| ConvaTec (Skillman, NJ) | DuoDERM ® CGF ® | 2 mm |
| CVS/Pharmacy ® | Elastic Bandage (generic) | 0.88 mm |
| CVS/Pharmacy ® | Silicone Scar Sheet (generic) | 0.64 mm |

*and adhesive, if any.

The above bandages underwent testing to assess their material properties with respect to their stress-strain curves. Each of the bandages was tensile strained to an engineering strain of 60% and then permitted to recover. To simulate conditions at least somewhat similar to use on human skin, the testing was performed at a temperature of 33 degrees Celsius and at a humidity of 50%. In some examples, use of elevated temperatures and/or humidity may better reflect real-world performance of the device or bandage when applied to a person. The measurements of the engineering stress and engineering strain were also calculated as true stress/strain curves and were also used to calculate the initial elastic modulus of the material.

Figures 14A, 14B:
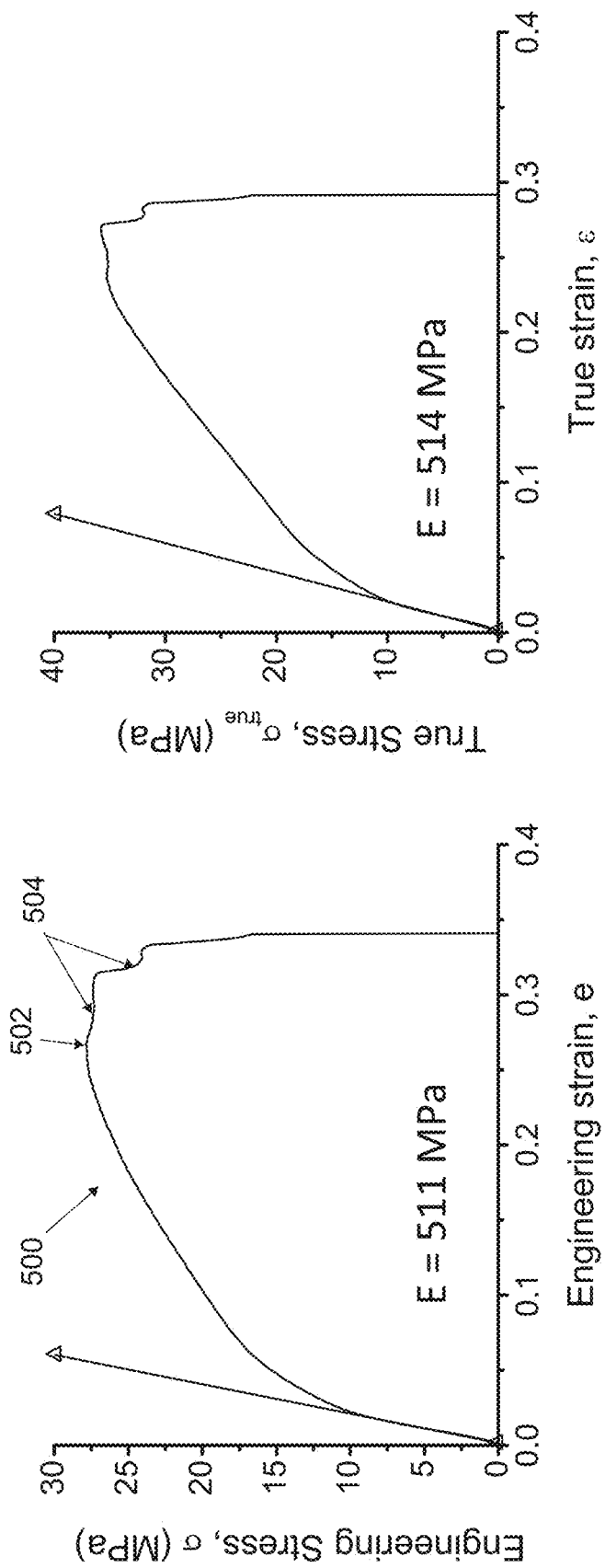
FIGS. 14A and 14B illustrate engineering and true stress/strain plots, respectively, of STERI-STRIP™ material.

Referring to FIGS. 14A and 14B, the stress-strain curves for a regular Steri-Strip™ demonstrated that the material failed to strain to 60%. As shown in the curve 500 in FIG. 14A, the Steri-Strip™ resulted in rupture 502 before reaching an engineering strain of 35%. Other evidence of structural failure included the downsloping, irregular segments 504 along the loading portion of the curve 500. Furthermore, substantial levels of engineering stresses of almost 15 MPa were needed to achieve an engineering strain of only about 5%. In some variations, use of high stresses to strain the wound treatment device may pose a safety risk to the user and/or the patient. Although the force used to strain a device will vary based upon the elastic modulus, thickness and width of the device, in some variations, the elastic modulus of the material used in the wound treatment device may be in the range of about 1 MPa to about 10 MPa, in some variations about 2 MPa to about 8 MPa, in other variations about 3 MPa to about 5 MPa, and in still other variations in the range of about 3 MPa to about 4 MPa. In some instances, a higher elastic modulus may generate a greater risk of skin blistering.

Figures 15A, 15B:
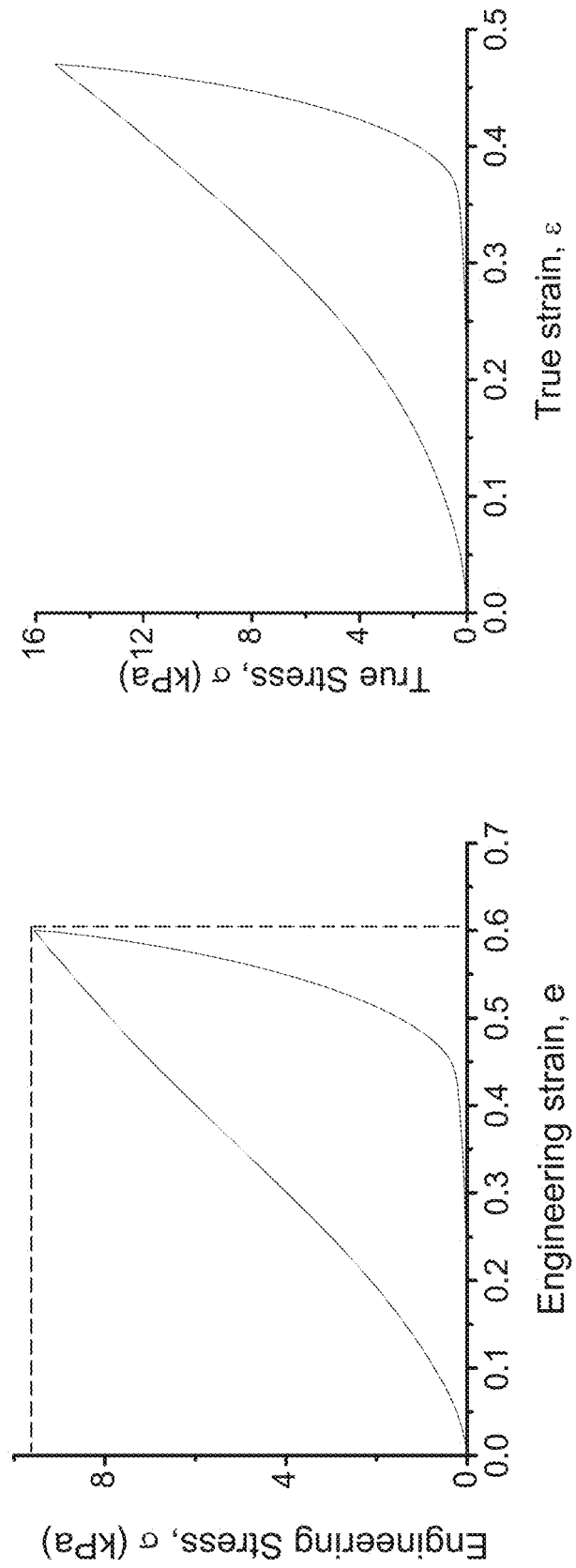
FIGS. 15A and 15B illustrate engineering and true stress/strain plots, respectively, of BAND-AID® Flexible Fabric backing material.
Figures 16A, 16B:
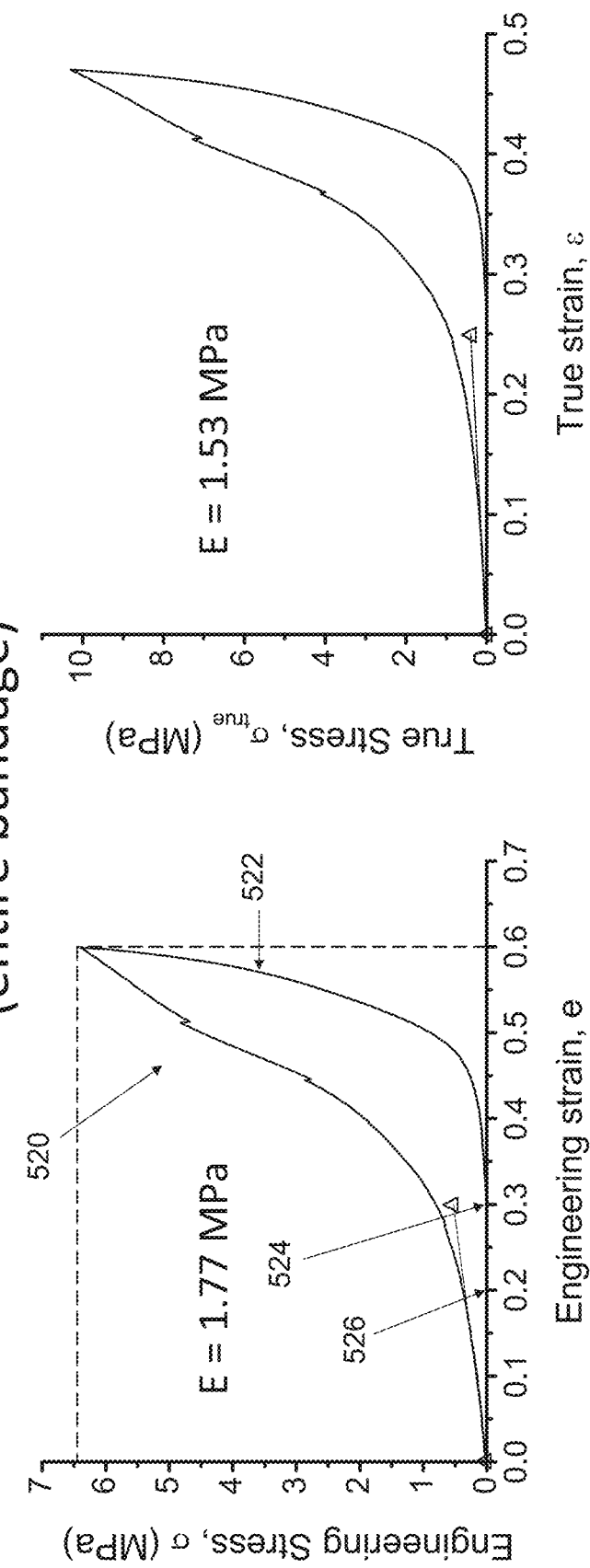
FIGS. 16A and 16B illustrate engineering and true stress/strain plots, respectively, of an intact BAND-AID® Flexible Fabric bandage.

Referring to FIGS. 15A and 15B, some backing materials, such as the flexible fabric used in Flexible Fabric BAND-AIDS®, are unable to impose substantial loads onto the skin when the backing material is strained and then permitted to recover the strain. As shown in the curve 510 in FIG. 15A, although the flexible fabric of this BAND-AID® was able to reach an engineering strain of 60%, upon unloading, engineering strains 512 fell quickly, and upon recovery to strains of 30% and 20%, respectively, the flexible fabric material was unable transfer significant forces 514 and 516, respectively, to the skin. This substantial difference may or may not reflect damage to the underlying material. As shown in FIGS. 16A and 16B, an intact Flexible Fabric BAND-AID® also had a stress-strain curve 520 with a recovery portion of the 322 in FIG. 16A showing substantial drop-off and limited residual force at strains 524 and 526 at 30% and 20%, respectively.

Figures 17A, 17B:
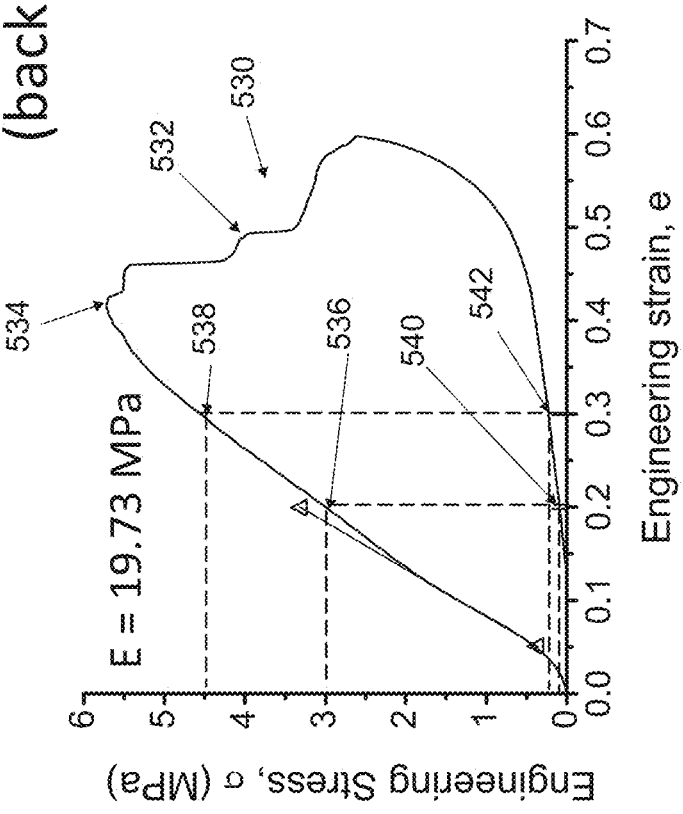
FIGS. 17A and 17B illustrate engineering and true stress/strain plots, respectively, of BAND-AID® TOUGH STRIP™ backing material.
Figure 18B:
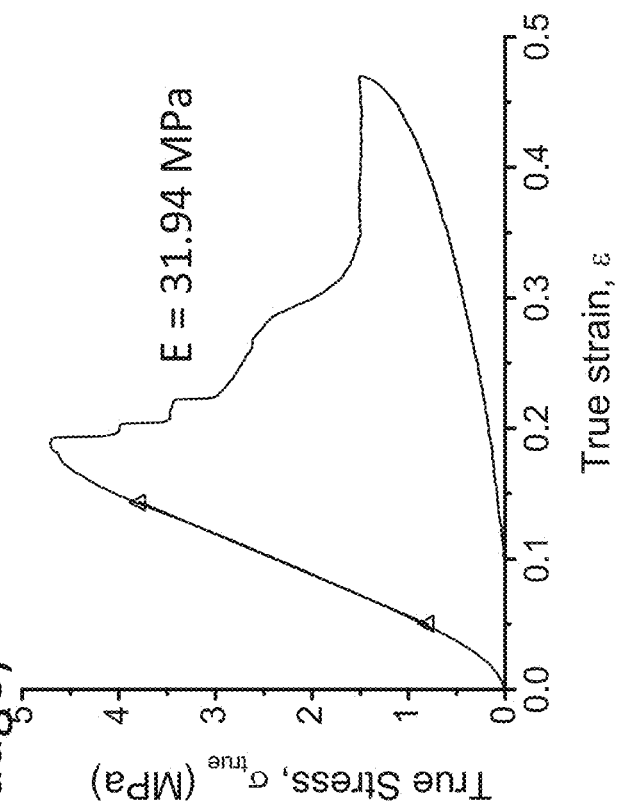
FIGS. 18A and 18B illustrate engineering and true stress/strain plots, respectively, of an intact BAND-MID® TOUGH STRIP™ bandage.
Figure 18A:
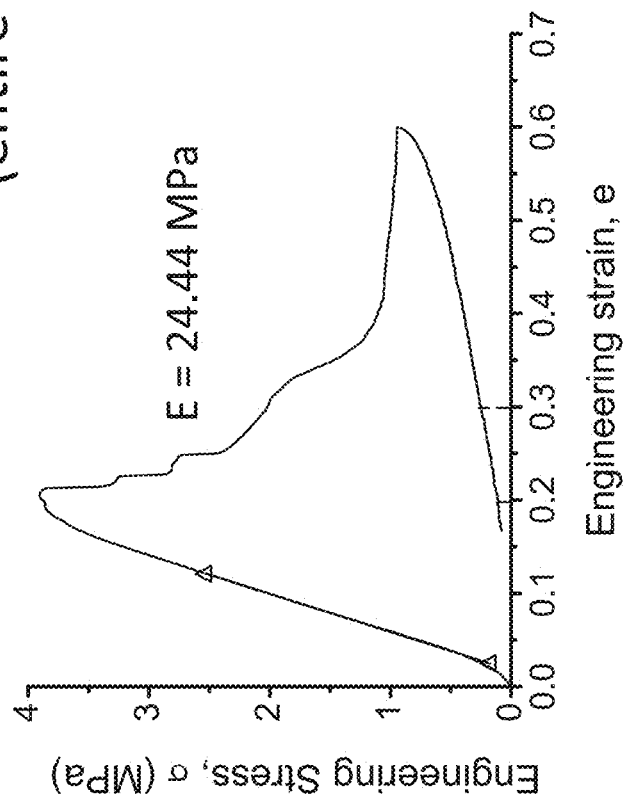
Figure 20A:
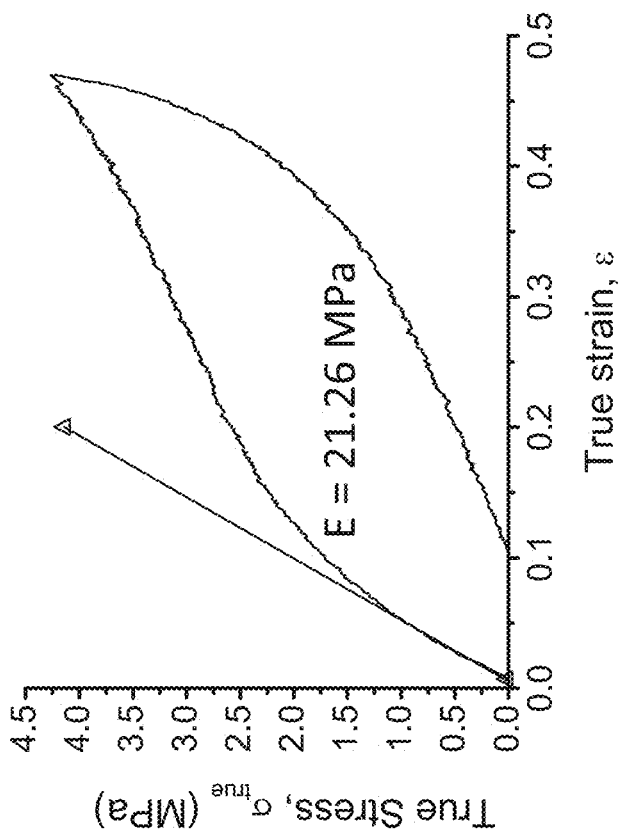
FIGS. 20A and 20B illustrate engineering and true stress/strain plots, respectively, of an intact NEXCARE™ TEGA-DERM™ bandage.
Figure 20B:
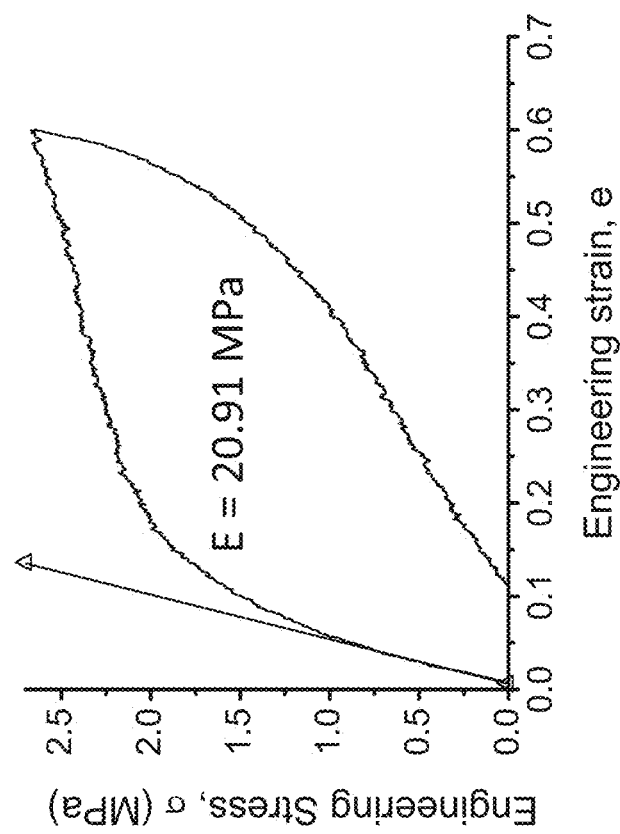

Another example of a material that failed to elastically strain to 60% is the backing material of Tough Strip™ BAND-AID®. As depicted in the engineering stress-strain curve 530 in FIG. 17A, structural damage is demonstrated by the downsloping, irregular segment 532 of the curve 530 during loading, with the peak engineering stress 534 occurring at about 40% strain rather than 60% strain. Relative to the peak engineering stress 534, or the corresponding loading stresses 536 and 538 at 20% and 30%, the recovery stresses 540 and 542 at 20% and 30% also illustrate that this material may be inefficient at transferring loads to the skin. As further depicted in FIGS. 18A and 18B, the stress-strain curves of an intact Tough Strip™ BAND-AID® continue to show evidence of structural damage at even earlier levels of strain.

Although the stress-strain curves depicted herein reflect certain intrinsic properties of the materials used in the tested bandages, the stress-strain curves alone may not be indicative of the suitability of a particular bandage to impose a strain on a skin location. The amount of stress and strain imposed on the skin may also vary depending upon the thickness, width, length, elastic modulus, and other material characteristics of the wound treatment device, as well as the amount of stress and strain placed on the wound treatment device. The force F exerted by the device may be generally characterized by the following equation, where E is the elastic modulus of the elastic material 4, A0 is cross-sectional area of the elastic material 4 transverse to the direction of stress, L0 is the initial length of the elastic material along the direction of stress and ΔL is the change in the length:

$$F = E \cdot A_0 \cdot \Delta L / L_0$$

This force may also be characterized in terms of the force per width of the elastic material 4:

$$\frac{F}{mm} = \frac{EA_0 \Delta L}{(L_0)(mm)} = \frac{E \cdot thickness_0 \cdot \Delta L}{L_0}$$

Figure 30A:
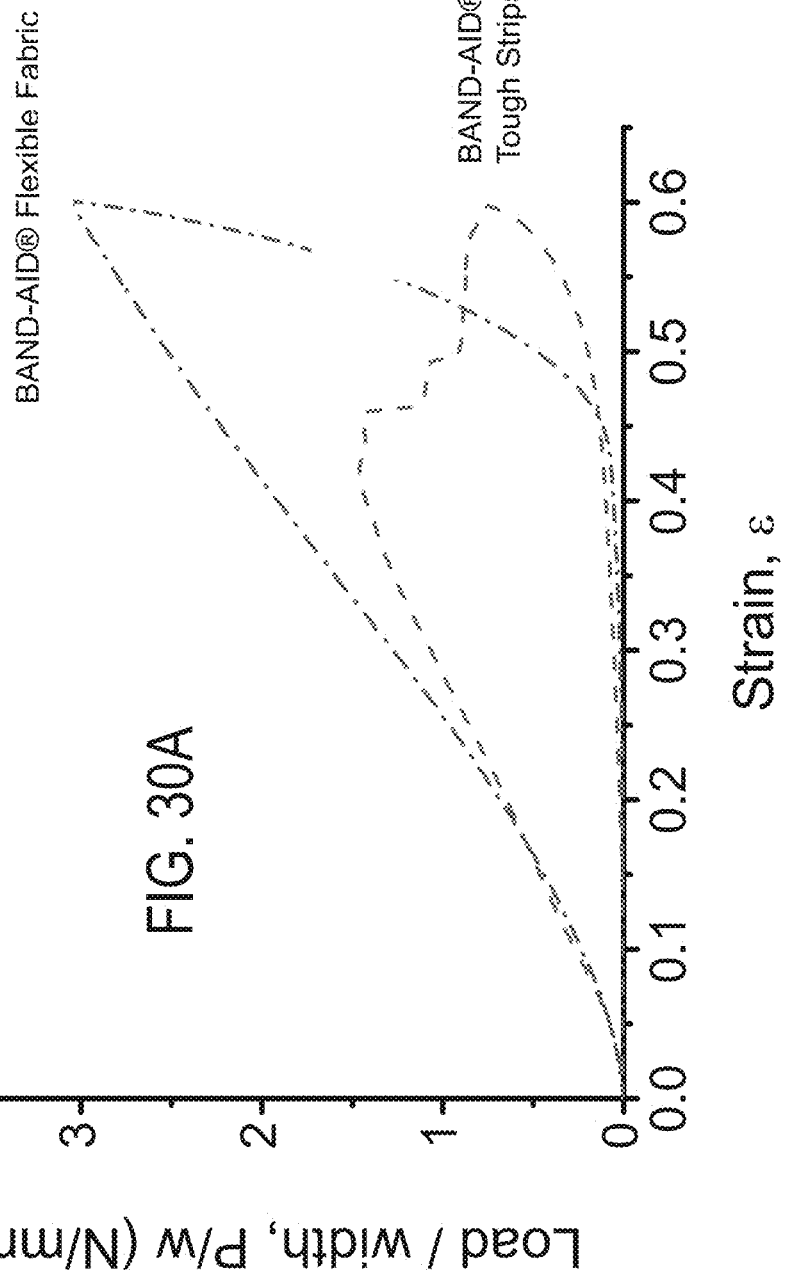
FIGS. 30A to 30C depict load per width plots of various bandage materials using three different Y-axis scales, respectively.
Figure 30B:
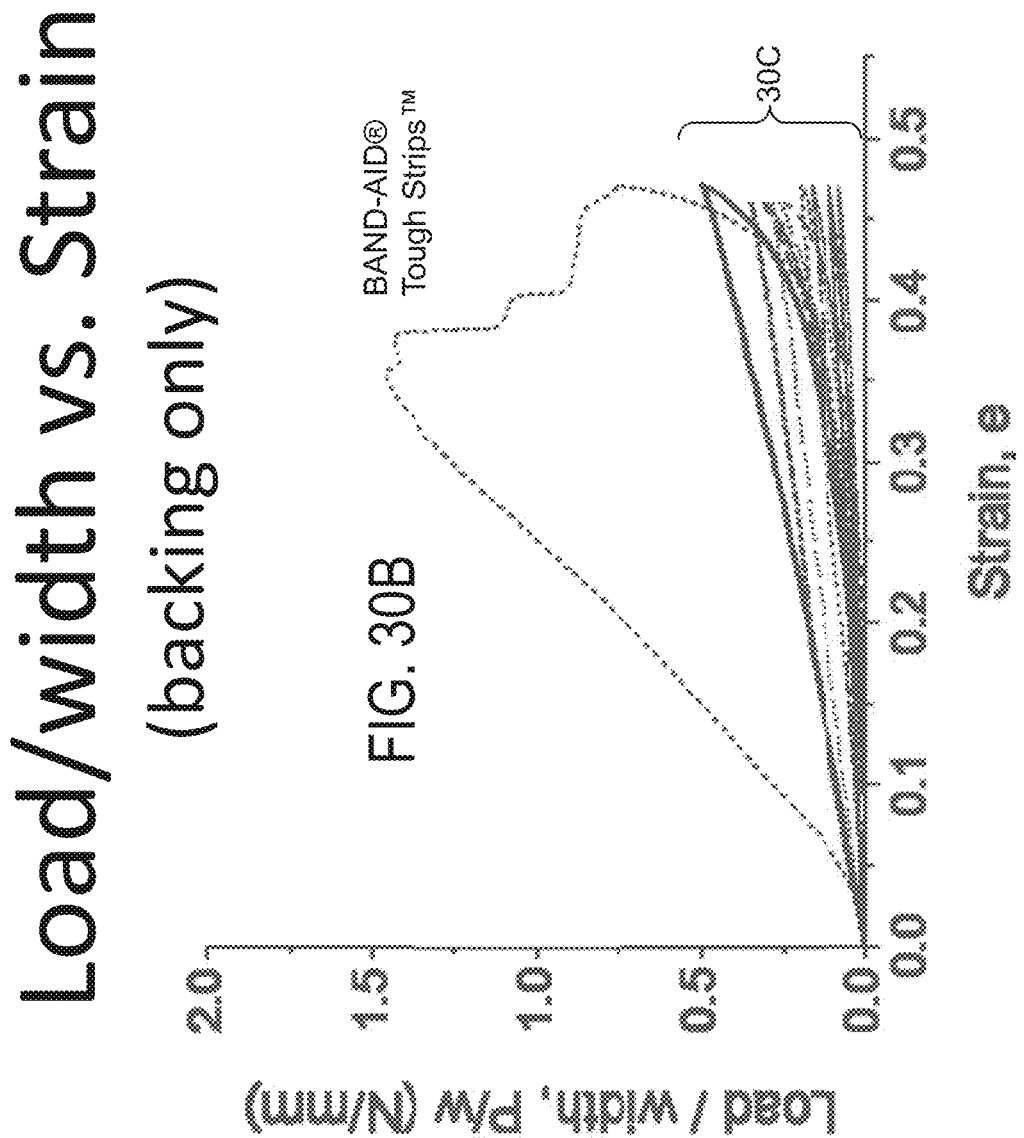
Figure 30C:
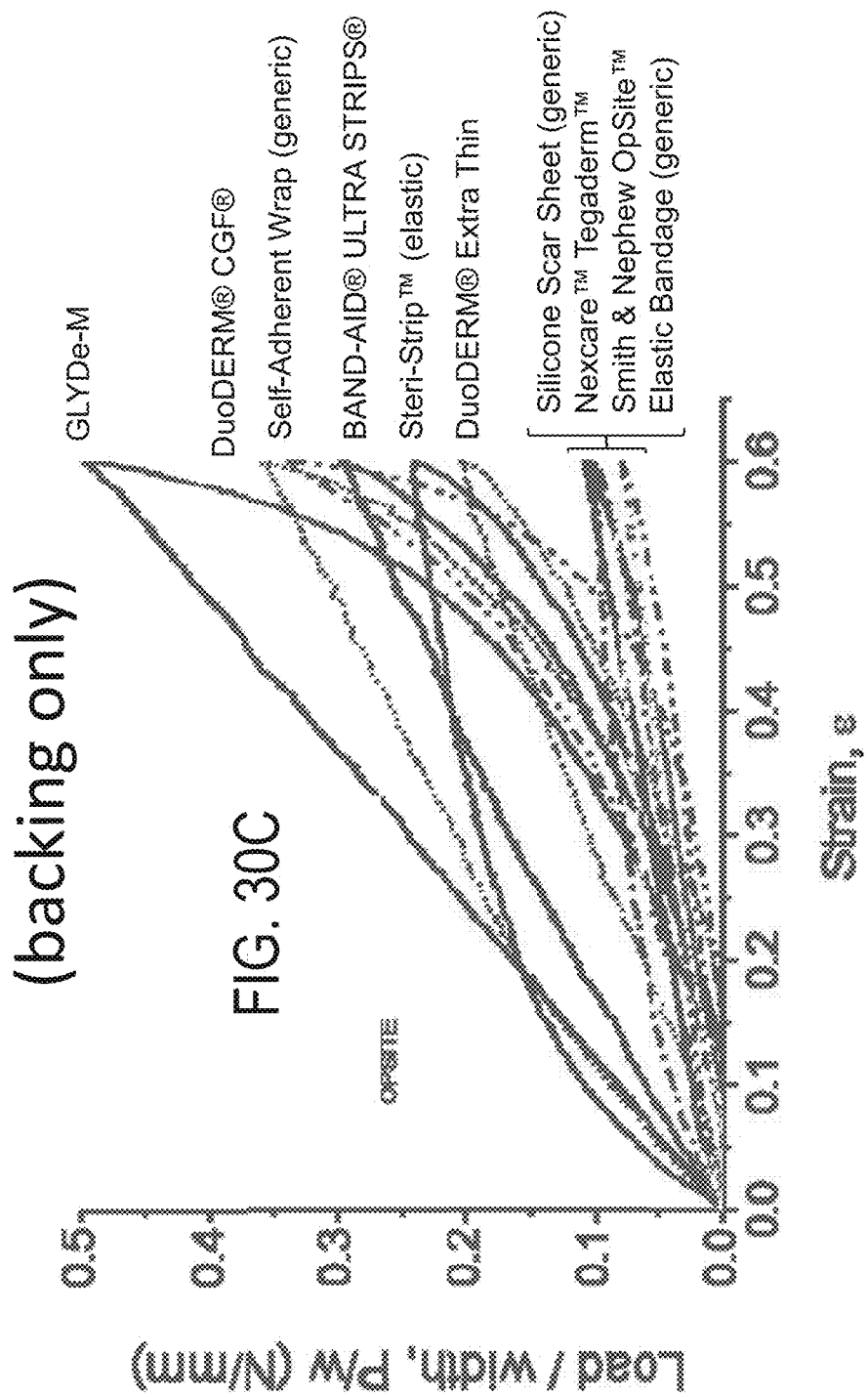

In one example depicted in FIGS. 19A and 19B, the stress-strain curves 550 and 552 for Nexcare™ Tegaderm™ occlusive bandages are provided. Although these curves do not indicate evidence of damage or rupture when loaded to 60% engineering strain 554 (or corresponding true strain 556), as did the Steri-Strip™, Flexible Fabric BAND-AID® and Tough Strip™ BAND-AID®, when the bandages are characterized in terms of their load-carrying capacity, as shown in FIG. 30C, Tegaderm™ exhibited substantially lower loads per millimeter width than many other tested bandages. Thus, the ability of some bandages to impose a stress onto the skin to generate skin strain may be limited. Also, as explained in greater detail below, many elastic materials was unable to sustain consistent levels of stress over time. This may be the result of stress relaxation in the backing material which was not intended to be strained to 30% as tested.

The stress-strain curves of still other bandages are provided in FIGS. 22A to 29B and 41A and 41B. Many of these bandages comprise materials with stress-strain curves that involve lower levels of stress, that result in lower load carrying capacity, as shown in FIG. 30C, while other bandages comprise materials that exhibit significant stress relaxation or other decreased in the strain imposed on the skin over time. As shown in FIG. 31A, the Nexcare™ Tegaderm™ backing material initially generated an engineering stress 560 of about 750 KPa when dropped to a strain of 30%, but over the course of 9 hours, the level engineering stress 562 continued to decrease, as shown in FIG. 31B with comparator line 564. In some examples, the backing material may be configured so that the engineering stress is tested at an engineering strain of 30% or some other level of strain over a period of time, the engineering stress levels decreases by less than about 15%, about 10%, about 8%, about 6%, about 5%, about 4%, about 3%, about 2%, or about 1% or less, or even effectively 0% for a particular time period.

The other backing materials tested generated an engineering stress of about 200 KPa or less at an engineering strain of 30% and/or demonstrated a decrease in the engineering stress over 9 hours, as depicted in FIGS. 34A to 40B. In some variations, this may indicate that the particular bandage may not be configured to generate consistent forces sufficient to impose sufficient stresses onto the skin to decrease skin tension, including high skin tension regions of the body such as the back and face.

Figures 37A, 37B:
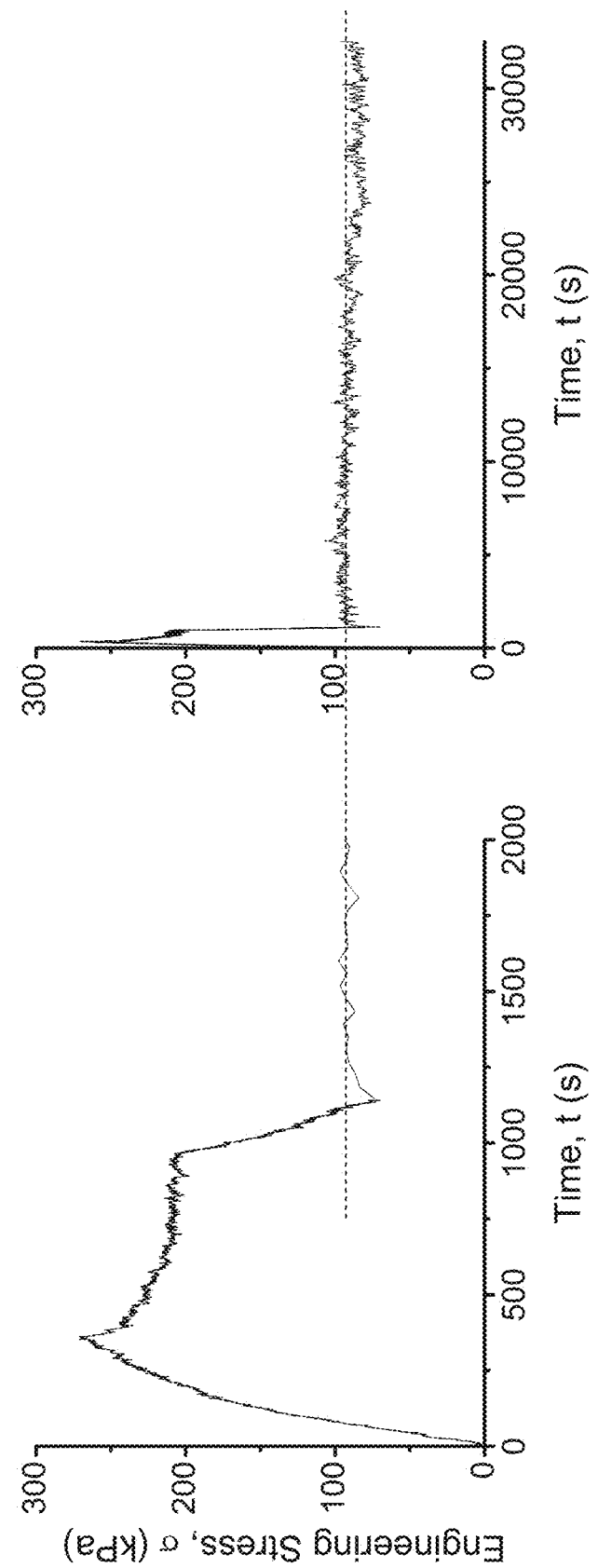
FIGS. 37A and 37B are engineering stress plots over time for DuoDERM® Extra. Thin under different loads using different X-axis scales, respectively.
Figures 38A, 38B:
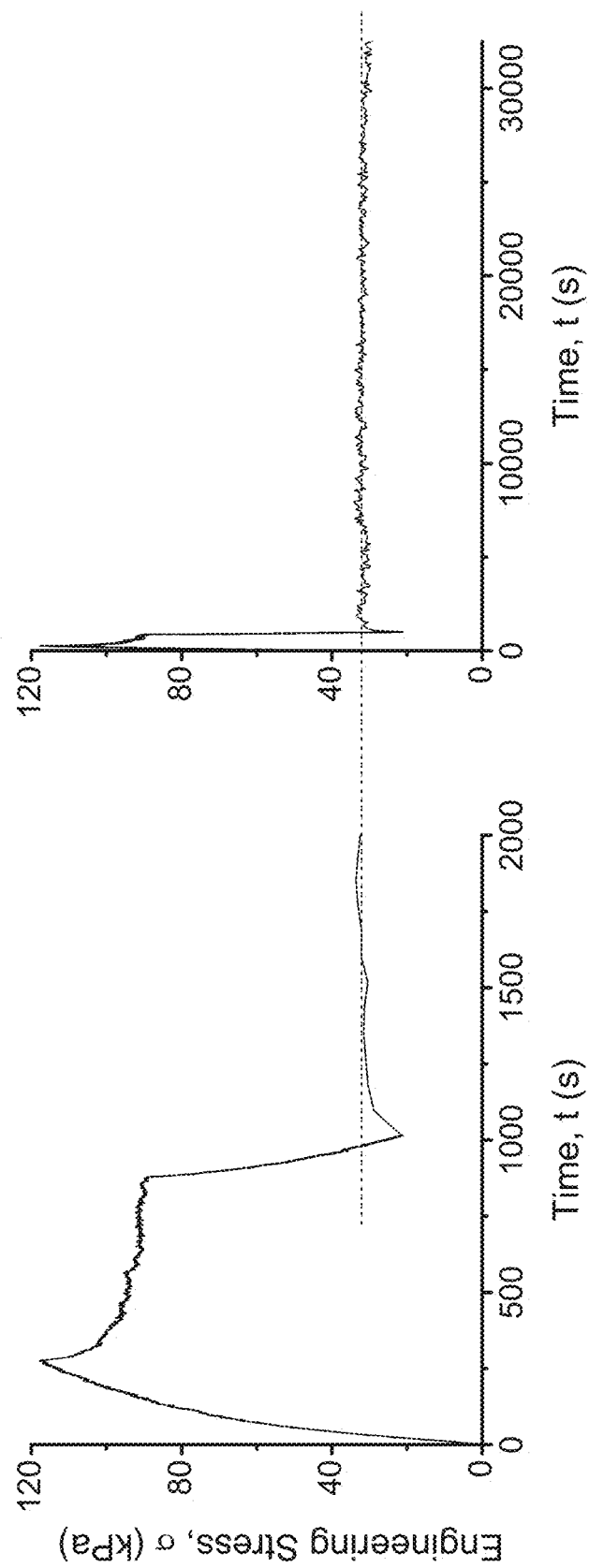
FIGS. 38A and 38B are engineering stress plots over time for DuoDERM® CGF® under different loads using different X-axis scales, respectively.
Figures 40A, 40B:
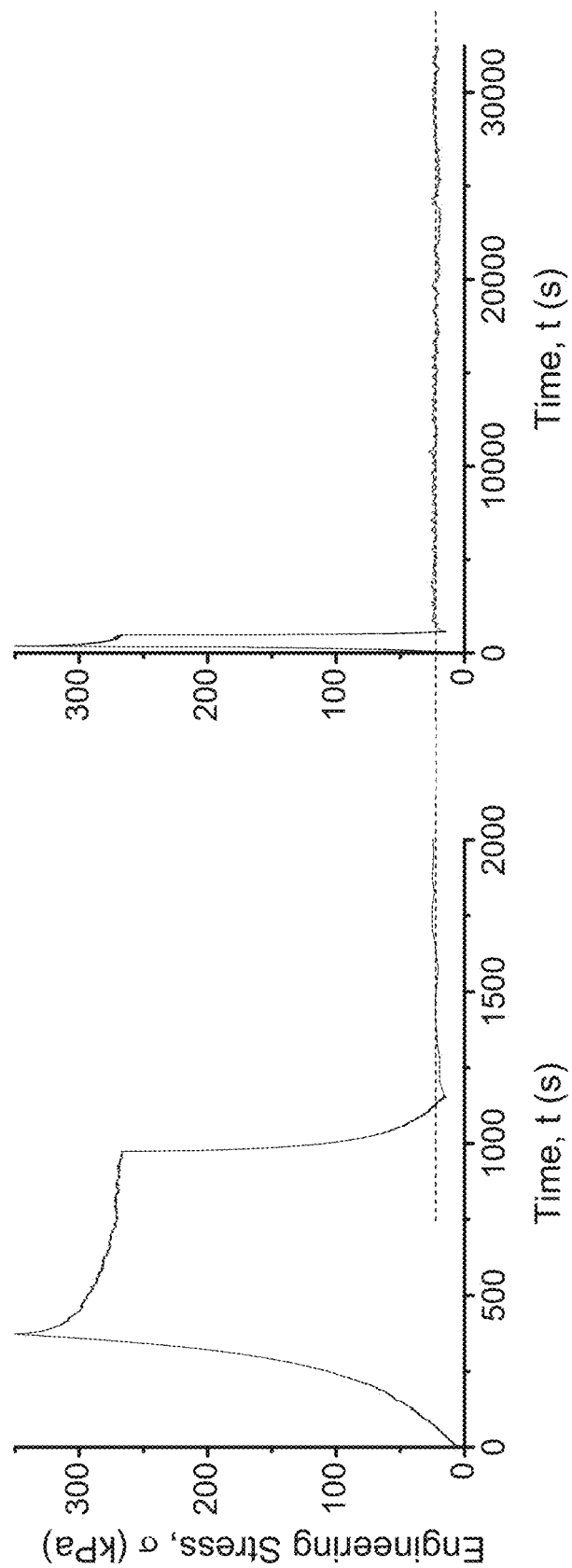
FIGS. 40A and 40B are engineering stress plots over time for the CVS/Pharmacy® self-adherent gentle wrap under different loads using different X-axis scales, respectively.
Figure 41A:
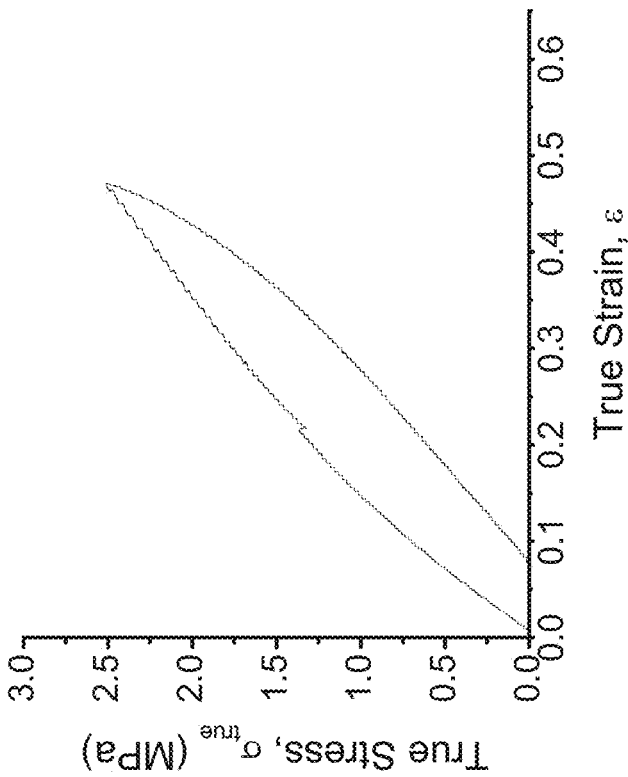
FIGS. 41A and 41B illustrate engineering and true stress/strain plots, respectively, of Smith & Nephew OpSite™.
Figure 41B:
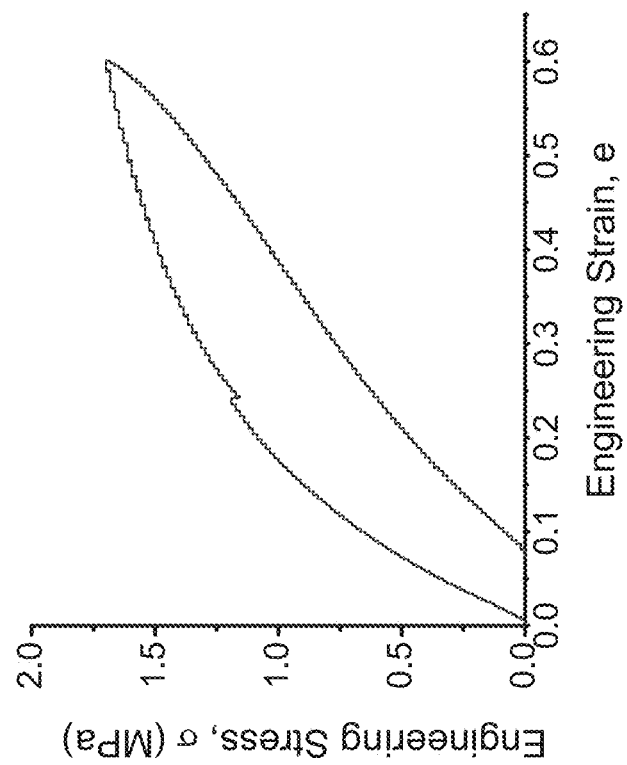

For example, as shown in FIGS. 33A to 34B, both the elastic Steri-Strip™ and the BAND-AID® ULTRA STRIP® generated an initial engineering strain of around 200 KPa at 30% strain, but also demonstrated at least some decrease in stress over time, with the ULTRA STRIP® decreasing more than the elastic Steri-Strip™. These decreases may be even greater if tested over longer periods of time, such as about 12 hours, about 24 hours, about 36 hours, about 48 hours, about 72 hours, about 96 hours, about 1 week, about 2 weeks, about 3 weeks, or about 4 weeks or greater, for example. As shown in FIGS. 35A to 40B, the backing materials of the other bandages generated substantially less than 200 KPa engineering stress, and some materials such as the DuoDERM® CGF®, the CVS/Pharmacy® elastic bandage, and the self-gripping CVS/Pharmacy® self-adherent gentle wrap, generated less than 50 KPa. Even at these lower levels of stress, however, some of the backing materials were unable to sustain consistent engineering stress levels over 9 hours, such as shown in FIGS. 37B, 38B, and 39B for DuoDERM® Extra Thin, DuoDERM® CGF® and CVS/Pharmacy® elastic bandage, respectively. Of further note is that the two bandages configured to be stretched when applied to the body, the CVS/Pharmacy® elastic bandage and the CVS/Pharmacy® self-adherent gentle wrap, are both designed to be wrapped circumferentially around a body part and to be attached back onto itself, exhibited the lowest engineering stresses when strained to 30%. This is also illustrated in FIG. 30C, where the portions of the unloading curves at 30% true strain are the lowest among the tested bandages, and at 20% true strain, are among the lowest along with DuoDERM® Extra Thin.

In addition to testing of the mechanical properties of the backing materials, the adhesive properties of the commercial bandages were also assessed. The testing was performed only with the bandages that had at least some adhesiveness or tackiness that permits measurement of slippage when applied to a test surface, excluding the CVS/Pharmacy® self-adherent gentle wrap and the CVS/Pharmacy® elastic bandage. Also, bandages that could not be elastically strained to 20% engineering strain, such as a regular Steri-Strip™ and the BAND-AID® Tough Strip, were excluded. To test the remaining materials, the backing material of each bandage was trimmed to a sample size of approximately 12 mm×50 mm. Each sample was stretched to either an engineering strain of 20% or 40% and then applied to polycarbonate sheeting and the degree of slippage was Observed up to 48 hours. Although the intrinsic properties of each adhesive used with each bandage may not be directly comparable based on this testing due to substantial differences in engineering stress generated at the specified levels of strain, and/or the degree of stress relaxation exhibited by each material, such testing may provide at least some indication of existing bandages to impose stresses onto skin.

TABLE 2

| Manufacturer | Product | Slippage at 20% Strain | Slippage at 40% Strain |
|---|---|---|---|
| — | Wound treatment device (GLYDe-M) | None @ 48 hrs. | None @ 48 hrs. |
| 3M (St. Paul, MN) | Steri-Strip ™ (elastic) | None @ 22 hrs. | None @ 22 hrs. |
| J&J (New Brunswick, NJ) | BAND-AID ® Flexible Fabric | None @ 46 hrs. | Slight @ 24 hrs Evident @ 46 hrs |
| J&J (New Brunswick, NJ) | BAND-AID ® Ultra Strip | Slight @ 24 hrs | Evident @ 2 hrs 40 min |
| 3M Nexcare ™ (St. Paul, MN) | Tegaderm ™ | None @ 24 hrs. | None @ 24 hrs. |
| ConvaTec (Skillman, NJ) | DuoDERM ® Extra Thin | Slippage @ 22 hrs. | Slippage @ 22 hrs. |
| ConvaTec (Skillman, NJ) | DuoDERM ® CGF ® | Edge peel @ 3 hrs Slippage at 24 hrs | Slippage @ 3 hrs More Slippage @ 24 hrs |
| CVS/Pharmacy ® | Silicone Scar Sheet | Slippage @ 3 min | Slippage @ 3 min |

As mentioned previously, although the actual force required to tensile strain a device may vary, depending upon the size of the device, in some variations, the device may be configured to achieve an engineering strain of about 60% using a load per millimeter width that is less than or equal to about 6 Newtons/millimeter (N/mm), about 5 N/mm, about 4 N/mm, about 3 N/mm, about 2 N/mm, about 1 1N/mm, about 0.8 N/mm, about 0.7 N/mm, about 0.6 N/mm, about 0.5 N/mm.

Each of the material or structural characteristics above may be mixed and matched to achieve the desired tensile stress/strain profile. In one specific example, the elastic material 4 may have an elastic modulus E in the range of about 2 MPa to about 4 MPa, exhibits a generally linear or curvilinear stress/strain loading curve (either engineering stress σ/strain e or true stress σ true/strain ε) with elastic deformation up to at least about 60% tensile engineering strain. In other examples, the elastic deformation property may be limited to about 20%, about 30%, about 40%, or about 50%. The elastic material 4 may also be configured with an average thickness in the range of about 100 microns to about 500 microns, about 200 microns to about 400 microns, or about 200 microns to about 300 microns. The elastic material 4 may also be configured to exert a minimum load per millimeter width at a particular strain. For example, when tensile strained to an engineering strain of 60%, the elastic material 4 may exert a compressive load/mm of at least about 0.3N, about 0.35N, about 0.4N, about 0.45N, or at least about 0.5N. In some examples, when tensile strained to an engineering strain of 40%, the elastic material 4 may exert a compressive load/mm of at least about 1.5N/mm, about 1.6N/mm, about 1.7N/mm, about 1.8N/mm, about 1.9N/mm, about 2 N/mm, about 2.1 N/mm, about 2.2 N/mm or about 2.3 N/mm, about 2.4 N/mm, about 2.5 N/mm or about 3 N/mm or greater. In still other examples, when tensile strained to an engineering strain of 30%, the elastic material 4 may exert a compressive load/mm of at least about 0.7N/mm, about 0.8N/mm, about 0.9N/mm, about 1N/mm, about 1.1N/mm, about 1.2 N/mm, or about 1.3 N/mm or greater. In yet other examples, when tensile strained to an engineering strain of 20%, the elastic material 4 may exert a compressive load/mm of at least about 0.4N/mm, about 0.45N/mm, about 0.5N/mm, about 0.55N/mm, about 0.6N/mm, about 0.65 N/mm, or about 0.7 N/mm or greater. On stress measurements at an engineering strain of about 30%, over a period of at least about 8 hours, about 12 hours, about 24 hours, or about 72 hours, the engineering strain may be at least about 175 KPa, about 200 KPa or about 225 KPa with a decrease in engineering strain that is no greater than about 12%, about 10%, about 8%, about 6%, about 5%, about 4%, about 3%, about 2% or less than about 1%.

Release Liner

Referring to FIGS. 2A and 2B, the wound treatment device 2 may be provided with one or more release liners 52, 54 and 56 to protect one or more of the adhesive regions 20, 22, 48 and 50. The release liners 52, 54 and 56 may be configured with one or more flaps or tabs 58, 60, 62, 64, 66 and 68 that project from the edges 10, 12 or surfaces 6, 8 of the treatment device 2 to facilitate grasping or removal of the release liners 52, 54 and 56. FIG. 2C depicts the liners 52, 54 and 56 without the wound treatment device 2. In some examples, the release liners may resist inadvertent adhesion of the wound treatment device to itself or other surfaces during loading of the device onto an applicator, or during application of the device to the skin. In variations where the device has multiple separate adhesive regions, separate release liners may be provided for each region, or some regions may be covered by the same release liner. Referring back to FIGS. 2A and 2B, the three release liners 52, 54 and 56 are provided to cover the four adhesive regions 20, 22, 48 and 50, with two end release liners 52 and 54 covering the flap regions 48 and 50, respectively and a single release liner 56 covering both inner adhesive regions 20, 22. The end release liners 52 and 54 each comprise two tabs 58 and 60 which project from the same edge 10 and 12, respectively, of the device, but in other variations, one or more tabs may project from the other edges 14 and/or 16, from multiple edges, or from no edges. The central release liner 56, for example, comprises tabs 66 and 68 that project from opposing edges 10 and 12 of the device. Although the tabs 58, 60, 62 and 64 are depicted as aligned with the edges 14 and 15 of the treatment device 2, in other variations the liners may be configured with tabs at other locations, or with a different number of tabs. In some variations, the tabs may also be folded or creased, which may facilitate grasping where the tabs are located against a surface rather than projecting from an edge.

In variations comprising multiple release liners, the liners may or may not be removed at different times or in a particular order. In some variations the liners may include indicia to facilitate removal in a particular order. The indicia may comprise alpha-numeric characters 70 and 72, color, graphic symbols and the like, and may be located on the body of the liner or on the tabs, if any. In FIGS. 2A and 2B, for example, users may be instructed to remove the central liner 56 during the loading of the treatment device 2 onto an applicator and/or for application to a skin site. After the initial adherence of the treatment device 2 to the skin, the outer release liners 52 and 54 covering the flap regions 48 and 50 may then be removed to permit adherence of the rest of the treatment device 2.

The release liners may comprise any of a variety of materials, including both opaque and transparent materials. The release liners may comprise Mylar or paper, or any other material with reduced adhesion to the adhesive material(s) of the device. In some examples, the central liner 56 (or a different liner) may be reapplied to the inner adhesive regions 20 and 22 after the treatment device 2 is loaded onto an applicator, which may protect the adhesive materials until actual application to the skin. The liners may comprise different surface geometries, e.g. surface roughness, and/or indicia that may permit identification of the original liner surface that was applied to the adhesive regions, which may reduce degradation of the adhesive regions from dust, dander and/or other substances if the incorrect side of the liner is reapplied to the device.

Applicator

As noted previously, an applicator, tensioning device and/or straining device may be provided in some embodiments to impart a strain to a skin treatment device with an external force and/or to maintain a strain imparted to the skin treatment device. In some examples, the straining device may be configured to impart and/or maintain a single predetermined or pre-set strain or a plurality of predetermined or pre-set strains. Features described herein with respect to an applicator may also be used in any tensioning or straining device that is used to strain a skin treatment device. An applicator, tensioning or straining device that is described as being in an unstrained configuration is in a configuration in which a skin treatment device may be unstrained or relatively less strained when attached to the applicator, tensioning or straining device. An applicator, tensioning, or straining device that is described herein has being in a strained configuration is in a configuration in which a skin treatment device may be strained or relatively more strained when attached to the applicator, tensioning or straining device. Features described herein with respect to an applicator may also be used in any tensioning or straining device that is used to strain a skin treatment device.

A skin treatment device that is described herein is a device that may be applied, attached to or coupled to one or more layers of the skin of a subject and may include without be limited to, a wound treatment device, a dressing, bandage, or other device.

Attachment structures of an applicator, tensioning or straining device may include any structures that are used to attach or couple an applicator, tension or straining device to a skin treatment device. Such devices may include but are not limited to pockets and tabs, hook and loop mechanism, hooks, angled bars, adhesives, removable adhesives, pegs, rip cords, towel bar configurations, sliding pins, friction locks, cam locks, vacuum or suction devices, snap connectors, carpet tack, press fit connections or other connections.

The attachment structure profile may be straight, curved or otherwise varied. For example, the shape of the attachment structures may be configured to follow the shape of the area of the subject's body to which the skin treatment device is to be attached. A tensioning device or applicator may be selected or configured to have a profile that has a desirable profile for a particular body location or profile where the skin treatment device is to be placed on a subject's skin. A tensioning device or applicator may be selected or configured to closely match a portion of a subject's body profile. The attachment structures may be curved, curvable, bendable, deformable, shapeable or movable to provide alternative shapes or profiles of an attached skin treatment device.

Attachment features or structures of a skin treatment device may include any of the attachment structures or corresponding structures to the attachment structures.

Attachment structures and corresponding attachment features may be configured to provide multi direction strain or additional strain in an orthogonal direction.

In some variations the applicator may comprise a mechanism configured to facilitate separation, release, removal or detachment of the attachment structures of the applicator from the attachment features of the skin treatment device, including but not limited to the separation devices and methods described herein. Releasing mechanisms may include but are not limited to pivoting, rolling, rocking or sliding features associated with or coupled to attachment structures of the applicator. They may be self-releasing latches or spring members. They may be actuated when a pressure member is applied to a skin treatment device prior to removing the applicator. They may be manually actuated. The mechanisms may include levers, latches, locking members, spring members, for example.

A variety of locking, latching or detent mechanisms may be used to maintain the applicator in a various configurations including but not limited to unstrained, partially strained, strained, unstamped, or stamped configurations. A variety of locking, latching or detent mechanisms may be used to maintain a skin treatment device in a variety of configurations including unstrained, partially strained, strained. By locking an applicator in a strained position a predetermined strain of a given skin treatment device may be achieved. Other locking mechanisms, including but not limited to other locking mechanisms described herein may be used. A variable locking mechanism may be used to vary the amount of strain for a given skin treatment device. Such mechanisms may be releasable to permit straining, stamping, release of the attachment structures from the skin treatment device, or to release various structures to permit reloading of the device.

An actuator, actuation force may be used or applied at any point during straining of a skin treatment device and is externally applied to the applicator, either manually or otherwise. Optionally, an actuator or handle may be provided that provides a mechanical advantage greater than 1 at least at some point when actuated. Optionally a mechanical advantage may increase as a device is strained.

Applicators configured with any of a variety of force transfer mechanisms may be used to transfer forces exerted onto the applicator to the skin treatment device, including but not limited to leaf springs, helical springs, pneumatic or hydraulic struts, sliders, helically threaded shafts, articulated linkages, pivoting levers, and the like. The force transfer mechanisms may be configured to transfer the resulting force onto the skin treatment device along the same direction as the originally exerted force, or in other configurations along a different direction. For example, the applicator 220 in FIG. 12A transfers force along the same direction as originally exerted by the user, while the applicator 1000 in FIG. 51A transfers the rotary force exerted by the user into a linear spreading force, and the applicator 1100 in FIG. 53A transfers a force that is perpendicular to the user exerted force. Also, while some force mechanisms provide the user with a mechanical advantage when straining a skin treatment device, e.g. applicator 1100 in FIG. 53A, others may not, e.g. applicator 200 in FIG. 6. These and other examples of applicators and force mechanisms are described in greater detail below.

Applicators described herein may provide accessible areas or spaces to access areas where the skin treatment device is applied to the skin so that the adhesive may be pressed on to the skin. The adhesive used may be, for example, a pressure activated adhesive (PSA), as a silicone, acrylic, styrene block copolymer, vinyl ether, nitrile or other PSA. In other variations, a non-pressure sensitive adhesive may be used, including but not limited a heat or light-cured adhesive.

In some variations, the applicator may comprise an attachment configuration that facilitates attachment of a device to the applicator, and a delivery configuration that stretches or strains the attached device by about 20%, about 30%, about 40%, about 50%, about 60%, about 70%, about 80%, about 90%, about 100%, or about 110% or more, relative to its unstretched or unstrained configuration. The applicator may have a greater strain in the attachment configuration than in the delivery configuration. The applicator may be configured such that the strain it imposes generally falls within with a one or two-sided tolerance of about 2%, about 3%, about 4%, about 5%, about 6%, about 7%, about 8%, about 9%, about 10%, about 15%, or about 20%, for example. The load per width imposed by the applicator onto the treatment device along its axis of tensile strain may vary, depending upon the amount of desired strain and the material characteristics of the device. For example, the applicator may be configured to exert a engineering strain of about 60% to the device using a load per millimeter width that is in the range of about 0.1N to about 1N, about 0.2N to about 0.8N, about 0.3N to about 0.6N, or sometimes in the range of about 0.4N to about 0.5N or 0.6N. In another example, the applicator may be configured to exert a strain of about 40% to the device using a load per millimeter width that is in the range of about 0.05N to about 0.6N, about 0.1N to about 0.5N, about 0.2N to about 0.4N, or about 0.3N to about 0.4N. In still another example, the applicator may be configured to exert a strain of about 30% to the device using a load per millimeter width that is in the range of about 0.05N to about 0.5N, about 0.1N to about 0.3N, or about 0.2N to about 0.3N.

The applicator may also be characterized by the force required to compressively strain the applicator to a particular strain level, and/or by the force the applicator exerts when the applicator is compressed to a particular strain level. For example, the applicator may be configured to be compressively strained to about 40% using a load per millimeter width (or dimension transverse to the direction of strain) that may be at least about 0.1N, about 0.2N, about 0.3N, about 0.4N, about 0.5N, about 0.6N, about 0.7N, or about 0.8N or greater. In other examples, the applicator may be configured to be compressively strain to about 20% using a load per millimeter width (or transverse dimension) that is at least about 0.05N, about 0.1N, about 0.2N, about 0.3N, about 0.4N, about 0.5N or greater. In some variations where the material exhibits little hysteresis on it stress/strain curves, the loading force and the unloading force at a particular level of strain may be the same or similar.

FIGS. 3A to 4D depict one example of an applicator 100 that may be used to generate the strain and/or maintain strain in the device for application to a treatment site. The applicator may comprise a resilient elastic or spring body comprising an expanded or relaxed configuration (as shown in FIGS. 3A to 3D) and a retracted or constrained configuration (as shown in FIGS. 4A to 4D). The applicator 100 may comprise an elastic body 102 with first and second device attachment structures 104 and 106 that are configured to releasably engage the applicator attachment structure 40 and 42 of the treatment device 2 illustrated in FIGS. 1A to 2B. Here, the attachment structures 104 and 106 comprise a plurality of projections 108 and 110 that may be inserted into the openings 44 and 46 of the devices. The projections may have any of a variety of shapes, orientations, sizes or thicknesses. In this particular variation, the projections 108 and 110 are angled upwards from the base structures 112 and 114 of the applicator 100 (e.g. away from an attached device). The angle may be anywhere in the range of about 0 degrees to about 90 degrees or more, in some variations about 15 degrees to about 75 degrees, and in other variations about 25 degrees to about 45 degrees. The angles of the projections 108 and 110 may be uniform or non-uniform between the two sets or between individual projections. The shape of the projections may be square, rectangular, triangular, bulbous, mushroom-like, or the like. In some variations, the transverse dimension of the projections may be greater than the corresponding transverse dimension of the openings 44 and 46 of the treatment device 2, which may result in stretching or deformation of the openings 44 and 46 when attached to the applicator 100. The resistance from the deformation of the openings 44 and 46 may reduce the rate of inadvertent detachment of the treatment device 2 from the applicator 100. In variations comprising a mushroom or bulbous configuration, the rounded distal end of the projection may reduce the risk of damaging the device during loading, while the increased transverse dimension of the projection distally and the reduced transverse dimension of the projection proximally may provide tactile feedback to the user during loading that may indicate proper loading, and may also reduce the risk of device damage by reducing stretching of the openings once loaded. The projections may have a length of about 500 microns to about 5 mm or more, in some variations about 1 mm to about 4 mm, and in other variations about 2 mm to about 3 mm. The thickness of the projections may be the same, lower or greater than the elastic body 102 of the applicator 100. The elastic body 102 may comprise any of a variety of elastic materials, including but not limited to polymeric and metallic materials. In other variations, generally malleable polymeric or metallic materials may be used.

To facilitate the application of pressure against the device 2 and onto the skin, the base structures 112 and 114 may further comprise pressure pads 116 and 118 or other padded/deformable structures that may conform to the contours of the skin surface, which may redistribute forces exerted onto the treatment device 2 through the applicator 100 across the surfaces of the pads 116 and 118. The pressure pads 116 and 118 may comprise any of a variety of deformable materials, including foams (open and closed cells), gels, and the like.

In some variations, the device may comprise further indicia that may be used to indicate proper loading and/or straining of the device. In FIGS. 1A and 2A, for example, the geometry of lines 74 and 76 may be remain generally linear when all of the openings 40 and 42 of the treatment device 2 are engaged by the projections 108 and 110, but may be deformed or become non-linear if one or more of the openings 40 and 42 are missed, due to variations in the degree of stretching across the treatment device 2. The lines 74 and 76 may also align with corresponding indicia on the applicator 100 (e.g. the base structures 112 and 114 and/or the pressure pads 116 and 118) to indicate proper loading and/or stretching of the treatment device 2.

In some variations, the applicators may be manually maintained in a retracted state by the user during loading by squeezing or otherwise exerting compressive forces onto the applicator. In other variations, as shown in FIGS. 3A to 4D, the applicator 100 may comprise a locking mechanism 120 that may be used to maintain the applicator 100 in one or more configurations. In this particular variation, the locking mechanism 120 comprises a latch 122 that releasably engages a tab 124 located in an opening 126 or recess of the elastic body 102. The latch 122 may be biased against the tab 124 such that as the tab 124 slides along the length of the latch 122 as the elastic body 102 is compressed, until the tab 124 engages a tab opening 134 (depicted in FIGS. 4A, 4C and 4D) on the latch 122 and locks in the compressed configuration of the elastic body 102. To resist complete disengagement between the latch 122 and the opening 126 in the elastic body 102, the opening 126 may comprise a retention bar 128 that the distal section 130 of the latch 122 may be wrapped around. The latch 122 may be attached to the elastic body 102 by a rivet 132, or by welding or gluing, for example. In other examples, the latch may be integrally formed by laser cutting or punching out the latch structure from the elastic body. In some variations, the applicator may be configured with two or more latches.

In other variations, the latch may not be biased against the tab and may be manually engaged the user at the desired locking position. In other variations, the latch may have a plurality of tab openings to permit locking into a variety of configurations. In still other variations, the latch may comprise a projection or tab that engages an opening or recess of the elastic body. In alternate variations, the locking mechanism may comprise a ratchet mechanism, locking pin mechanism, or resistance screw, for example.

Figure 5A:
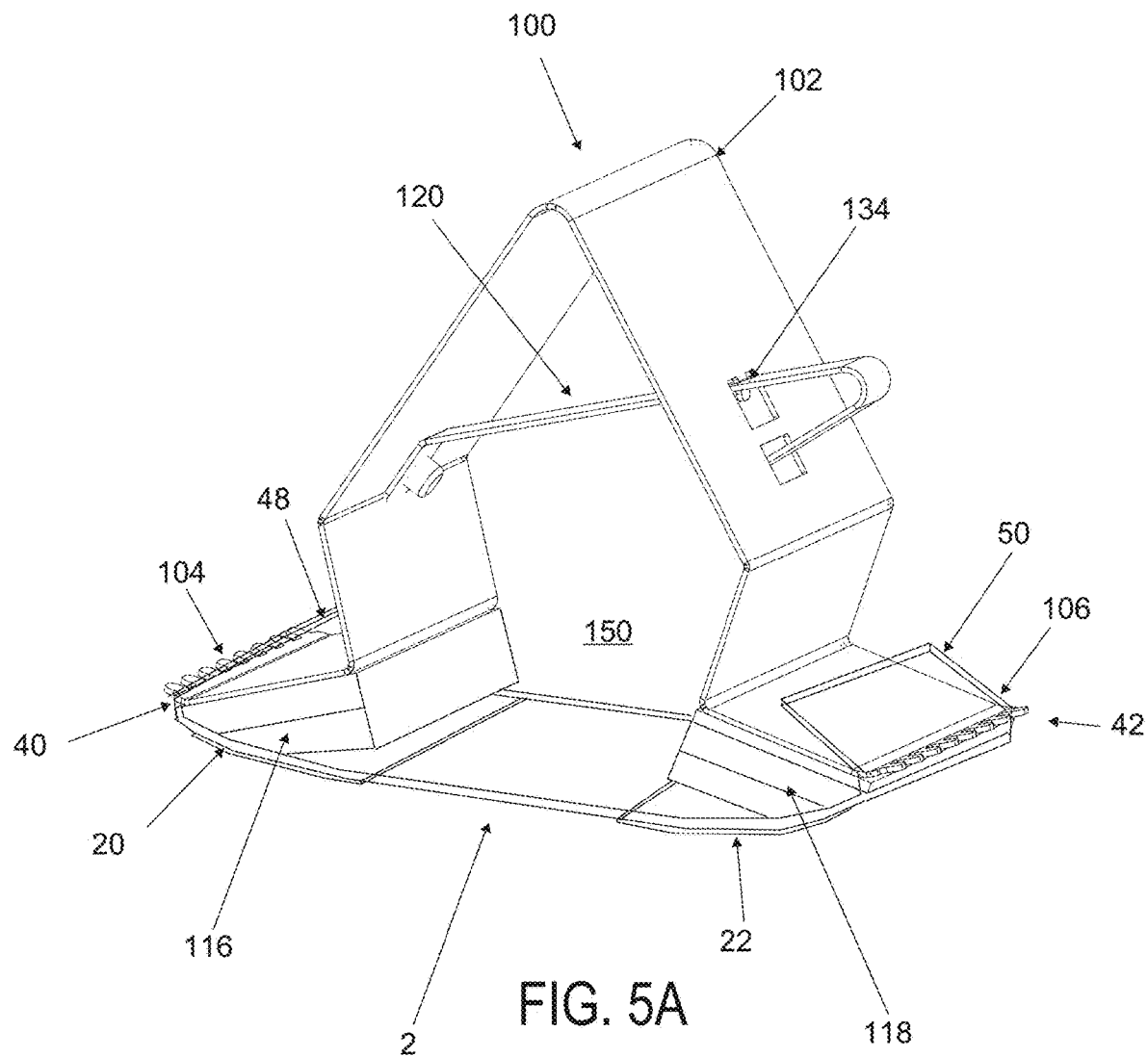
FIGS. 5A and 5B are schematic perspective and side elevational views of the applicator in FIGS. 4A and 4B loaded with a wound treatment device.
Figure 5B:
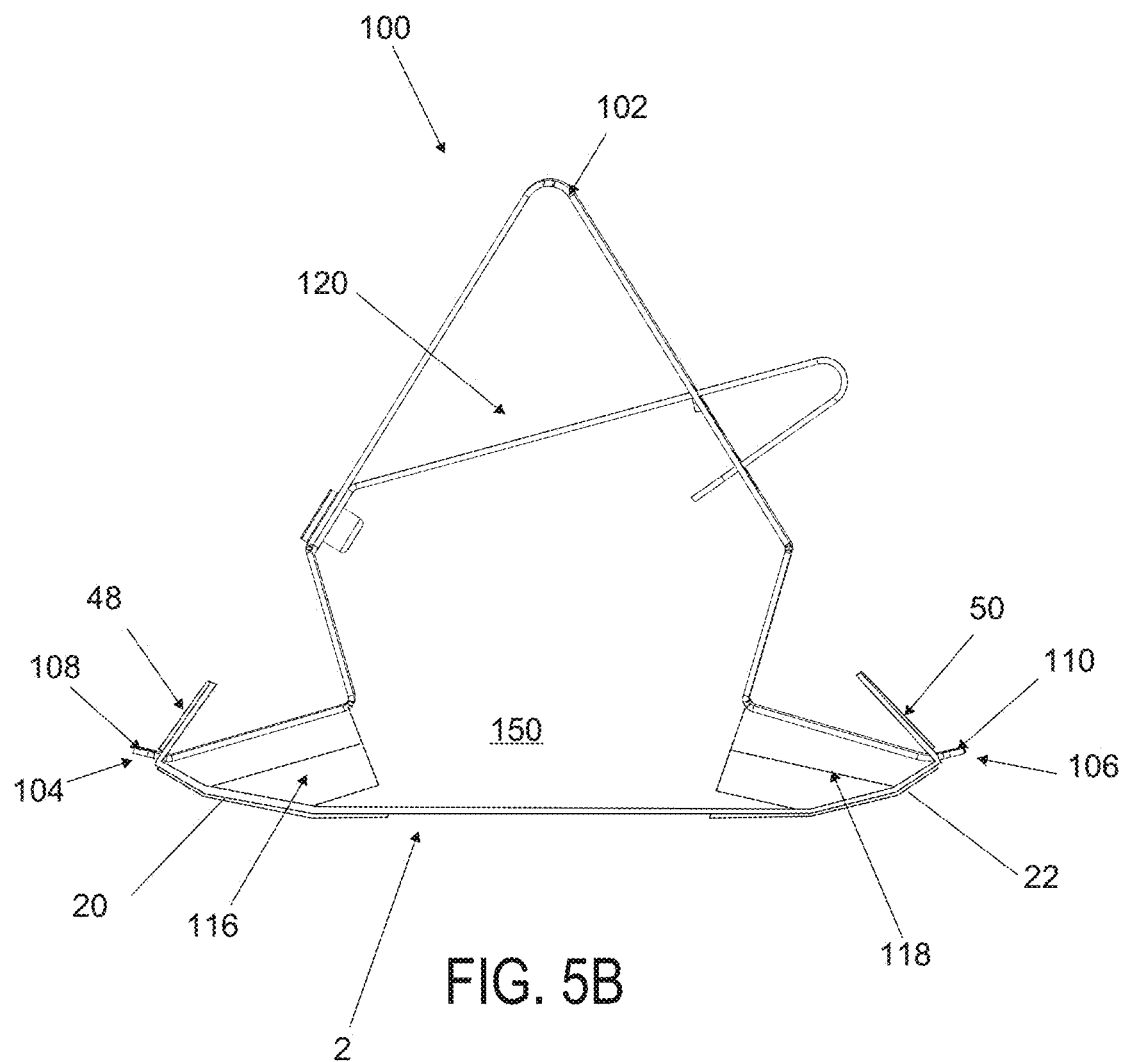

FIGS. 3A to 3D depict the applicator 100 in its base configuration with reduced strain, if any. To facilitate loading of the treatment device 2, the applicator 100 may be compressed, until the applicator 100 is locked into a compressed configuration, as illustrated in FIGS. 4A to 4D, which may reduce the degree of stretching, if any, needed to load the device onto the applicator 100, as depicted in FIGS. 5A and 5B. Once the device is loaded, the locking mechanism 120 may be disengaged by pressing the latch 122 away from the locking tab 124. The potential energy in the elastic body 102 from its compression is then released to permit stretching of the attached treatment device 2 and is ready for adhesion to the skin. As shown, the elastic body 102 comprises a sheet of semi-rigid material, but in other variations, may have a frame-like configuration. In some variations, the elastic body may comprise stainless steel with a thickness in the range of about 500 microns to about 3 mm or more, in some variations about 1 mm to about 2 mm, and in other variations about 1 mm to about 1.5 mm. The elastic body 102 may be configured with as a number of angled panel regions, as depicted in FIGS. 3A to 4D, with generally horizontal base structures 112 and 114 that may be generally orthogonal to side panels 140 and 142, which in turn form an angle of about 135 degrees each (as measured from the inferior surface of the elastic body 102) with the central panels 144 and 146 which in turn may be generally oriented at about a 90 degree angle with each other. The angles between the panels may be sharp angles or rounded angles, and may be configured differently depending upon the particular skin site (e.g. limb vs. torso), or degree of desired strain (e.g. a more obtuse angle between the central panels 144 and 146). In other variations, the angle between any two panels or base structure may be in the range of about 0 to about 360 degrees, in some variations about 45 to about 135 degrees, and in other variations about 75 to about 90 degrees (as measured from the underside or topside of the elastic body 102). The latch mechanism 120 may be attached or involve the central panels as shown in FIGS. 3A to 4D, but in other variations may be attached or involve the side panels or base structures. In other variations, the elastic body may comprise a curved structure, including but not limited to an omega-shaped structure. As illustrated in FIGS. 3A to 5B, the non-planar configuration of the applicator 100 provides an open region 150 between the pressure pads 116 and 118 and side panels 140 and 142, which permits access to the superior surface of an attached device to facilitate positioning of the device to a treatment site and/or to permit direct access or the application of pressure to the central portion of a device by the user (e.g. using fingers or other instrument). As shown in FIGS. 5A and 5B, the treatment device 2 and the applicator 100 may be configured so that the inner adhesive regions 20 and 22 are generally located underneath the pressure pads 20 and 22 when the treatment device 2 is loaded onto the applicator 100.

Figure 6:
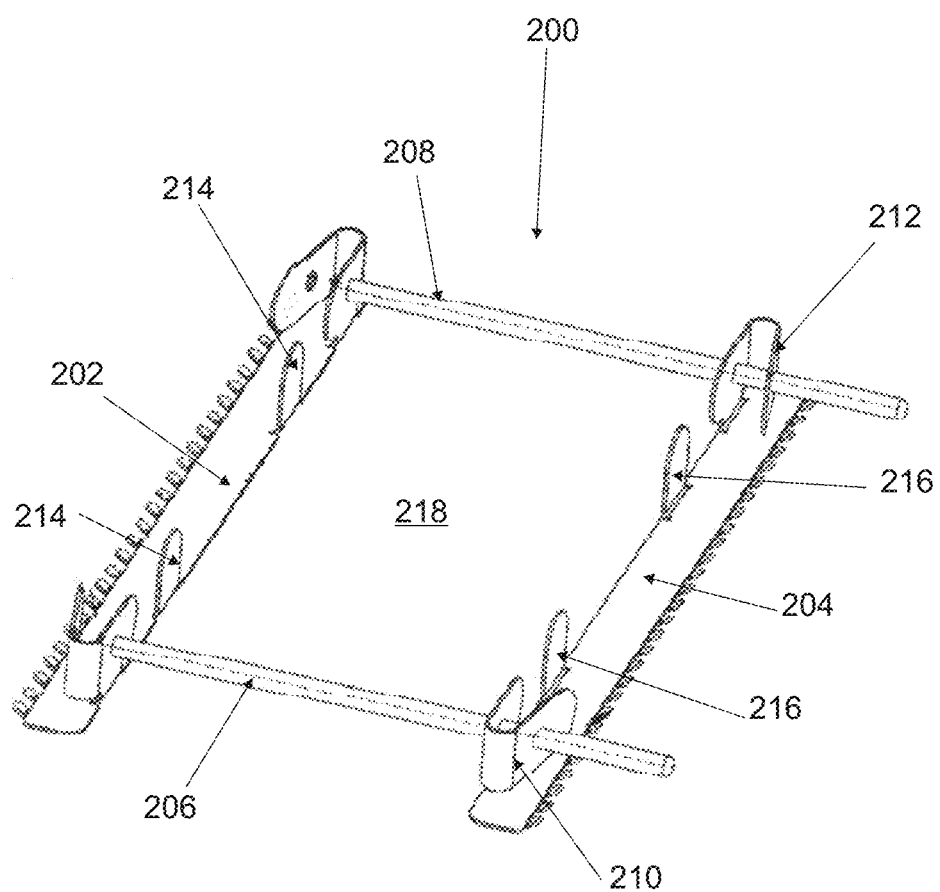
FIG. 6 depicts another variation of an applicator.

In other variations, the applicators usable with the wound treatment device may not be configured to actively exert force onto the device, and/or need not have a generally angled or curved design. In FIG. 6, for example, the applicator 200 has a generally planar configuration and comprises two device attachment structures 202 and 204 that are connected by strut or frame members 206 and 208 that are configured to slide or move with respect to at least one of the device attachment structures 204, if not both. In FIG. 6, for example, the strut or frame members 206 and 208 may be fixedly mounted to one of the attachment structure 202, but are slidably mounted to the other attachment structure 206 by clamps 210 and 212. The clamps 210 and 212 depicted in FIG. 6 are friction clamps that may be pinched or compressed to at least partially release or relieve the frictional resistance between the frame members 206 and 208 and the clamps 210 and 212, which permits separation or contraction of the applicator 200. The attachment structures 206 and 208 may further comprise tabs 214 and 216 or handles to facilitate manipulation and/or positioning of the applicator 220. In use, the user will attach a device 2 to the applicator 200, and then manually stretch the device 2 by pulling apart the clamps 210 and 212. To use this applicator 200, the attachment structure 204 is slid toward the other attachment structure 202 along frame members 206 and 208 until the spacing between the attachments structures 202 and 204 is sufficiently reduced to facilitate attachment of a complementary treatment device (not shown) without requiring significant stretching, if at all. Once attached, the attachment structure 204 is pushed or pulled away from the other attachment structure 202 until the desired degree of stress or strain in the treatment device is achieved. The treatment device is then applied to the treatment site, and then the attachment structure 204 is slid along the frame members 206 and 208 again to relieve the stress and strain in the treatment device and to permit separation of the applicator 200 from the treatment device.

In the particular variation depicted in FIG. 6, the applicator 200 comprises two frame members 206 and 208 located on the periphery of the applicator 220 to provide a central access region 218 that may facilitate positioning of the attached device or to direct access to the device. In other variations, the applicator may comprise a single frame member or three or more frame members, and the applicator may comprise one or more frame members that are centrally located or otherwise spaced away from the periphery of the applicator. In other variations, other types of movable or lockable mechanical interfaces may be provided between the frame members and the attachment structures, including but not limited to locking pins, thumbscrews, and the like. In another variation, helical springs may be provided along the frame members to 206 and 208 to bias or exert a separation force between the attachment members 202 and 204. In still other variations, such as the applicator 220 depicted in FIG. 12A, force members 222 and 224, which may be coil or pneumatic struts, for example, may also be used.

FIGS. 11A and 11B depict another variation of an applicator 320 comprising bendable or deformable frame members 322 that may or may not be biased to a configuration that exerts a stretching force on an attached device. In this particular variation, the bendable frame members 322 comprise a frame member 322 with a hinge 324, but in other variations, other mechanical joints, or a malleable or other deformable frame member may be used. The applicator 320 may be bent or angled to facilitate loading of a device onto its attachment structure 326. Once attached, the device may be strained by straightening the configuration of the frame member 322, as shown in FIG. 11B. The frame member 322 may be maintained in the straight configuration using a locking sleeve 328 that is positioned over the hinge joint to restrict motion. The sleeve 328 may be configured to slide and/or rotate in and out of locking position, and may or may not reduce the risk of inadvertent unlocking.

Figure 7:
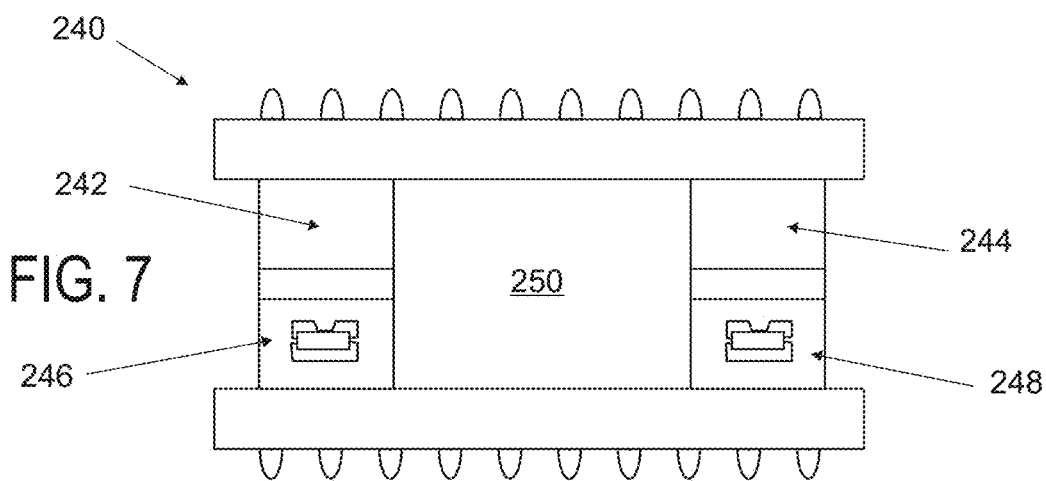
FIG. 7 schematically depicts another variation of an applicator with two sets of central panels and locking mechanisms.

The length of the attachment structures of the applicator may vary, and as depicted in FIG. 7, the applicator 240 may comprise two or more elastic bodies 242 and 244, each of which may have a locking mechanism 246 and 248, and a central access region 250 between the elastic bodies 242 and 244, which may facilitate device placement by permitting visualization of the treatment site. In other variations, such as the applicator 220 in FIGS. 12A and 12B, the force members 222 and 224 may be separately coupled to the attachment members 226 and 228 from the locking mechanism 230, e.g. the locking mechanism may be attached to the attachment members 226 and 228 rather than the force members 222 and 224. In FIG. 12A, the locking mechanism 230 comprises complementary ratchet/toothed members 232 and 234 that engage once the applicator 220 is sufficiently squeezed or retracted. In contrast to the locking mechanism 120 described in FIGS. 3A to 5B, the locking mechanism 230 in FIG. 12A is able to lock the applicator configuration across a range according to the degree of overlap or engagement between the ratchet/toothed members 232 and 234. To release or separate the locking mechanism 230, a tab, handle, or ring 236 may be provided on one or both ratchet members 232 and 234 to facilitate disengagement.

Figure 8:
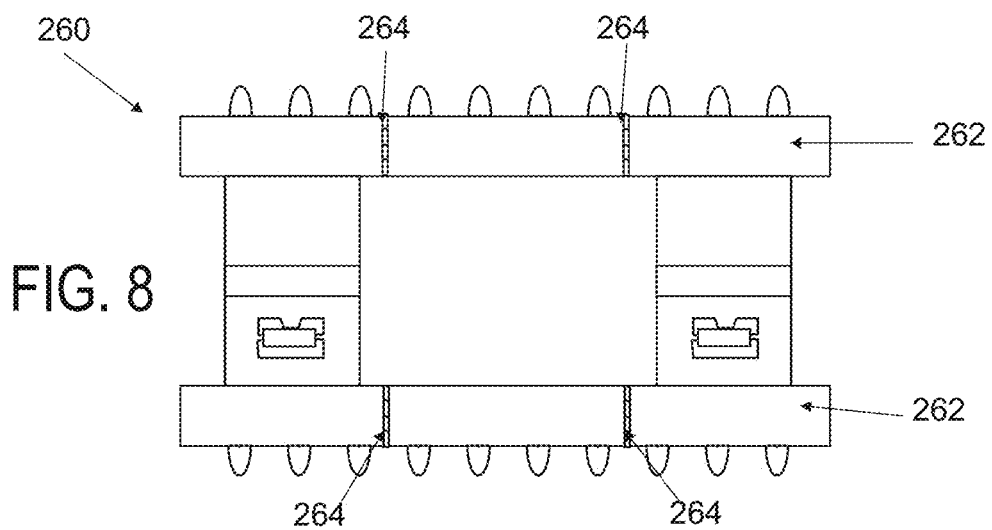
FIG. 8 schematically depicts another variation of an applicator with hinged base structures.
Figure 9:
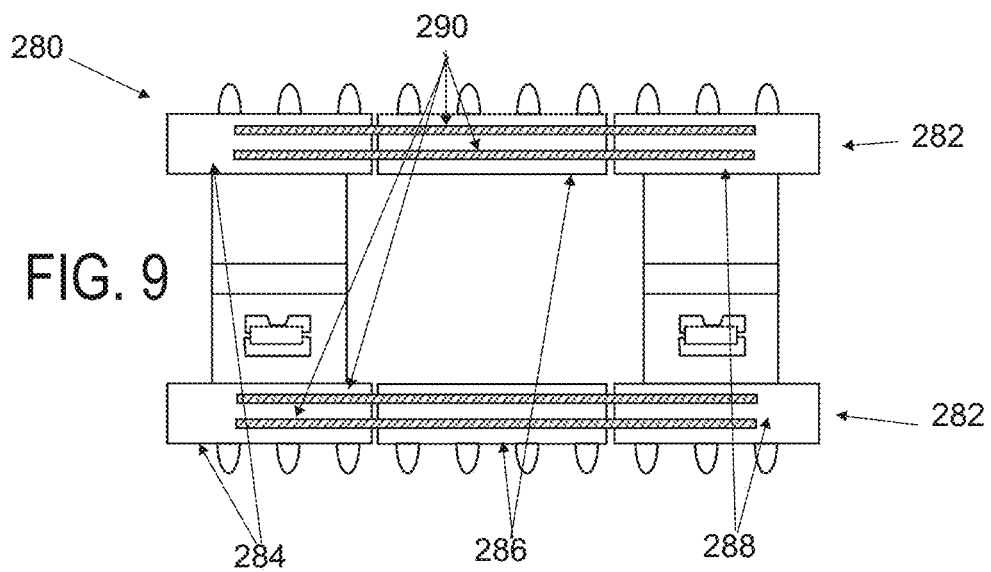
FIG. 9 schematically depicts another variation of an applicator with bendable wire-supported base structures.

As illustrated in FIGS. 8 and 9, to facilitate conforming a wound treatment device to a treatment site, the applicators 260 and 280 may be configured with attachment structures 262 and 282, respectively, that are able to bend or deform along their longitudinal lengths. In FIG. 8, for example, the attachment structures 262 comprise hinge mechanisms 264 that permit bending at one or more locations. The hinges 264 may or may not be configured to limit the degree or range of bending. In FIG. 9, the applicator 280 comprises attachment structures 282 with segments 284, 286 and 288 that are attached by bendable or deformable wires 290 or struts. In this particular variation, each wire 290 spans all three segments 284, 286 and 288, but in other variations, one or more wires may be configured to span two or less than all of the segments.

In some variations, the attachment structures of the applicator may or may not comprise discrete segments but may comprise a material or configuration that permits flexion along their longitudinal length. In still other variations, the attachment structures may have non-linear or non-planar configurations. In FIG. 10, for example, the applicator 300 comprises an attachment structure 302 with a fixed curvature or curvilinear configuration. In still other examples, the applicator may have a curved or curvilinear base configuration, but may elastically deform in one or more directions. The degree of curvature may vary and may or may not comprise an arc of a circle or oval structure. The curved attachment structures may be used with applicators 300 comprising frame members 304, for example, or with applicators with comprising sheet or leaf spring members, for example.

In one variation, to use the wound treatment system, the patient may be positioned so that the incision site is in a non-stressed, tension free position. For an abdominoplasty incision site, for example, the patient may be standing up or lying in supine position, and for a breast incision site, the patient may be lying in the supine position. The incision site may then be cleaned with an agent alcohol or other cleaning agent. In some further variations, a separate skin adhesive or adjunctive agent (e.g. tincture of benzoin) may be applied adjacent to the incision site prior to the application of a bandage.

Figure 13A:
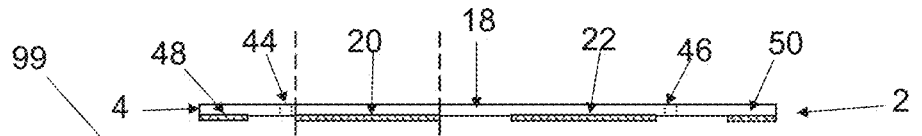
FIGS. 13A to 13D schematically depict one variation of the use of the wound treatment device depicted in FIGS. 1A and 1B.
Figure 13B:
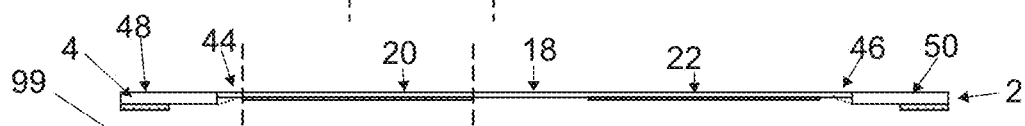
Figure 13C:
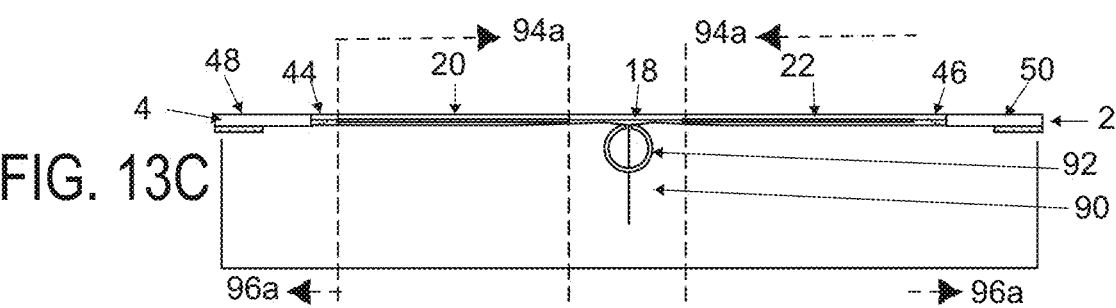
Figure 13D:
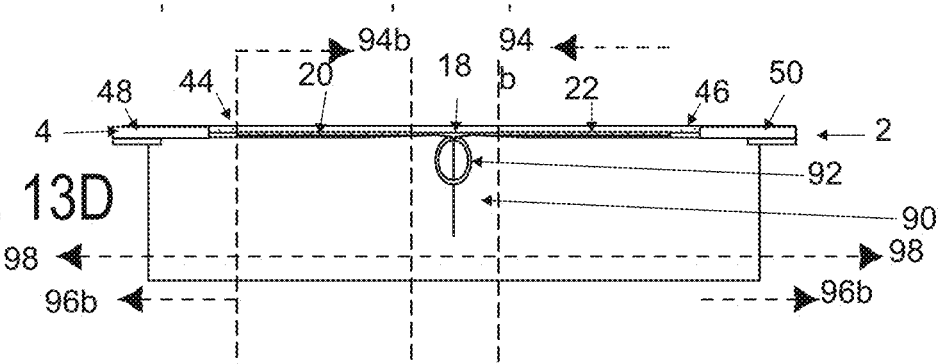

An applicator may be manipulated into a retracted position and then locked to that position. In some variations, the locking occurs automatically, while in other variations, the locking is manually actuated. Referring to FIGS. 13A to 13D, and using the treatment device 2 in FIG. 1A and the applicator (not shown), for example, the applicator may be squeezed or compressed until the latch automatically snaps into position. A treatment device 2 is oriented with the adhesive surface (or release liner 56) facing away from the applicator and then attached to the device attachment structures of the applicator, e.g. by inserting the attachment projections and through the retention openings 44 and 46 of the treatment device 2. In some variations, some stretching of the device may occur as the device is attached to the applicator, and in some instances, the release liner of at least the inner adhesive regions 20 and 22 may be removed to facilitate the stretching. This may be performed between the engagement of the two sets of openings 44 and 46 of the treatment device 2, for example, or after the attachment of the treatment device 2 to the applicator is completed. Once the attachment of the treatment device 2 has been confirmed, the applicator may be released from the locked position, e.g. by actuating the latch to strain the device, as depicted in FIG. 13B. In some variations, markings or indicia on the treatment device 2 (e.g. lines 74 and 76 of the treatment device 2 in FIG. 2A) may be used to assess proper attachment of the device to the applicator. In some examples, the applicator may be squeezed to facilitate unlatching. Once unlocked, the applicator exerts a separation force that pushes apart the attachment sites of the device to a pre-determined strained configuration.

To apply the device 2, the device 2 may be oriented by identifying the central non-adhesive region 18 of the treatment device 2 and aligning this region with a wound or incision site 90. Pressure is applied to the applicator to secure the treatment device 2 to the site 90. In some variations, the foam structures (or other pad structures) of the applicator are compressed or otherwise deformed as the applicator is pushed against the skin. In some examples, the user may also apply manual pressure directly to the device and against the skin by inserting his or her fingers between the device attachment sites of the applicator. The site 90 may or may not already be closed using sutures 92 or other wound closure devices, e.g. staples, glues, and the like. In variations, the site 90 may be closed with subcutaneous sutures but not cutaneous sutures.

Once the treatment device 2 is secured to the site 90, the applicator may be disengaged from the device by squeezing the applicator. In some variations, one device attachment site of the applicator may be held in place (e.g. the "thumb" side of the applicator as it is held by the user) while the other device attachment site is released from the retention apertures of the device (e.g. displacing the "finger" side of the applicator toward the "thumb" side of the applicator). Once one side of the device is released, the applicator may be detached from the other side of the device, e.g. by withdrawing the attachment projections of the applicator from the remaining retention apertures. In examples where multiple devices are placed, the above steps may be repeated until the entire incision site is covered. In some variations, the multiple devices are placed edge-to-edge with adjacent devices while reducing any overlap or gaps between the devices. The release liner of the end flaps may be removed and the end flaps 48 and 50 may be secured to the skin using finger pressure. The end flaps may or may not be stretched or tensioned by the user before being pressed against the skin.

Figure 64A:
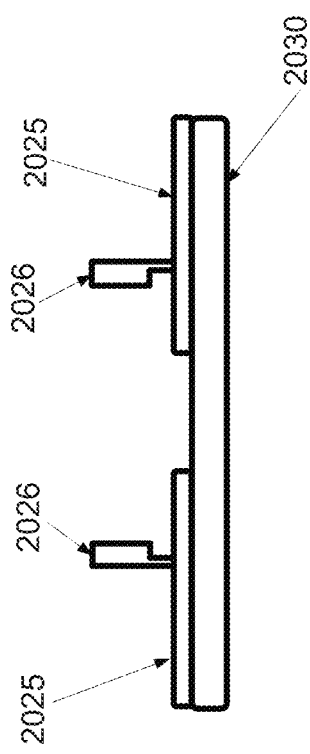
FIGS. 64A to 64Q illustrate variations of an attachment system.

FIGS. 50A to 50F illustrate one variation of a tensioning device, straining device or applicator 900. The applicator 900 comprises an actuator or handle 901 having a first handle member 902 with pivot arm 904 and a second handle member 903 with second pivot arm 905. Attachment structures 906, 907 are respectively coupled to distal portions of pivot arms 904, 905. Attachment structures 906, 907 each comprise an elongate portion 908 having one or more tabs or extensions 909 extending from the elongate portion 908. The extensions 909 may be used to attached to a skin treatment device such as, for example, as described with respect to the skin treatment device 2010 and attachment device 2003 illustrated in FIGS. 64A and 64B herein. Alternative attachment structures may be used as discussed in further detail herein.

The handle members 902, 903 are pivotally coupled by connector 910 at the pivot anus 904, 905 to provide a pivot point or fulcrum, to transfer force from the handle 901 of applicator 900 to a skin treatment device when coupled to the attachment structures 906, 907, to thereby strain the skin treatment device prior to placement on skin.

Figure 50A:
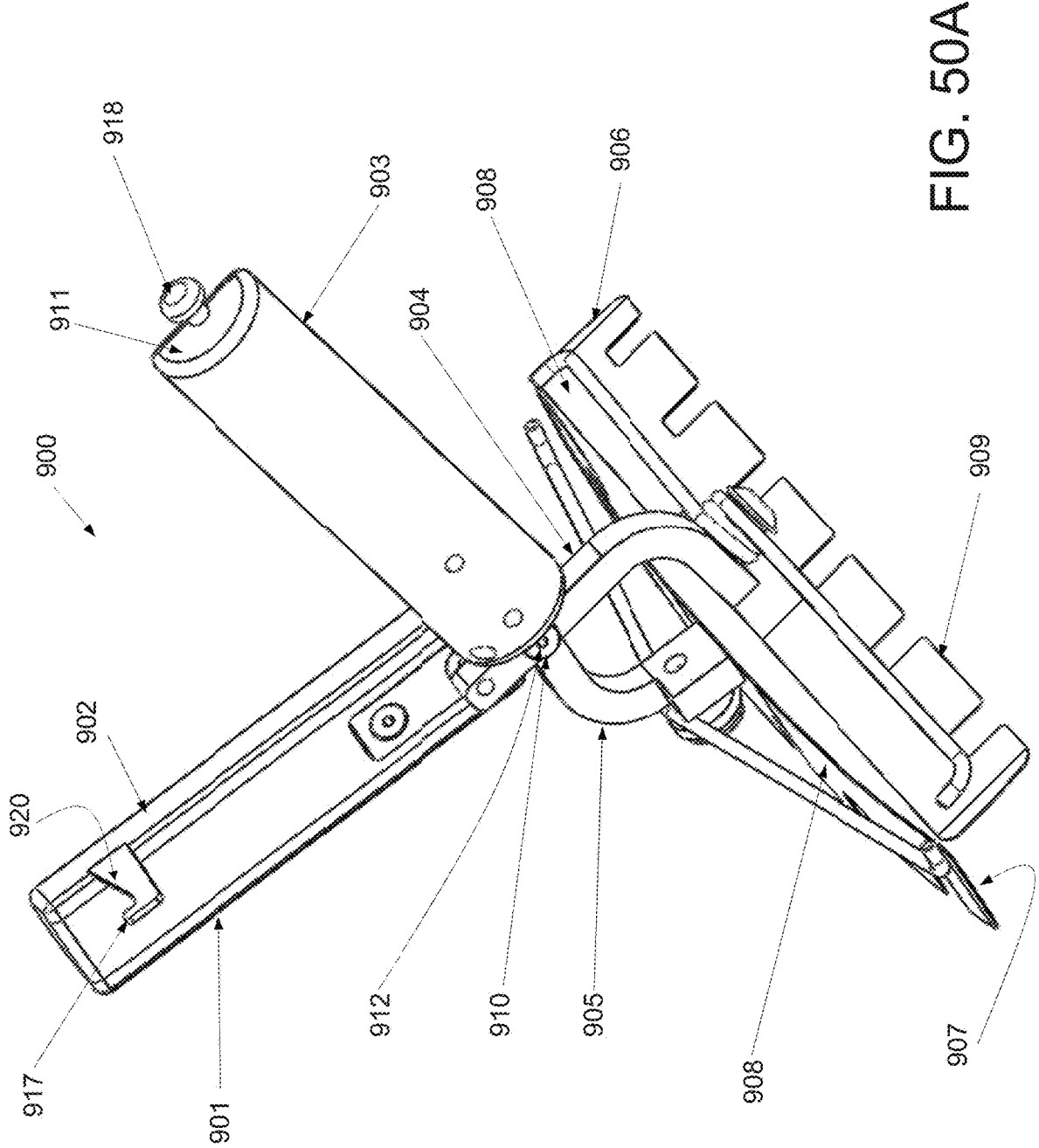
FIG. 50A is a perspective view of an applicator in an unstrained configuration.
Figure 50B:
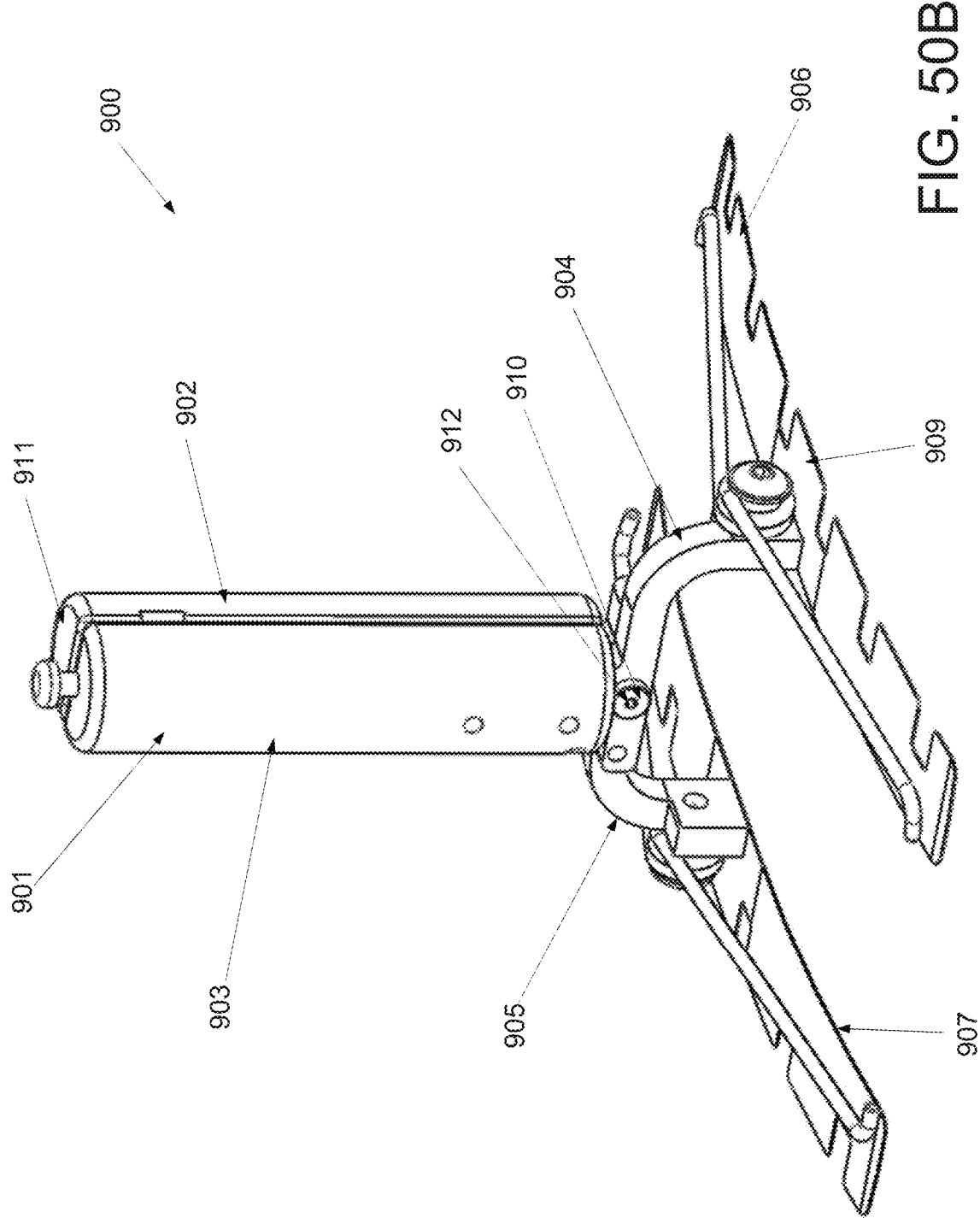
FIG. 50B is a perspective view of the applicator of FIG. 50A in a strained configuration.

FIG. 50A illustrates an actuator or handle configuration prior to straining a skin treatment device for application to the skin of a subject. A skin treatment device may be attached to the attachment structures 906, 907. When an external force is applied to the actuator, e.g., the handle members 902, 903 of the handle 901 are squeezed together, the force is transferred to provide a separation force between the attachment structures 906, 907 coupled respectively to pivot arms 904, 905. Optionally, the handle may be provided with a distance d2 from the top 911 to the fulcrum or pivot point 912 that is greater than the distance d1 from the pivot point 912 to an attachment structure 906 or 907. Thus, the actuator or handle may provide a mechanical advantage greater than 1 when actuated. In some variations, d2 may be greater than d1 by at least about 10%, about 20% about 30%, about 40%, about 50% about 76% or about 100% or more. In other examples, d2 may be measured from the midpoint of the handle, rather than the top of the handle.

Figure 50C:
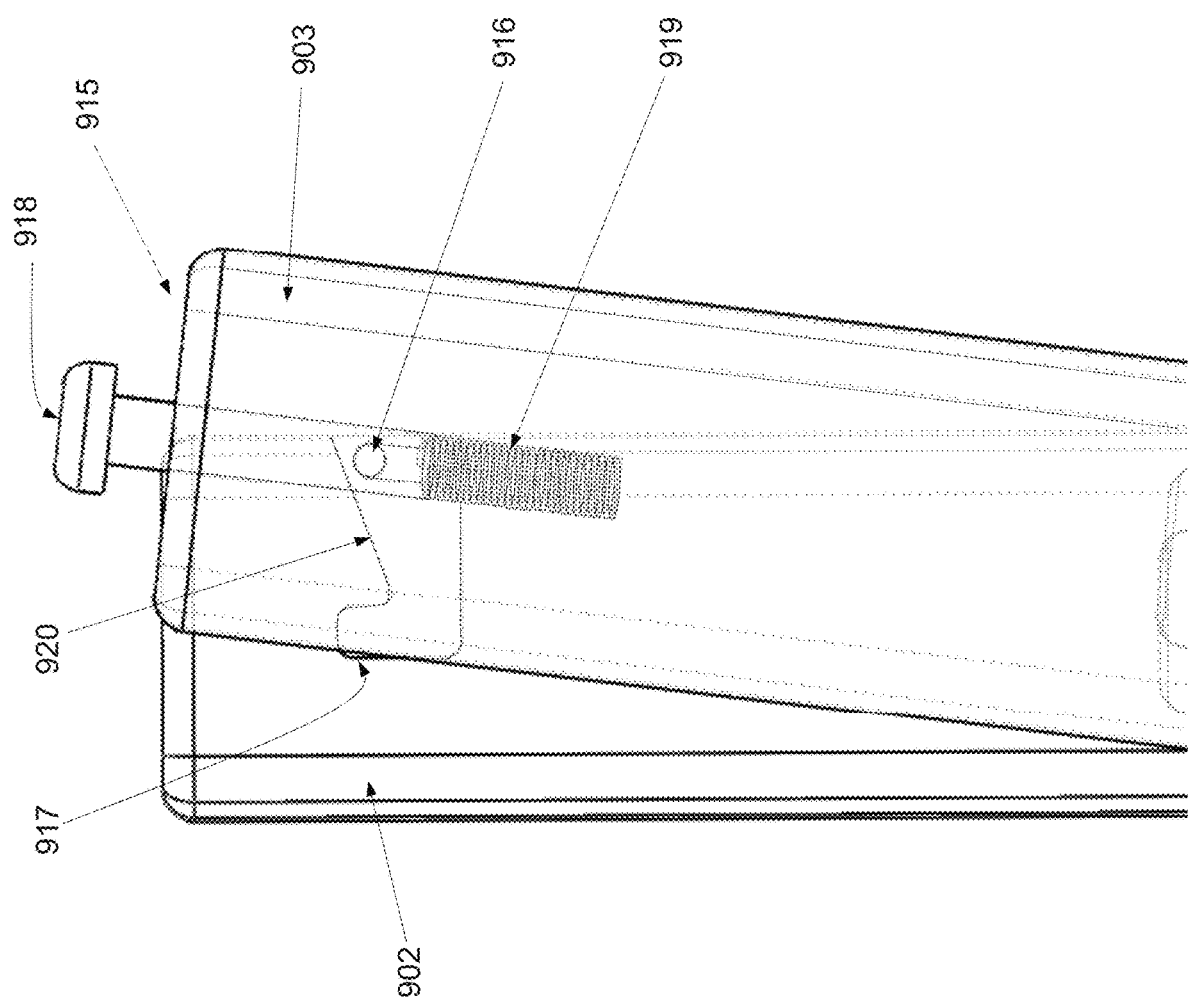
FIG. 50C is a side elevational view of a handle and locking mechanism of the applicator of FIG. 50A in an unstrained configuration.

FIG. 50I3 illustrates the applicator 900 in a strained configuration. For purposes of clarity, an attached skin treatment device is not shown, but the pocketed skin treatment devices illustrated in FIGS. 43A to 43C, for example, may be adapted for use with applicator 900. The handle members 902, 903 have been squeezed together and a separation force has been exerted between the attachment structures 906, 907 to strain an attached skin treatment device 930 (shown in FIG. 500. The applicator 900 may or may not have a mechanism to lock to maintain the skin treatment device in a strained configuration. In the variation depicted in FIGS. 50A to 50F, the handle members 902, 903 are lockable together by a locking mechanism 915 that may be locked to prevent or resist separation of the handle members 902, 903 and unlocked to release the strain exerted on the skin treatment device. FIG. 50C depicts the locking mechanism 915 is prior to closure of the handle members 902, 903, and FIG. 50D depicts it after closure of the handle members 902, 903.

Referring to FIGS. 50C and 50D, the locking mechanism 915 comprises a spring loaded catch 916 in handle member 902 that is depressed by caromed surface 920 of cavity in handle member 903, as the handle members 902, 903 close. The catch 916 may be biased upward into notch 917 after handle members 902, 903 close. The catch 916 may be released from engagement in notch 917 by depressing release member 918 to compress spring 919 and separating handle members 902, 903. Thus the attachment structures 906, 907 may be released from an attached skin treatment device after application to the skin. By locking the applicator in a strained position a predetermined strain of a given skin treatment device may be achieved. Other locking mechanisms, including but not limited to other locking mechanisms described herein may be used. A variable locking mechanism may be used to vary the amount of strain for a given skin treatment device.

Figure 50E:
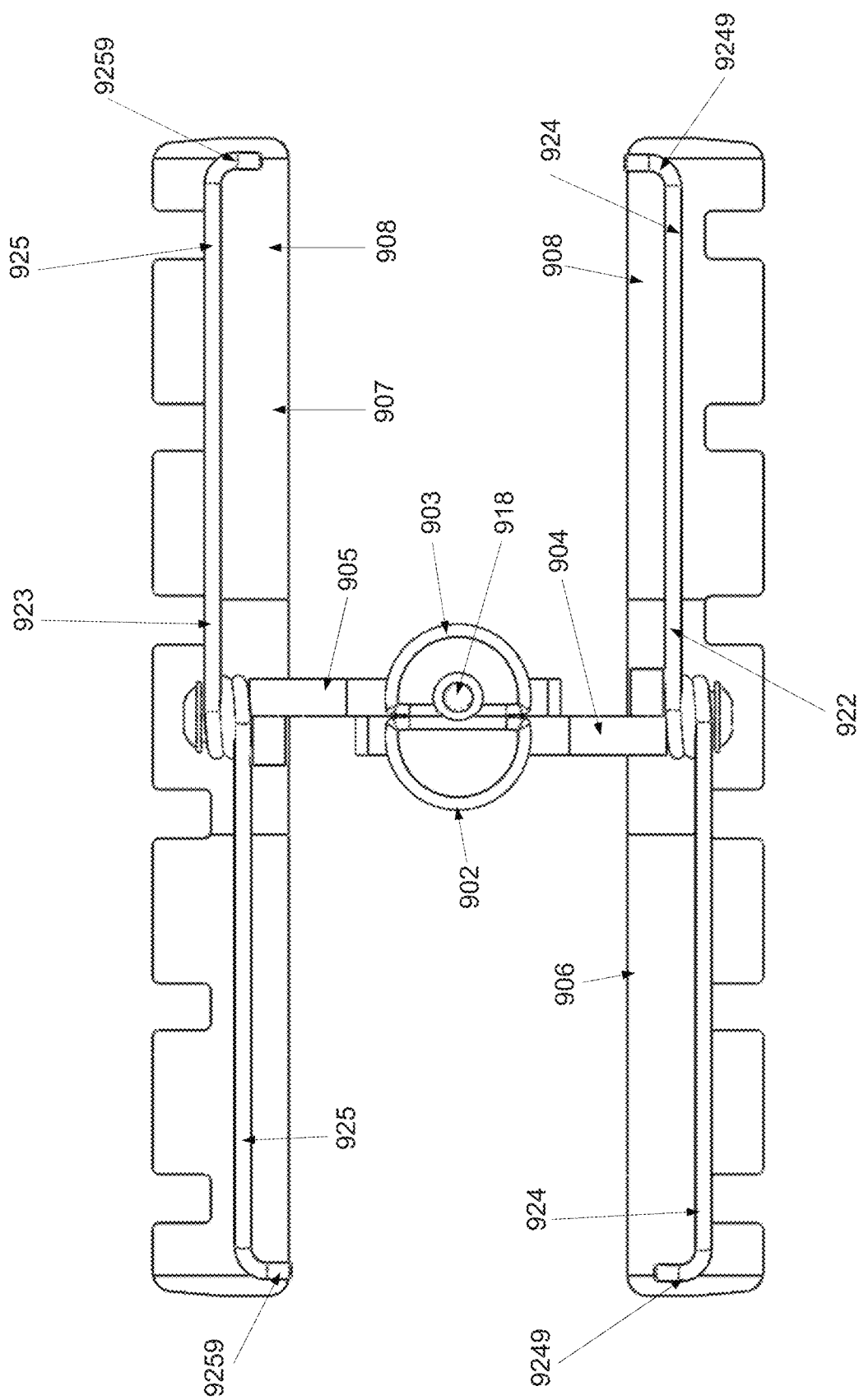
FIG. 50E is a superior view of the applicator of FIG. 50A in a strained configuration.

The attachment structure profile may be straight, curved or otherwise varied. For example, the shape of the attachment structures may be configured to follow the shape of the area of the subject's body to which the skin treatment device is to be attached. In accordance with another variation the applicator 900 is illustrated with curved or curvable attachment structures 906, 907. As shown in FIG. 50E torsion springs 922, 923 are respectively coupled to pivot arms 904, 905. Torsion spring arms 924, 925 (with spring tips 924a, 925a to apply a downward force) extend along elongated portions 908 of attachment structures 906, 907 respectively. The biases of the spring arms 924, 925 and tips 924a, 925a, apply a downward force to cause the attachment structures 906, 907 to bend to form a curved skin treatment device 930. As shown in FIG. 50F, a curved or shaped skin treatment device 930 may be applied to a curved or shaped surface 928 of a subject's skin. The amount of torsion in the springs 922, 923 may be varied to provide a varying degree of curvature. A tensioning device or applicator may be selected or configured to have a profile that has a desirable profile for a particular body location or profile where the skin treatment device is to be placed on a subject's skin. A tensioning device or applicator may be selected or configured to closely match a portion of a subject's body profile, as shown in FIG. 50F, where a concavely shaped side of the skin treatment device generally matches the convex shape of the subject's body profile where the device is to be attached. The attachment structures may be curved, curvable, bendable, deformable, shapeable or movable to provide alternative shapes or profiles of an attached skin treatment device.

To remove the handle 901 from the skin treatment device, the release member 918 may be actuated so that the handle members 902, 903 may be separated, thereby separating the attachment structures from the attachment features of the skin treatment device. A variety of methods and devices may be used to provide for an easy separation of the attachment structures of an applicator from the attachment features of the skin treatment device including but not limited to the separation devices and methods described herein.

FIGS. 51A to 51D illustrate another variation of a tensioning device, straining device, or applicator 1000. Here, the applicator 1000 comprises an actuator or handle 1001 having a screw handle 1002 and threaded post 1003. The screw handle 1002 comprises a complementarily threaded lumen that may be rotated to advance it up or down the threaded post 1003. A stop 1005 at the top of threaded post 1003 may be provided to resist or prevent the screw handle 1002 from advancing beyond the top of the threaded post 1003. A sliding collar 1004 is positioned on the post 1003 below the screw handle 1002. Lever arms 1010, 1011 have first end portions 1012, 1013 respectively that are pivotally coupled to the sliding collar 1004 at pivot points 1020, 1021. Second or opposite end portions 1014, 1015 are pivotally coupled to attachment structures 1006, 1007 by way of attachment bars 1016, 1017 at pivot points 1022, 1023 respectively. Attachment bars 1016, 1017 are also pivotally attached to the bottom of the post 1003 at pivot points 1024, 1025.

Attachment structures 1006, 1007 may be respectively coupled to distal portions 1014, 1015 of pivot arms 1010, 1011. Attachment structures 1006, 1007 each comprise an elongate portion 1008 having one or more tabs or extensions 1009 extending from the elongate portion 1008. The extensions 1009 may be used to attached to a skin treatment device such as, for example, as described with respect to the skin treatment device 2010 and attachment device 2003 illustrated in FIGS. 64A and 64B herein. Alternative attachment structures, and corresponding attachment configurations on the skin treatment devices that may be used are discussed in further detail herein. The attachment structure profile may be straight, curved or otherwise varied. For example, the shape of the attachment structures may be configured to follow the shape of the area of the subject's body to which the skin treatment device is to be attached, may be curved, curvable, bendable, deformable, shapeable or movable to permit various skin treatment device shapes to be formed including but not limited to, as shown in FIG. 50F herein.

Figure 51A:
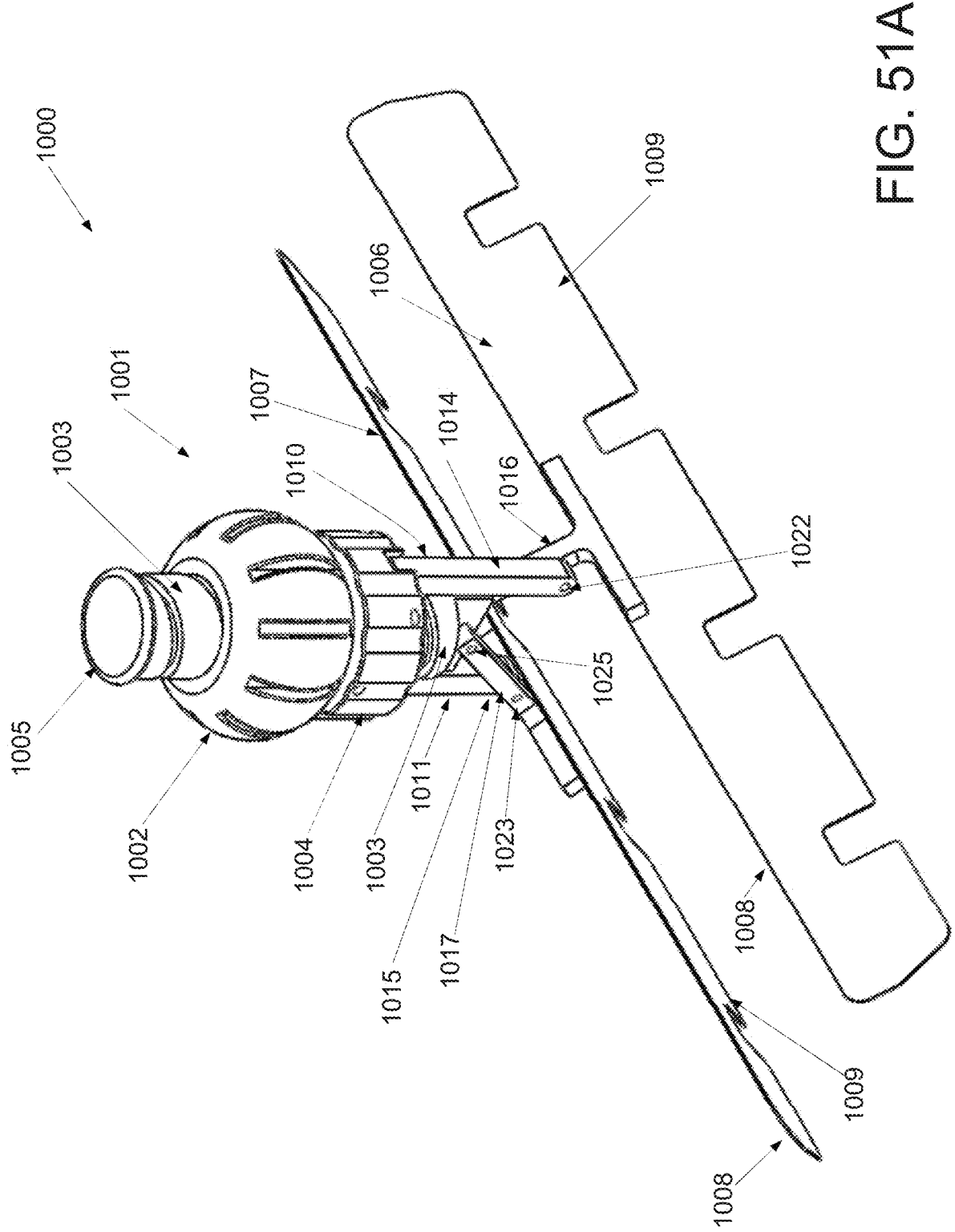
FIG. 51A is a perspective view of an applicator in an unstrained configuration.
Figure 51B:
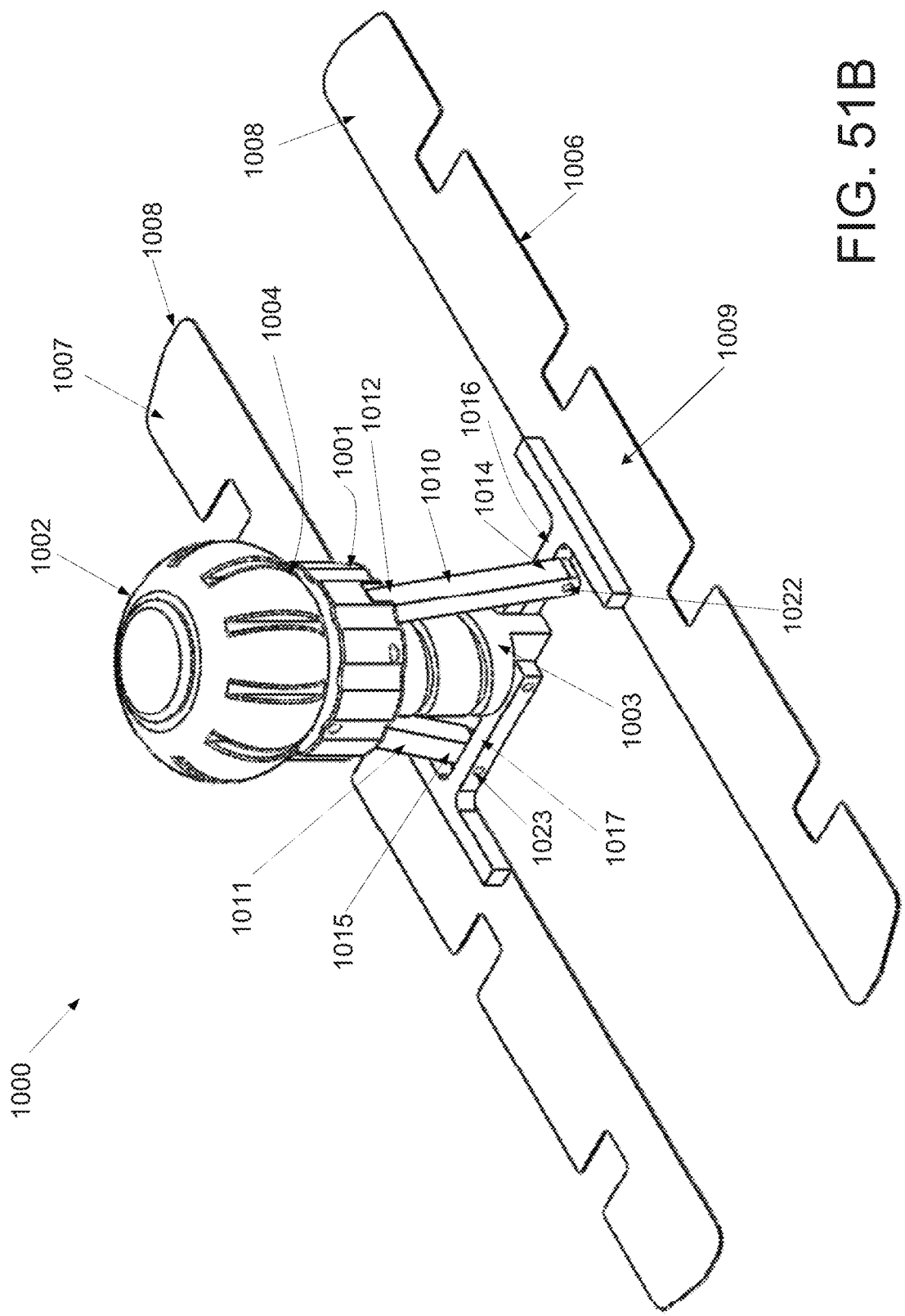
FIG. 51B is a perspective view of the applicator of FIG. 51A in a strained configuration.
Figure 51C:
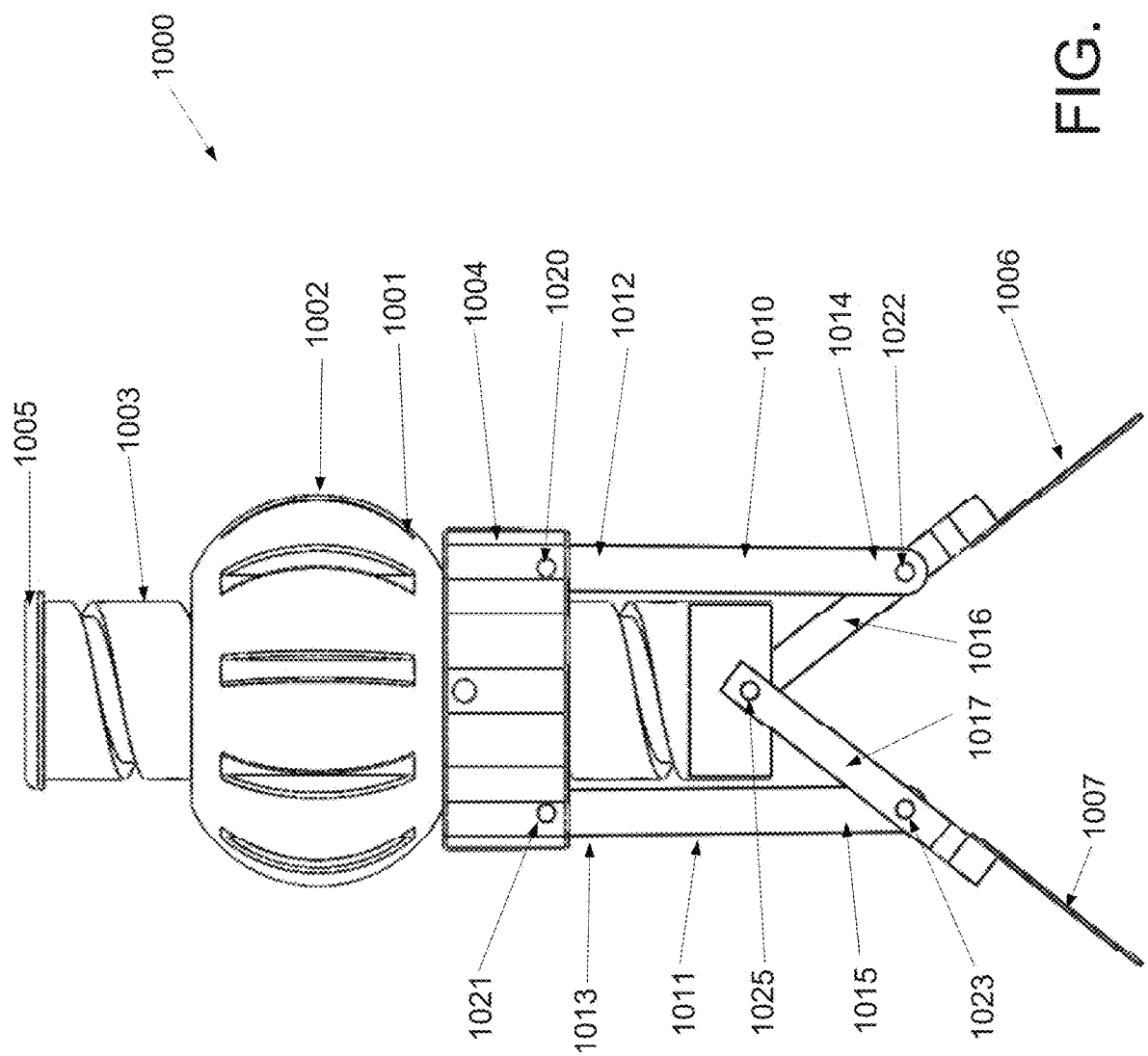
FIG. 51C is a anterior view of the applicator of FIG. 51A in an unstrained configuration.

FIGS. 51A and 51C depicts the applicator 1000 in an unstrained position, with the screw handle 1002 is in a relative position advanced downward from the stop 1005 of the post 1003. The attachment structures 1006, 1007 are pivoted or angled in with respect to each other and are in a closed position where the distance between them is smaller than when strained. This position facilitates loading or release of a skin treatment device from the applicator.

Figure 51D:
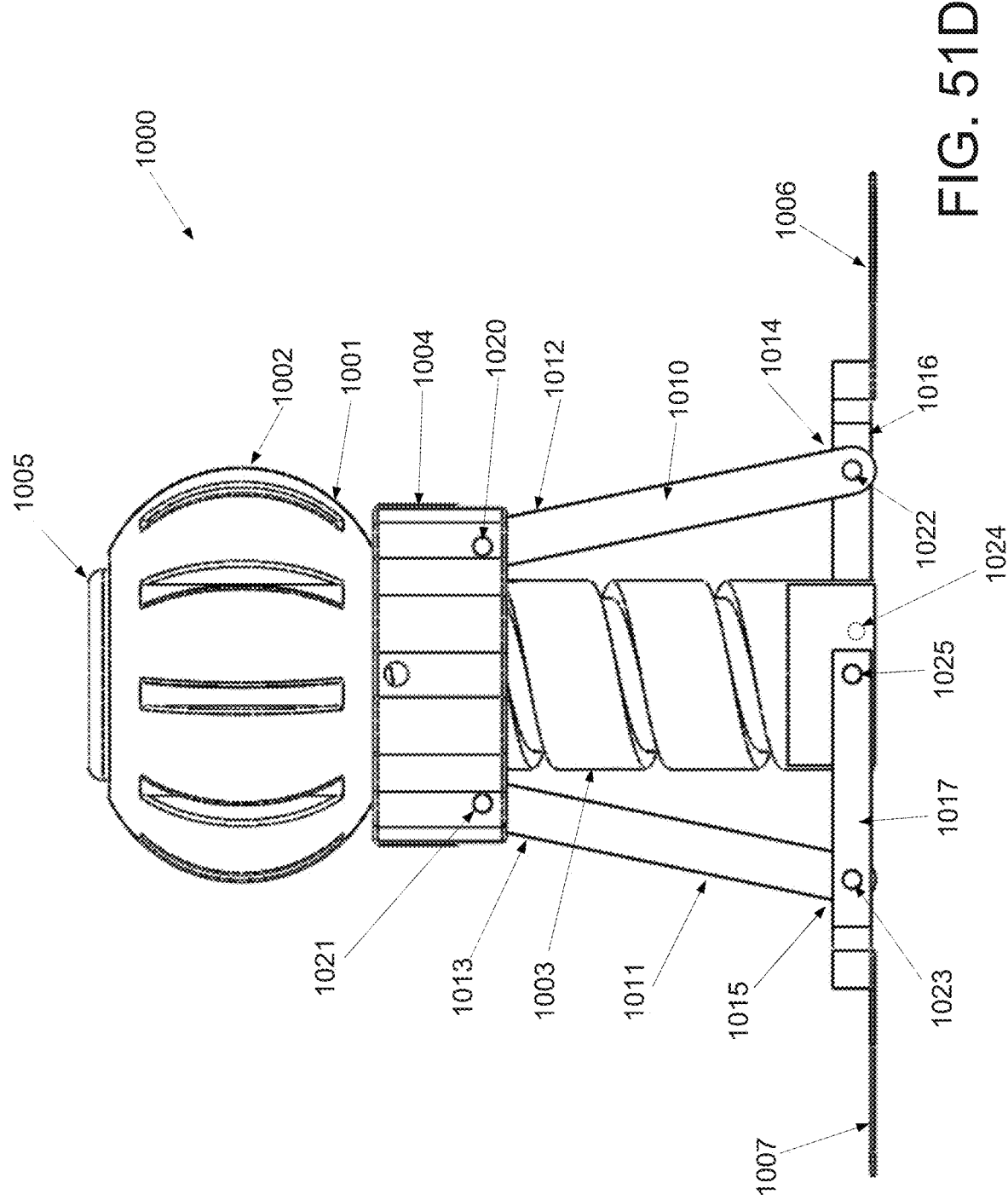
FIG. 51D is a front side view of an applicator of FIG. 51A in a strained configuration.

As shown in FIGS. 51B and 51D, when the screw handle 1002 is rotated to advance the post 1003 inferiorly, the post 1003 pushes relatively downward on attachment bars 1016, 1017 at pivot points 1024, 1025 while lever arms 1010, 1011 move relatively upward with collar 1004, thereby pulling up on attachment bars 1016, 1017 at pivot points 1022, 1023 and applying forces that separate and outwardly rotate the attachment structures 1006, 1007 into a flatter more planar configuration with respect to each other. As the screw handle 1002 is rotated moving the device from an unstrained towards a more strained configuration, the structures of the handle 1001 hold the attachment structures 1006, 1007 in position. Thus the handle 1001 holds or locks the applicator 1000 in its relative strained position. Various positions of the screw handle 1002 on the post 1003 may correspond to various degrees of strain of a particular skin treatment device. Markings may also be made on the post to identify a relative strain of a skin treatment device with respect to screw handle 1002 positions.

To remove the handle 1002 from the skin treatment device, the screw handle 1002 may be rotated in an opposite direction so that the attachment structures move inward and rotate to separate them from the attachment features of the skin treatment device. The number of handle turns to move applicator 1000 from an unstrained to strain position, and vice versa, may vary from about a half-turn to about 1, 2, 3, 4, 5, 6, 7, 8, 9, 10 or more turns, depending upon the pitch of the threading. The pitch of the helical threading (i.e. the width of one complete turn) may be selected depending upon the desired mechanical advantage and/or self-locking effect, e.g. resisting rotation that may occur from an attached skin treatment device squeezing attachment bars 1016, 1017. Typically, smaller pitches may be used to increase the mechanical advantage or self-locking feature, but may be more tedious to manipulate.

FIGS. 52A to 52H, illustrate another variation of a tensioning device, straining device, or applicator 1030, comprising an actuator or handle 1031 having a body 1033 with a cam handle 1032 and locking tabs 1050. The cam handle 1032 may be rotatably positioned on top of the body 1033 and attached to a cam 1055 which is positioned under the body 1033. At least one of parallel u-bars 1040, 1041 is slidably mounted on at least one of posts 1034, 1035, which are attached to the handle body 1033 with mounts 1045. As shown, in FIGS. 52A and 52C, post 1034 extends through and can slide through opening 1048 in u-bar 1040. Post 1035 extends through and can slide through opening 1049 in the u-bar 1041. U-bars 1040, 1041 further comprise inner surfaces 1042, 1043 that interact with cam surfaces 1052, 1053 or cam 1055.

Figure 52A:
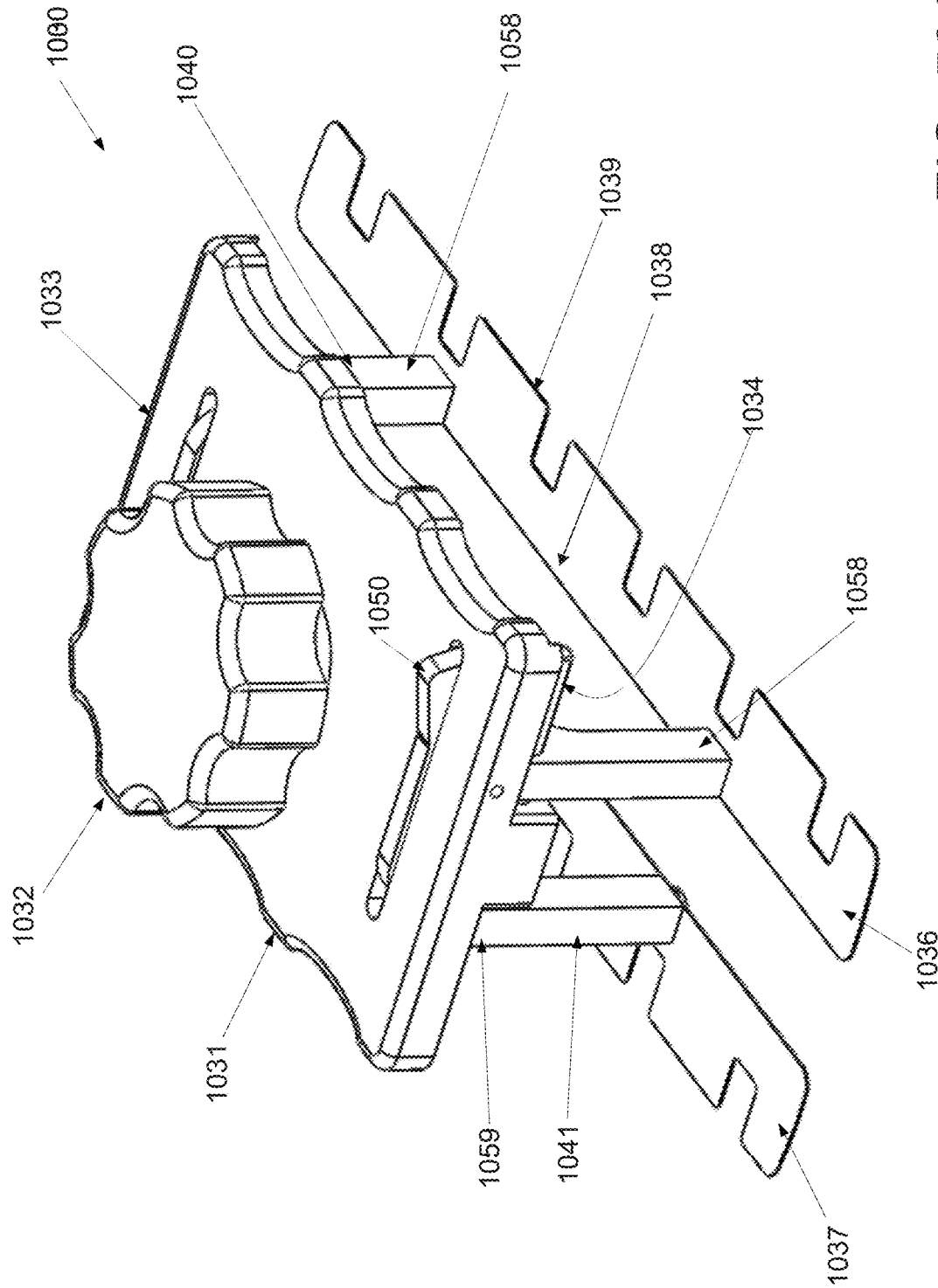
FIG. 52A is a perspective view of an applicator in an unstrained configuration.

The bars 1040, 1041 couple skin treatment device attachment structures 1036, 1037 to body 1033 of the applicator 1030. Attachment structures 1036, 1037 are coupled to struts or legs 1058, 1059 of u-bars 1040, 1041. In other variations, rather than a u-shaped bar, a single strut or a group of three or more joined struts may be provided, and the struts may or may not be parallel relative to one another, or perpendicular to the body of the applicator 1030, e.g. the struts may be acutely or obtusely angled. As illustrated in FIG. 52A, attachment structures 1036, 1037 each comprise an elongate portion 1038 having one or more tabs or extensions 1039 extending from the elongate portion 1038. The extensions 1039 may be used to attach to a skin treatment device such as, for example, as described with respect to the skin treatment device 2010 and attachment device 2003 illustrated in FIGS. 64A and 64B herein. Alternative attachment structures may be used as discussed in further detail herein. The attachment structure profile may be straight, curved or otherwise varied. For example, the shape of the attachment structures may be configured to follow the shape of the area of the subject's body to which the skin treatment device is to be attached, may be curved, curvable, bendable, deformable, shapeable or movable to permit various skin treatment device shapes to be formed including but not limited to, as shown in FIG. 50F herein.

FIGS. 52A, 52C, 52E and 52G show the applicator 1030 in an unstrained position. The u-bars 1040, 1041 are in relatively close parallel position with respect to each other. Thus the attachment structures 1036, 1037, coupled to the bars are relatively close with respect to each other to facilitate the loading of an unstrained skin treatment device on to the attachment structures 1036, 1037.

Figure 52B:
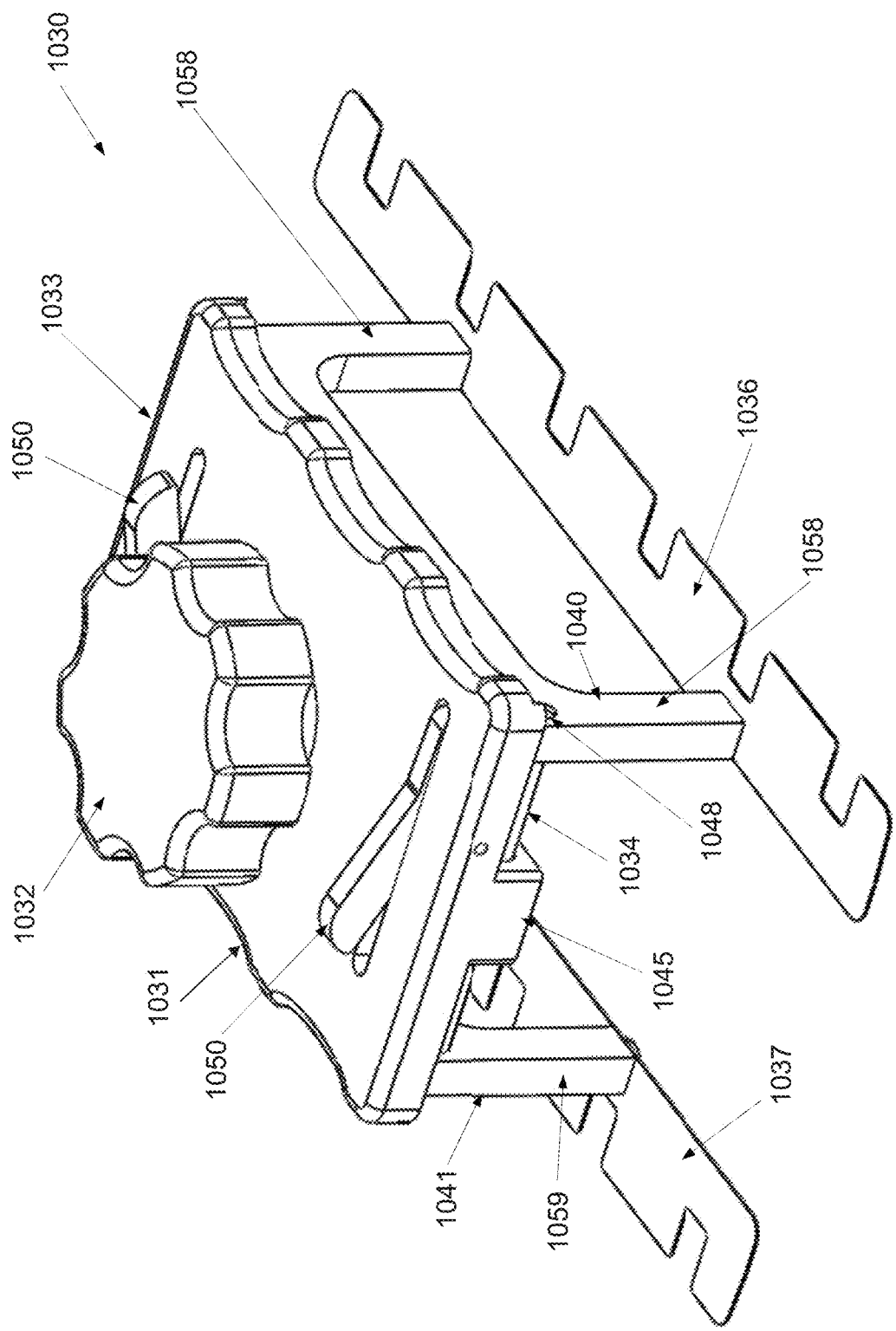
FIG. 52B is a perspective view of the applicator of FIG. 52A applicator in a strained configuration.
Figure 52C:
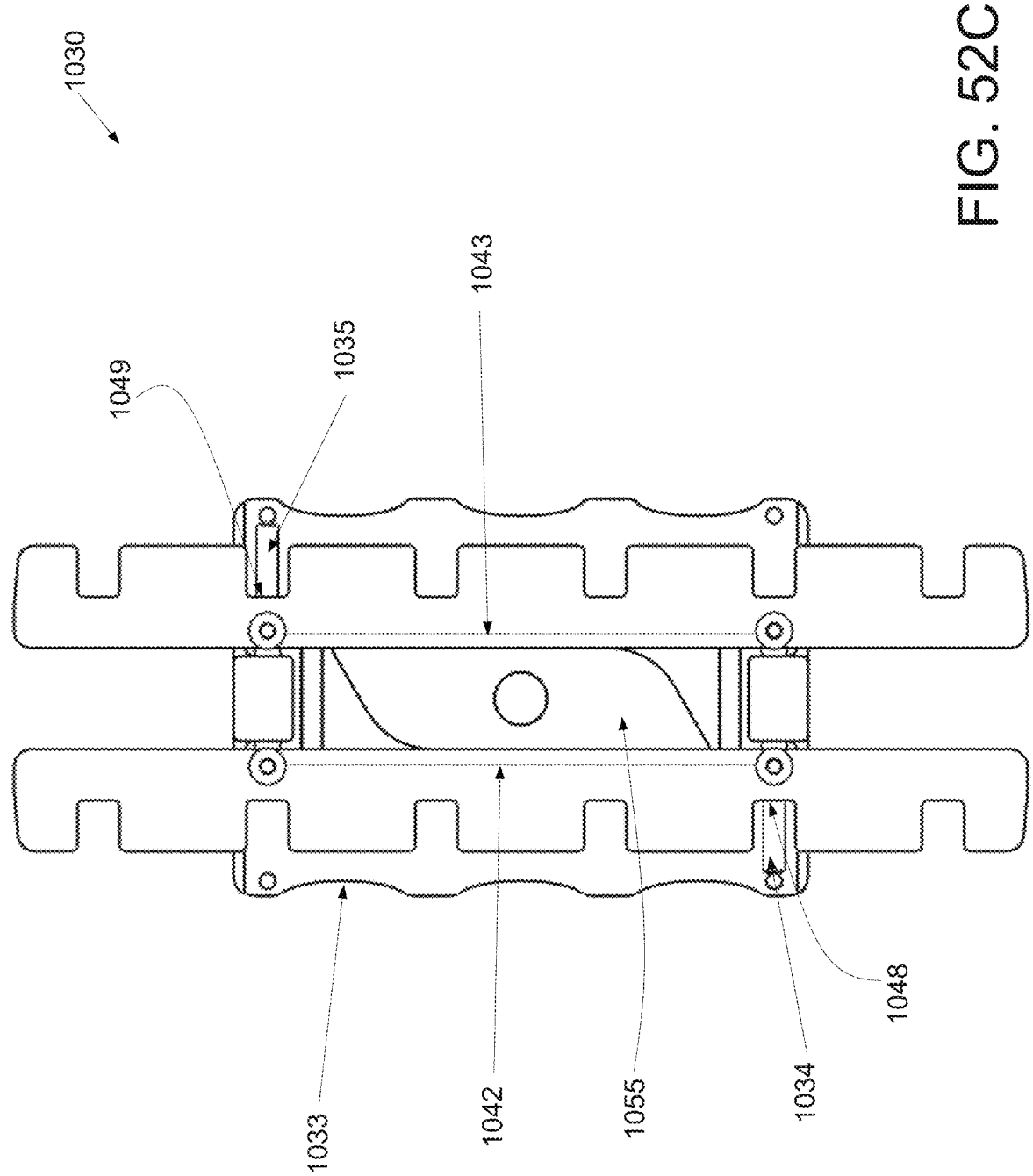
FIG. 52C is an inferior view of the applicator of FIG. 52A in an unstrained configuration.

As shown in FIGS. 52B and 52D, the cam handle 1032 is rotated, the cam surfaces 1052, 1053 interact with the inner surfaces 1042, 1043 of the bars 1040, 1041 to apply a separating force between the u-bars 1040, 1041 and thus to attachment structures 1036, 1037 to thereby strain an attached skin treatment device (not shown). The skin treatment devices illustrated in FIGS. 43A to 43C may be adapted for use with applicator 1030. As the cam handle 1052 is rotated about point 1051 using an external force, the cam 1055 moves the device from an unstrained towards a more strained configuration where bars 1040, 1041 are in a more separated, generally parallel position with respect to each other. The locking tabs 1050 may be depressed to lock the applicator 1030 in its relative strained position, i.e. to maintain the strain of the skin treatment device. The locking tabs 1050 when moved to the locking position as shown in FIG. 52H interfere with movement u-bars 1040, 1041 by engaging inner walls 1042, 1043 When the applicator 1030 is in an unstrained position, the locking tabs extend above housing 1033 (as depicted in FIG. 52G).

To remove the handle 1031 from the skin treatment device, the locking tab 1050 is released to the position illustrated in FIG. 52G so that the cam handle 1030 may be rotated in an opposite direction. This moves the attachment structures 1036, 1037 closer together and permits the attachment structure 1036, 1037 to separate from the attachment features, e.g., pockets or hook or loop structures, of the skin treatment device.

FIGS. 53A to 53E depicts another variation of a tensioning device, straining device, or applicator 1100, comprising a handle 1101 or actuator configured to be actuated to strain a skin treatment device and/or to apply the device to the skin of a subject. The applicator 1100 includes attachment structures 1106, 1107. In the variation illustrated in FIGS. 53A to 53E, the attachment structures comprise spring loaded binder type clips that grasp or pinch ends of a skin treatment device or an attachment structure on ends of the skin treatment device, but the applicator or skin treatment device attachment structures may comprise other types of attachment structures or features, including but not limited to other attachment structures and features set forth herein.

The applicator 1100 may further comprise a moveable, slideable or a collapsing or expanding top frame structure 1102, opposing stationary walls 1108, 1109 and opposing movable, pivotable or hinged walls 1110, 1111. Frame structure 1102 comprises a pair of slideable elements 1120, 1121 and pair of slidable elements 1122, 1123. Each of the pair of slidable elements 1120, 1121 and 1122, 1123 can slide together into a closed position (FIGS. 53A and 53C) where there is a first distance d1 (depicted in FIG. 53C) between walls 1108 and 1109. The pairs of slidable element 1120, 1121 and 1122, 1123 can slide apart into a second open position where there is a second distance d2 (depicted best in FIG. 53D) between the walls 1108, 1109 and where the distance d2 is greater than the distance d1.

Hinged wall 1110 comprises a first and second wall portions or segments 1112a, 1113a that are movably, pivotally or hingedly connected to each other by connector 1114a, at a pivot point. Hinged wall 1111 comprises a first and second wall segments 1112b, 1113b that are movably, pivotally or hingedly connected to each other by connector 1114b at a pivot point. Wall segments 1112a and 1113b are movably, pivotally or hingedly coupled respectively to opposite end sides 1108a, 1108b of wall 1108. Wall segments 1112b and 1113a are movably, pivotally or hingedly coupled respectively to opposite end sides 1109b, 1109a of wall 1109. The walls 1108, 1109, 1110, 1111 are coupled to the frame structure 1102 to form a box-like structure with an opening (when in the strained configuration) to provide access to a skin treatment device attached across the bottom of the applicator to attachment structures 1106, 1107. The access allows a user to apply pressure to a skin treatment device as or after it is applied to a skin surface before removing the applicator 1100. Alternatively, a pressure application device may be coupled to the applicator and actuable to provide pressure through the opening to a skin treatment device as or after it is being applied.

Figure 53A:
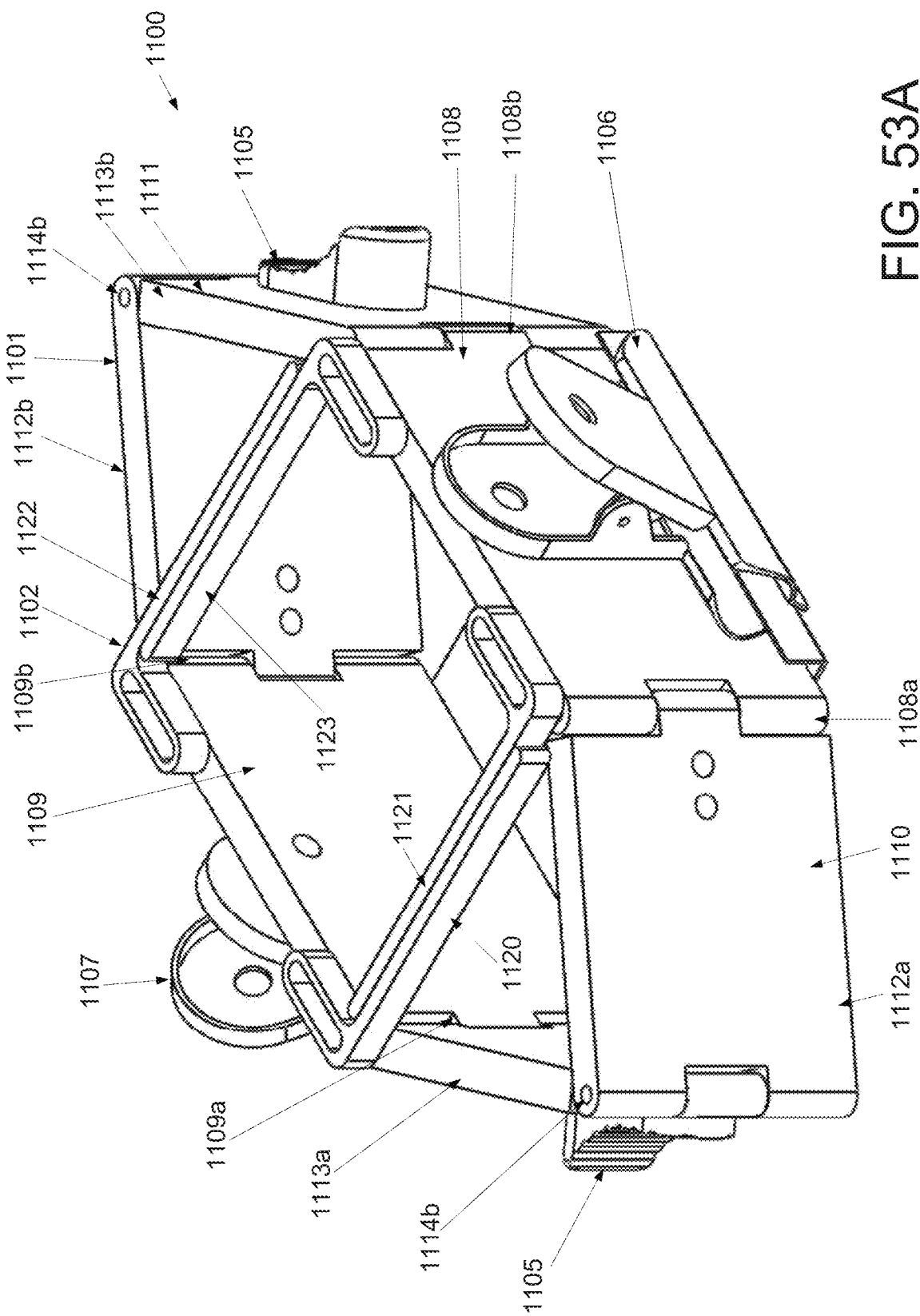
FIG. 53A is a perspective view of an applicator in an unstrained configuration.
Figure 53B:
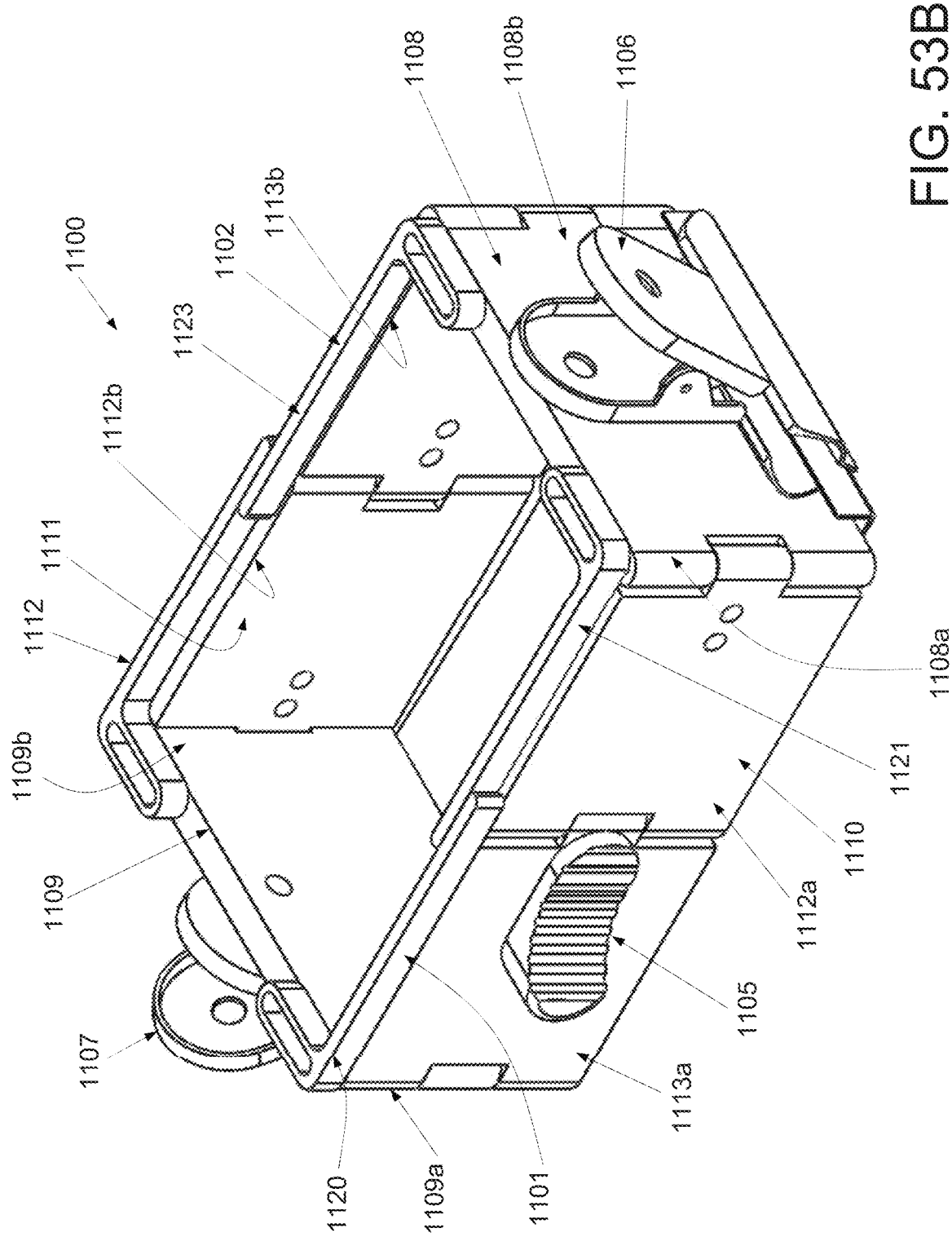
FIG. 53B is a perspective view of the applicator of FIG. 53A applicator in a strained configuration.
Figure 53C:
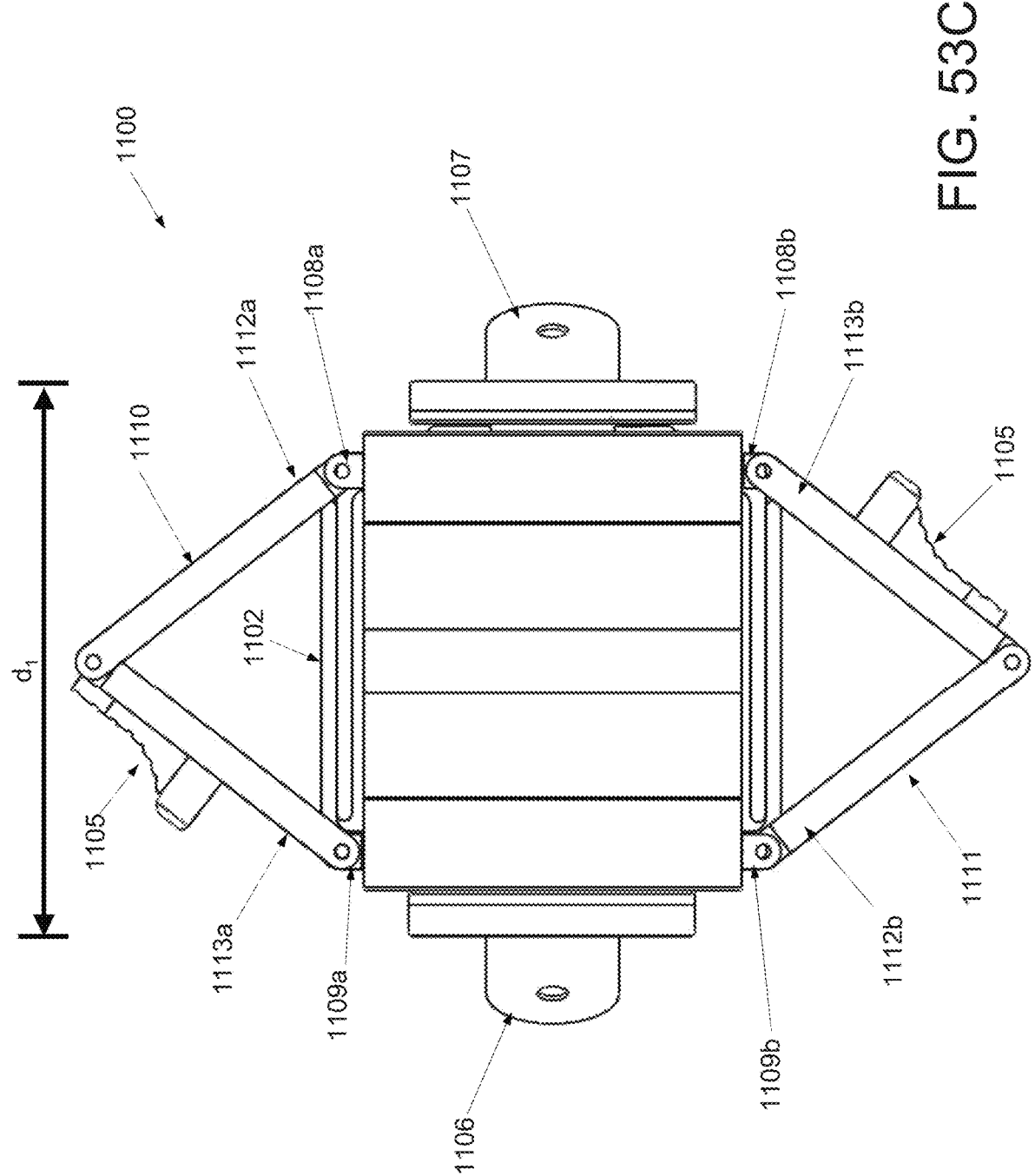
FIG. 53C is an inferior view of the applicator of FIG. 53A in an unstrained configuration.
Figure 53D:
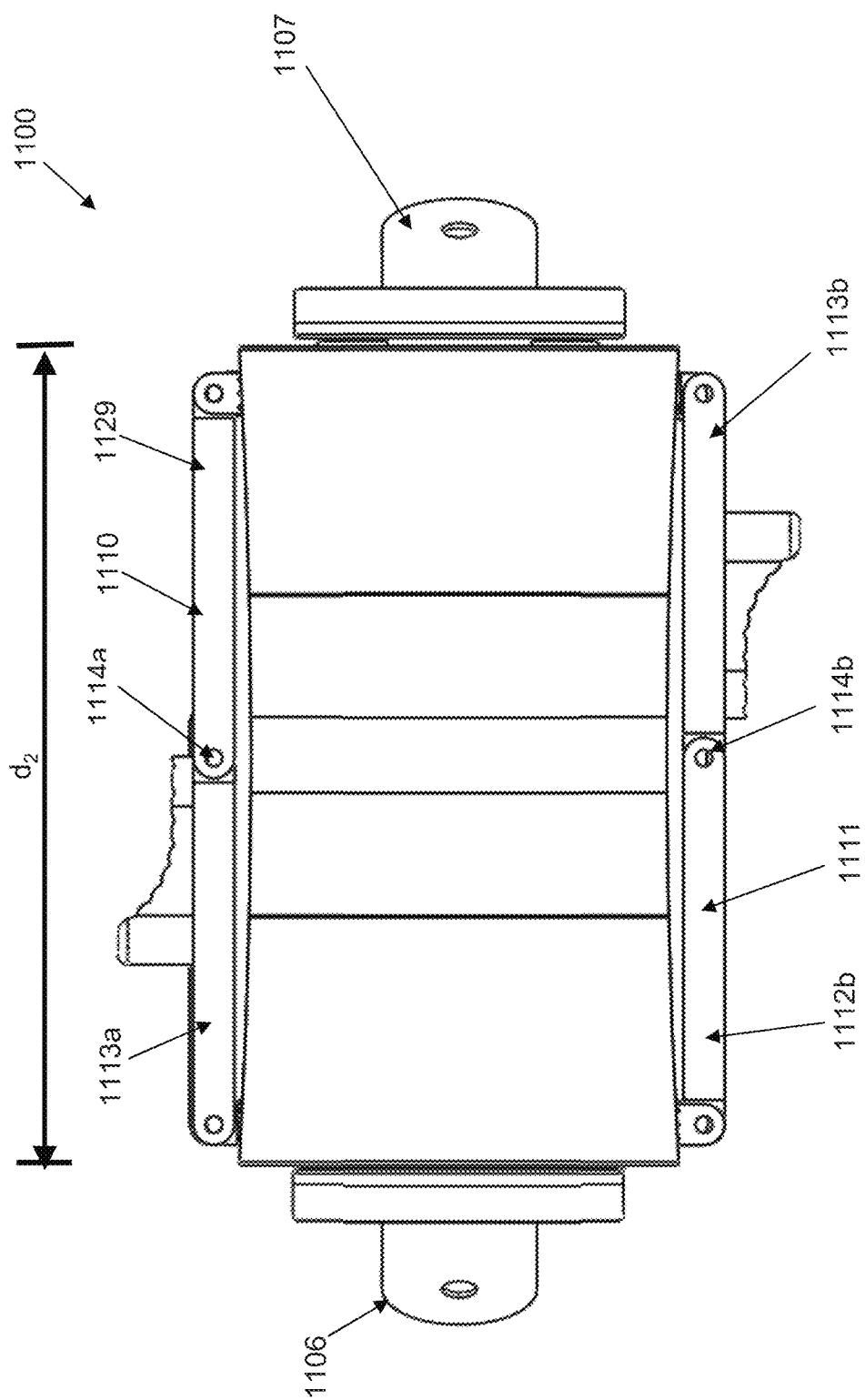
FIG. 53D is an inferior view of the applicator of FIG. 53A in a strained configuration.
Figure 53E:
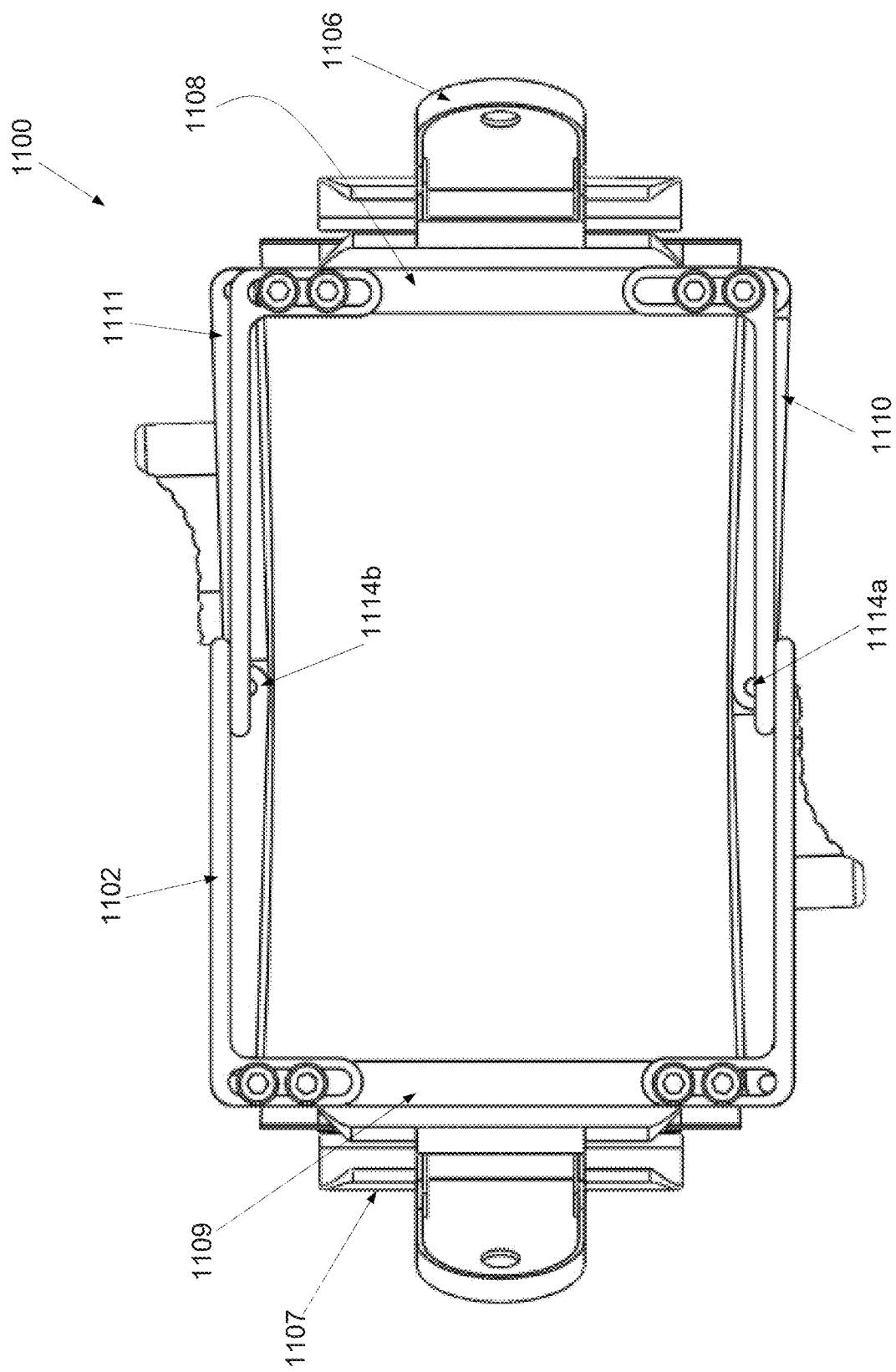
FIG. 53E is a superior view of the applicator of FIG. 53A in a strained configuration.

FIGS. 53A and 53C illustrate the applicator 1100 in a first, unstrained position. The frame structure 1102 is in a collapsed position where slidable supports or elements 1120, 1121 and slidable elements 1122, 1123 are in a folded closed position. In this position, subsupports or wall segments 1112a and 1113a are pivoted to form a v-shape extending outward of the applicator, and wall segments 1112b and 1113b are pivoted to form a v-shape extending outward of the applicator 1100 so that the distance between end walls is a distance d1. This configuration may facilitate loading of an unstrained skin treatment device. After an unstrained device is loaded, the skin treatment device is strained by applying pressure to the v-shaped walls 1110, 1111 (for example by manually squeezing the v-shaped or collapsed walls shown in FIGS. 53A and 53C). This action forces the pairs of sliding elements 1120, 1121 and 1122, 1123 into a spread, elongated or open position, as shown in FIGS. 53B, 53D and 53E. In the spread or open position, the frame structure 1102 transferring a separation force from the wall segments 1112a and 1113a to the skin treatment device to strain the skin treatment device along a strain axis. When the applicator 1100 is in the strained position, as shown in FIG. 53E, the wall segments 1112a, 1113a and 1112b, 1113b of walls 1110 and 1111 may be configured to pivot slightly inward and/or off-center to lock the applicator 1100 into place or to resist collapse of the walls back into the v-shaped configuration. Thus, the applicator 1100 and an attached strained skin treatment device may be configured to maintain or lock in a strained configuration without continuous user applied force.

Grasping members 1105 may be provide to facilitate grasping of the device when applying a skin treatment device to the skin of a subject. Although each of the grasping member 1105 are depicted to opposite sides of their respective pivot connectors 1114b, in other example, the grasping members may be located on the same sides of their respective pivot connectors, or lie across or on both sides of the pivot connectors.

In sonic variations, the use of two opposing and collapsible walls to separate to slidable walls of a fixed configuration, as illustrated in the applicator 1100 depicted in FIGS. 53A to 53E, as wells similar applicators such as those illustrated in FIGS. 54A to 54I, FIGS. 56A to 57I, for example, may provide a mechanical advantage when applying a strain to a skin treatment device. A mechanical advantage may be characterized by an output force that is greater than the input force, and may be described as a ratio of the output force divided by the input force that is greater than 1. In some variations, the mechanical advantage may be at least about 1.1, about 1.2, about 1.3, about 1.4, about 1.5 about 1.7, or about 2 or more. The mechanical advantage may or may not be provided throughout the entire movement range of the applicator.

Figure 54A:
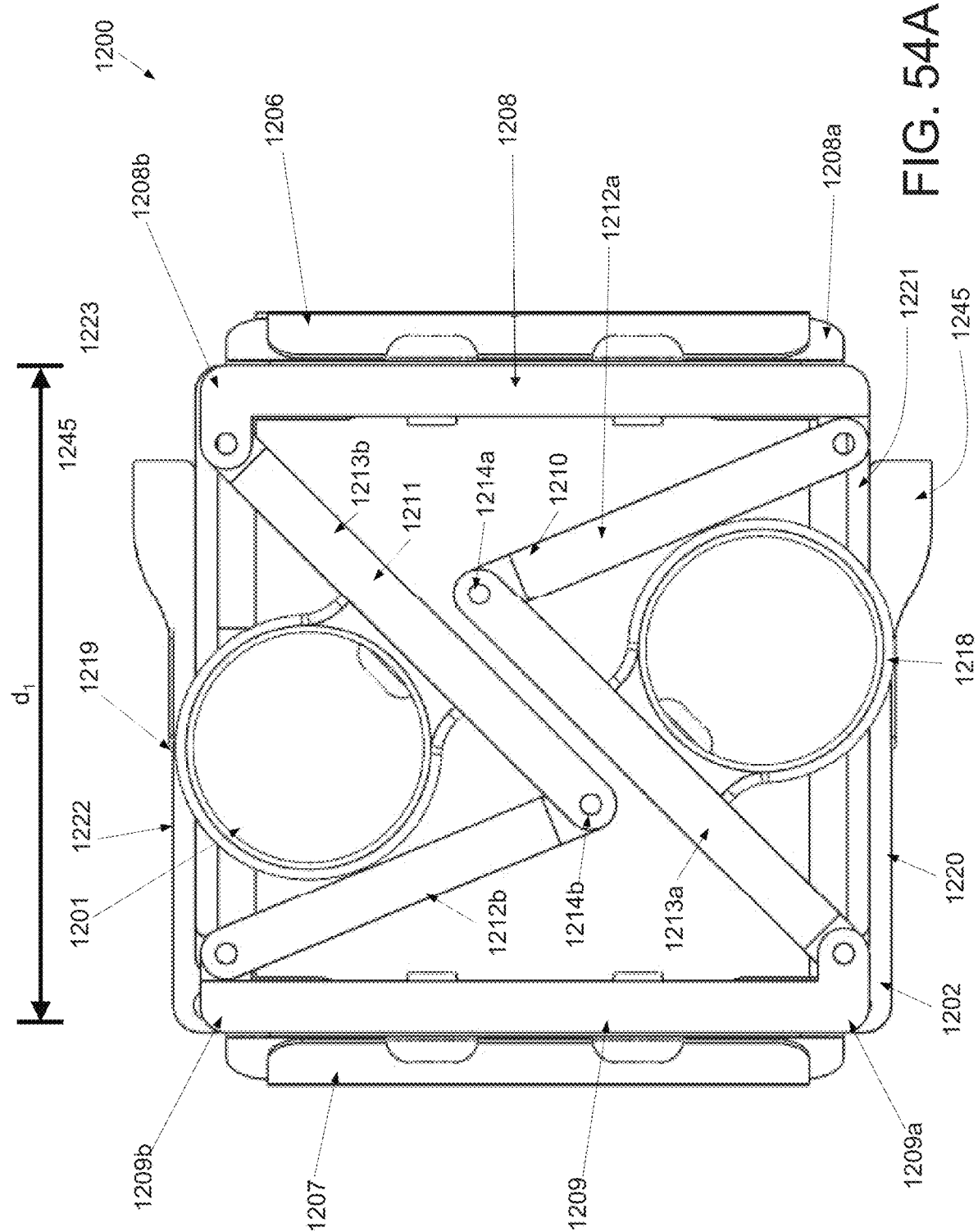
FIG. 54A is a superior view of an applicator in an unstrained configuration.
Figure 54B:
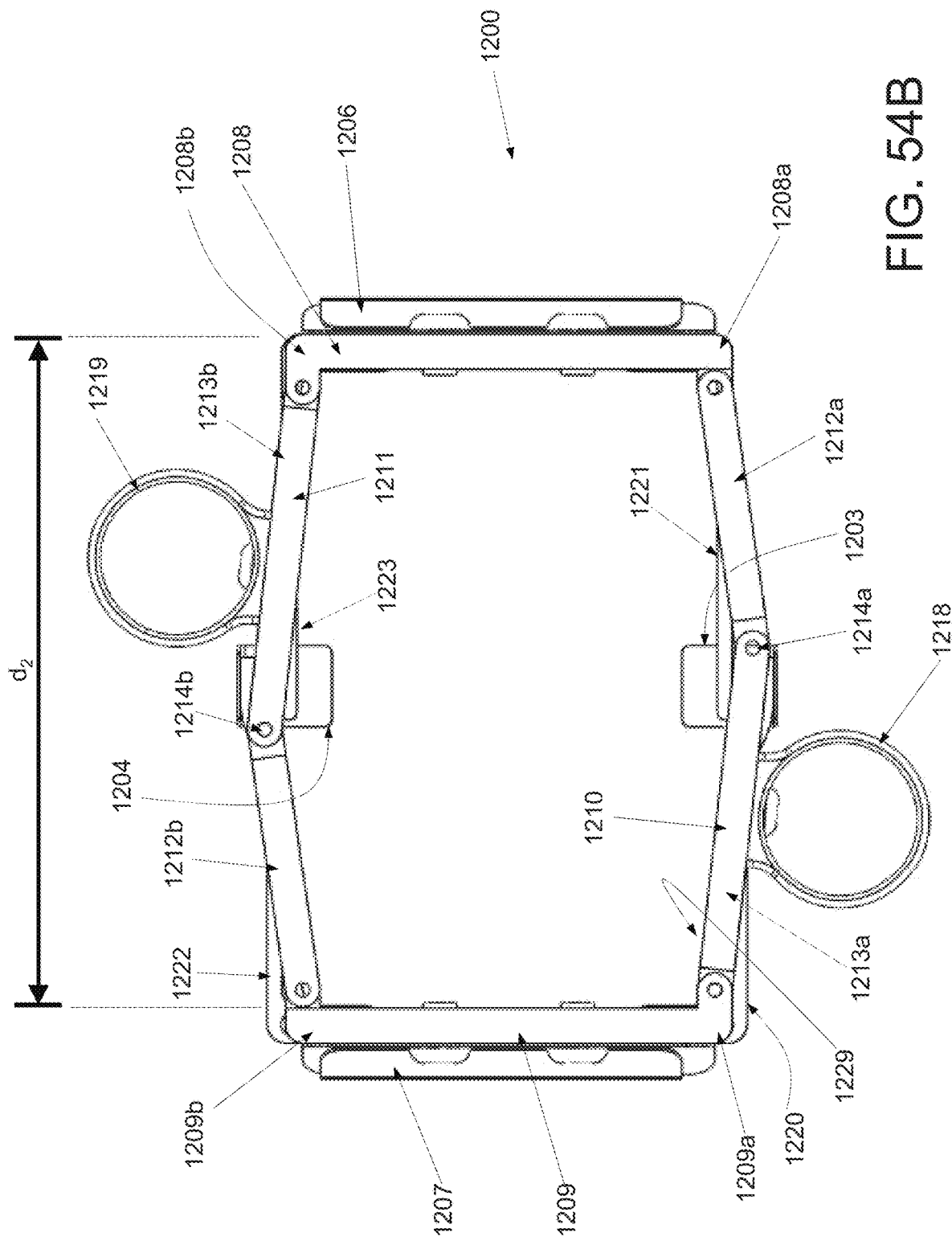
FIG. 54B is a superior view of the applicator of FIG. 54A in a strained configuration.
Figure 54C:
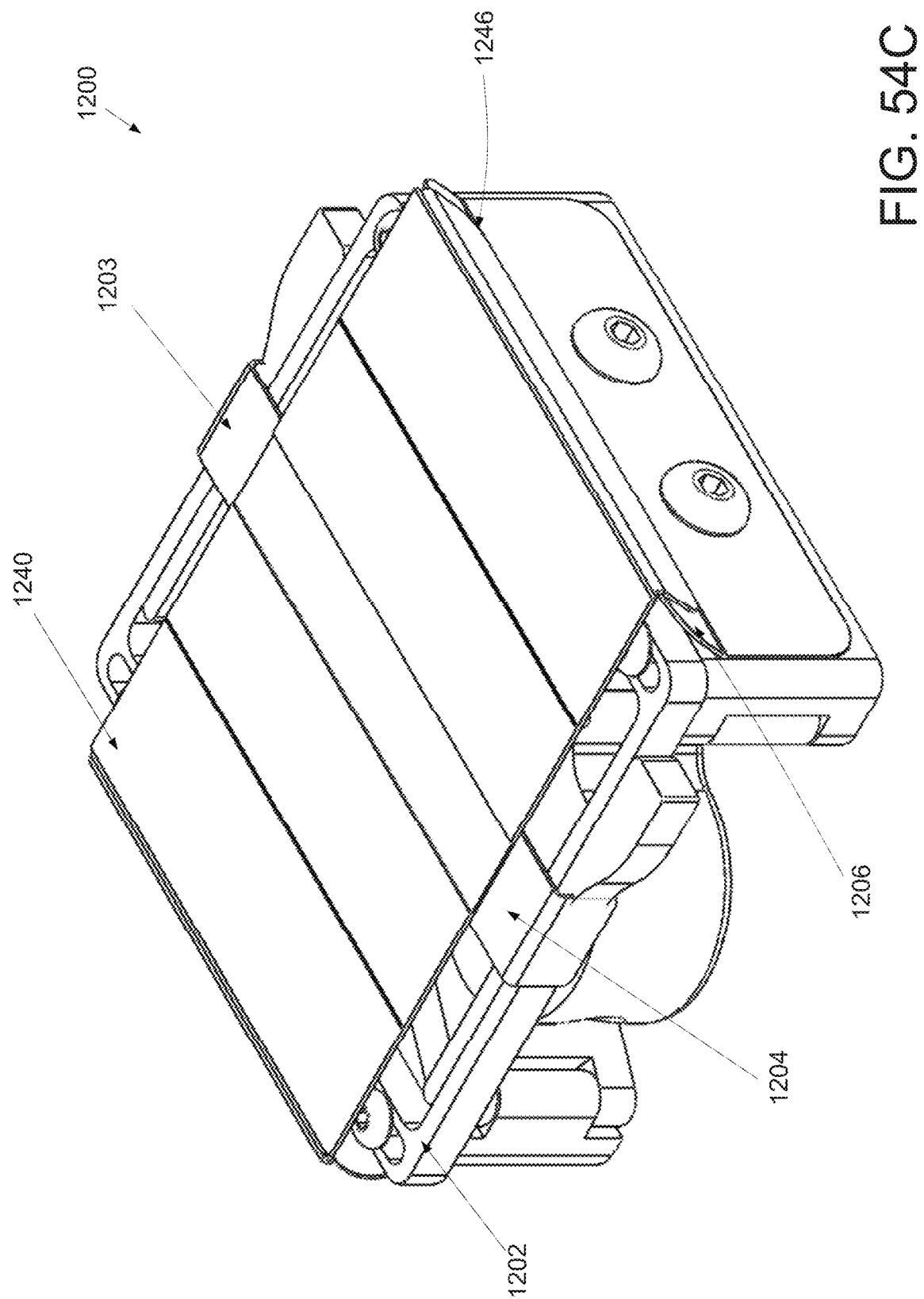
FIG. 54C is an inferior perspective view of the applicator of FIG. 54A in an unstrained configuration.
Figure 54D:
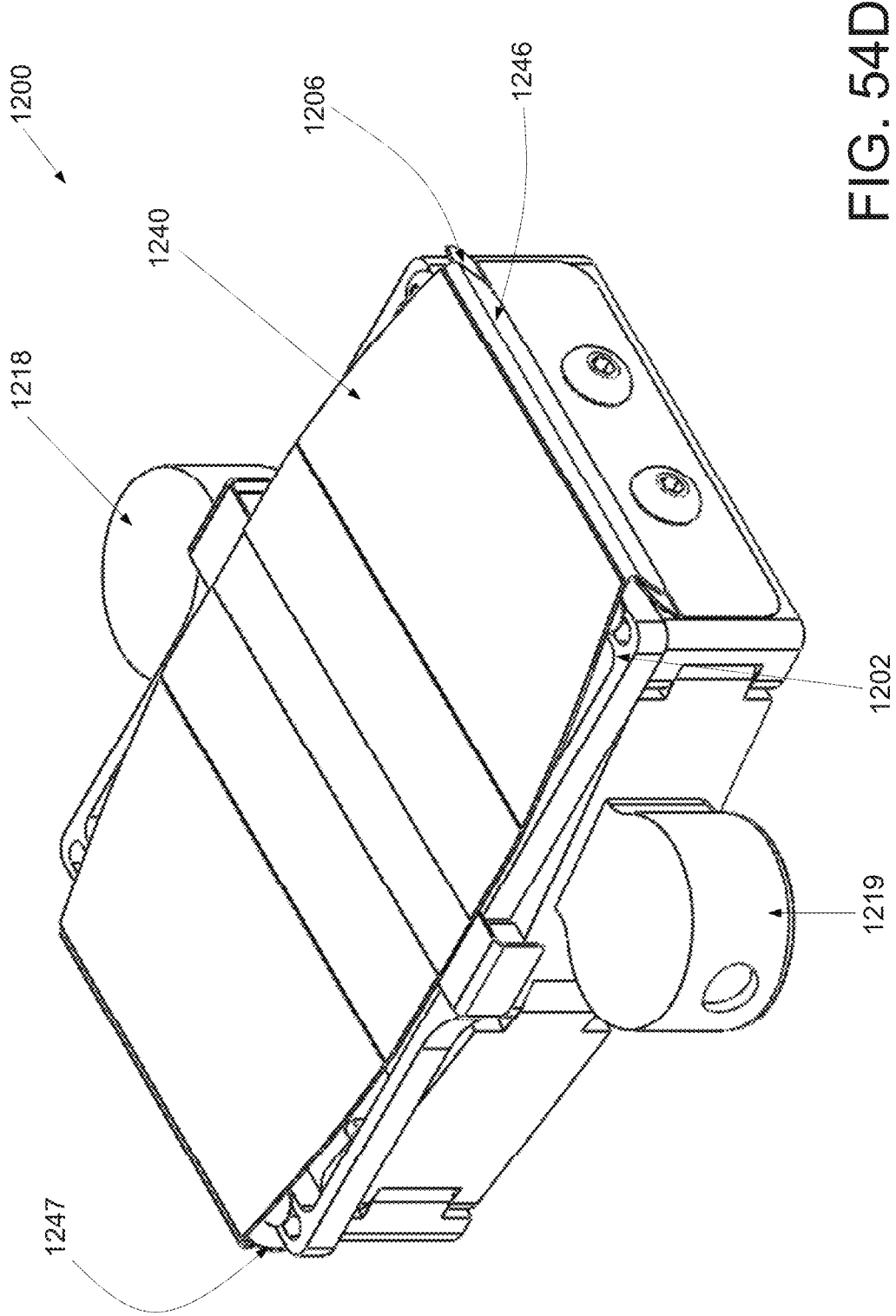
FIG. 54D is an inferior perspective view of the applicator of FIG. 54A in a strained configuration.
Figure 54E:
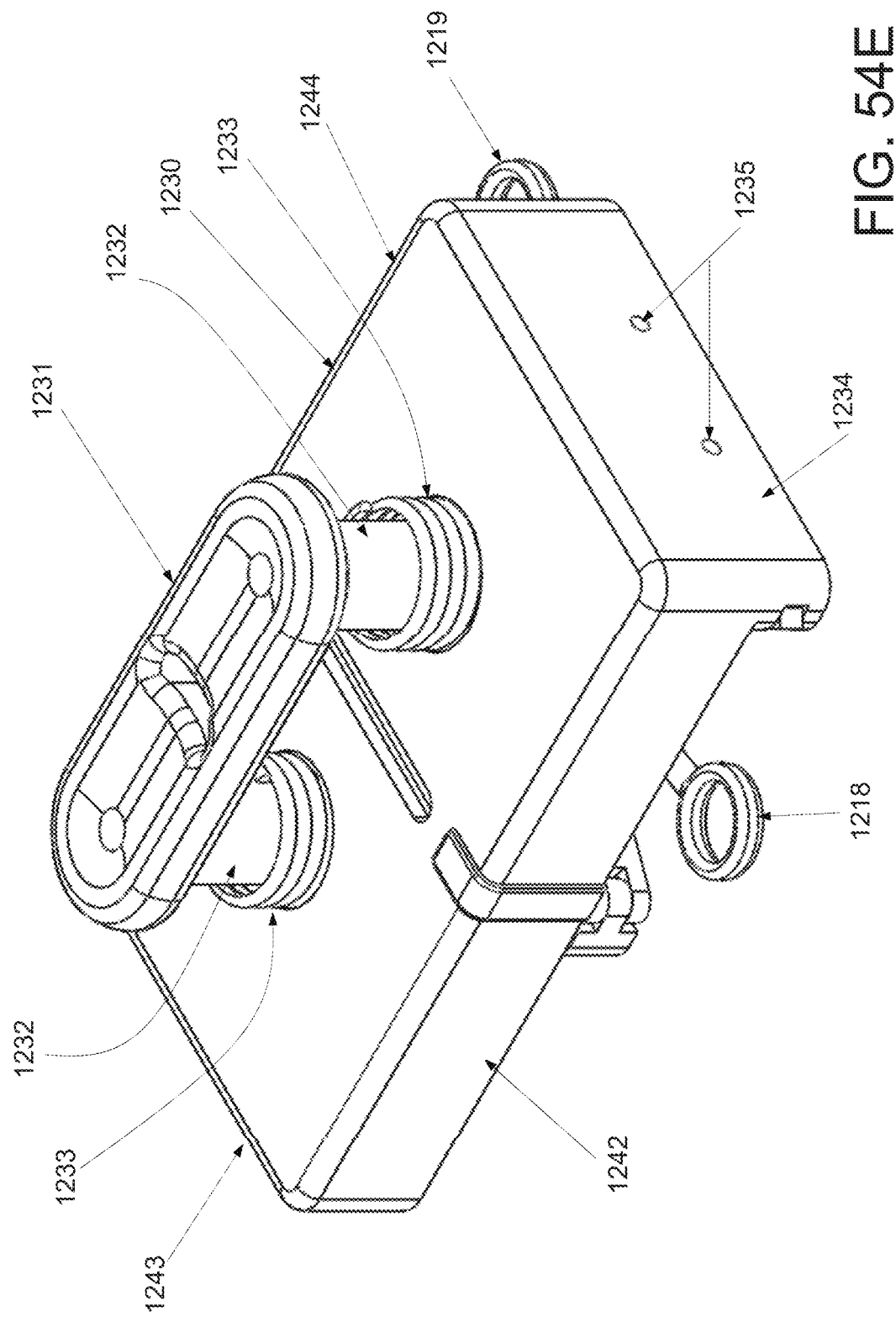
FIG. 54E is a perspective view of the applicator with integrated stamper, in an unstrained configuration.
Figure 54F:
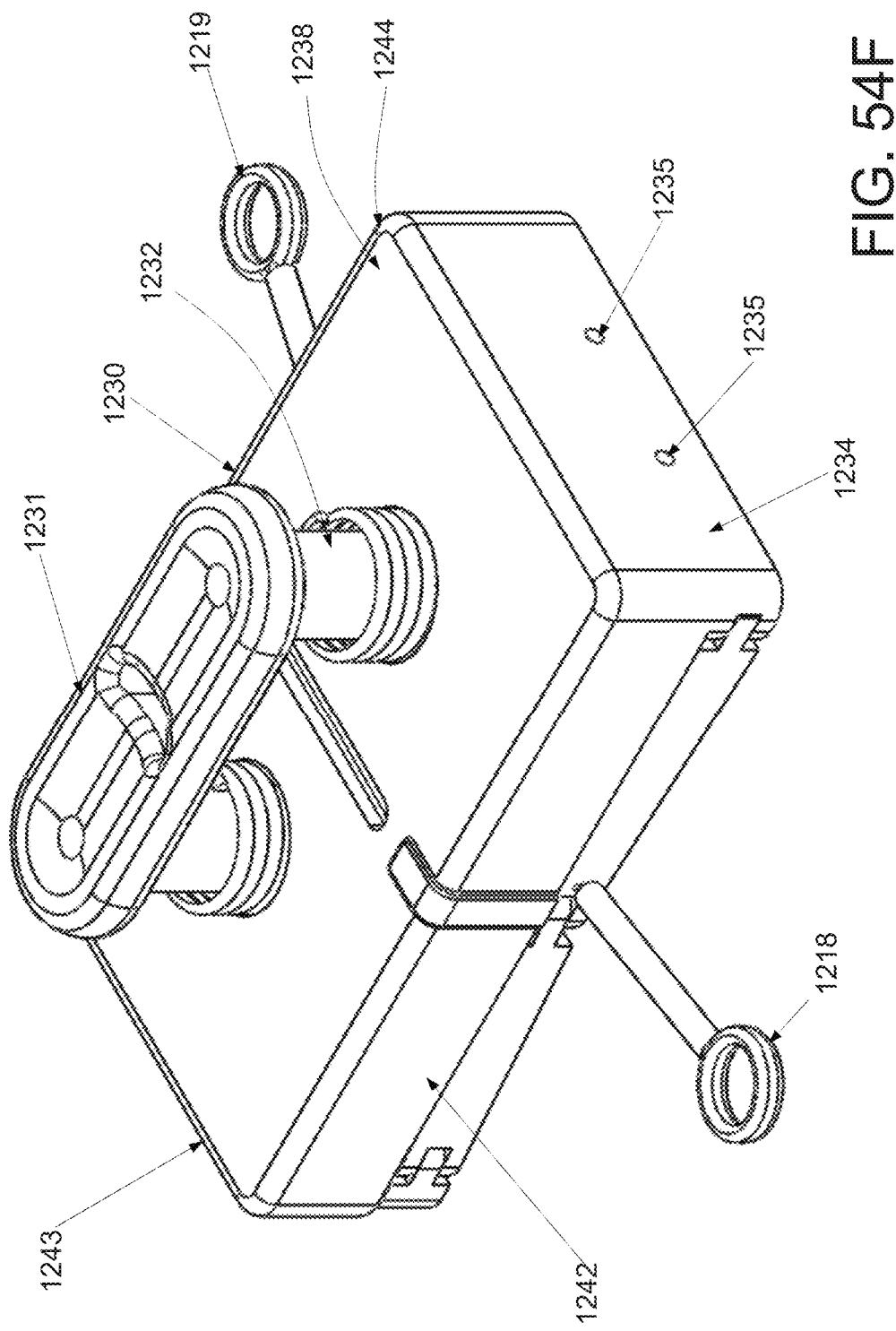
FIG. 54F is a perspective view of the applicator of FIG. 54E in a strained configuration.
Figure 54G:
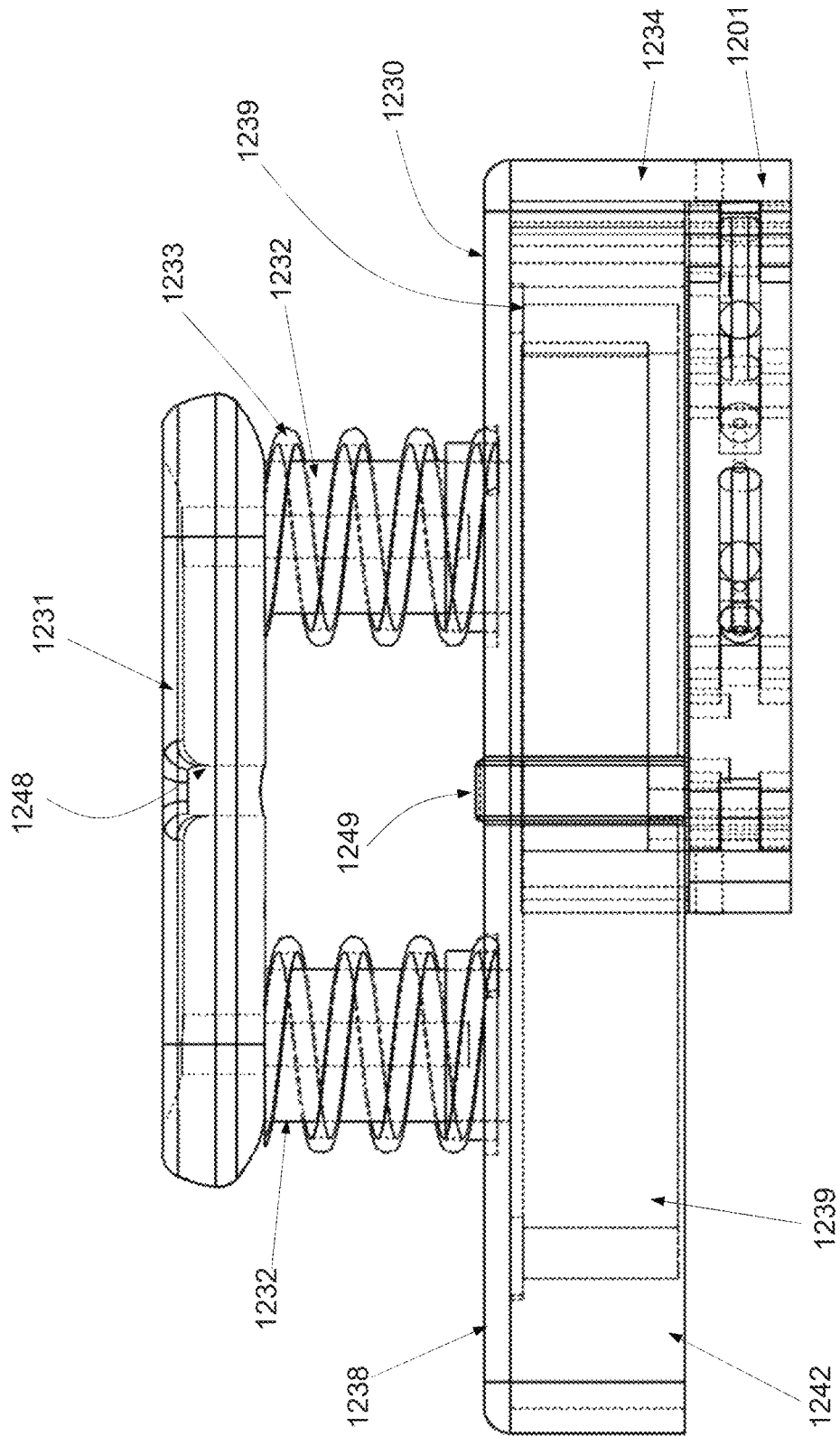
FIG. 54G is a side view of the applicator of FIG. 54E in an unstrained configuration.
Figure 54I:
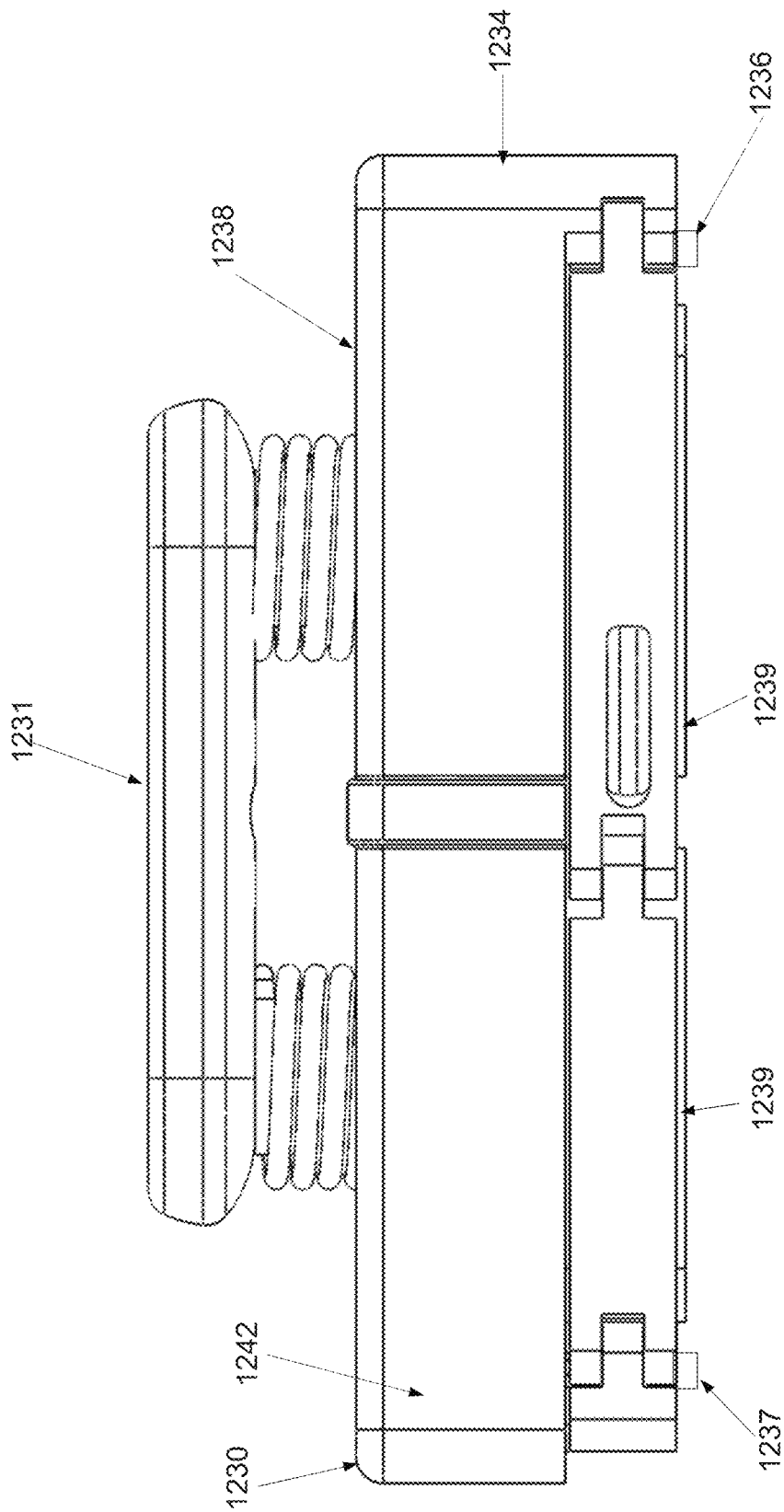
FIG. 54I is a side view of the applicator of FIG. 54E in a strained configuration with a deployed stamper.
Figure 54J:
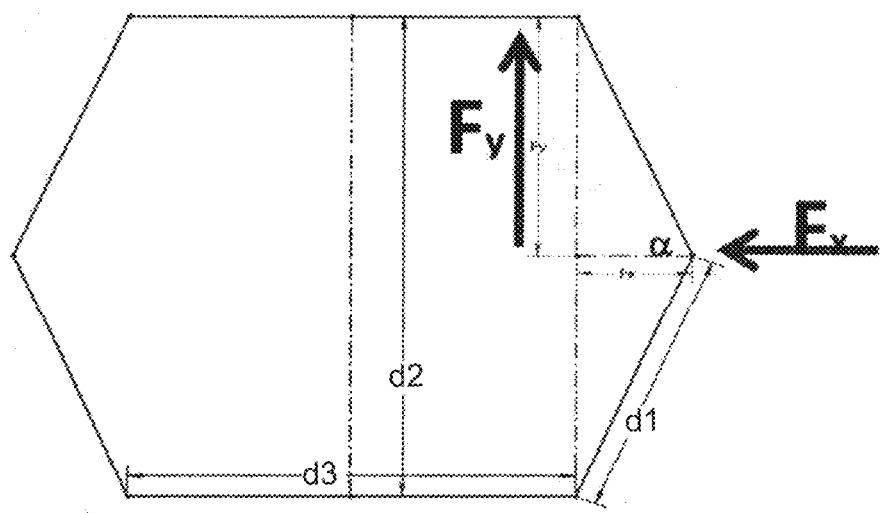
FIG. 54J is a schematic illustration and equation to determine the mechanical advantage of a collapsing box applicator design.

Referring to FIG. 54J, the mechanical advantage of the collapsing box, with two opposing slidable walls having a fixed configuration separated by initial distance d2 and two collapsible opposing walls, each comprising two wall segments of length d1 and forming an angle α between a wall segment and an intersecting midline may be calculated as:

$$F_x = F_y / \tan \alpha$$

The width of the slidable walls d3 permits skin treatment devices of up to a comparable width d3, which may affect the absolute level of force necessary to strain the attached skin treatment device, but may not direct impact the mechanical advantage provided by the collapsing box design. It is noted from the above equation that where angle α is initially 45 degrees at a 0% strain, a mechanical advantage is provided along the entire strain process. Thus, in some variations, the applicator may be configured to have an initial angle α of about 45 degrees, but in other examples, the initial angle α may be in the range from about 1 degree to about 90 degrees, sometimes about 15 degrees to about 75 degrees, and other times about 30 degrees to about 60 degrees, and still other times about 30 degrees to about 45 degrees. However, use of an initial angle α that is less than about 45 degrees at 0% strain may permit a greater degree of straining, compared to designs with an initial angle α of about 45 degrees or more. In some designs where an initial angle α of less than about 45 degrees is used, although no initial mechanical advantage, the absolute level of force to be exerted by the user to generate the initial, smaller strains (e.g. up to about 10% or about 20% strain) in the skin treatment device may not be significant compared to the absolute greater strains needed for higher levels of strain (e.g. about 40% or about 60% strain).

Figures 54K, 54L:
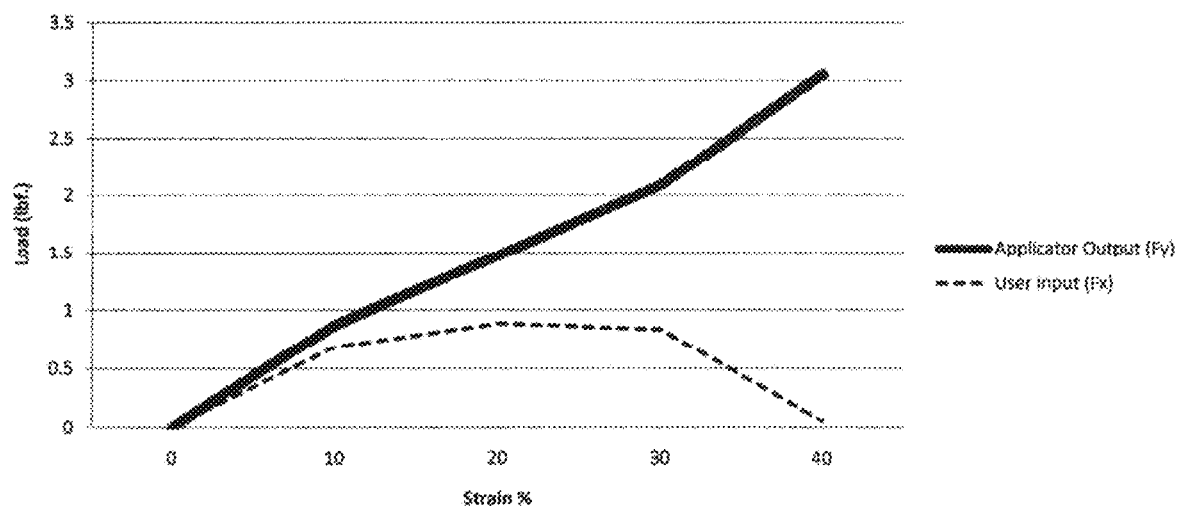
FIG. 54K is a table listing the input load and output load of one embodiment of a collapsing box applicator for strains from 0% to 40%.
FIG. 54L is a graph of the input and output loads per strain of the data from FIG. 54K.

FIG. 54K is a table that lists the resulting load based upon a collapsing box applicator design attached to a 6 cm dressing, where the collapsible walls are configured with an angle α of about 45 degrees at a strain of o%. As depicted in the graph of FIG. 54L, the plot of the force exerted by the user at each level of strain (10%, 20%, 30% and 40%) is generally at or below the level of force generated by the applicator. In this particular configuration, the user input force gradually increases from about 0% to about 20%, then plateau to about 30%, and then decreases toward zero at a strain of about 40%.

Figures 54M, 54N:
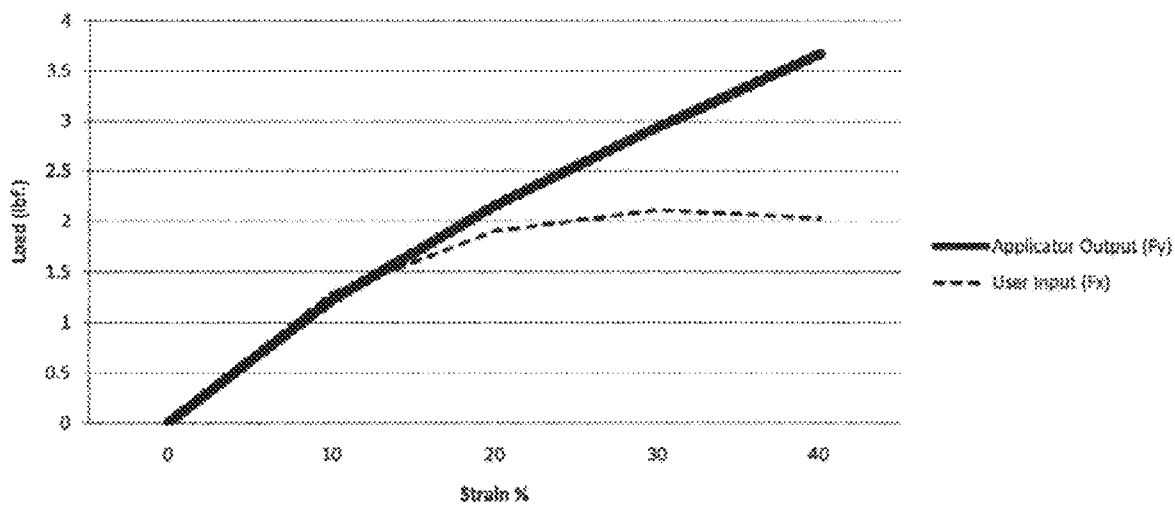
FIG. 54M is a table listing the input load and output load of another embodiment of a collapsing box applicator for strains from 0% to 60%.
FIG. 54N is a graph of the input and output loads per strain of the data from FIG. 54M up to 40% strain.

FIG. 54M is a table that lists the resulting load for a collapsing box applicator design attached to a 6 cm dressing, where the collapsible walls are configured with an angle α of about 40 degrees at a strain of 0%, and also where strains up to 60% were measured. As shown in the graph of FIG. 54N, the plot of the force exerted by the user at each level of strain (10%, 20%, 30%, 40%, 50% and 60%) at or slightly above the output force until angle α is about 45 degrees (approximately 12% strain) but is at or below the level of force generated by the applicator for greater strains (e.g. about 20% to about 60%).

Figures 54O, 54P:
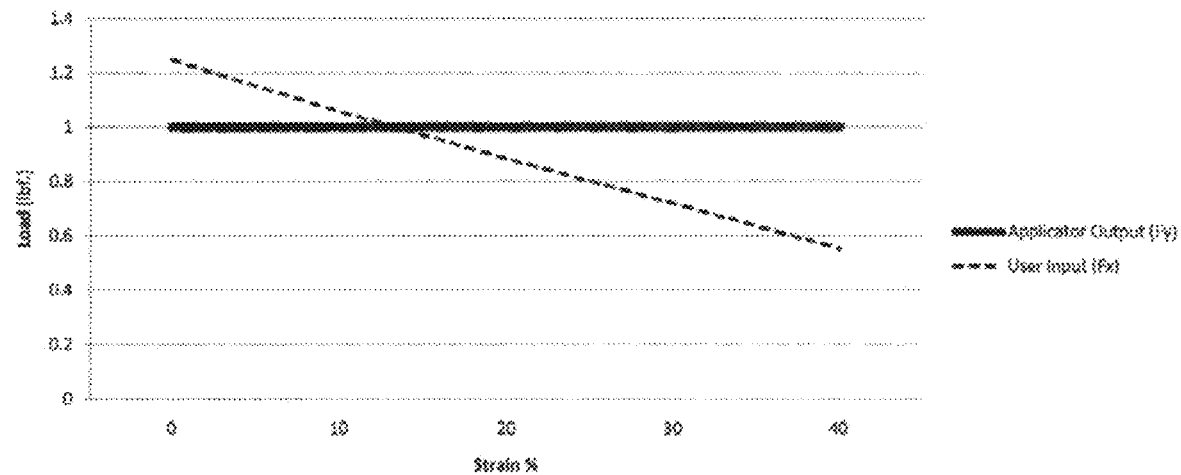
FIG. 54O is a table listing the input load against a constant output load of the collapsing box applicator embodiment from FIGS. 54M and 54N for strains from 0% to 60%.
FIG. 54P is a graph of the input and output loads per strain of the data from FIG. 54O.

FIG. 54O is a table that lists the user input force required to maintain a constant output force (here normalized to 1 Lbf) from a strain of 0% to 60%. As shown in the graph of FIG. 54P, to generate a constant force across for strain up to 40%, the required user input force is initially greater until angle α is about 45 degrees (approximately 12% strain), then gradually decreases (at a generally constant slope) as the level of strain increases (up to a strain of 40% is depicted in FIG. 54P).

Other examples of applicator designs that may be configured with a mechanical advantage are described elsewhere herein.

FIGS. 54A to 54D illustrate another variation of a tensioning device, straining device or an applicator 1200. The applicator 1200 comprises a handle 1201 or actuator configured to be actuated to strain a skin treatment device 1240 and/or to apply the device to the skin of a subject. The applicator 1200 includes end attachment structures 1206, 1207. In some variations, the applicator may also include side attachment structures 1203, 1204, 1220, 1222 that may interface with structures 1203 and 1204 be attached to the sides of a skin treatment device. This interface may provide a second dimension or axis to the tension or strain applied to the skin treatment device. Thus the skin treatment device may be strained in orthogonal directions or at least two directions, i.e., the applicator provides a bi-directionally or multi-directionally strained skin treatment device. The attachment structures may be located on the bottom of bump features 1245 on wall segments 1220, 1222. The attachment structures 1206, 1207 may comprise engagement flaps having edges that engage attachment features 1246, 1247 of a corresponding skin treatment device 1240. Attachment structures 1203, 1204 as shown are hook or loop structures that have corresponding hook or loop structure attachment features on the back side of the skin treatment device. The applicator or skin treatment device attachment structures may comprise other types of attachment structures, including but not limited to other attachment structures described or set forth herein.

The applicator 1200 may further comprise moveable, slidable or a collapsing or expanding bottom frame structure 1202, opposing fixed configuration walls 1208, 1209 and opposing movable, pivotable or hinged walls 1210, 1211. Frame structure comprises a pair of slidable elements 1220, 1221 and pair of slidable elements 1222, 1223. Each of the pair of slidable elements 1220, 1221 and 1222, 1223 can slide together into a closed position (FIGS. 54A and 54C) where there is a first distance d1 between walls 1208 and 1209. The pairs of slidable element 1220, 1221 and 1222, 1223 can slide apart into a second open or strained position where there is a second distance d2 between the walls 1208, 1209 and where the distance d2 is greater than the distance d1 (as depicted in FIGS. 54B and 54A, respectively).

Hinged wall 1210 comprises first and second wall portions or segments 1212a, 1213a that are movably, pivotally or hingedly connected to each other by connector 1214a, at a pivot point. Hinged wall 1211 comprises a first and second wall segments 1212b, 1213b that are movably, pivotally or hingedly connected to each other by connector 1214b at a pivot point. Wall segments 1212a and 1213b are movably, pivotally or hingedly coupled respectively to opposite end sides 1208a, 1208b of wall 11081208. Wall segments 1212b and 1213a are movably, pivotally or hingedly coupled respectively to opposite end sides 1209b, 1209a of wall 1209. The walls 1208, 1209, 1210, 1211 are coupled to the frame structure 1202 to form a box-like structure with an opening (when in the strained configuration) to provide access to a skin treatment device 1240 attached across the bottom of the applicator to attachment structures 1203, 1204, 1206, 1207, 1246, 1247. This access allows a user to apply pressure to a skin treatment device as or after it is applied to a skin surface, before removing the applicator 1200 from the skin treatment device. Alternatively, a pressure application device may be coupled to the applicator and actuable to provide pressure through the opening to a skin treatment device as or after it is being applied.

FIGS. 54A and 54C illustrate the applicator 1200 in a first, unstrained position. The frame structure 1202 is in an unstrained position where slidable elements 1220, 1221 and slidable elements 1222, 1223 are in a closed position. Wall segments 1212a and 1213a are pivoted to form a v-shape collapsed into the box structure of the applicator 1200, and opposing wall segments 1212b and 13b are pivoted to form a v-shape collapsed into the box so that the distance between end walls is a distance d1. This position facilitates loading of an unstrained skin treatment device onto the applicator 1200.

After an unstrained device is loaded, the skin treatment device is strained by applying opposing, outward forces to pulling rings 1218, 1219, respectively attached to wall segments 1213a, 1213b. This force straightens side walls 1210, 1211 and pairs of sliding elements 1220, 1221 and 1222, 1223 into an elongated or open position as shown in FIGS. 54B and 54D, thus transferring a separation force to the skin treatment device to strain the skin treatment device widthwise (relative to its orientation and use on along a length of an incision). In other variations, a single collapsible wall attached generally about the midpoints of the fixed configuration walls so only a single pulling force is used to separate the fixed configuration walls.

When the device is in the strained position as shown in FIGS. 54B, and 54D the wall segments 1212a, 1213a and 1212b, 1213b of walls 1210 and 1211 are pivoted. As shown in FIGS. 54B and 54D, the side walls are over center or slightly hyper-extended or pivoted outward to provide a strain in a width wise direction with the force transferred to the skin treatment device through attachment structures 1203, 1204. Thus the skin treatment device may be strained in orthogonal directions or at least two directions, i.e., the applicator provides a bi-directionally or multi-directionally strained skin treatment device. The applicator 1100 may be locked or maintained in a strained configuration by way of over center side walls. A latch or other stop such as a spring loaded pin may engage one or more of inside surfaces of wall segments 1212a, 1213a and 1212b, 1213b to maintain the applicator in its over center locked position.

FIGS. 54E to 54I illustrate other variations of a tensioning device, straining device or an applicator 1200 as previously described with respect to FIGS. 54A to 54D, including an integrated stamper 1230. The stamper 1230 is attached to the top of the handle, actuator or tensioning device 1201 of FIG. 54A with connectors 1235 that attach the device 1201 to the inside of the stamper side wall 1234. The stamper comprises a handle 1231 coupled to posts 1232 that extend through the top wall 1238 of the stamper 1230. Posts 1232 are coupled to pressure members 1239 inside the stamper 1230. Prior to actuation, the pressure members 1239 are positioned within walls 1234, 1242, 1243, 1244 of stamper 1230 above and the tensioning device 1201 as shown in FIG. 53G. Springs 1233 around the posts 1232 bias the handle 1231 in an upward (not stamping) configuration. Visibility openings 1248, 1249 respectively in the handle 1231 and the top wall 1238 of the stamper 1230 provide an opening through which the skin treatment device and/or wound can be seen, for positioning of the applicator 1200 in an appropriate location.

As shown in FIGS. 54E, and 54G, when the tensioning device 1201 is in an unstrained configuration, the length of its side walls 1210, 1211 are less than the length of the side walls 1242, 1244 of the stamper 1230.

In FIGS. 54F and 54H, the tensioning device 1201 is in a strained configuration where the side walls 1242, 1244 of the stamper 1230 are approximately that of the side walls 1210, 1211 of the tensioning device 1201. In a strained configuration, an opening 1229 is provided in the tensioning device 1201 sized to receive the pressure members 1239 therethrough. When a force is applied to the handle 1231 and the tensioning device 1201 is in a strained configuration, the pressure members 1239 extend down into and through the opening 1229 in the applicator handle 1201, towards the skin treatment device (not shown), to apply a force to areas of the dressing where an adhesive interfaces with the skin of the subject. (FIG. 54I) Thus, where the adhesive is pressure activated, the stamper 1230 applies a generally even pressure to the skin treatment device. All stampers described herein may be constructed of a foam or other compressible, conformable material which translates the force applied to handle 1231 to the skin treatment device (not shown). These other materials include silicones and styrenic block copolymers (e.g. Kraton®), in a solid or porous form.

As an option or alternative, the applicator 1200 may be provided with attachment structures 1236, 1237 that comprise a hook or loop structure of a hook and loop attachment mechanism, or any other attachment structure described herein. Likewise, side attachment structures 1203, 1204 may also be a hook or loop structure or any other attachment structure.

Figure 55B:
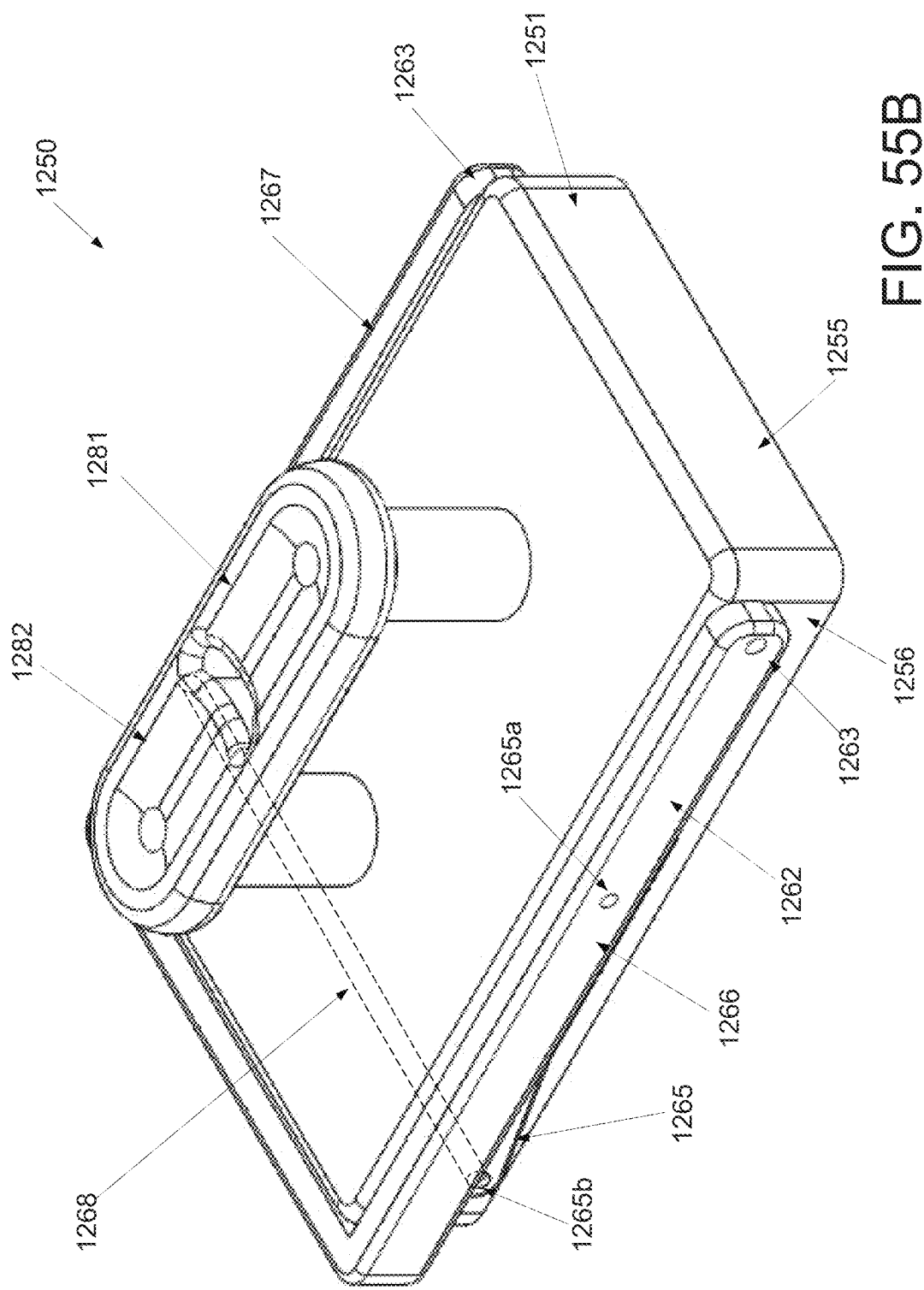
FIG. 55B is a perspective view of the applicator of FIG. 55A in a strained configuration.
Figure 55C:
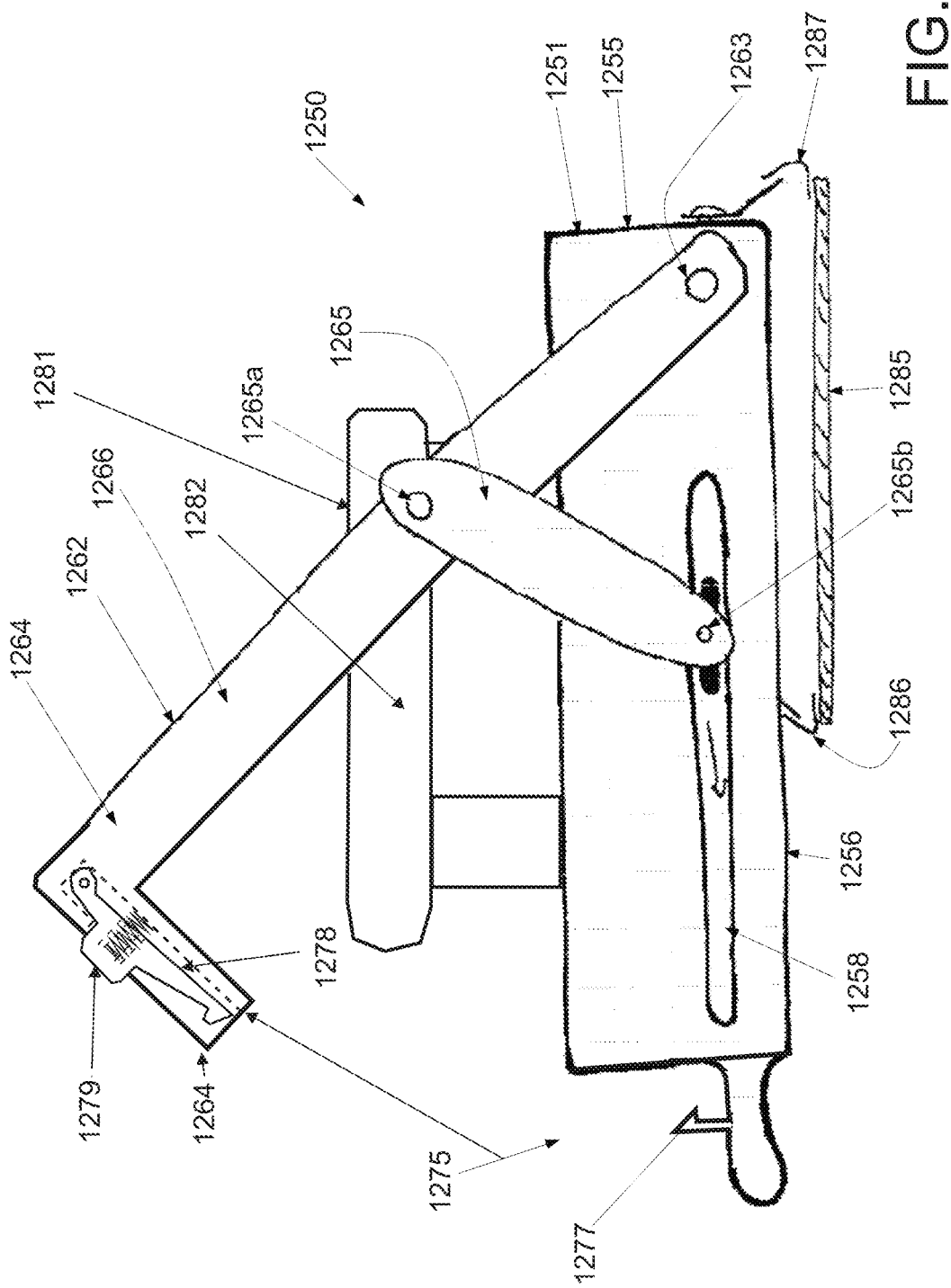
FIG. 55C is a side partial cut-away view of the applicator of 55A in an unstrained configuration.
Figure 55D:
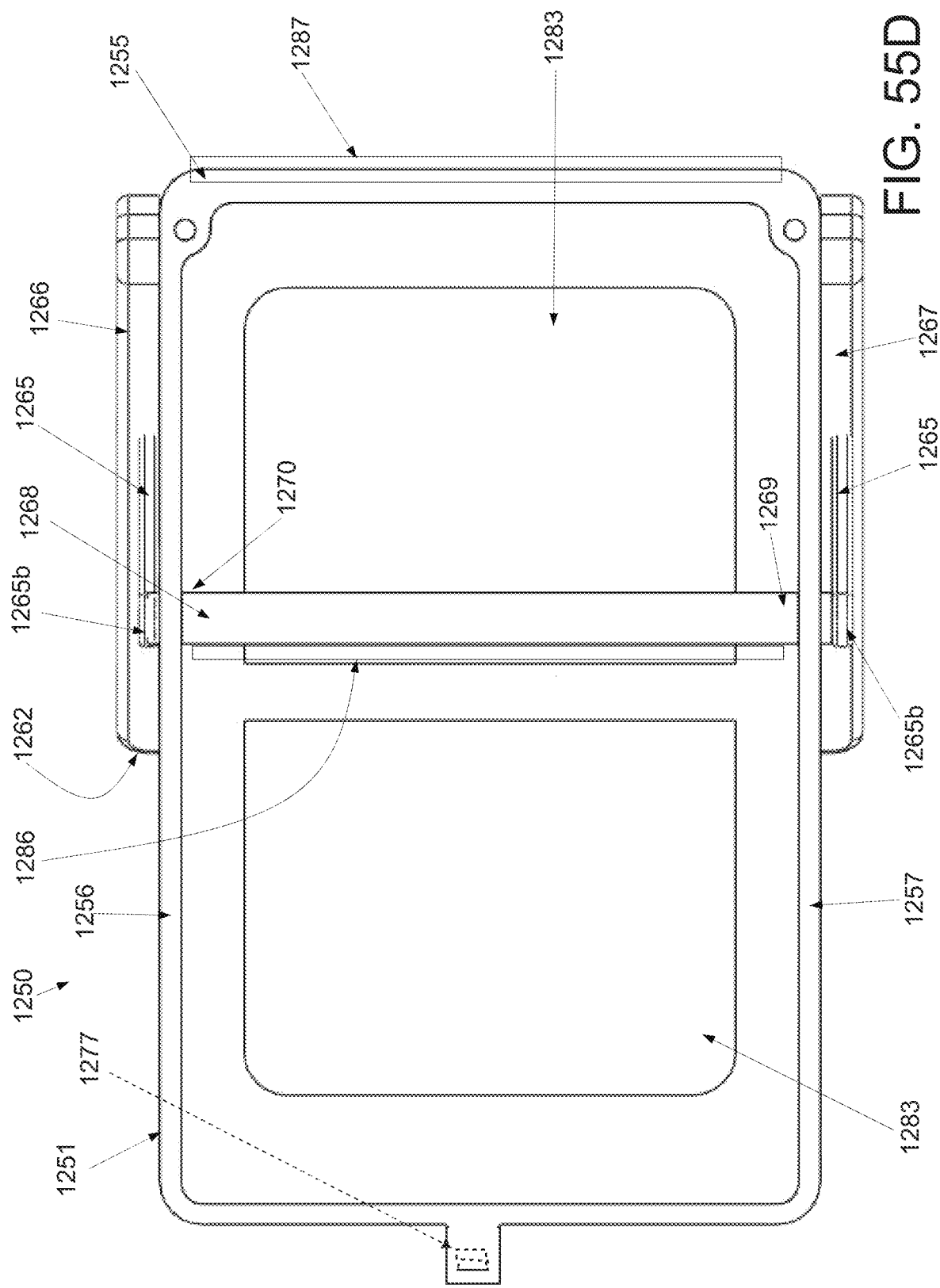
FIG. 55D is an inferior view of the applicator of FIG. 55A in a strained configuration.

FIGS. 55A to 55E illustrate a variation tensioning device, straining device or applicator 1250 comprising a frame 1251 and a pivoting handle 1262 that is used to strain a skin treatment device loaded on to the applicator 1250. The handle 1262 is pivotally attached at a first end 1263 to side walls 1256, 1257 near end wall 1255 of the frame 1251. An opposite second end 1264 of the handle 1262 extends above the frame 1251 when the applicator 1250 is in an unstrained configuration as shown in FIGS. 55A, 55C and 55D. The handle 1262 further comprises tensioning arms 1265 pivotally coupled to sides 1266, 1267 of handle 1262 at first ends 1265a and pivotally coupled to a sliding tensioning bar 1268 at a second opposite ends 1265b. Each end 1269, 1270 of the sliding tensioning bar 1268 is configured to slide in slots 1258 extending along a portion of the length of side walls 1256, 1257 of frame 1251. When the handle 1262 is squeezed so that its second end 1264 is moved towards the frame 1251, a forced is transmitted from the handle 1262 through pivot point at first end 1265a to tensioning arms 1265 which translate the force to the sliding tensioning bar 1268 which slides in the slots 1258 from the middle towards the end of the frame 1251.

Figure 55E:
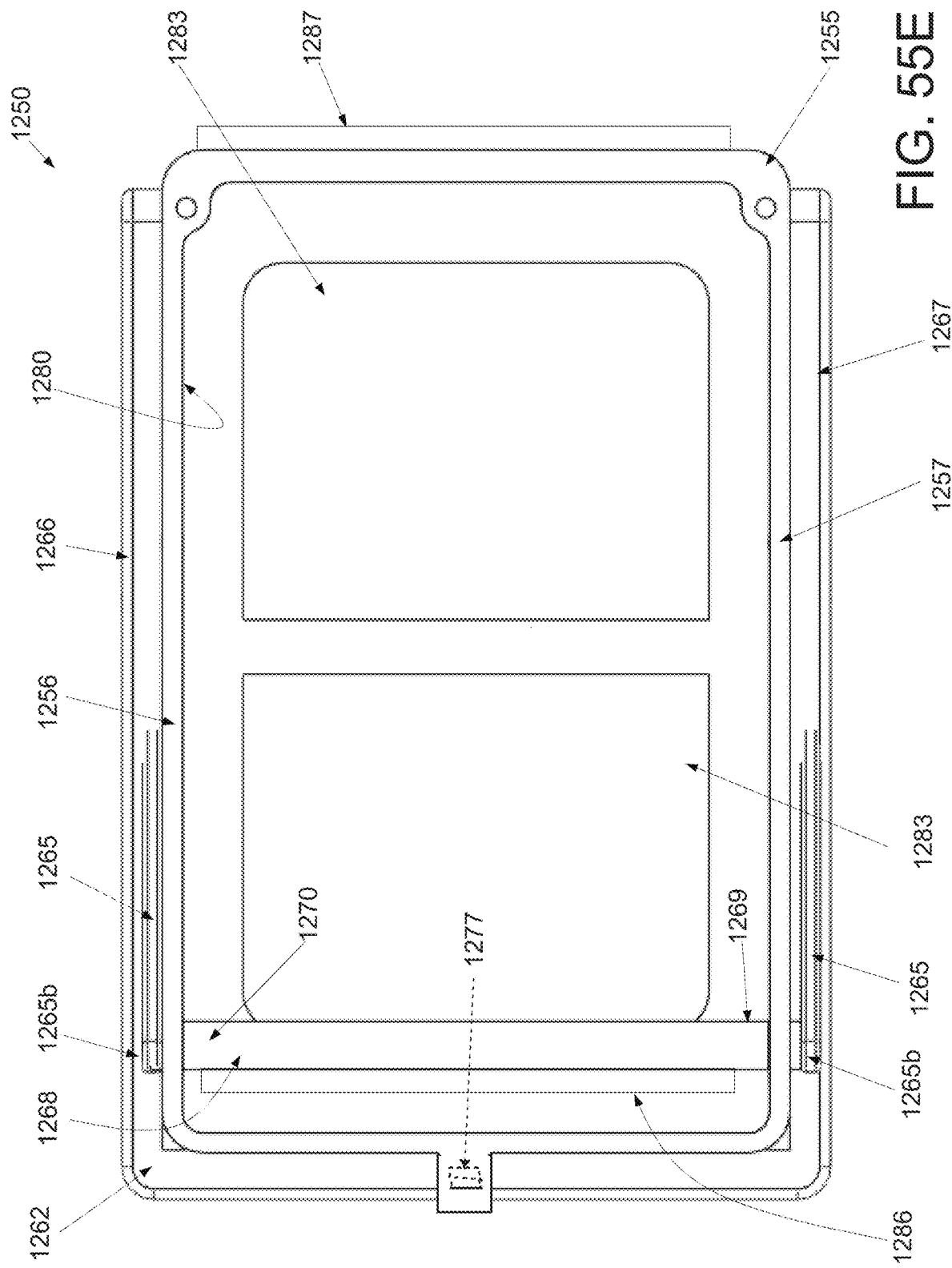
FIG. 55E is an inferior view of the applicator of FIG. 55A in a strained configuration

The sliding bar 1268 may further comprise a first attachment structure 1286 to which one end of a skin treatment device may be attached. A second attachment structure 1287 is positioned on the bottom of the stationary end wall 1255 of the frame 1251. As shown in FIGS. 55A, 55C, and 55D, when in an unstrained position, the sliding tensioning bar 1268 is located at the inner end of the slots 1258 where the attachment structure 1286 is a shorter distance from the second attachment structure 1287 to facilitate attaching or loading of an unstrained skin treatment device. As shown in FIGS. 55B and 55E, in a strained configuration, the sliding tensioning bar 1268 is located at the outer end of the slots 1258 where the first attachment structure 1286 is a greater distance from the second attachment device 1287. In use, the handle 1262 is moved from the open unstrained position to a second strained position transferring the force to the tensioning arms 1265 which slide the sliding tensioning bar 1268 the length of the slots 1258. When the handle 1262 is closed, it is latched or locked into a strained position by locking or latching mechanism 1275. As shown in FIG. 55C, the locking mechanism 1275 comprises a latch 1277 on the frame 1251 which engages a spring biased catch 1278 on the end 1264 of the handle 1262. A release button 1279 on the end 1264 of the handle 1262 may be used to depress the spring loaded catch 1278 to release it from the latch 1277.

After the skin treatment device is strained, the applicator 1250 may be used to press the skin treatment device to the skin. As shown in FIGS. 55A to 55E, a stamper 1281 with one or more pressure members 1283 may be used to apply a relatively even pressure to portions of the skin treatment device 1285 where an adhesive interfaces with the skin. The stamper 1281 includes a spring loaded plunger handle 1282 that may be used to apply pressure to the skin treatment device while or after the skin treatment device has been applied to the skin. In other variations, the frame may provide an opening on the superior surface of the applicator to provide access to the superior surface of the skin treatment device, which allows a user to apply manual pressure to the skin treatment device as or after it is applied to the skin.

The applicator 1250 may also be configured to provide a mechanical advantage by providing a substantially longer pivoting handle relative to the coupling location of the tensioning arms from the pivot point of the pivot handle. In some variations, the coupling location as a percentage of the distance from the pivot point to the distal end of the pivoting handle farthest away from the pivot point may be less than about 50%, less than about 40%, less than about 30%, or less than about 20%, for example.

FIGS. 56A to 56E illustrate another variation of a tensioning device, straining device or an applicator 1300 with a stamper 1330. The applicator 1300 comprises a tensioning device 1305 enclosed by a housing 1331, a plunger 1332 on the top of the housing 1331, to actuate the stamper 1330 which includes pressure members 1339 positioned or positionable within or through the tensioning device 1305. Slide actuators or side buttons 1301, 1302 extend from each side 1333, 1334 of the housing. The side buttons 1301, 1302 may be manipulated by squeezing them together to strain an attached skin treatment device in a manner otherwise similar to that described with respect to actuator 1100 of FIG. 53A.

The applicator 1300 includes a tensioning structure 1305 comprising a moveable, slidably or a collapsing or expanding frame structure 1325. Frame structure 1325 comprises a pair of arms elements 1320, 1321 and pair of arms elements 1322, 1323. Arm elements 1320, 1321 and arm elements 1322, 1323 respectively are slidably coupled so they can expand or collapse the frame structure 1325 by increasing or decreasing the distance between sides or side walls 1308, 1309 of the frame structure 1325. The walls 1308, 1309 may also slide together into a closed or unstrained position (FIGS. 56A, 56C, 56E) or expand to an open or strained position (FIGS. 56B and 56D).

Attachment structures 1306, 1307 are coupled to and move with side walls 1308, 1309. In an unstrained configuration (FIGS. 56A, 56C, 56E), the walls 1308, 1309 area first shorter distance from each other to facilitate loading of an unstrained skin treatment device. In a strained configuration (FIGS. 56B, 56D,) the opposing walls 1308, 1309 are a second greater distance from each other.

The tensioning structure 1305 may further comprise opposing movable, pivotable or hinge members 1310, 1311. Hinged member 1310 comprises a first and second hinge segments 1312a, 1313a that are movably, pivotally or hingedly connected to each other by way of side button 1301, at pivot points 1314a and 1314b, respectively. Hinged member 1311 comprises first and second hinge segments 1312b, 1313b that are movably, pivotally or hingedly connected to each other by way of side button 1302 at pivot points 1315a, 1315b respectively. Segments 1312a and 1313b may be movably, pivotally or hingedly coupled respectively to opposite end sides 1308a, 1308b of wall 1308. Segments 1312b and 1313a may be movably, pivotally or hingedly coupled respectively to opposite end sides 1309b, 1309a of wall 1309.

The tensioning structure 1305 further comprises guide structures 1343, 1344 coupled to walls 1308, 1309. (FIG. 56E). Guide rods 1341, 1342 are attached to side buttons 1301, 1302 and extend inwardly through guide slots 1345, 1346 of guide structures 1343, 1344 to align movement of the hinge members 1310, 1311 with respect to the frame structure 1325.

Figure 56A:
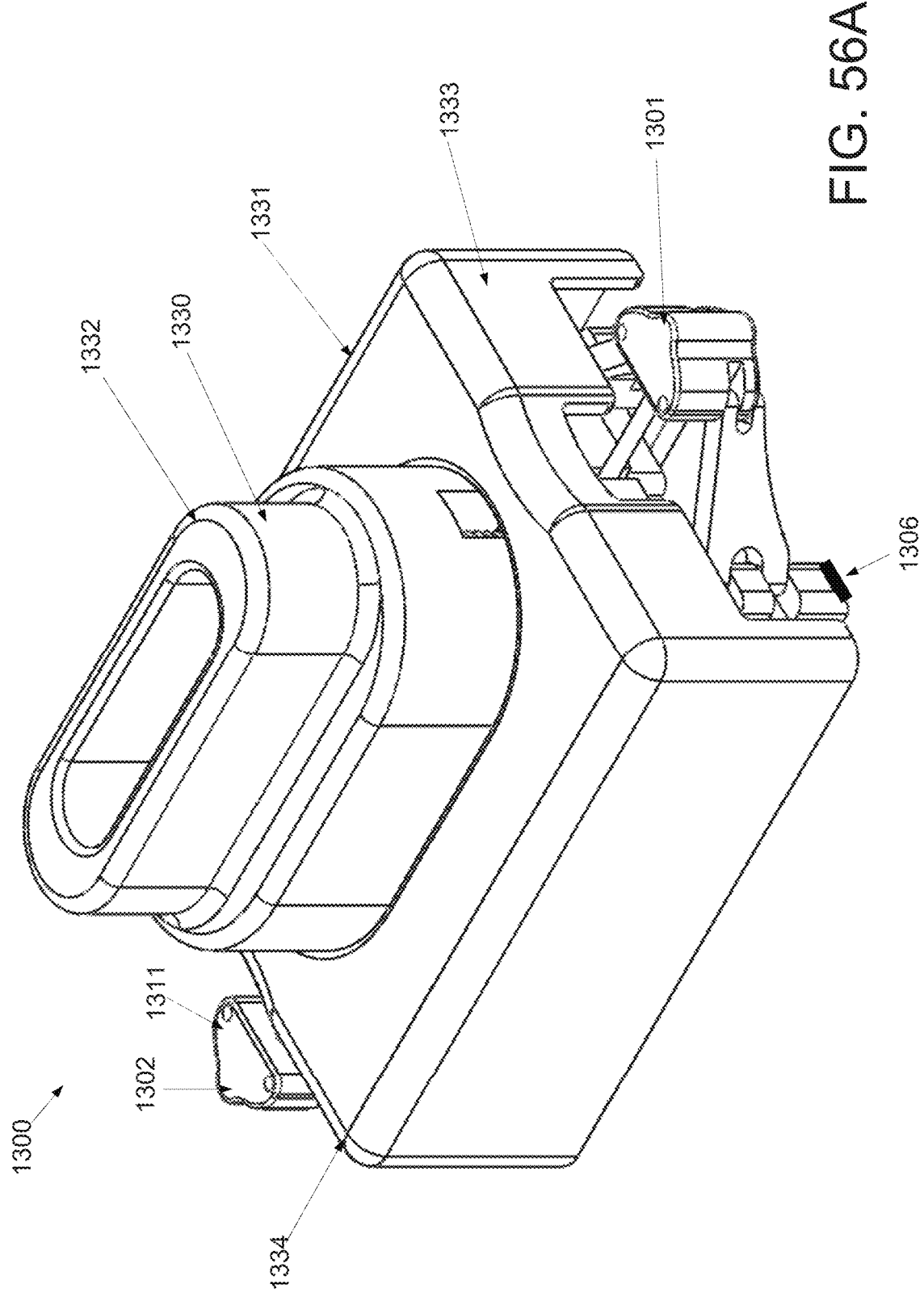
FIG. 56A is a perspective view of an applicator with an integrated foam stamper in an unstrained configuration.
Figure 56B:
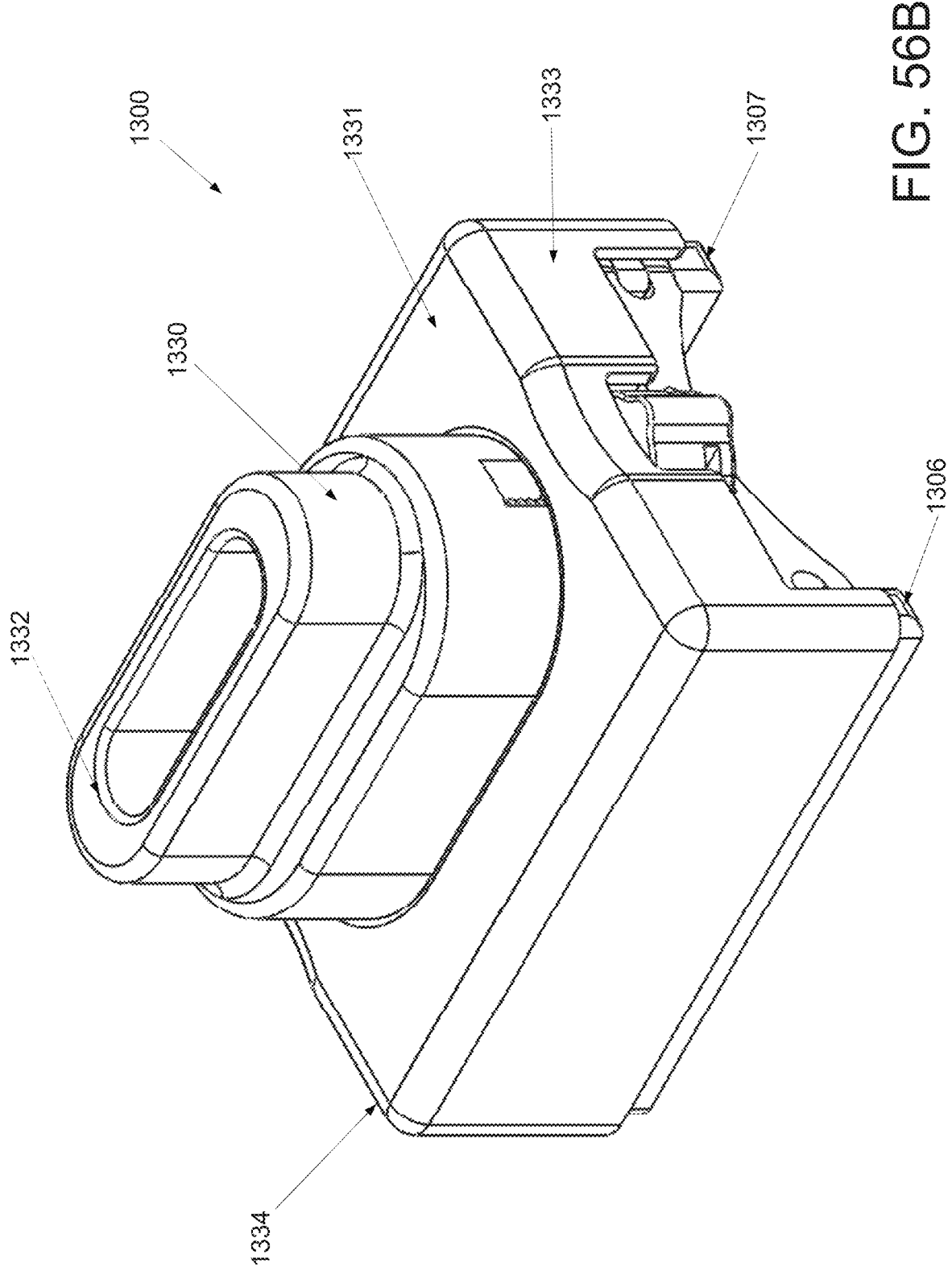
FIG. 56B is a perspective view of the applicator of FIG. 56A in a strained configuration.
Figure 56C:
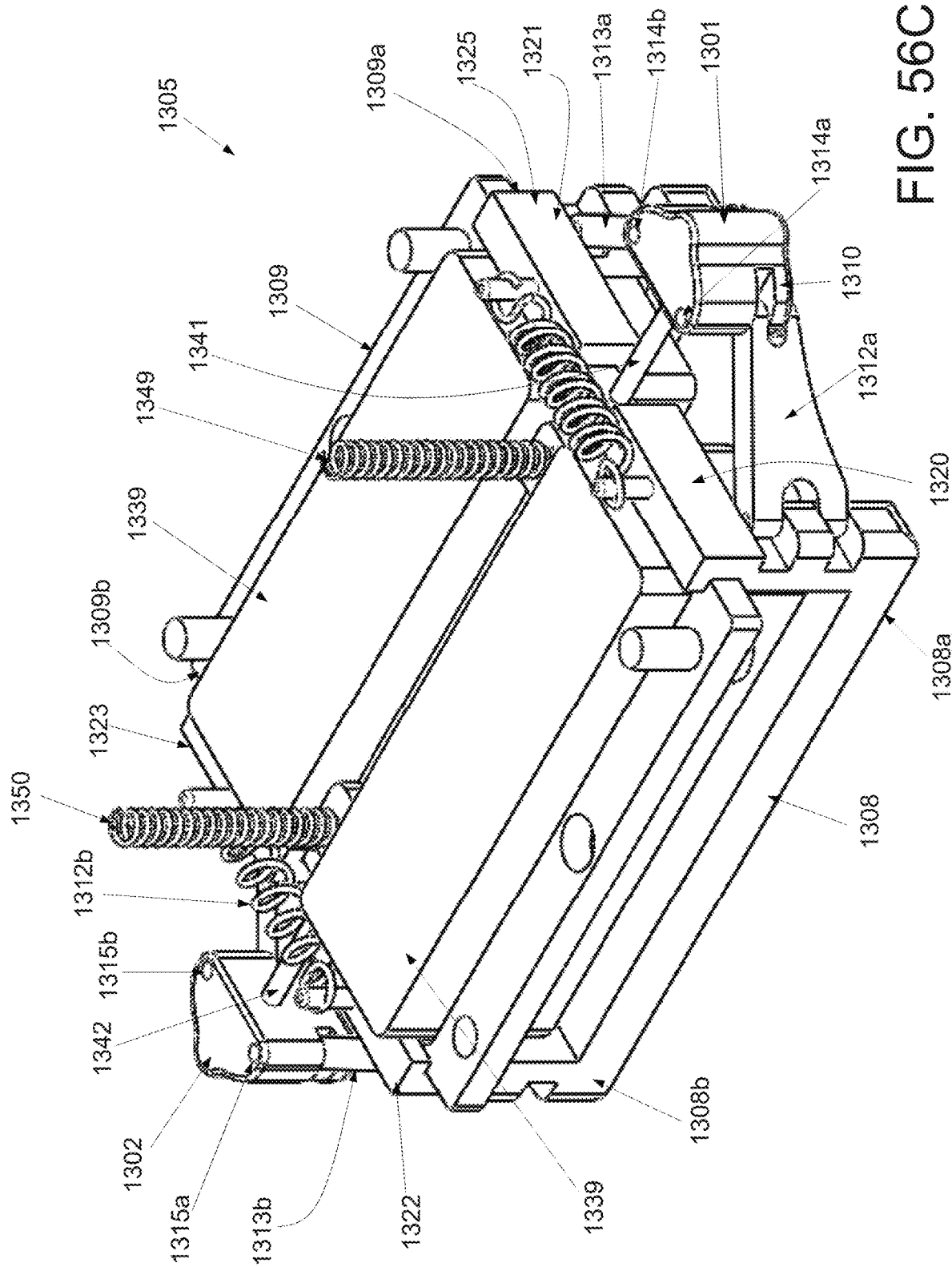
FIG. 56C is a perspective view of the tensioning device of the applicator of FIG. 56A in an unstrained configuration.
Figure 56D:
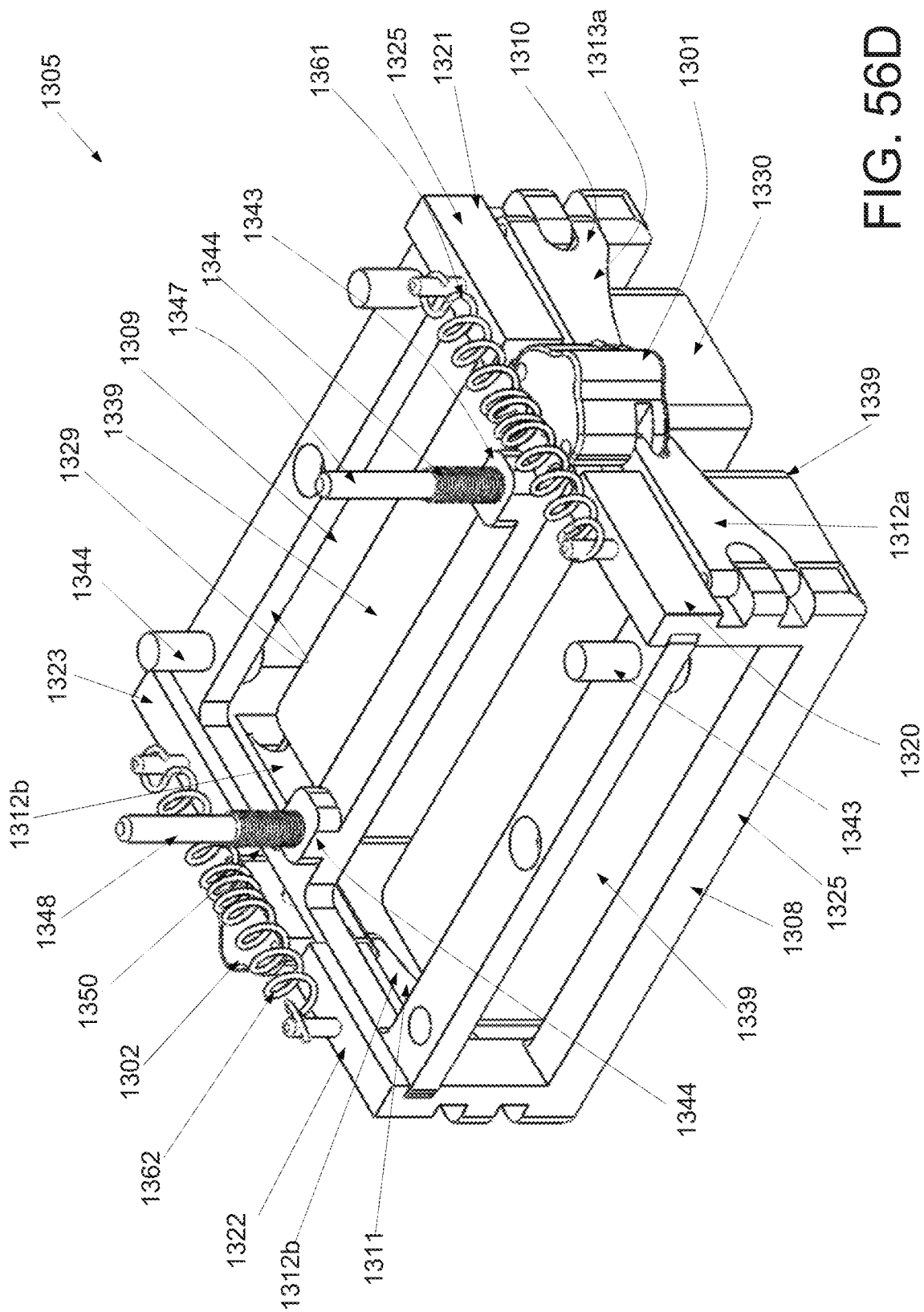
FIG. 56D is a perspective view of the tensioning device of the applicator of FIG. 56A in a strained configuration.
Figure 56E:
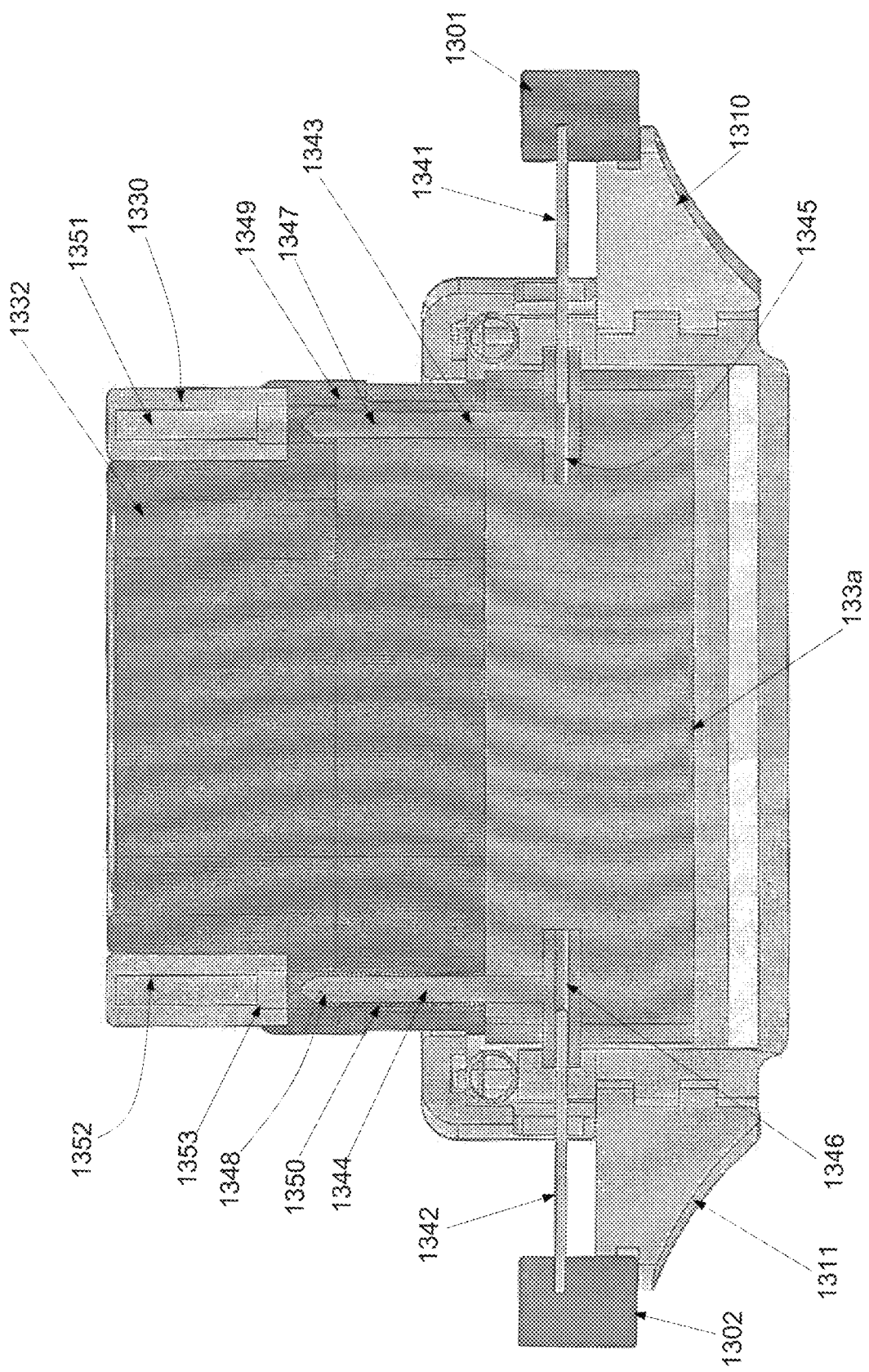
FIG. 56E is a side cross sectional view of the applicator of FIG. 56A in an unstrained configuration.

FIGS. 56A, 56C and 56E illustrate the applicator 1300 in a first, unstrained position. The tensioning structure 1305 is in a collapsed position. Segments 1312a, 1313a and side button 1301 are pivoted to form a collapsed, folded or v-shape extending outward of the applicator, and segments 1312b, 1313b and side button 1302 are pivoted to form a convex or v-shape extending outward of the applicator 1300 so that the distance between walls 1308, 1309 is relatively shorter. This facilitates loading of an unstrained skin treatment device. After an unstrained device is loaded, the skin treatment device is strained by applying pressure to the side buttons 1301, 1302. This forces segments 1312a, 1313a and segments 1312b, 1313b to pivotally move into a straightened, elongated or open position as shown in FIGS. 56B and 56D and thus transferring a separation force to the skin treatment device to strain the skin treatment device.

The walls 1308, 1309, and arms 1320, 1321, 1322, 1323 form a box-like structure with an opening 1329 (when in the strained configuration) to provide access to a skin treatment device when attached across the bottom of the applicator 1300 to attachment structures 1306, 1307. The stamper 1330 may be actuated to apply pressure to the skin treatment device by depressing the plunger 1332 to advance the pressure members 1339 through the opening 1329 and against a skin treatment device, as and/or after it is being applied. The tensioning device 1305 stays fixed when the plunger 1332 is pressed. The pressure members are configured to compress over the skin treatment device to distribute even force including over non-planer surfaces or body areas. A mechanical, visual, electrical, audible or other indicator may be included in the stamper to signal when the correct amount of pressure has been applied to the plunger, e.g. a MEMS pressure sensor or a mechanical strain gauge coupled to the stamper mechanism. As shown, the stamper 1330 may be guided with guide posts 1347, 1348 of guide structures 1343, 1344 that are received by slots 1351, 1352 in plunger 1332. Guide posts 1347, 1348 may include spring members 1349, 1350 that interact with lip 1353 in slots 1351, 1352 to bias the stamper 1330 upward. This resists or prevents the pressure members 1339 from deploying without applying a force and facilitates reloading by springing stamper 1330 back in to a loading position.

The applicator 1300 is shown in an open or unlocked position in FIGS. 56A, 56C and 56E. When the device is in the strained position as shown in FIGS. 56B and 56D, the hinge segments 1312a, 1313a and 1312b, 1313b of side structures 1310 and 1311 may be configured to pivoted slightly inward and off-center to lock the device into place or to resist or prevent collapse of the walls back into the v-shaped or folded configuration. Springs 1361, 1362 attached to posts 1363, 1364 on arm members 1320, 1321, and 1322, 1323 respectively bias the arm member 1320, 1321, and 1322, 1323 together. Thus, where the tensioning member 1305 is in the locked position, the springs 1361, 1362 prevent the sliding members from opening or unlocking. Thus the applicator 1300 may be maintained or locked in a strained configuration. The springs 1361, 1362 also spring the tensioning device back to a loading or unstrained position when the device is unlocked for reloading. The springs 1361, 1362 help maintain the device in the unstrained configuration to facilitate loading.

Alternatively, without the stamper 1330, the opening 1329 may provide access to a user to apply pressure to a skin treatment device as or after it is applied to a skin surface. In variations without a stamper, the opening may be enlarged to facilitate manipulation of the skin treatment device manually.

In a variation Illustrated in FIGS. 56A to 56E the attachment structures 1306, 1307 comprise hook or loop mechanisms. The applicator or skin treatment device attachment structures may comprise other types of attachment structures, including but not limited to other attachment structures described or set forth herein.

FIGS. 57A to 57I illustrate another variation of a tensioning device, straining device, or applicator with a stamper. The applicator 1400 comprises a tensioning device 1405 enclosed by a housing 1431; a plunger 1432 on the top of the housing 1431 to actuate the stamper 1430. The stamper 1430 includes pressure members 1439 positioned or positionable within or through the tensioning device 1405. Side buttons 1401, 1402 extend from each side 1433, 1434 of the housing. The side buttons 1401, 1402 are actual* by squeezing them together to strain a skin treatment device attached to the applicator in a manner similar to that described with respect to actuator 1100 of FIG. 53A and actuator 1300 of FIG. 56A.

The applicator 1400 includes a tensioning structure 1405 comprising a fixed frame structure 1424 and moveable, slidable or a collapsing or expanding frame structure 1425. Frame structure 1424 comprises opposing side walls 1413, 1414 and end walls 1415, 1416, and middle support structure 1417 extending from end wall 1415 to end wall 1416, which in combination form openings 1427, 1428 in frame structure 1424. Openings 1427, 1428 may receive one or more pressure members 1439 therethrough. End walls 1415, 1416 include rails 1418 for slidably receiving rails 1404 of side walls 1408, 1409. Frame structure 1425 comprises side walls 1408, 1409 and opposing movable, pivotable or hinge members 1410, 1411. Hinged member 1410 comprises first and second hinge segments 1420, 1421. Hinged member 1411 comprises first and second hinge segments 1422, 1423. Hinge segments 1420, 1421 and hinge segments 1422, 1423 are movably, pivotally or hingedly connected to each other by way of side buttons 1401, 1402 respectively at a pivot points so they can expand or collapse the frame structure 1425, increasing or decreasing the distance between sides or side walls 1408, 1409 of the frame structure 1425. The walls 1408, 1409 may slide together into a closed or unstrained position (FIGS. 57A, 57C, 57E and 57F) or expand to an open or strained position (FIGS. 57B, 57D), Rails 1404 of walls 1408, 1409 engage rails 1418 to maintain the walls 1408, 1409 of frame structure 1425 in alignment with the frame structure 1424 when sliding back and forth.

Attachment structures 1406, 1407 are coupled to and move with side walls 1408, 1409. In an unstrained configuration (FIGS. 57A, 57C, 57E and 57F), the walls are a first shorter distance from each other facilitating loading of an unstrained skin treatment device. In a strained configuration (FIGS. 57B, 57D, 57G, 57H, 57I) the opposing walls are a second greater distance from each other.

The moveable frame structure 1425 is further coupled to the stationary structure 1424 with latching guide rods 1441 that are attached to side buttons 1401, 1402. Latching guide rods 1441 slide inward or outward through guide slots 1443 in middle support structure 1417. Latching guide rods 1441 serve to align movement of the hinge members 1410, 1411 with respect to the frame structure 1424 and frame structure 1425. Latching guide rods 1441 include latch members 1442 at their distal ends. The latch members 1442 engage catches 1444 at the ends of guide slots 1443 when the buttons 1401, 1402 are pushed in and the device is in a strained position.

Figure 57A:
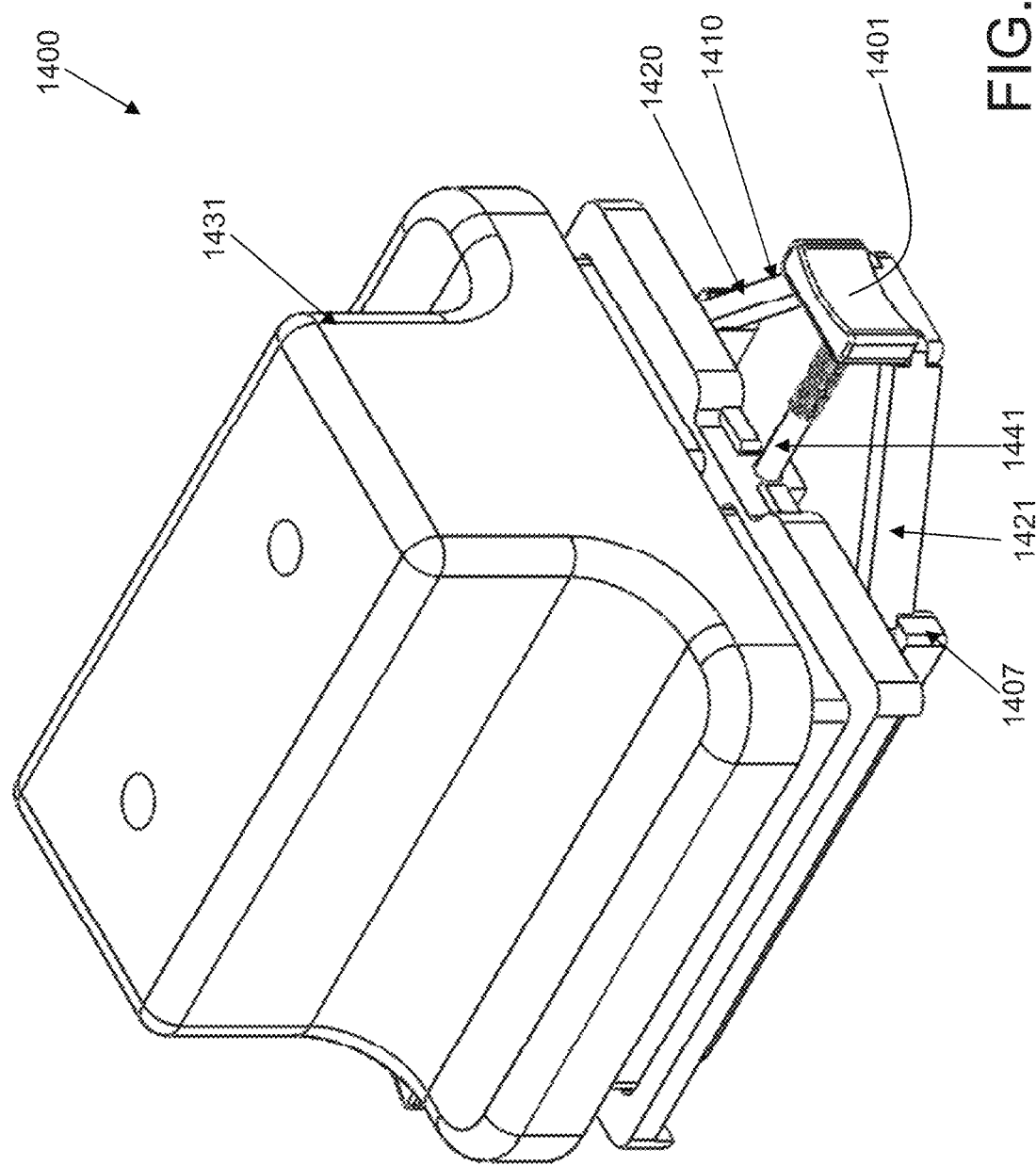
FIG. 57A is a perspective view of an applicator with an integrated foam stamper in an unstrained configuration.
Figure 57C:
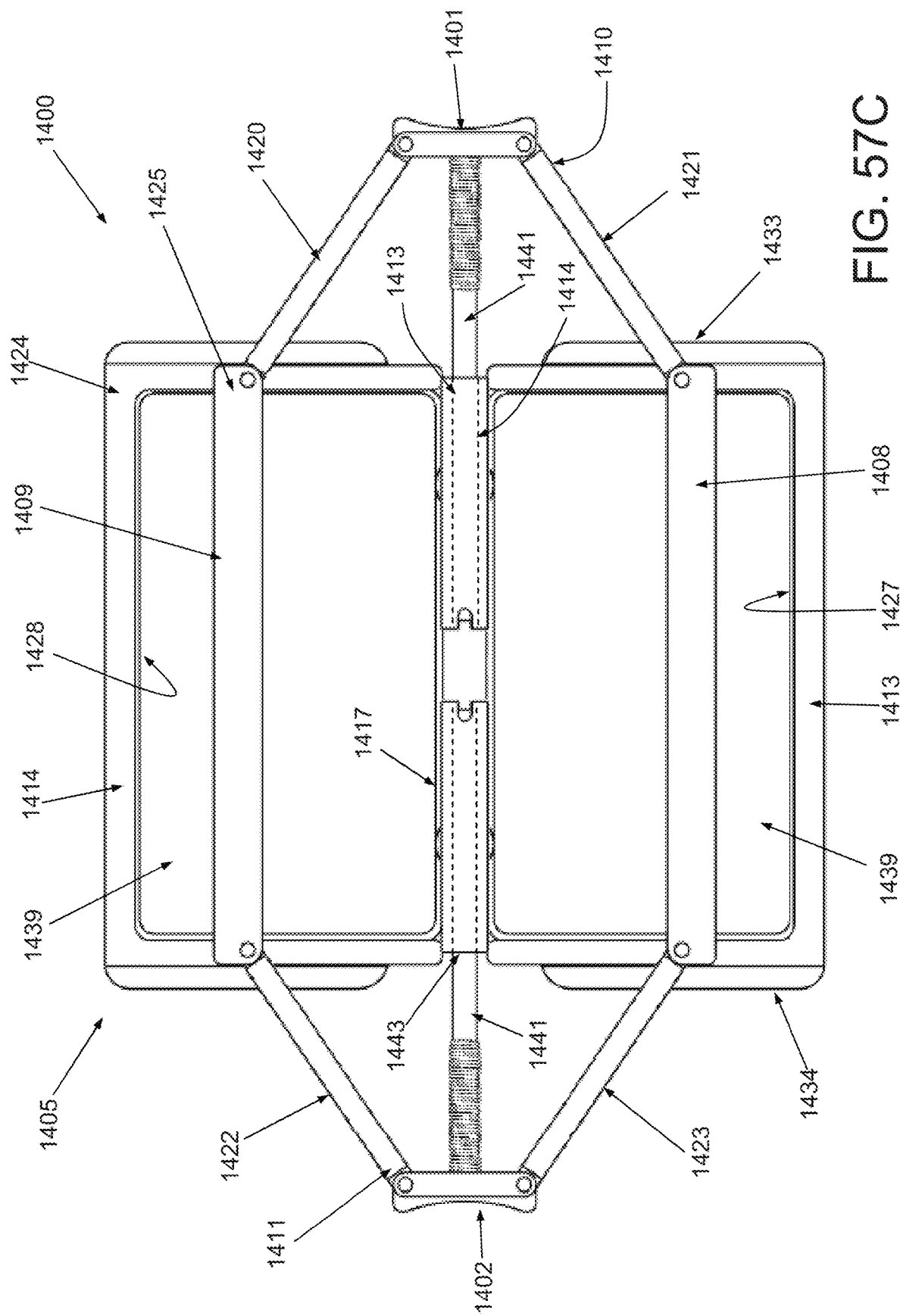
FIG. 57C is an inferior view of the tensioning device of the applicator of FIG. 57A in an unstrained configuration.
Figure 57D:
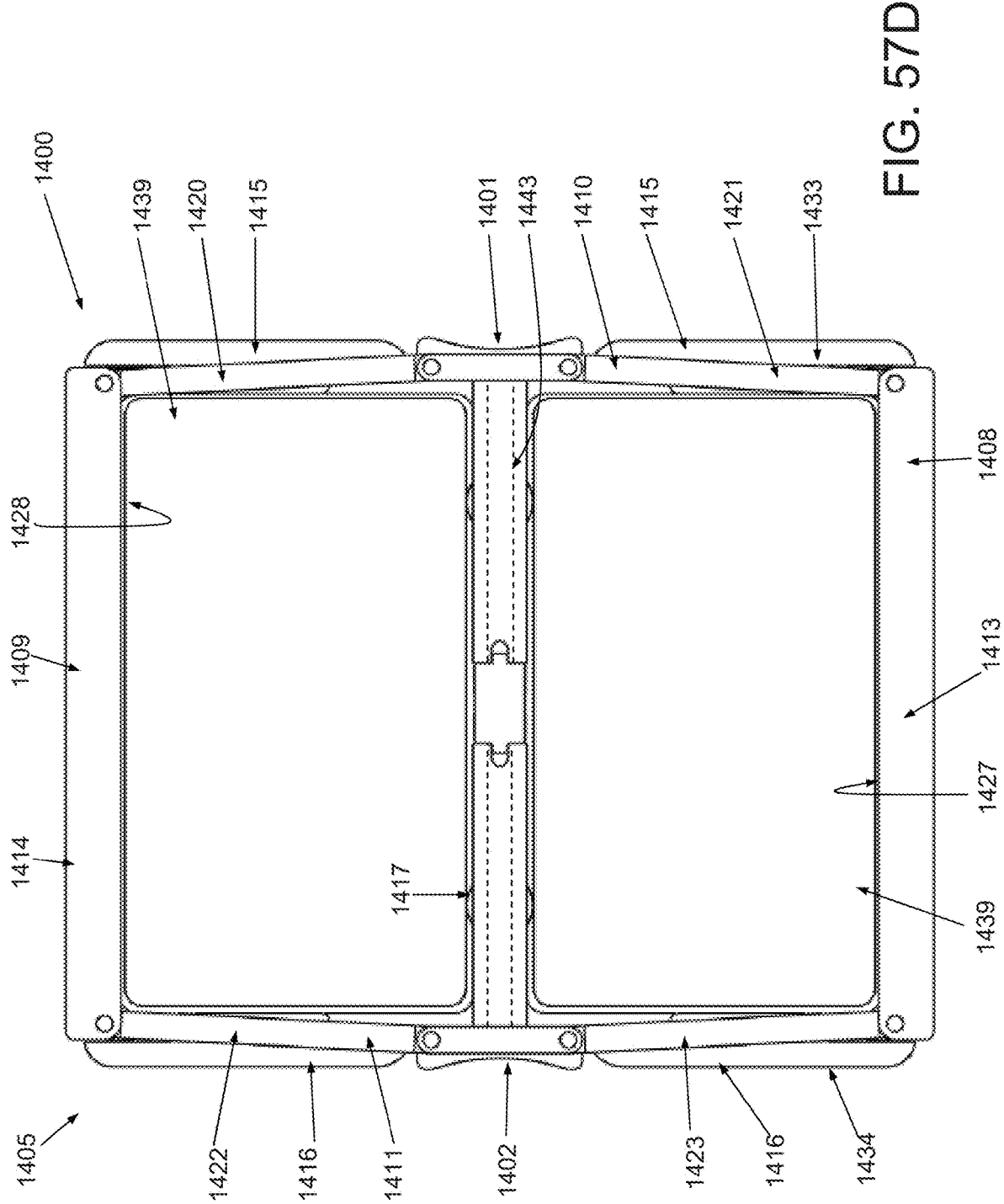
FIG. 57D is an inferior view of the tensioning device of the applicator of FIG. 57A in a strained configuration.
Figure 57E:
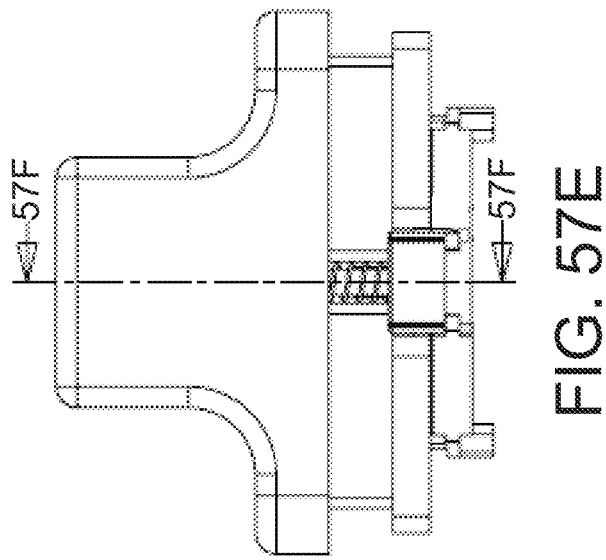
FIG. 57E is a front elevational view of the tensioning device of the applicator of FIG. 57A in an unstrained configuration.
Figure 57F:
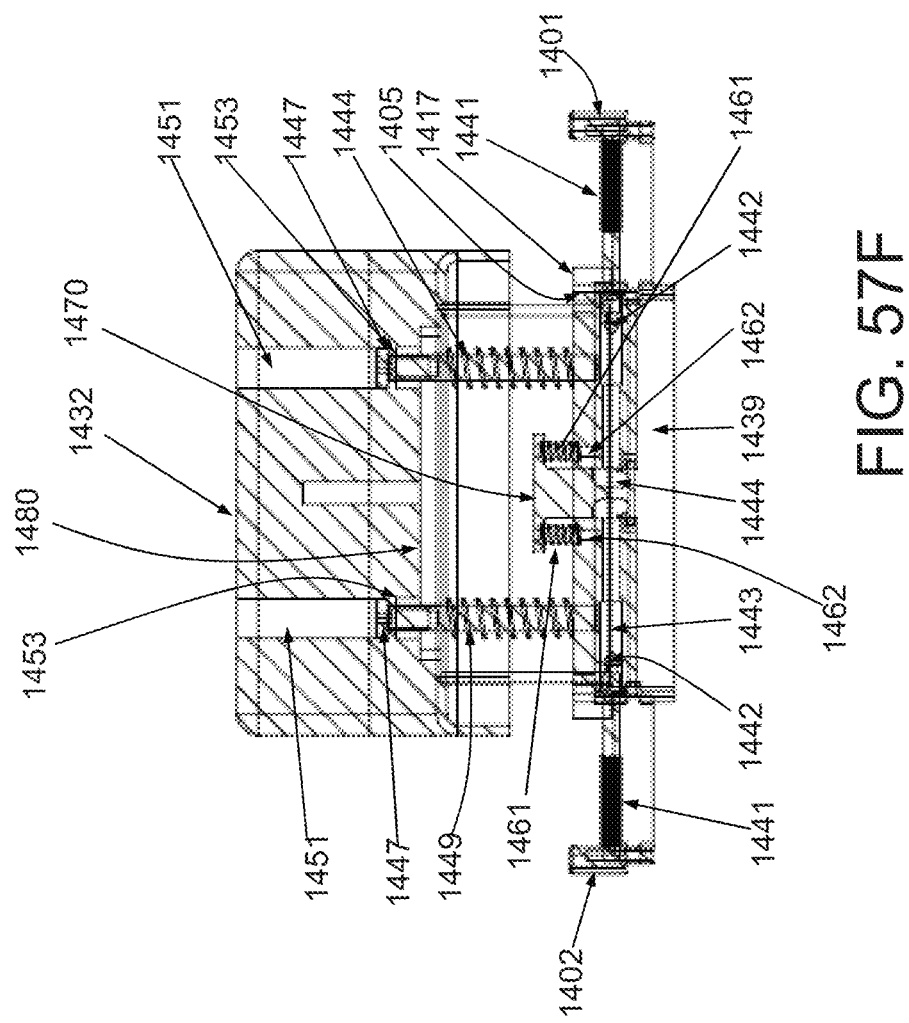
FIG. 57F is a cross sectional view of the device as indicated in FIG. 57E.
Figure 57G:
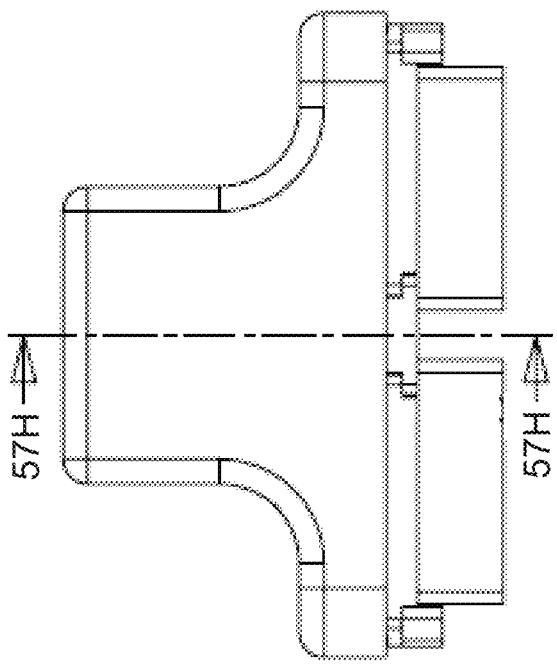
FIG. 57G is a side elevational view of the tensioning device of the applicator of FIG. 57A in a strained and stamped configuration.
Figure 57H:
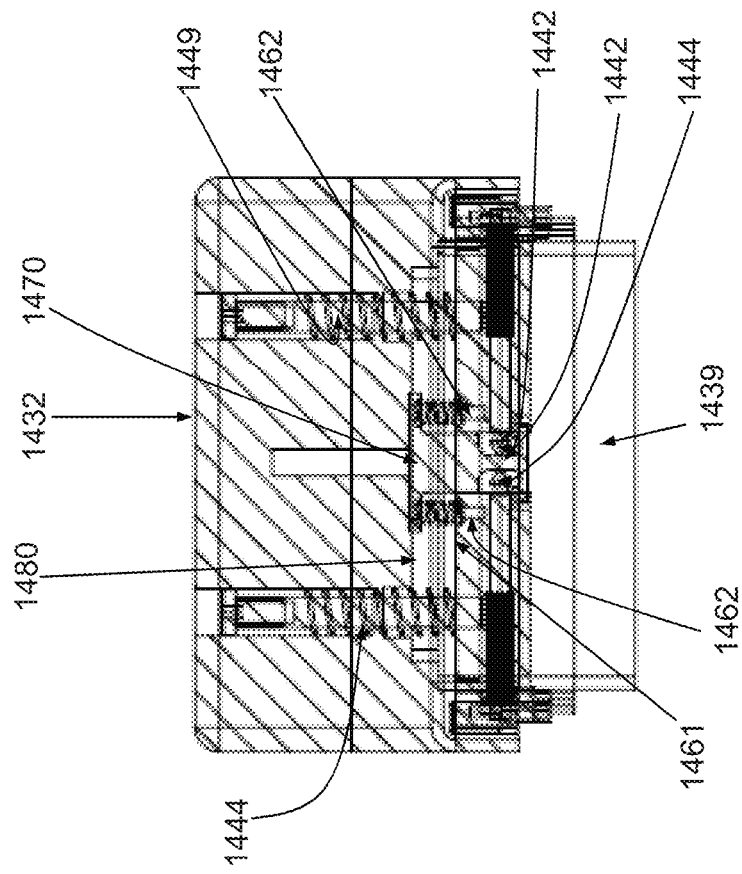
FIG. 57H is a cross sectional view of the device as indicated in FIG. 57G.
Figure 57I:
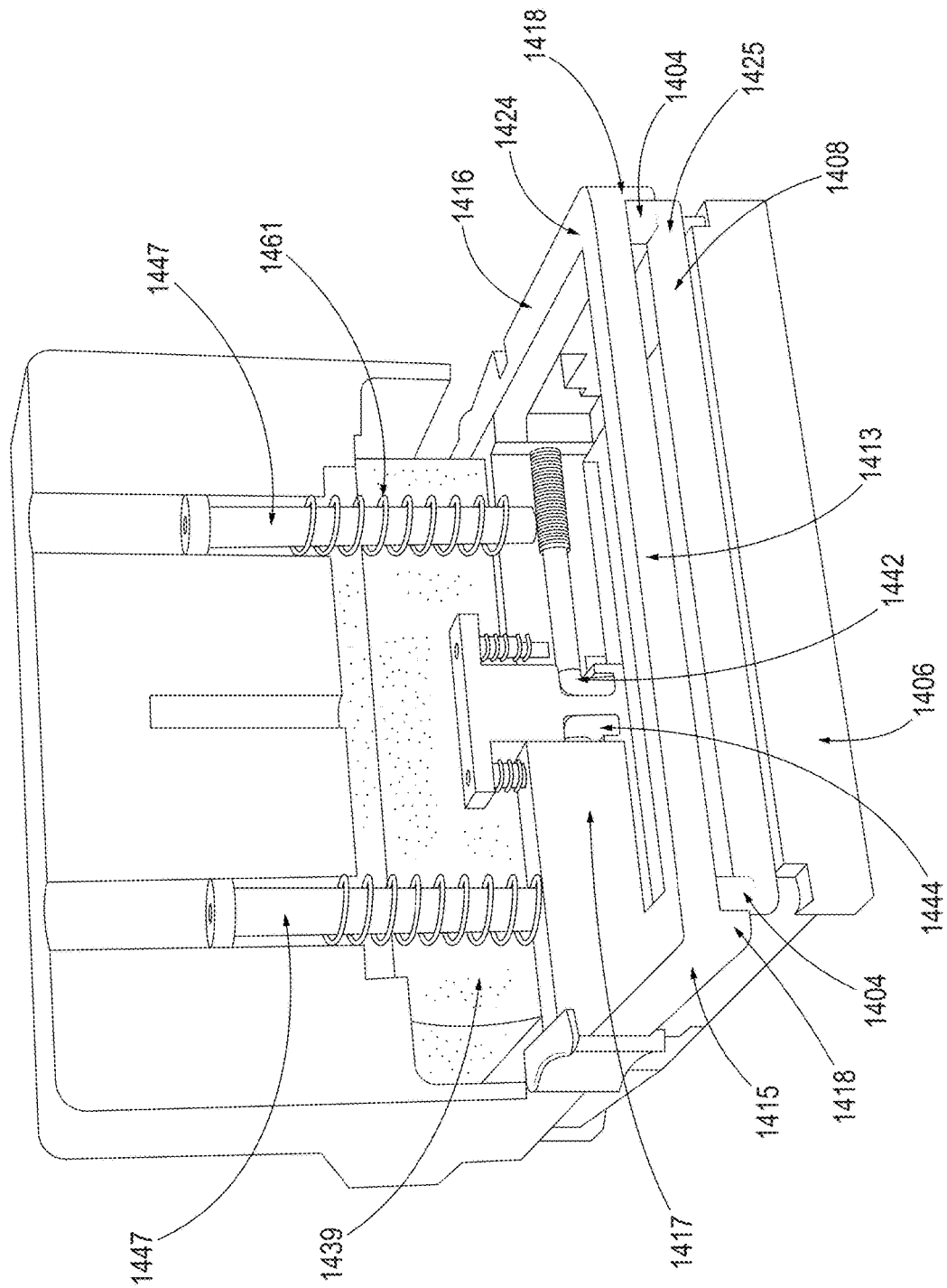
FIG. 57I is a partial cut-away perspective view of the tensioning device of the applicator of FIG. 57A in a strained configuration.

FIGS. 57A, 57C, 57E and 57F illustrate the applicator 1400 in a first, unstrained position. The tensioning structure 1405 is in a collapsed position. Hinge segments 1420, 1421 and side button 1401 are pivoted to form a convex or v-shape extending outward of the applicator, and hinge segments 1422, 1423 and side button 1402 are pivoted to form a collapsed, folded or v-shape extending outward of the applicator 1400 so that the distance between end walls 1408, 1409 is relatively shorter. This facilitates loading of an unstrained skin treatment device. After an unstrained skin treatment device is loaded, it is strained by applying pressure to the side buttons 1401, 1402. This forces hinge segments 1420, 1421 and hinge segments 1422, 1423 to pivotally move into a straightened, elongated or open position as shown in FIGS. 579 and 57D and thus transferring a separation force to the skin treatment device to strain the skin treatment device.

The walls 1408, 1409, and hinge members 1410, 1411 form a box-like structure with an opening 1429 through moveable frame structure 1425 (when in the strained configuration) to provide access to a skin treatment device attached across the bottom of the applicator 1400 to attachment structures 1406, 1407. The stamper 1430 may be actuated to apply pressure by depressing the plunger 1432 to advance the pressure members 1439 through the opening 1429 and openings 1427, 1428 to a skin treatment device as or after it is being applied. As shown, the stamper 1430 may be guided with guide posts 1447 fixed to middle support structure 1417. Guide posts 1447 are received by slots 1451 in plunger 1432. Guide posts 1447 may include spring members 1449 that interact with lip 1453 in slots 1451 to bias the stamper 1430 upward. This resists or prevents the pressure members 1339 from deploying without applying a force and facilitates reloading by springing stamper 1430 back in to a loading or unstrained position.

The device is shown in an open or unlocked position in FIGS. 57A, 57C, 57E and 57F. When the device is in the strained position as shown in FIGS. 57B, 57D, 57G, 57H and 57I, buttons 1401, 1402 are pressed inward and latching members 1442 on the guide rods 1441 engage with catches 1444 in the T-bar 1470 (contiguous with the guide slots 1443) to lock the buttons 1401, 1402 into place in a strained position. Springs 1449 bias guides rods 1441 outward so that when the latch members 1442 are released from the catches 1444, the buttons 1401, 1402 spring open. The latching members 1442 remain latched until a sufficient stamping force is applied as described below.

A T-bar release 1470 may be slidably positioned in the middle of middle support structure 1417. The T-bar. 1470 may be biased upward by spring members 1461 that are positioned over alignment pins 1462 for aligning T-bar 1470 over guide slots 1443. In an upward biased position, the T-bar has openings with catches 1444 that are contiguous with guide slots 1443. The tensioning member 1405 remains in the locked position, until the stamper 1430 is depressed, and a ceiling 1480 of the stamper engages the top of the t-bar 1470 to depress the T-bar 1470 typically biased upward by spring members 1461. The catches 1444 move downward to release the latching member 1442 and the guide rods 1441 from locking engagement with the catches 1444. When released, springs 1449 bias guide rods 1441 outward to thereby spring buttons 1401 1402 back into a loading or unstrained configuration.

Alternatively, without the stamper 1430, the opening 1429 may provide access to a user to apply pressure to a skin treatment device as or after it is applied to a skin surface.

In a variation illustrated in FIGS. 57A to 57I, the attachment structures 1406, 1407 comprise a hook or loop mechanism. The applicator or skin treatment device attachment structures may also comprise other types of attachment structures, including but not limited to other attachment structures described or set forth herein.

Referring to FIGS. 58A to 58I, other variations of a tensioning device, straining device or applicator 1500 may include an integrated stamper 1530 and release mechanism. The applicator 1500 comprises a first pivoting frame portion 1501a having a first handle member 1502 with lower frame portion 1504 and a second pivoting frame portion 1501b with a second handle member 1503 with lower frame portion 1505. Attachment structures 1506, 1507 are respectively coupled to bottom of lower frame portions 1504, 1505. Attachment structures 1506, 1507 each comprise a pivoting, or rotating structure, e.g. roller 1508 having an attachment mechanism such as e.g., hooks or loops 1509 attached to a plurality of locations on the roller 1508. The hooks or loops 1509 may be used to attached to a skin or wound treatment device such as, for example, as described with respect to the skin treatment device 700 and attachment devices 716, 718, 732, 734 illustrated in FIGS. 47 and 48 herein. Alternative attachment structures may be used as discussed in further detail herein.

The pivoting frame portions 1501a, 1501b are pivotally coupled by connector 1510 to provide a pivot point 1512 to transfer force from the applicator 1500 to a skin treatment device coupled to the attachment structures 1506, 1507, to thereby strain the skin treatment device prior to placement on skin.

Figure 58A:
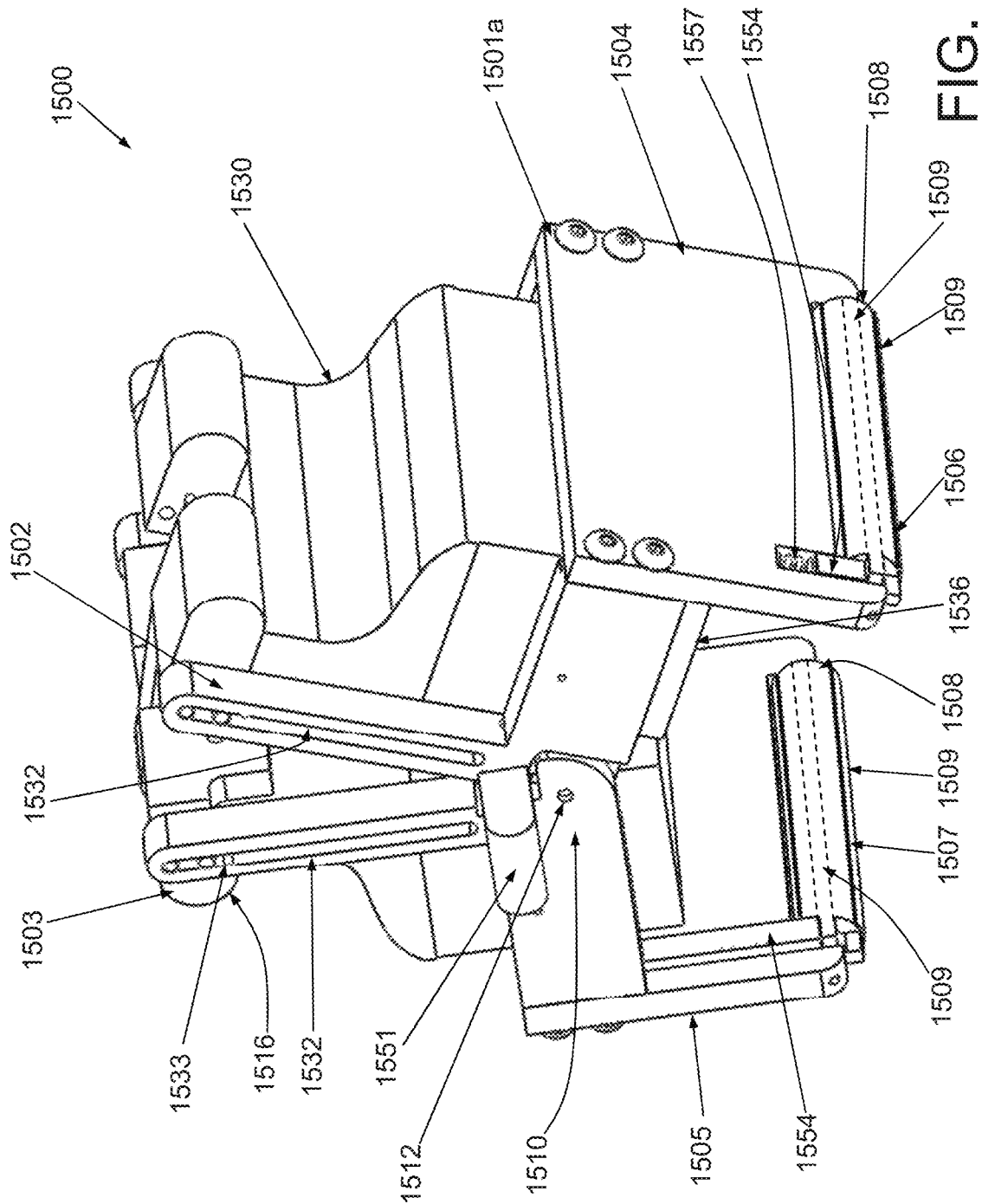
FIG. 58A is a perspective view of an applicator in an unstrained configuration.
Figure 58B:
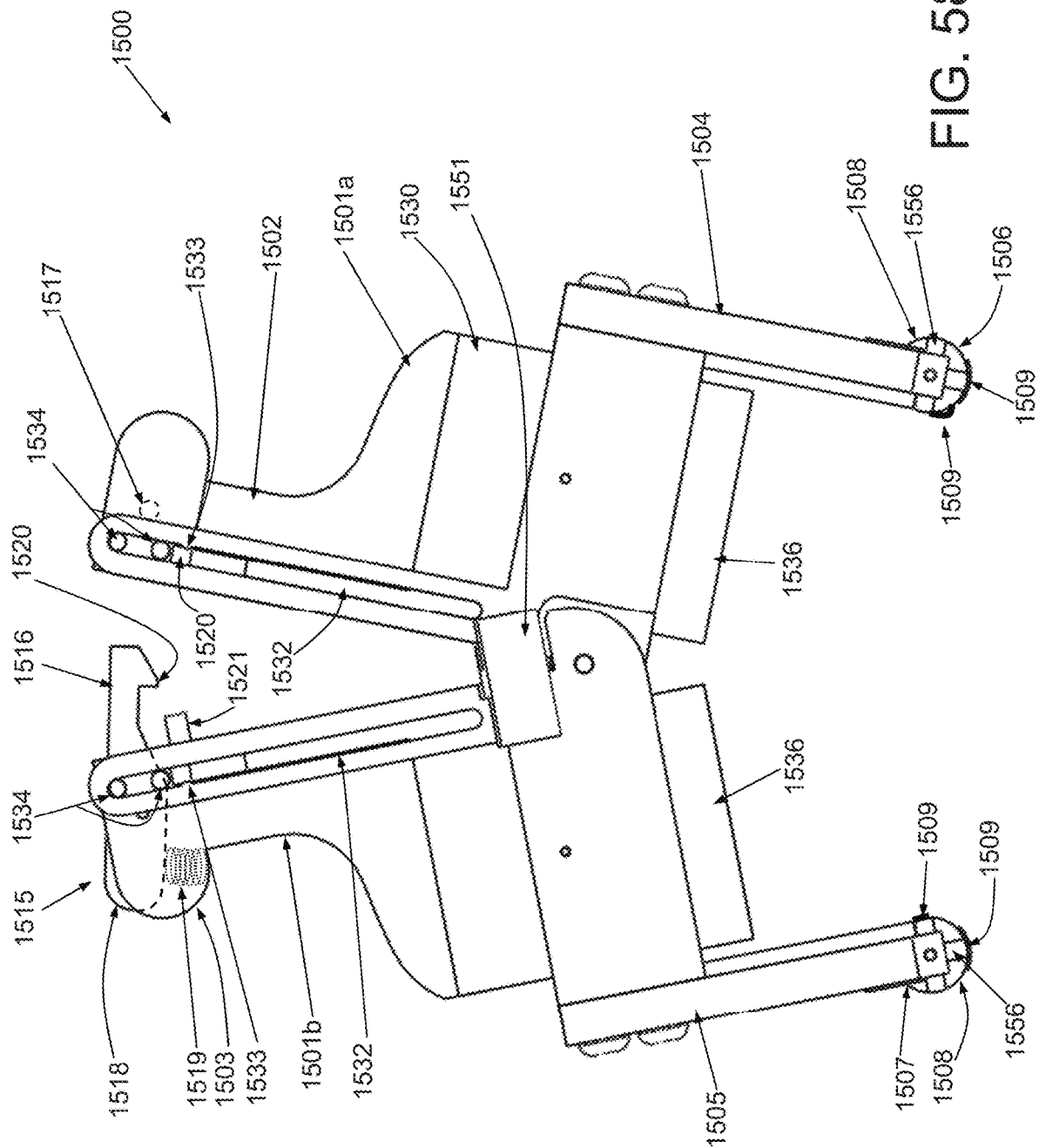
FIG. 58B is a side view of the applicator of FIG. 58A in an unstrained configuration.

FIGS. 58A and 58B illustrate an actuator or handle configuration prior to straining a skin treatment device for application to the skin of a subject. A skin treatment device may be attached to the attachment structures 1506, 1507. When an external force is applied to the actuator, e.g., the handle members 1502, 1503 of the applicator 1500 are squeezed together, the force is transferred to provide a separation force between the attachment structures 1506, 1507, coupled respectively to the bottom of the lower frame portions 1504, 1505. Optionally, the handle may be provided with a distance from the top 1511 to the pivot point 1512 that is greater than the distance from the pivot point 1512 to an attachment structure 1506 or 1507. Thus, the actuator or handle may provide a mechanical advantage greater than 1 when actuated.

Figure 58C:
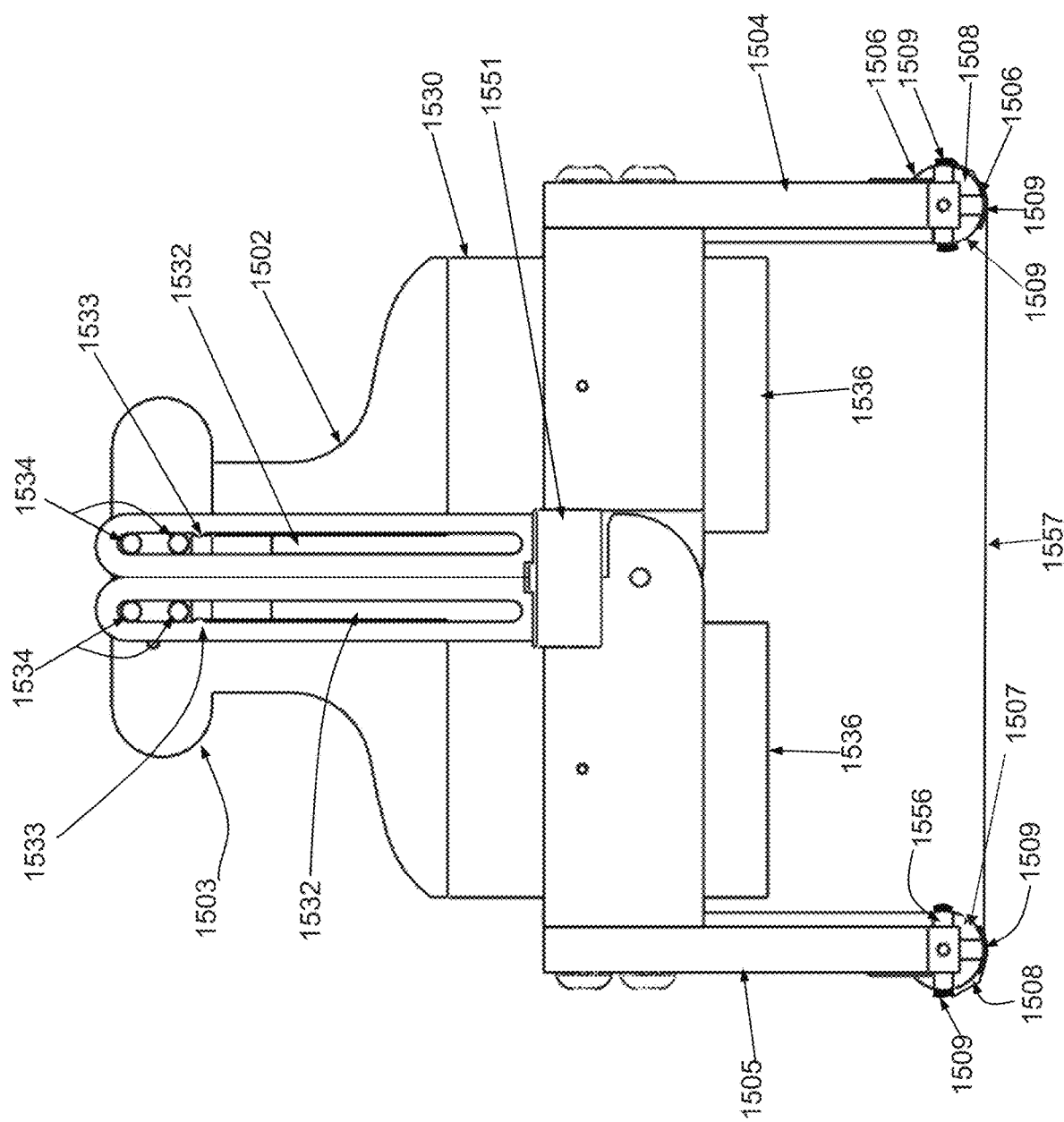
FIG. 58C is a side view of the applicator of FIG. 58A in a strained configuration.
Figure 58E:
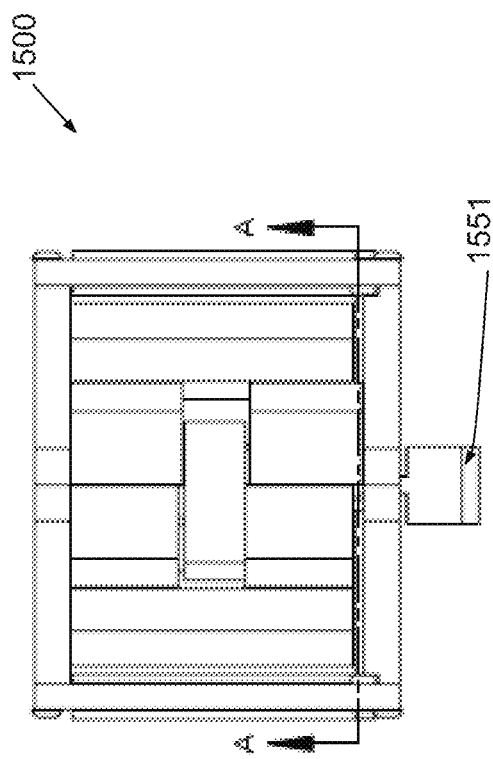
FIG. 58E is a superior view of the applicator of 58A in a strained, stamped and unreleased configuration.
Figure 58F:
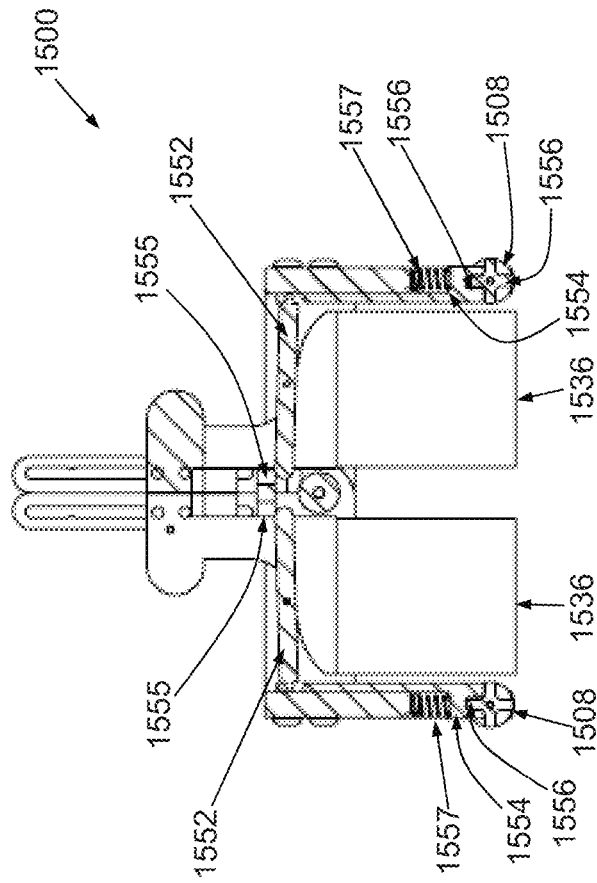
FIG. 58F is a cross-sectional view of the applicator of FIG. 58E along the lines A-A.
Figure 58I:
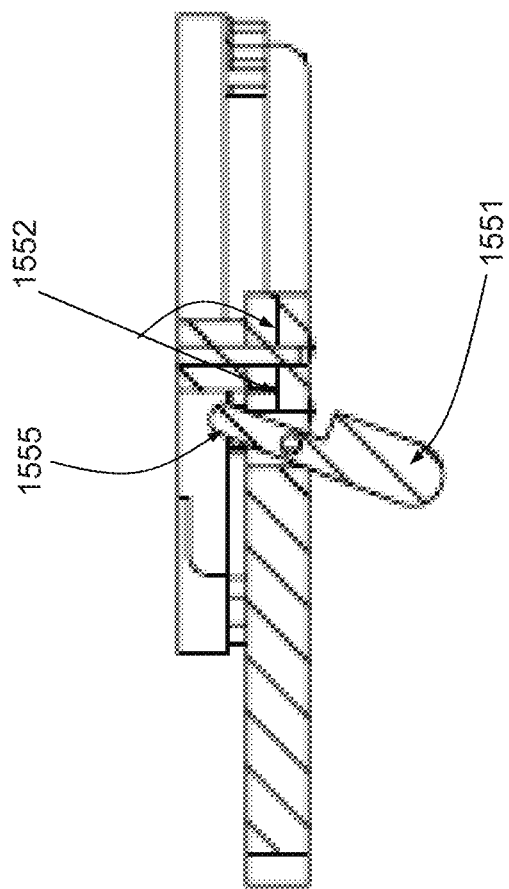
FIG. 58I is a cross-sectional view of the applicator of FIG. 58G along the lines B-B.

FIG. 58C schematically illustrates an actuator or handle configuration of the applicator 1500 where an attached skin treatment device 1557 is in a strained configuration prior to applying the stamper. The handle members 1502, 1503 have been squeezed together and a separation force has been exerted between the attachment structures 1506, 1507 to strain the attached skin treatment device.

The applicator 1500 includes a mechanism to maintain the skin treatment device in a strained configuration. Any of a variety of skin treatment devices may be used with this applicator 1500, including but not limited to skin treatment devices illustrated in FIGS. 43A to 43C and others described herein. In accordance with a variation, the handle members 1502, 1503 are releasably lockable together by a locking or latching mechanism 1515 that prevents separation of the handle members 1502, 1503 and thus the release of the strain exerted on the skin treatment device. As shown in FIG. 5813, the locking mechanism 1515 is depicted prior to closure of the handle members 1502, 1503. Alignment pin 1521 of handle 1503 fits into alignment opening 1520 of handle 1502. The locking mechanism 1515 comprises a spring loaded latch 1516 that has a hook 1520 that latches on to catch 1517 as the handle members 1502, 1503 close. The latch 1516 may be released by depressing release member 1518 to compress spring 1519 and separating handle members 1502, 1503. By locking the applicator in a strained position, a predetermined strain of a given skin treatment device may be achieved. Other locking mechanisms, including but not limited to other locking mechanisms described herein may be used. A variable locking mechanism may be used to vary the amount of strain for a given skin treatment device.

Pivoting frame portions 1501a, 1501b each further comprise guide slots 1532 coupled to the lower frame portions 1504, 1505. When the handle members 1502, 1503 are coupled together, they form a plunger for actuating the stamper 1530. The stamper 1530 comprises handle members 1502, 1503 which are attached to pressure members 1536 on their distal ends. Slots 1532 are coupled to the lower frame members 1504, 1505 and pegs 1534 on the handle members 1502, 1503 are slidable within the slots 1532.

When the device has been strained and the handle members have been latched (FIG. 58C) the dressing may be applied to the skin of a subject. The handle members 1502, 1503 that are coupled together may be depressed to apply a pressure to the back of the dressing with pressure members. Prior to stamping the dressing, detents 1533 within the guide slots 1532 prevent the stamper from self-deploying by engaging with pegs 1534. When the handle members 1502, 1503 are depressed, the force overcomes the detents 1533 and the pegs 1534 slide distally through the slots 1532. The stamper 1530 applies pressure with pressure members 1536 to the skin treatment device 1557 to activate the adhesive.

The applicator 1500 may further includes releasable attachment structures 1506, 1507. According to a variation shown in FIGS. 58A to 58I, the attachment structures 1506, 1507 each comprise lockable releasable rollers 1508. The rollers 1508 are locked when loading and applying a skin treatment device. They may be released to provide for easy release of the attachment structures.

The release and locking structure 1550 comprises a release button 1551, pivoting lifter arms 1552, and fork members 1554 biased into a locking position (e.g. downward) with springs 1557. The pivoting lifter arms 1552 are movably coupled to a first end of the fork members 1554. Fork members 1554 include roller engaging forks on the opposite end. The locking structure 1550 further comprises tabs 1556 on the rollers 1508 that engage the fork members 1554 to lock the rollers 1508. The release button 1551 has a lever end 1555 which may be pivotably moved with the release button 1551 to actuate the pivoting lifter anus 1552, which that in turn lift the attachment forks members 1554 from engagement with one of the tabs 1556 on each of the rollers 1508.

To remove the applicator 1500 from the skin treatment device, after the stamper 1530 has been used to apply sufficient pressure to the skin treatment device, the release button 1551 may be lifted to release the fork members 1554 from tabs on the roller 1508. (FIGS. 58G to 58I) The internal strain on the skin treatment device places a tangential force on the rollers 1508 causing them to rotate towards the skin treatment device. This rotation replicates a peel motion that releases the Hook and loop connection.

Each roller 1508 has four tabs 1556 and four corresponding hook or loop mechanisms 1509. After the roller 1508 is released it rotates and the fork member 1554 engages an adjacent tab 1556 and an adjacent hook or loop mechanism 1509 is positioned on the bottom of the roller 1508 for reloading the next skin treatment device.

Figure 59A:
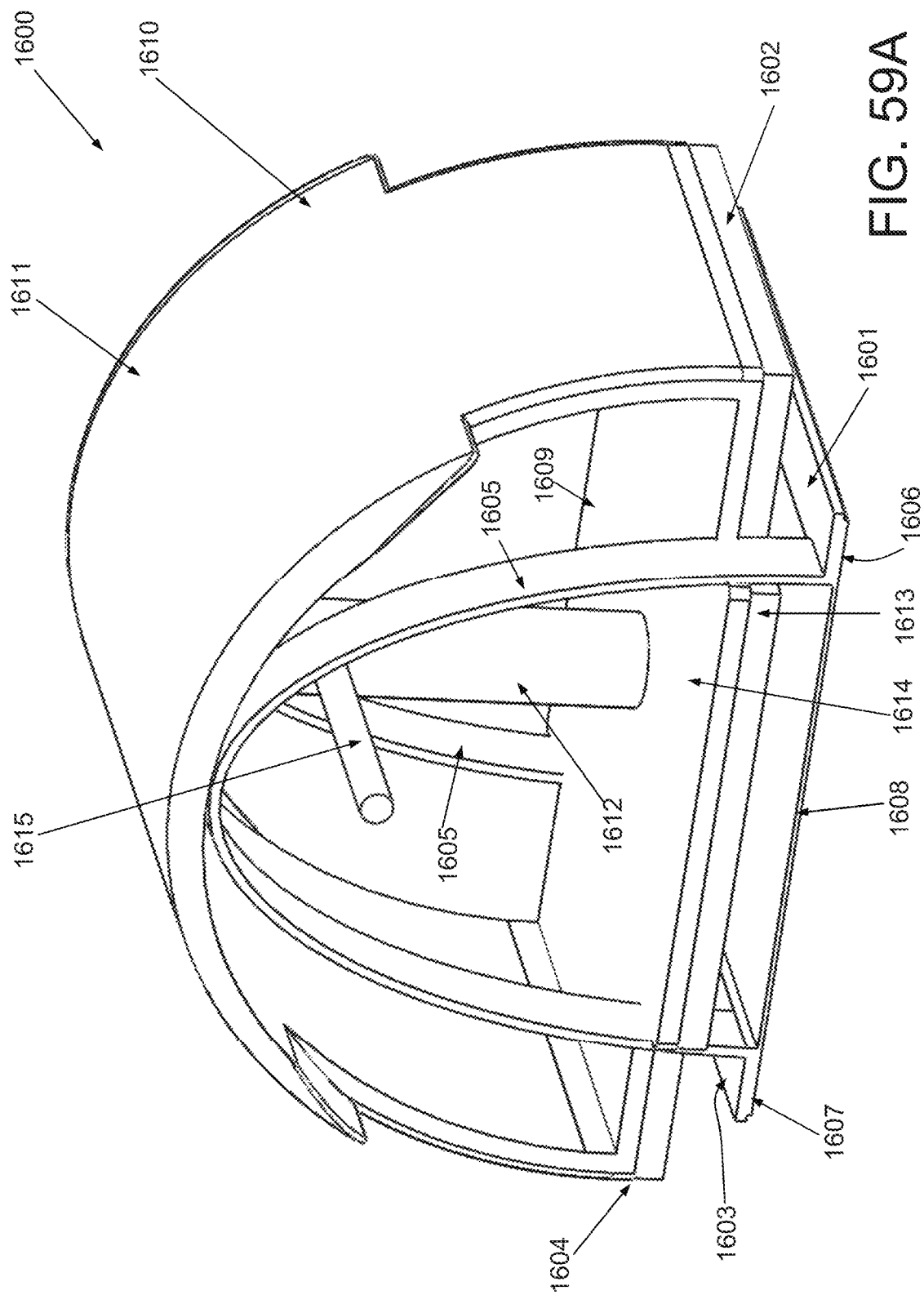
FIG. 59A is a perspective view of an applicator in an unstrained configuration.
Figure 59B:
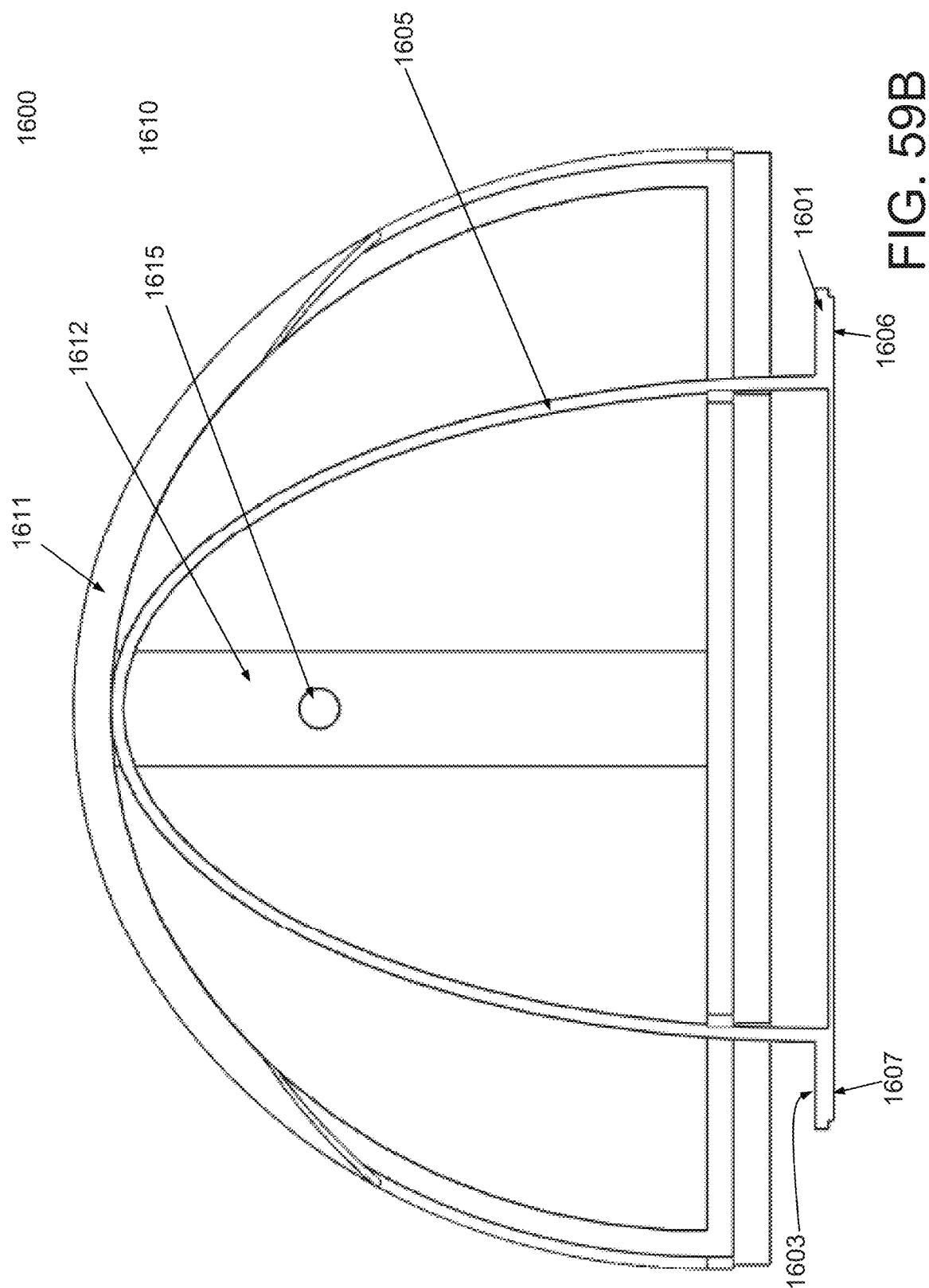
FIG. 59B is a side view of the applicator of FIG. 59A in an unstrained configuration.
Figure 59C:
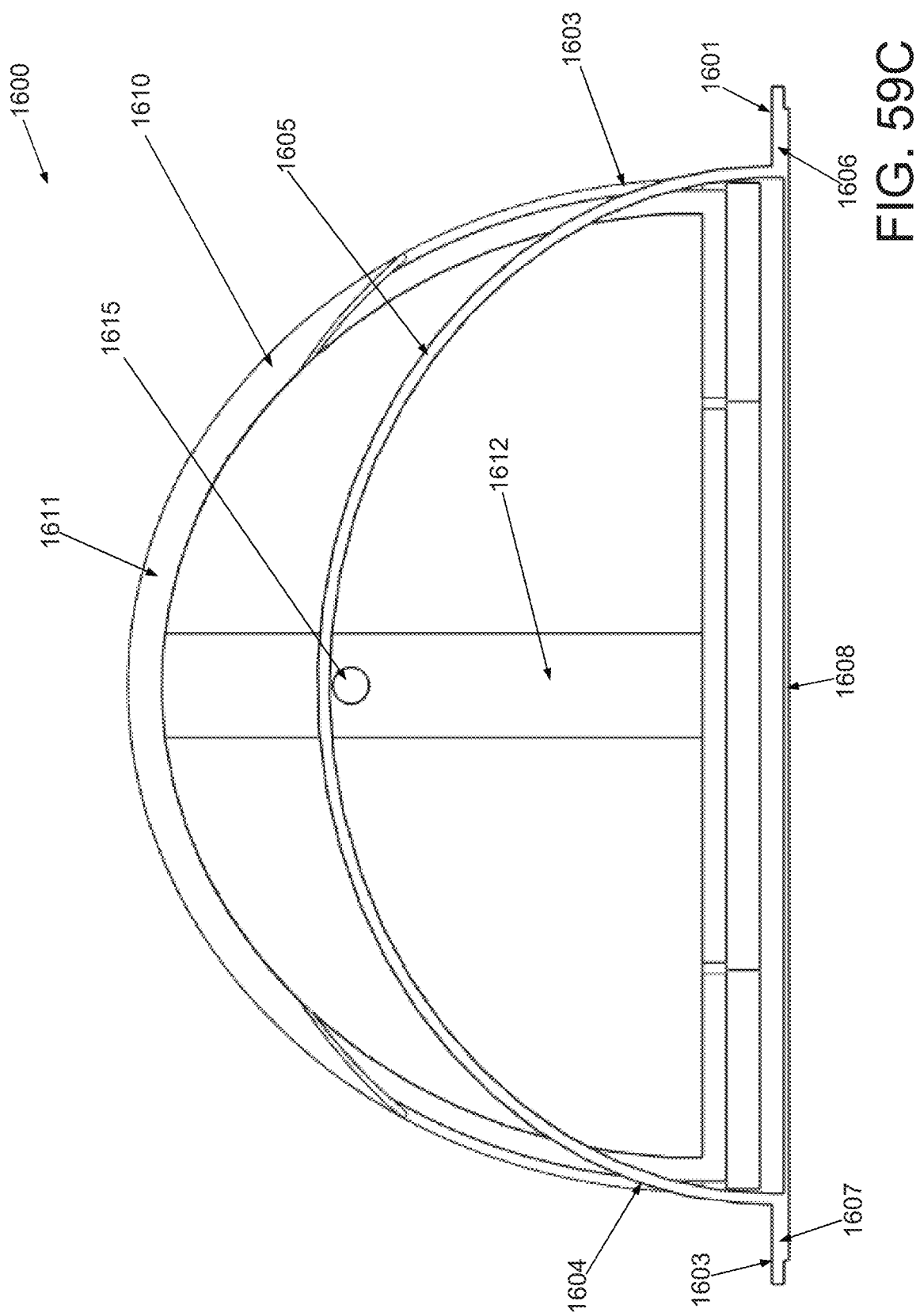
FIG. 59C is a side view of the applicator of FIG. 59A in a strained an unstamped configuration.
Figure 59D:
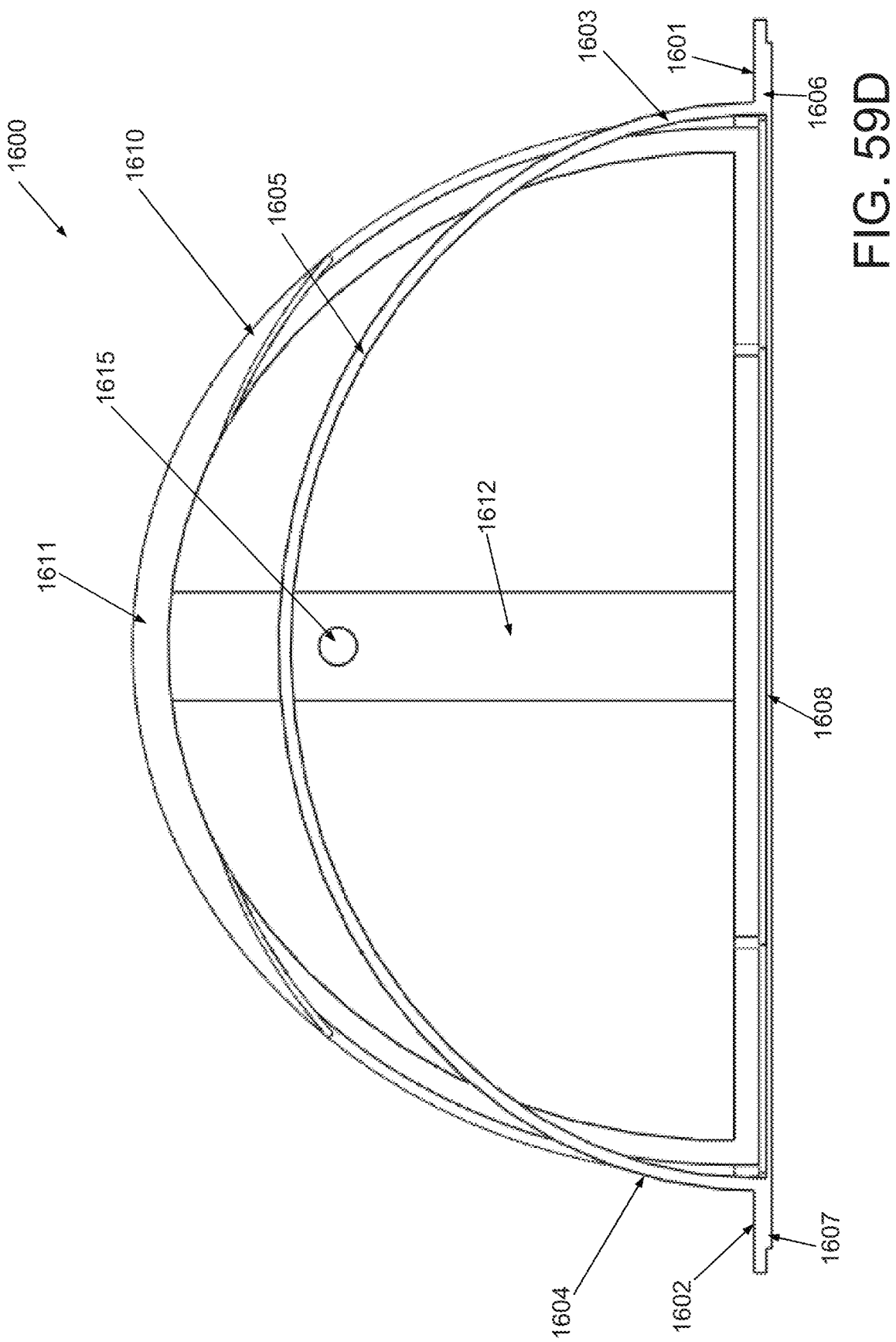
FIG. 59D is a side view of the applicator of FIG. 59A in a strained and stamped configuration.

FIGS. 59A to 59C illustrate another variation of an applicator 1600. Applicator 1600 comprises a pair of spring or resilient members 1605. Each resilient member 1605 extends from attachment foot 1601 on a first end 1602 to attachment foot 1603 on an opposite end 1604. Each resilient member 1605 is positioned on sides 1608, 1609 of applicator 1600. A stamper 1610 is positioned between resilient members 1605. Stamper 1610 includes handle 1611 comprising an arching member extending from first end 1602 to second end 1604 and attached to planar support 1614. The handle 1611 is coupled to plunger 1612 attached to planar support 1614. A pressure member 1613 is attached to the bottom of the planar support 1614. When the stamper 1610 is actuated, the pressure member 1613 applies pressure to a strained skin treatment device attached to the attachment structures, 1606, 1607. Plunger 1612 has laterally extending rods 1615 that prevent separation of the stamper 1610 from the resilient members 1605. As shown in FIG. 59A, the resilient members 1605 are compressed to load an unstrained skin treatment device on to attachment structures 1606, 1607 which may comprise one or more variation of attachment structures. The skin treatment device may be loaded on to a carrier that holds the resilient members until they are released to strain the skin treatment device. The resilient members may also be manually compressed and released to strain the skin treatment device. FIG. 59B shows the applicator 1600 in a strained configuration prior to stamping. FIG. 59C shows the applicator 1600 in a strained and stamped configuration.

FIGS. 60A to 60D illustrate variations of tensioning device, straining device, or applicator 1650 in which the applicator 1650 is self-releasing from an applied skin treatment device. The applicator 1650 comprises a handle 1651 and a resilient member 1654 coupled to the handle 1651, attachment feet 1652 with upwardly curved ends 1653 and coupling edges 1658, 1659, and attachment structures 1656, 1657 on the bottom of the attachment feet 1652. A skin treatment device 1660 for use with the applicator is illustrated loaded on a carrier device 1670. The skin treatment device has an adhesive side 1661; an attachment side 1662; end portions 1664, 1665 with attachment features 1666, 1667 for attaching to attachment structures 1656, 1657 of the applicator 1650. The adhesive side 1661 is positioned on the carrier device 1670. Carrier device 1670 comprises a rigid planar backing 1671 with coupling structures 1678, 1679 on each end. A releasable locking tab 1673 is located on coupling structure 1678 to help peel or remove the carrier 1670 from the skin treatment device 1660.

Figure 60B:
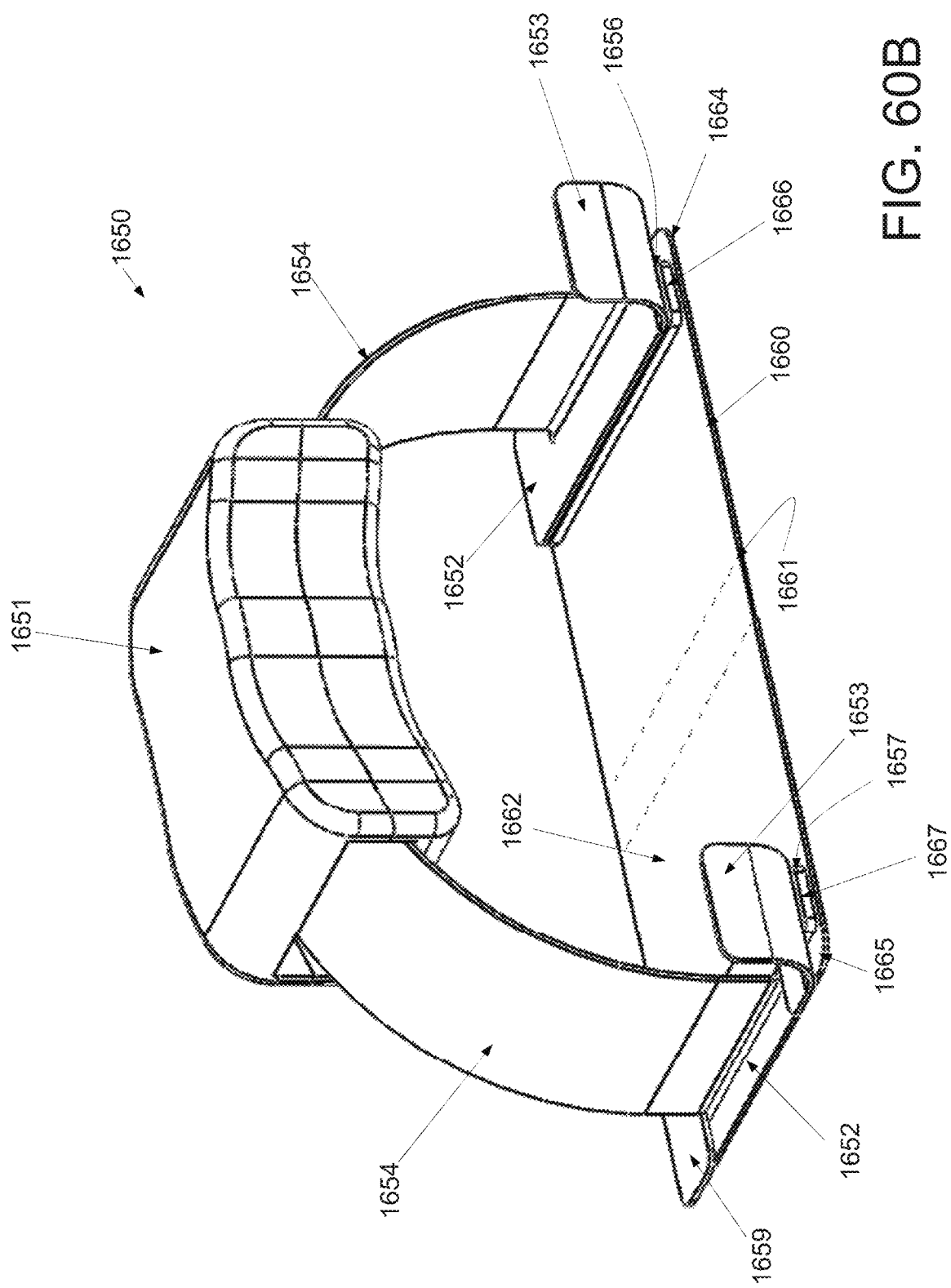
FIG. 60B is a perspective view of the applicator and skin treatment device of FIG. 60A in a strained configuration.
Figure 60C:
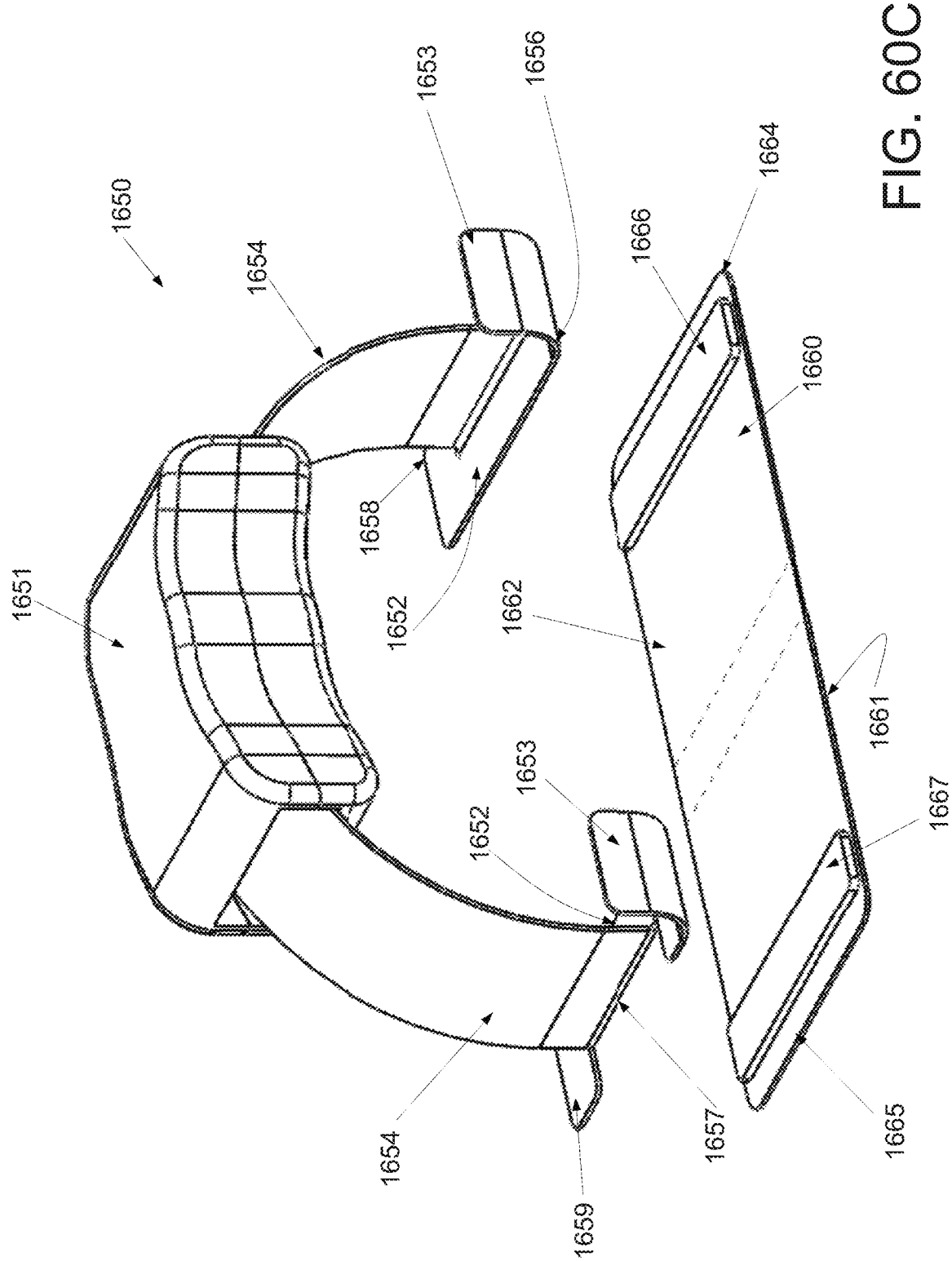
FIG. 60C is a perspective view of the applicator and skin treatment device of FIG. 60A in an applied and released configuration.

In use, the resilient member 1654 may be squeezed by hand to reduce the distance between the attachment feet 1652 and to load a carrier 1670 and unstrained skin treatment device 1660 on to the applicator 1650. The coupling edges 1658, 1659 of the applicator engage with the coupling structures 1678, 1679 of the carrier device 1670. The carrier device 1670 maintains the skin treatment device 1660 in an unstrained configuration until it is removed from the skin treatment device 1660. The locking tab 1673 is rotated upward to lock the skin treatment device in an unstrained position. (FIG. 60A) To strain the skin treatment device, the resilient member 1654 is released and then when the locking tab 1673 is released by rotating it downward and the carrier 1670 is removed from the skin treatment device. The resilient member 1652 applies a separation force to strain the skin treatment device 1660 which may then be applied to the skin of a subject. (FIG. 60B). The device may then be released by rotating the applicator 1650 forward on to the curved ends 1653. (FIG. 60C) The removal feature may be used with various attachment structures including hook and loop combined attachment structures. The applicator 1650 may also include a stamper 1680 where the handle 1651 acts as a plunger handle and is used to depress stamper 1680 to apply pressure with pressure members 1681 (FIG. 60D).

Figure 61A:
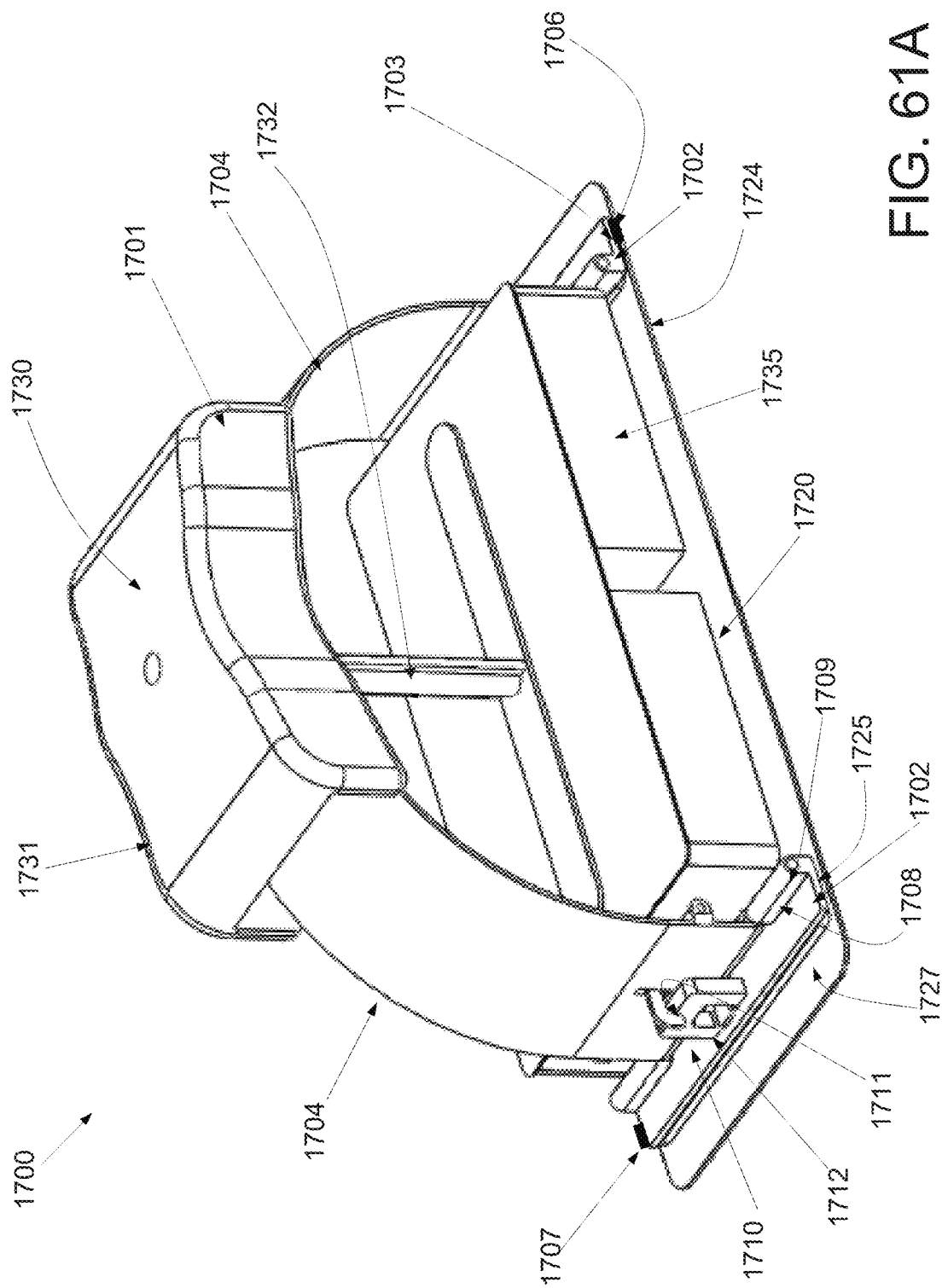
FIG. 61A is a perspective view of an applicator in a strained configuration.
Figure 61B:
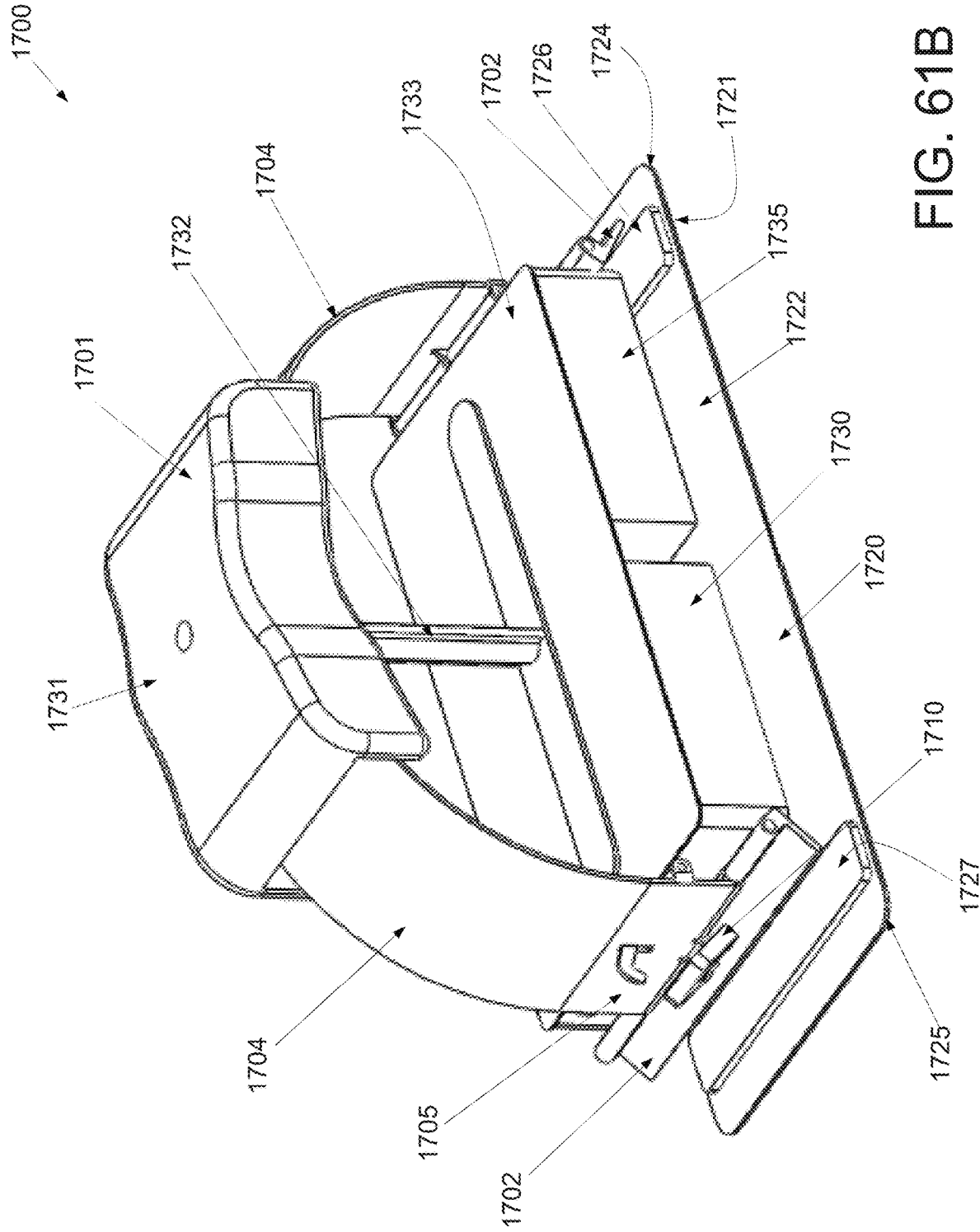
FIG. 61B is a perspective view of the applicator of FIG. 61A in an unstrained configuration with the attachment feet released (unconstrained)
Figure 61C:
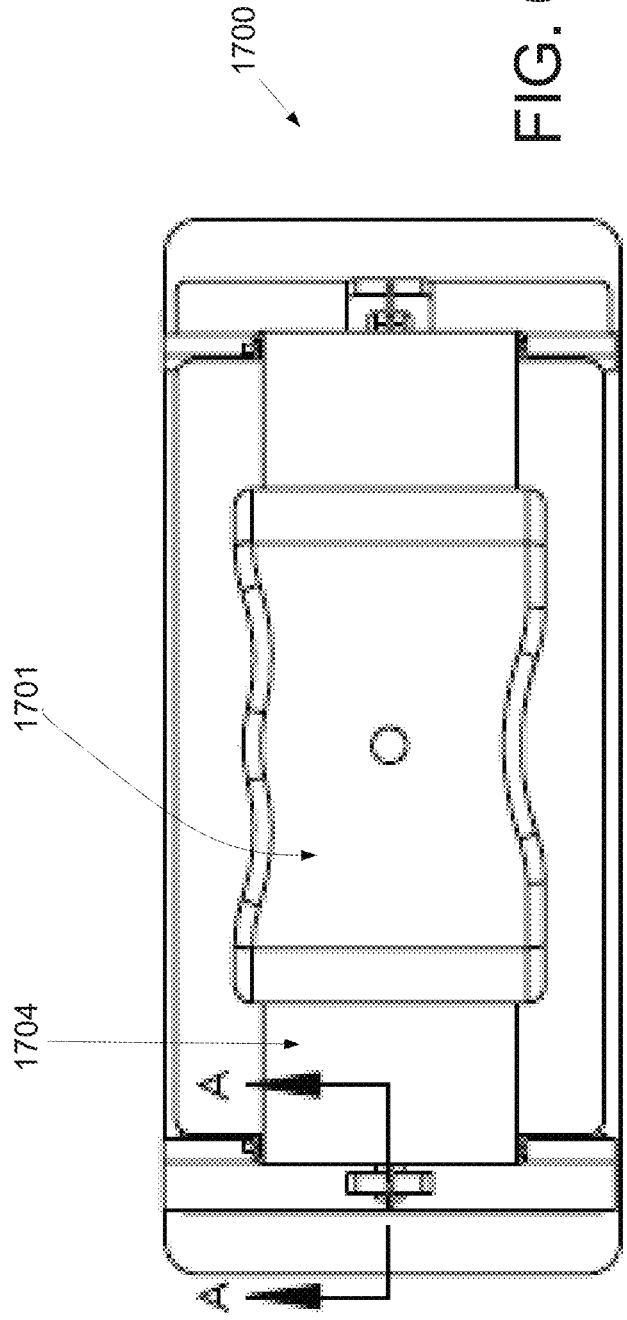
FIG. 61C is a superior view of the applicator of FIG. 61A in a strained configuration.
Figure 61D:
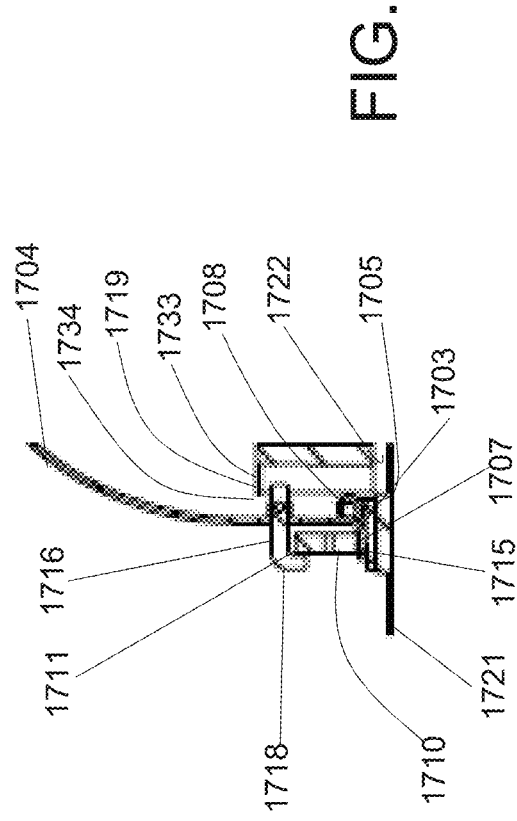
FIG. 61D is a side cross section view across the lines A-A of a portion of the applicator of FIG. 61C.
Figure 61E:
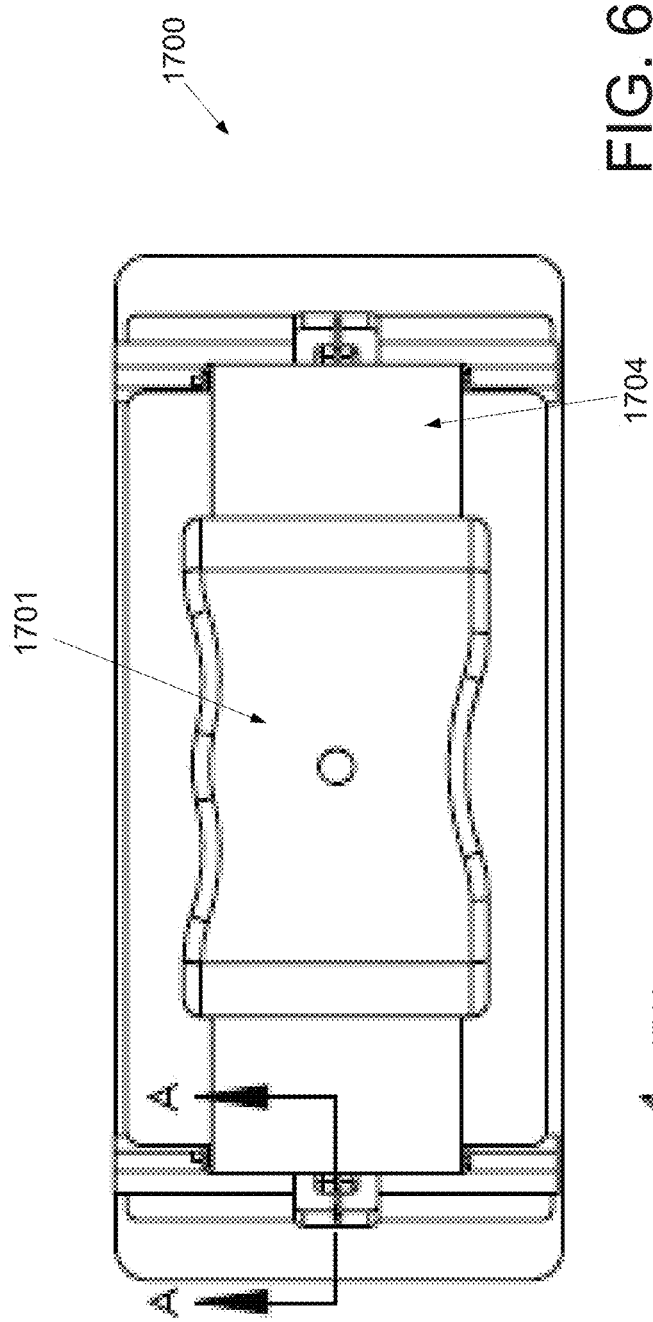
FIG. 61E is a superior view of the applicator of FIG. 61A in an unstrained configuration.

FIGS. 61A to 61F illustrate still another variation of a tensioning device, straining device or applicator 1700 in which the applicator 1700 is self-releasing from an applied skin treatment device. The applicator 1700 comprises a handle 1701 and a resilient member 1704 coupled to the handle 1701, pivoting attachment feet 1702 coupled to the ends 1705 of the resilient member 1704. As shown in FIG. 61D, the resilient member 1704 comprises a latch 1716 pivotally coupled to the each end portion 1705 of the resilient member 1704. The latch 1716 includes a latching finger 1718 extending laterally outward of the resilient member 1704 and a release bar 1719 extending laterally inward of the resilient member 1704. The resilient member also includes a resilient tab 1715 extending laterally outward from each end portion 1705. The pivoting attachment feet 1702 each comprise a hinge 1708 attached with a pin 1709 to an end portion 1705 of the resilient member 1704. The pivoting feet 1702 each further comprise a planar bottom portion 1703 with attachment structures 1706, 1707 thereon. The pivoting feet 1702 each further comprise a locking structure 1710 on the top of the feet 1702 having a top edge 1711 for engaging a latching finger 1718 of a latch 1716, and a window 1712 for receiving a tab 1715 extending laterally outward from each end portion 1705 of the resilient member 1704.

A stamper 1730, comprising a plunger handle 1731 which may be coupled to a T-bar 1732 which in turn is coupled to a backing 1733 with pressure members 1735. The backing 1733 may be configured to extend laterally around the pressure members 1735, at least around ends 1734 of backing 1733. The stamper 1730 may be used to apply pressure to an applied skin treatment device with pressure members 1735.

In use, the resilient member 1704 is squeezed by hand to reduce the distance between the pivoting feet 1702 and to load an unstrained skin treatment device 1720 on to the applicator 1700. The skin treatment device 1720 has an adhesive side 1721; an attachment side 1722; end portions 1724, 1725 with attachment features 1726, 1727 for attaching to attachment structures 1706, 1707 of the applicator 1710. To strain the skin treatment device 1720, the resilient member 1704 is released. The resilient member 1704 applies a separation force to strain the skin treatment device 1720 which may then be applied to the skin of a subject.

FIG. 61A shows a skin treatment device 1720 loaded onto and strained by the applicator 1700 before the skin treatment device 1720 has been stamped. The latch fingers 1718 of the latches 1716 are hooked over the top edges 1711 of locking structures 1710 while receiving tabs 1715 extend laterally outward from each end portion 1705 of the resilient member 1704 and through windows 1712. (FIGS. 61A and 61D) The latch fingers 1718 hold the pivoting feet 1702 in a flat position and prevent downward rotation of the pivoting feet 1702. The tabs 1715 act as alignment pins and resist or prevent upward rotation of pivoting feet 1702.

Figure 61F:
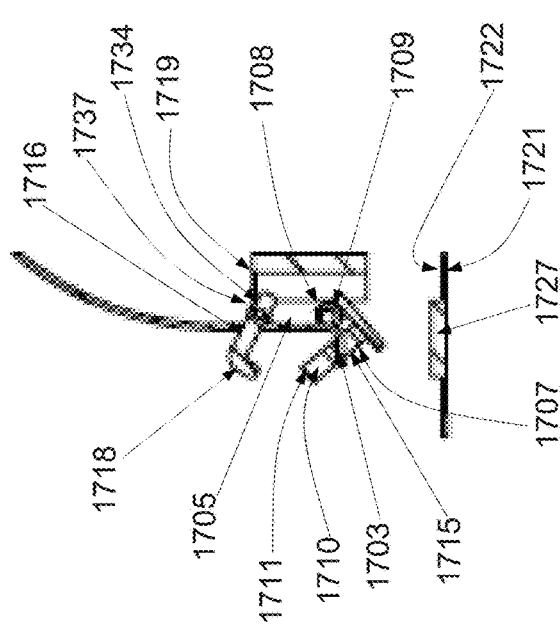
FIG. 61F is a side cross sectional view across the lines A-A of a portion of the applicator of FIG. 61E.

FIGS. 61B and 61F depict the stamper 1730 depressed. The stamper 1730 releases the pivoting feet 1702 and attachment structures 1706, 1707 from engagement with the attachment features 1726, 1727 of the skin treatment device 1720. When the stamper 1730 is depressed, the pressure members 1735 apply pressure to the back of the skin treatment device and the ends 1734 of backing 1733 engage the release bars 1719 moving them down and lifting the latching finger 1718 which permits the pivoting feet 1702 to rotate down as the plunger handle 1731 is pulled up to remove the applicator 1700 from the skin treatment device 1720. As the pivoting feet 1702 are released, both feet 1702 pivot inward due to the internal strain in the skin treatment device. This rotational motion breaks the contact between the hook and loop of attachment structures 1706, 1707 and attachment features 1726, 1727, at a lower face allowing the applicator 1700 to detach without substantially pulling the skin treatment device 1720 off of the skin or reducing the amount the skin treatment device may be pulled off of the skin. The removal feature may be used with various attachment structures including hook and loop combined attachment structures.

FIGS. 62A to 62D illustrate an example of a self-expanding tensioning device, straining device or applicator 1750. The applicator 1750 comprises opposing end supports or bars 1752 have a fixed shape and opposing sliding side bars 1754. Bars 1752, 1754, form an open frame structure 1751 with opening 1769. Each of side bars 1754 comprises an inner tube 1755 with an end 1756 that slides within an outer tube 1757. A spring 1758 is positioned in each outer tube 1757 and interfaces with end of inner tube 1755 to bias inner tube 1755 and outer tube 1757 apart. Stationary end bars 1752 have attachment structures 1753 along the bottom.

Figure 62A:
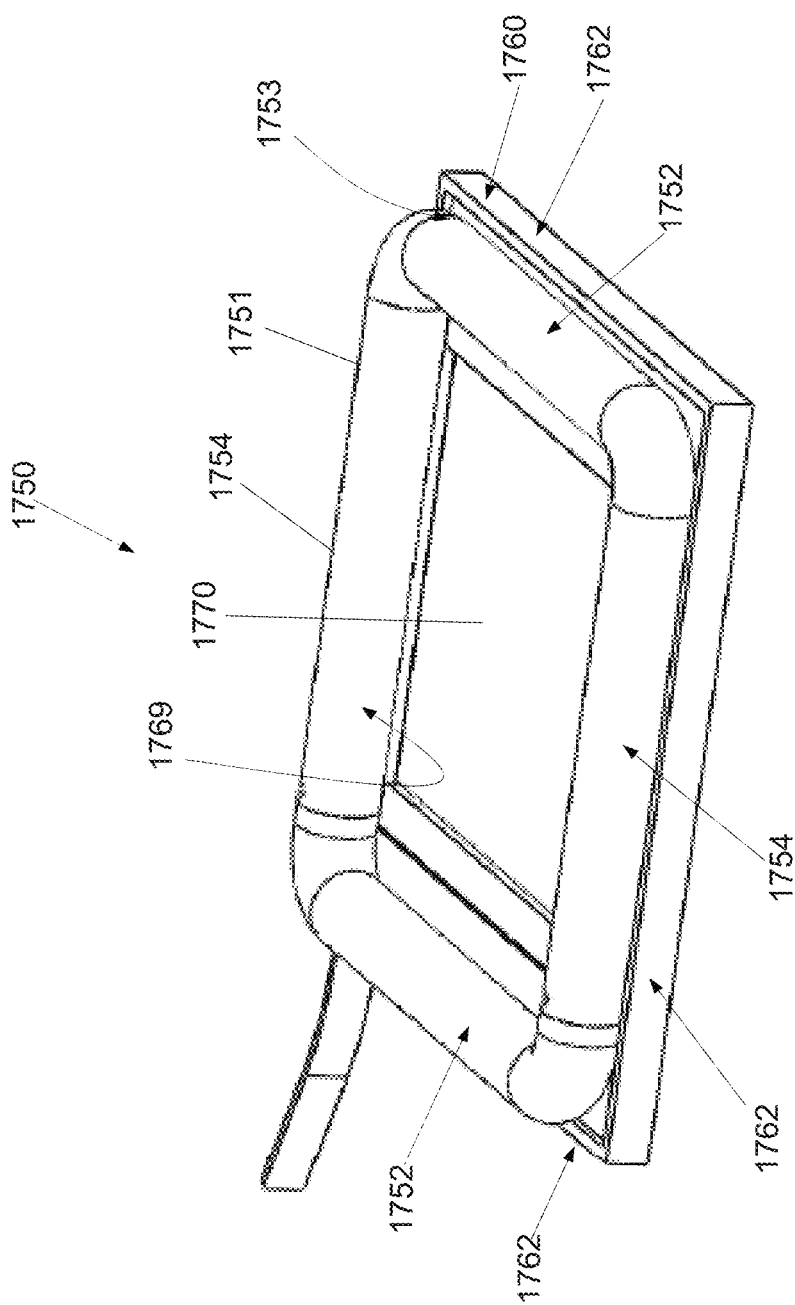
FIG. 62A is a perspective view of an applicator and skin treatment device in an unstrained configuration.
Figure 62C:
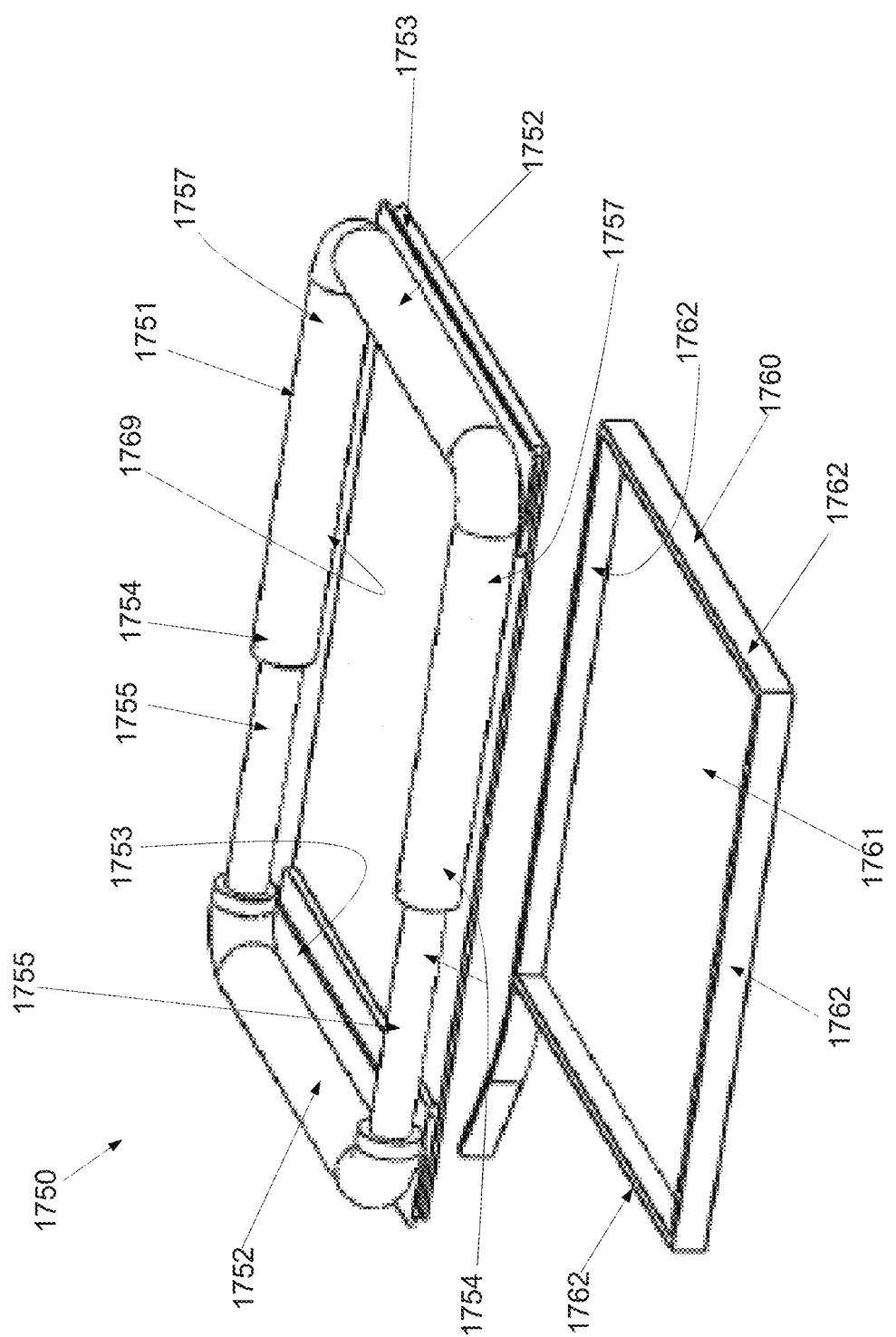
FIG. 62C is a perspective view of the applicator and skin treatment device of FIG. 62A in a strained configuration.
Figure 62D:
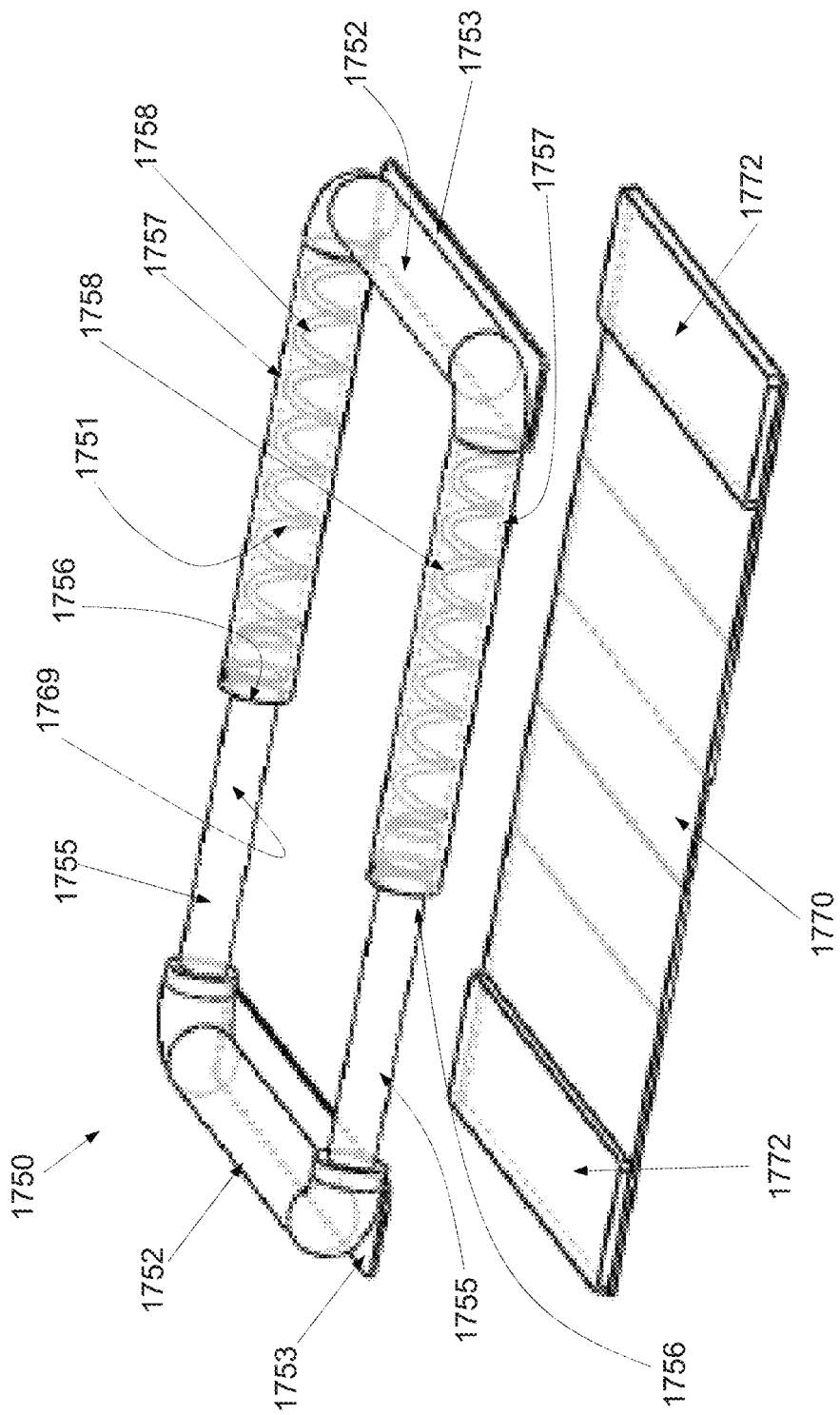
FIG. 62D is a perspective view of the applicator and skin treatment device of FIG. 62A in an applied configuration.

A loader or dispenser 1760 comprises a planar bottom 1761 and side walls 1762 forming an open box. The box is sized to receive an unstrained skin treatment device 1770 having attachment features 1772 for engaging with attachment structures 1753 of the applicator 1750. As shown in FIG. 62A, an unstrained skin treatment device 1770 is placed within the loader 1760 with the attachment features 1772 facing up. The side bars 1754 of the applicator 1750 are compressed together and the applicator 1750 is placed within loader 1760 with the end bars 1752 and sliding side bars 1754 engaging the inside of side walls 1762 to prevent the side bars 1754 from sliding open. Attachment structures 1753 of applicator 1750 are facing down and aligned with the attachment features 1772 of the skin treatment device 1770 so that they are coupled together. As shown in FIG. 62B, the applicator 1750 and skin treatment device 1770 are removed from the loader 1760 and as shown in FIG. 62C, the applicator 1750 self-expands with biasing force of springs 1758 and strains the attached skin treatment device 1770 by applying a separating force. The skin treatment device 1770 is then applied to the skin of a subject using applicator 1750, and as shown in FIG. 62D, the applicator 1750 is separated from the skin treatment device 1770.

Figure 63A:
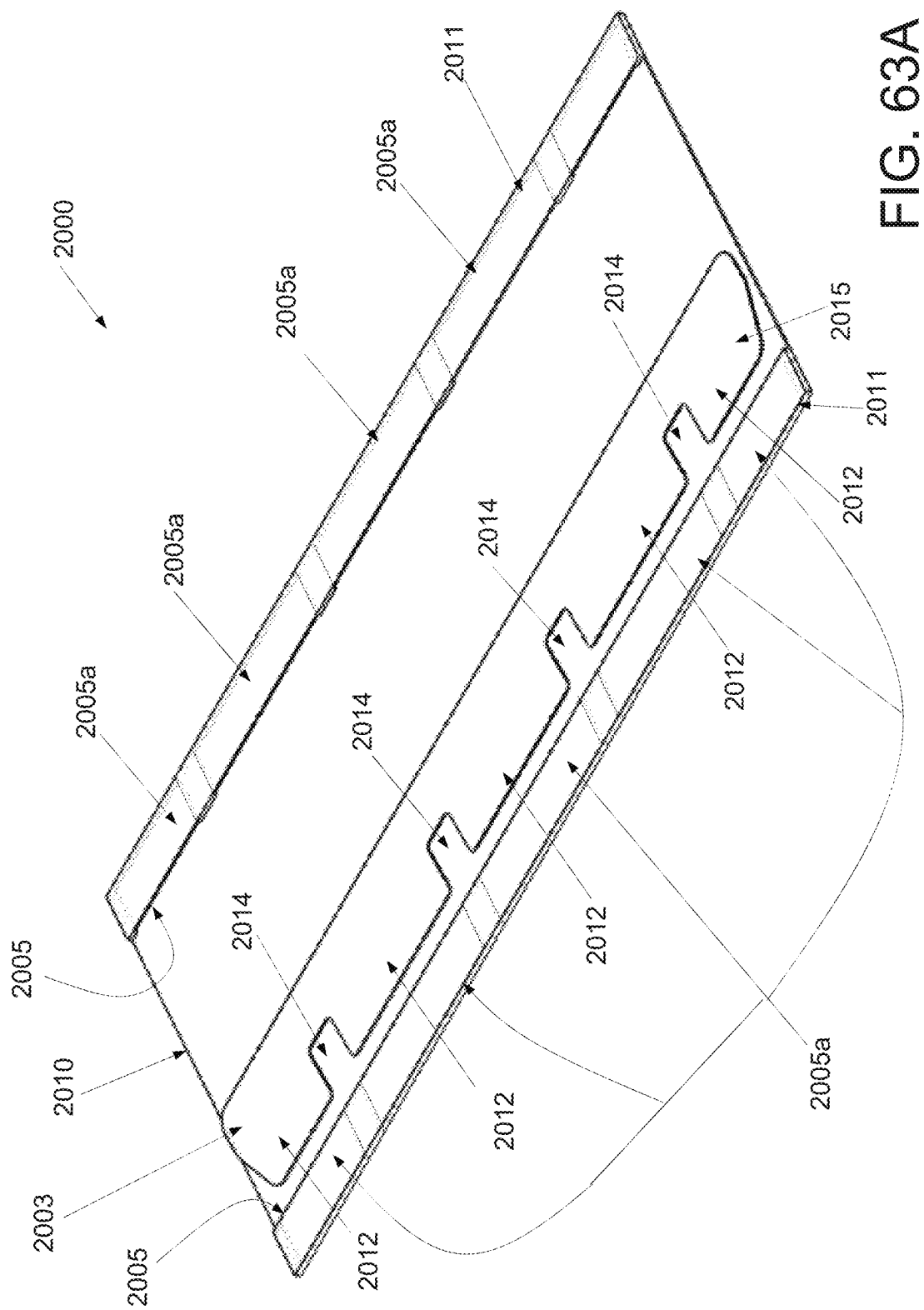
FIG. 63A is a perspective view of a variation of an attachment system in an unloaded configuration.

FIGS. 63A and 63B illustrate a variation of an attachment system 2000 to attach a skin treatment device to an applicator or tensioning device and to strain the skin treatment device that includes an attachment structure for an applicator or tensioning device and an attachment feature for a skin treatment device. The attachment system includes pockets 2005 that are formed on and extend the length of the sides 2011 of a skin treatment device 2010. The pockets 2005 may be formed by folding over edges of the skin treatment device and bonding the folds on the outer edges and at various points along the length to form a plurality of pocket portions 2005a. An attachment structure 2003 that may be used on an applicator or tensioning device in accordance with one or more variations of an applicator or tensioning device is shown comprising a side 2015 with a plurality of tabs 2012 or a plurality of cutouts 2014. In use, an applicator or tensioning device has a plurality of attachment structures 2003 which are placed in a plurality of pockets 2005 of a skin treatment device 2010. The tabs 2012 fit into pocket portions 2005a. A separation force is applied with attachment structures 2003 to the skin treatment device to strain it in one or more directions. In accordance with variations of the invention, multiple tabs or fingers may be provided on the attachment structures to adapt or conform to uneven or undulating skin.

Figure 64B:
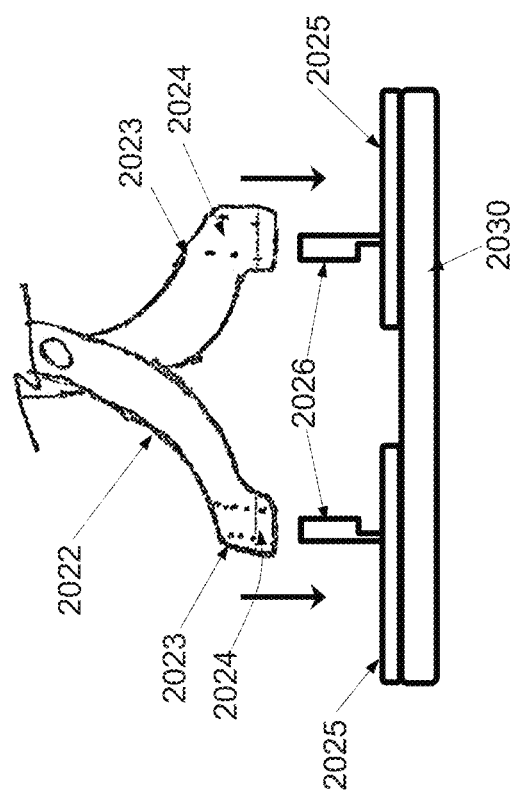

FIGS. 64A to 64E illustrate variations of an attachment system to attach a skin treatment device to an applicator or tensioning device and to strain the skin treatment device that includes an attachment structure for an applicator or tensioning device and an attachment feature for a skin treatment device. A skin treatment device 2030 is pre-mounted to plastic feet 2025 which may be attached to the skin treatment device 2030 in one of several manners. For example, the plastic feet 2025 may be inserted into a pocket, or attached by a hook or loop mechanism or other attachment structure. The plastic feet 2025 have notched attachment pegs 2026 that are easily accessible to a tensioning device or applicator. Any one or more of the applicators described herein may be used, for example. FIG. 64B shows an applicator 2022 with attachment structures 2023 comprising mating features 2024 for snapping pegs 2026 on to applicator 2022. The applicator then applies a separation force to the plastic feet to strain the skin treatment device 2030. The applicator may apply the separation force a variety of ways including but not limited to those described in the various embodiments herein. FIG. 64B shows pivot arms that may be pivoted e.g. using a handle to exert a separation force.

Figure 64D:
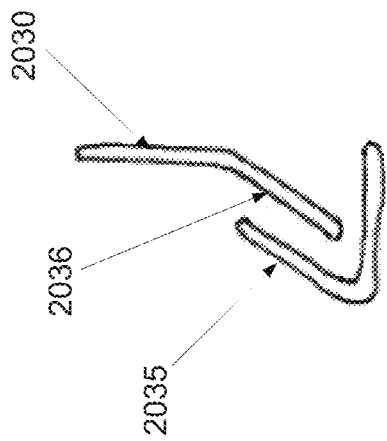
Figure 64E:
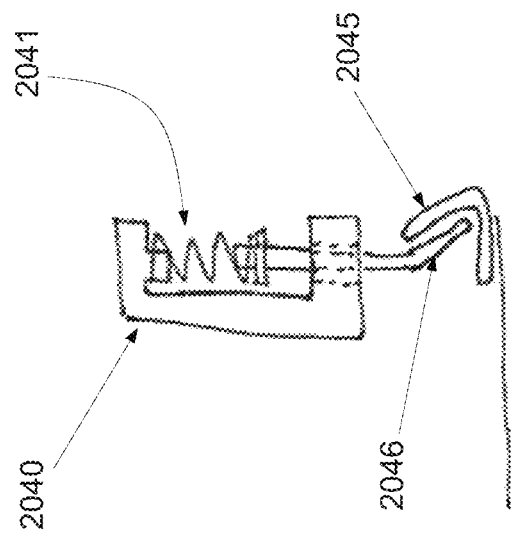
Figure 64C:
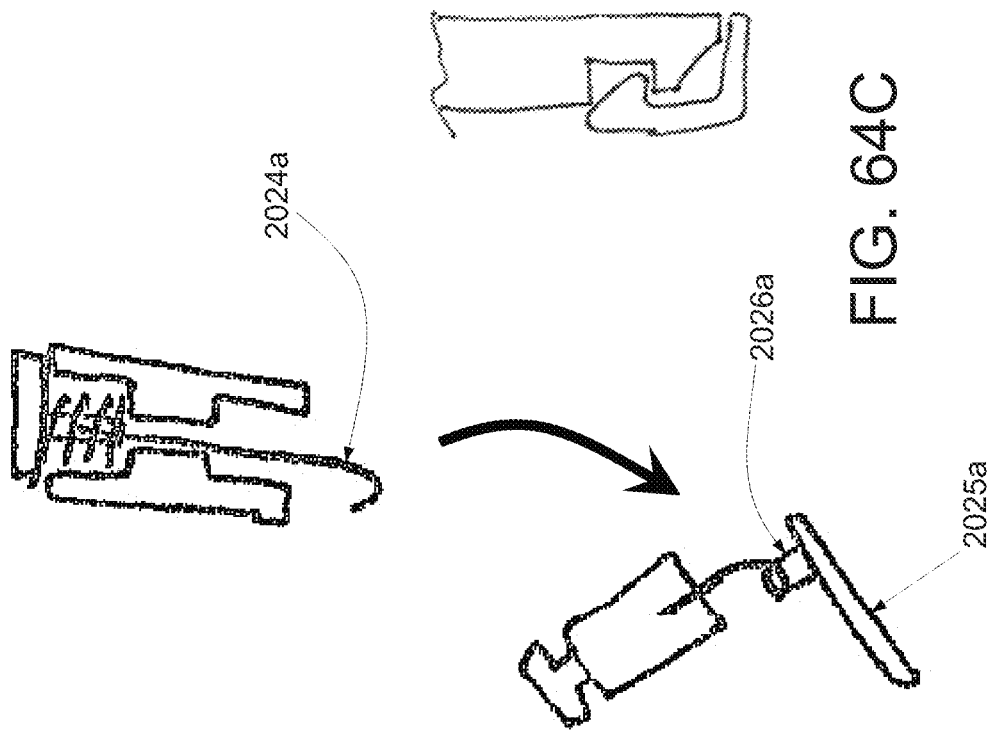
Figure 64G:
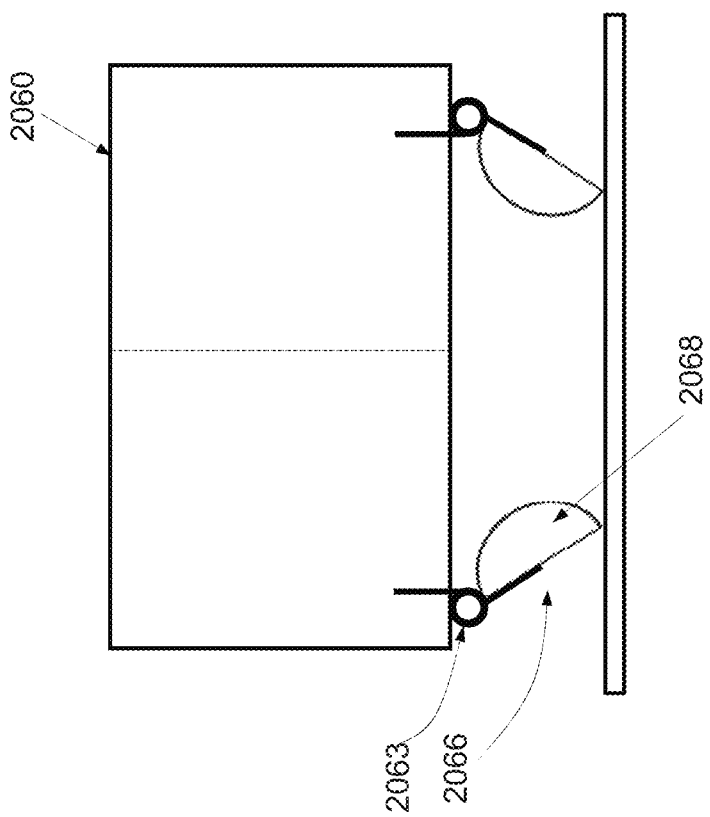

FIG. 64C illustrates variations of system that includes an attachment structure for an applicator or tensioning device and an attachment feature for a skin treatment device. Attachment structure 2024a comprises a spring biased hook 2024a that may hook on to a wire loop 2026a on a plastic foot 2025a.

FIG. 64D illustrates an alternative attachment system that includes an attachment structure for an applicator or tensioning device and an attachment feature for a skin treatment device. Attachment structure 2030 comprises an angled attachment feature 2036 that engages an angled attachment feature 2035 of a skin treatment device.

FIG. 64E illustrates an alternative attachment system that includes an attachment structure for an applicator or tensioning device and an attachment feature for a skin treatment device. Attachment structure 2040 comprises an angled attachment feature 2046 that engages an angled attachment feature 2045 of a skin treatment device. Angled attachment feature 2046 is coupled to a spring mechanism 2041 that biases the attachment feature 2046 and attachment feature 2045 downward. This may assist in applying a skin treatment device to an uneven area of skin or body profile.

Figure 64F:
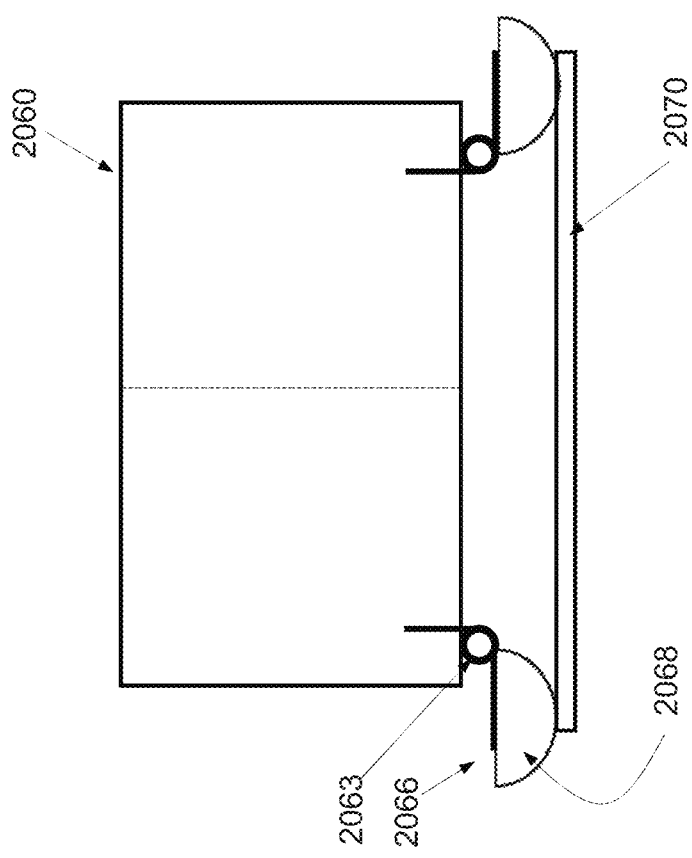
Figure 64I:
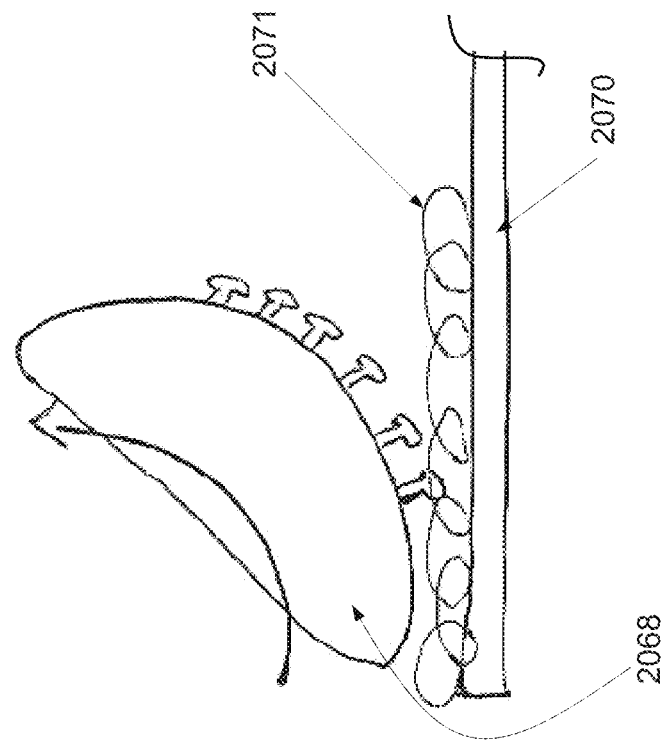
Figure 64H:
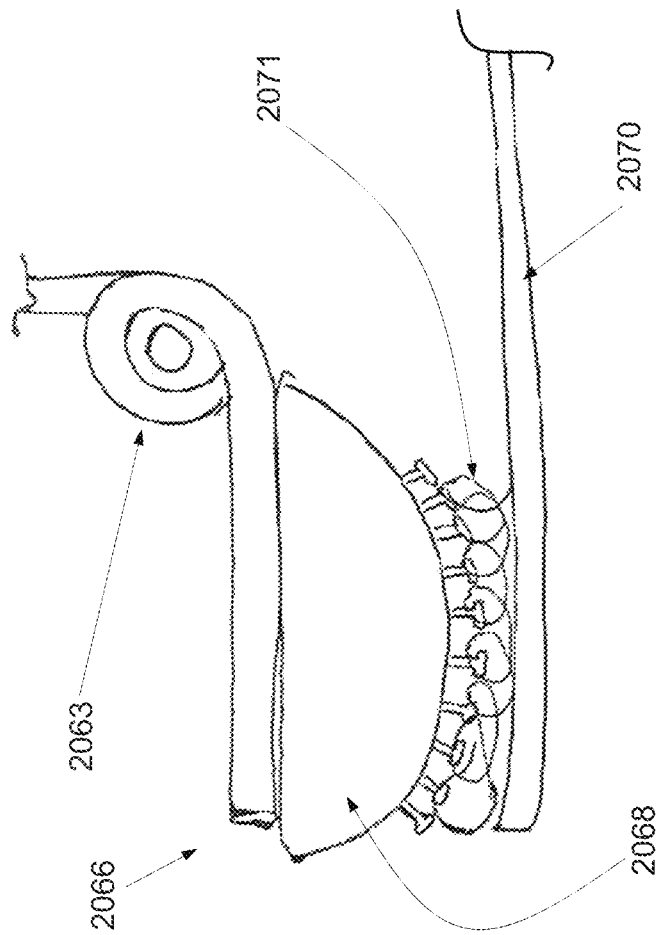

FIGS. 64F to 64I illustrate an alternative attachment system that includes an attachment structure for an applicator. The applicator 2060 includes attachment structures 2066 coupled by way of torsion springs or spring loaded pivots 2063 to the applicator 2060. Each attachment structure 2066 comprises a convex foot 2068 with hooks (of a hook and loop attachment mechanism). In FIGS. 64F and 64H, a skin treatment device 2070 is loaded onto attachment structures 2066 and the spring loaded pivot 2063 is locked in position using a locking mechanism for example as described herein. The convex foot 2068 may serve to apply a generally more uniform pressure on the skin treatment device 2070 when applied to uneven skin. As shown in FIGS. 64H and 64I, the attachment feature 2071 on the skin treatment device 2070 comprises a loop (of a hook and loop mechanism). When the spring loaded pivots 2063 are released, the convex feet 2068 rotate so that fewer rows of hooks are peeled from the loop at a time to reduce the required force at the time of removal, release or detachment of the hooks form the loops or of the attachment structures 2066 of the applicator 2060 from the attachment features 2071 of the skin treatment device 2070.

Figure 64K:
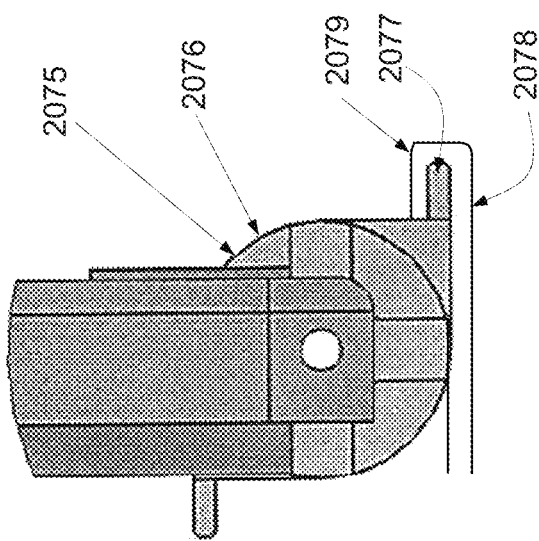
Figure 64J:
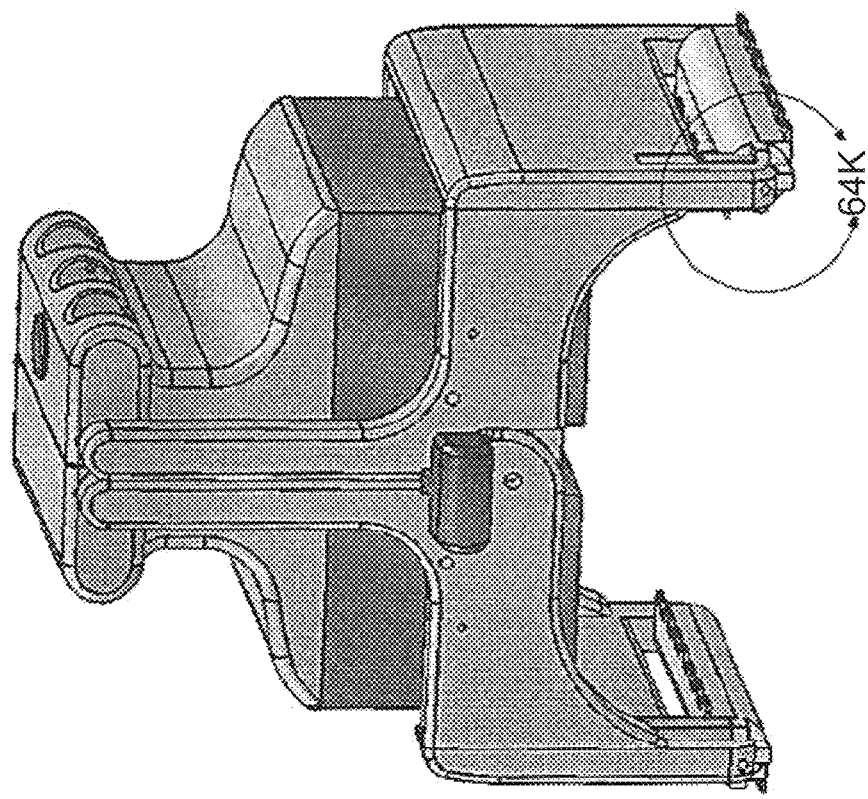

FIGS. 64J and 64K illustrate variations of an attachment system for a tensioning device, straining device or applicator. Attachment structure 2075 comprises a roller 2076 that may be locked and unlocked in a manner similar to roller 1508 as described with respect to FIGS. 58A to 58I. The roller 2076 comprises a plurality of attachment fingers 2077 for engaging openings or pockets in a skin treatment device. As shown in FIG. 64J, fingers 2077 may be positioned in openings 2079 of skin treatment device 2078. In the loaded and locked position, the roller 2076 is positioned with the fingers 2077 facing away in a horizontal plane from the middle of the skin treatment device 2078. After the skin treatment device 2078 is applied, the rollers 2076 are released, unlatched or unlocked. The internal tension of the strained skin treatment device pulls or rotates, the fingers 2077 and roller 2076 in a manner that translates the fingers so they are closer to perpendicular to the skin and the attachment structure 2075 can be removed from the skin treatment device.

Figure 64M:
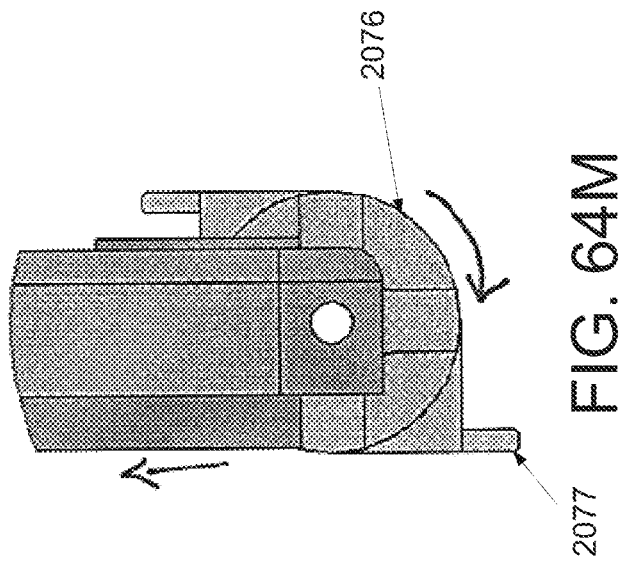
Figure 64L:
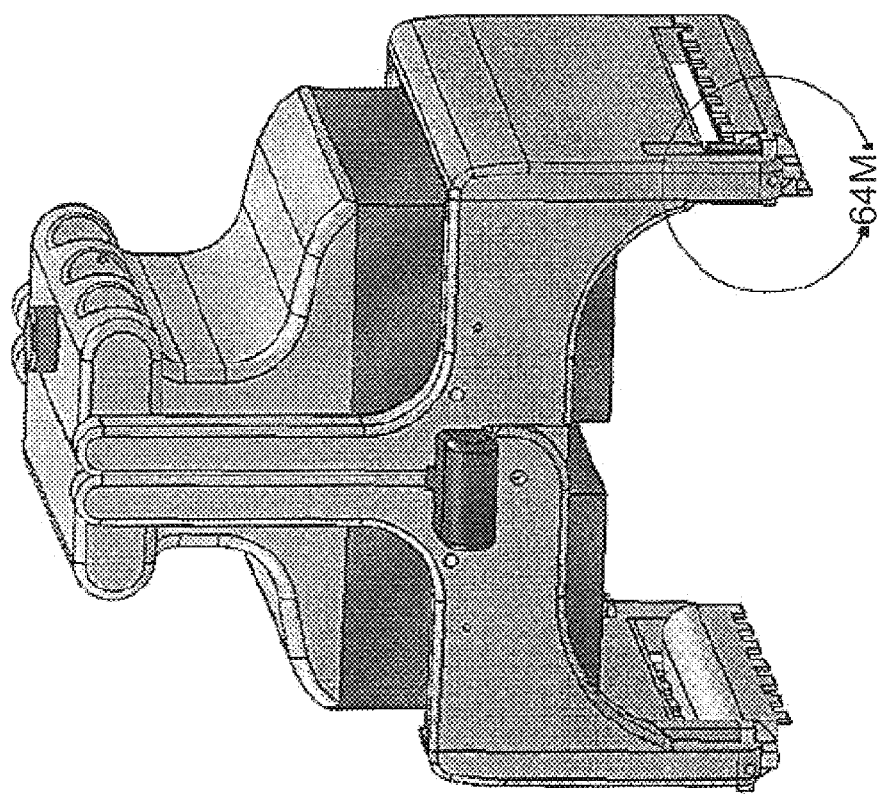
Figure 64O:
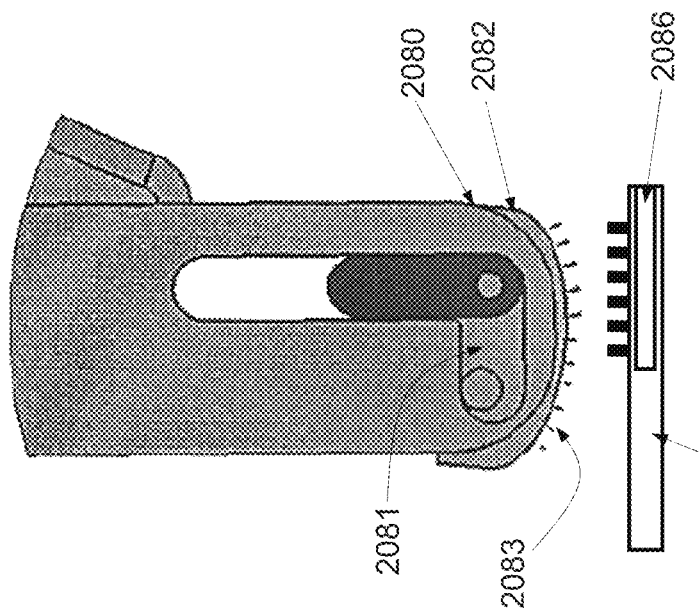
Figure 64N:
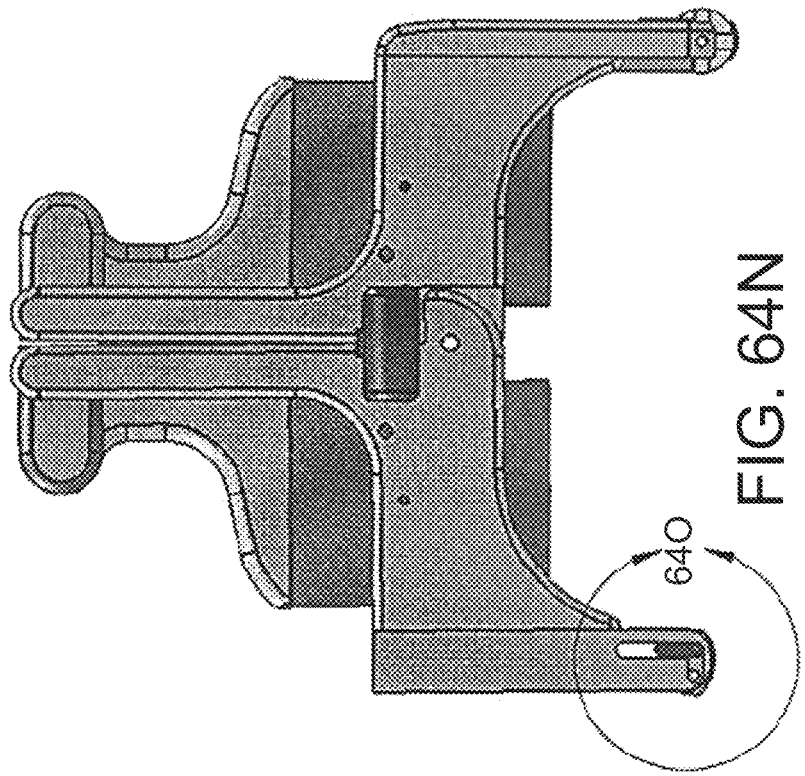
Figure 64Q:
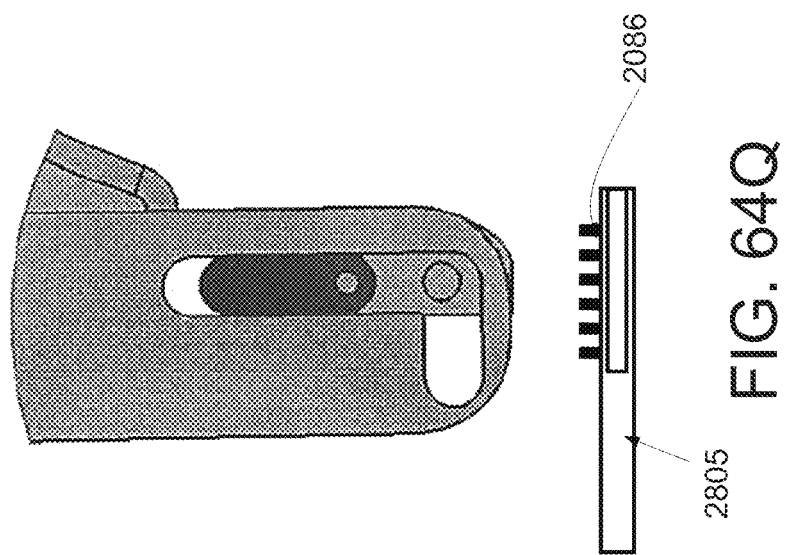
Figure 64P:
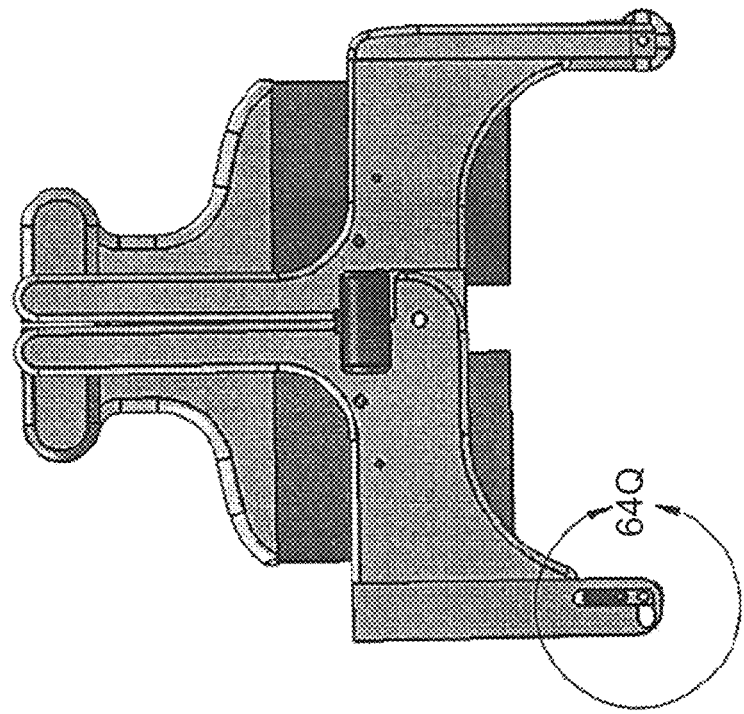

FIGS. 64L and 64M illustrate variations of an attachment system for a tensioning device, straining device or applicator. As shown in FIG. 64L, a linked locking bar 2081 is coupled to a translating foot 2082 with hook or loop material 2083, in a locked position facing an attachment feature 2086 of a skin treatment device 2085. As shown in FIG. 64M, the linked locking bar 2081 is pulled up and out of the locking position, for example using lifter arms 1552 as described with respect to FIGS. 58A to 58I. The translating foot 2082 which is moved by the locking bar 2081 to a position more perpendicular with respect to attachment feature 2086 of a skin treatment device 2085.

Figure 65A:
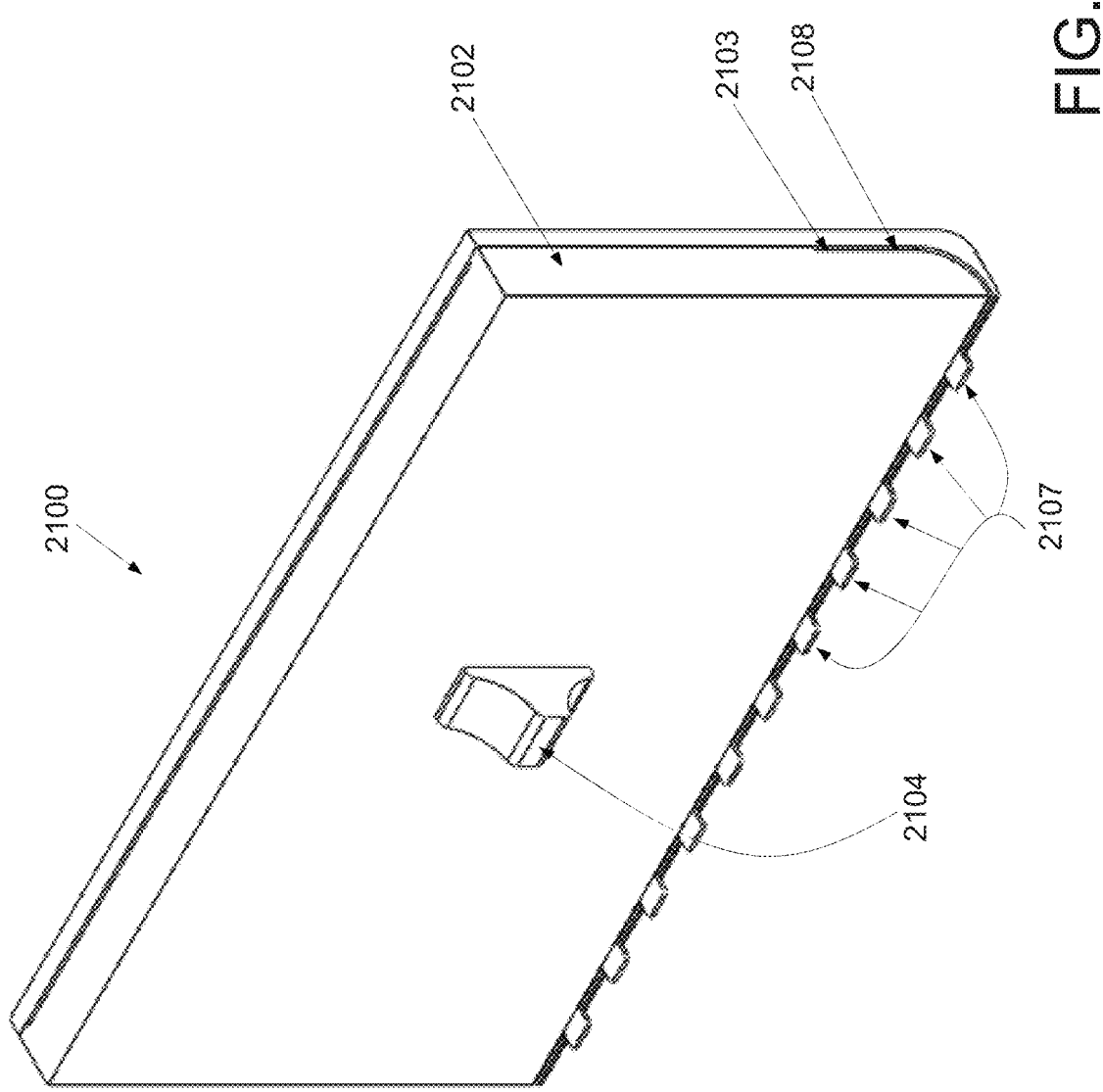
FIG. 65A is a perspective view of an attachment structure system in a first position.
Figure 65C:
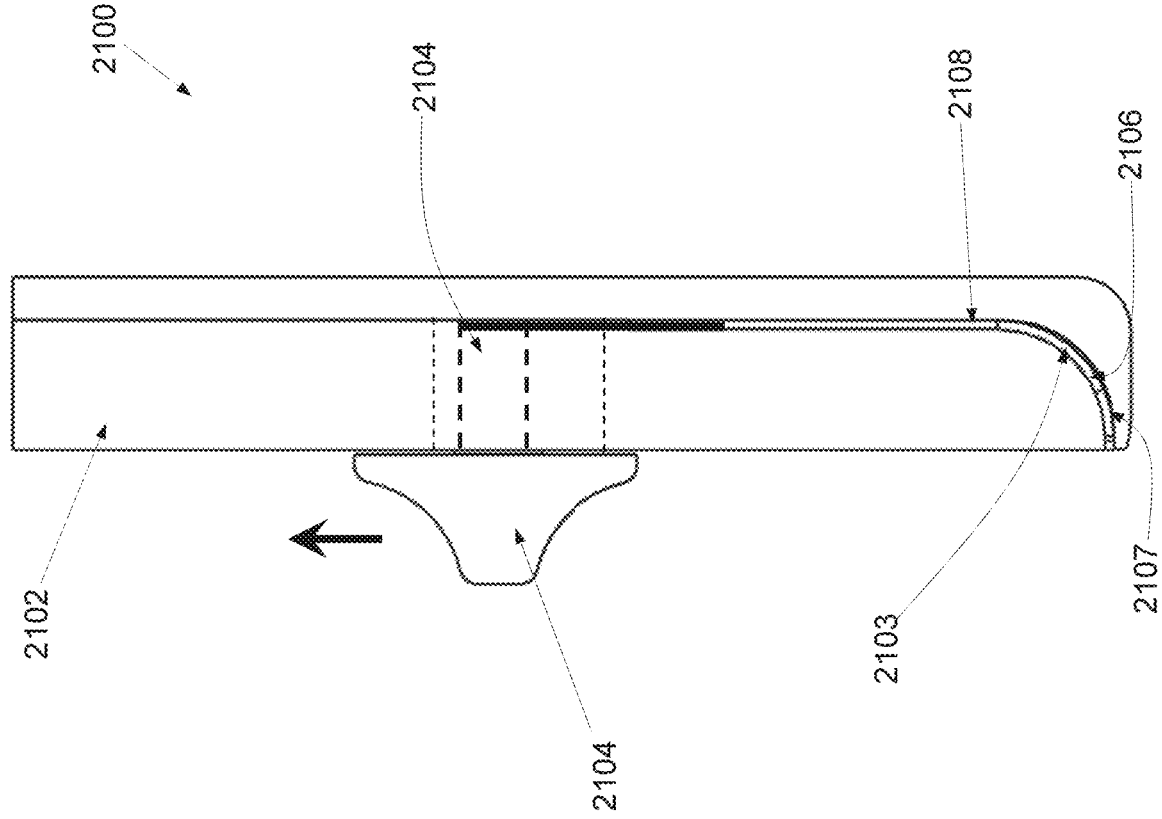
FIG. 65C is a side view of the attachment structure system of FIG. 65A in a second, retracted position.

FIGS. 65A to 65C illustrate variations of system that includes an attachment structure for an applicator or tensioning device and an attachment feature for a skin treatment device. An attachment structure system 2100 is illustrated having an attachment structure 2106 comprising attachment, tabs 2107 at the end of a sliding planar member 2108 that slides within slot 2103 of housing wall 2102. Button 2104 is attached to the outside of the housing wall 2102 extends into housing wall 2102 and is attached to the sliding planar member 2108. The button is slidable up and down in the housing wall to extend or retract the tabs 2107 at the end of the sliding planar member. In use, the tabs 2107 extend out of the housing wall and are used to engage an attachment structure such as, e.g. a pocket, of a skin treatment device (not shown) in a manner similar to that described with respect to attachment structure 2003 and skin treatment device 2010 of FIG. 63A. A second attachment structure system (not shown) attaches to an attachment structure on another side of the skin treatment device. A separation force is applied through the attachment systems to strain the skin treatment device. After the strained skin treatment device is applied to the skin, the buttons 2104 on each housing wall of each attachment system 2100 may be used to retract the attachment structures to provide for release, removal or detachment of the applicator or straining device from the skin treatment structure.

Figure 66A:
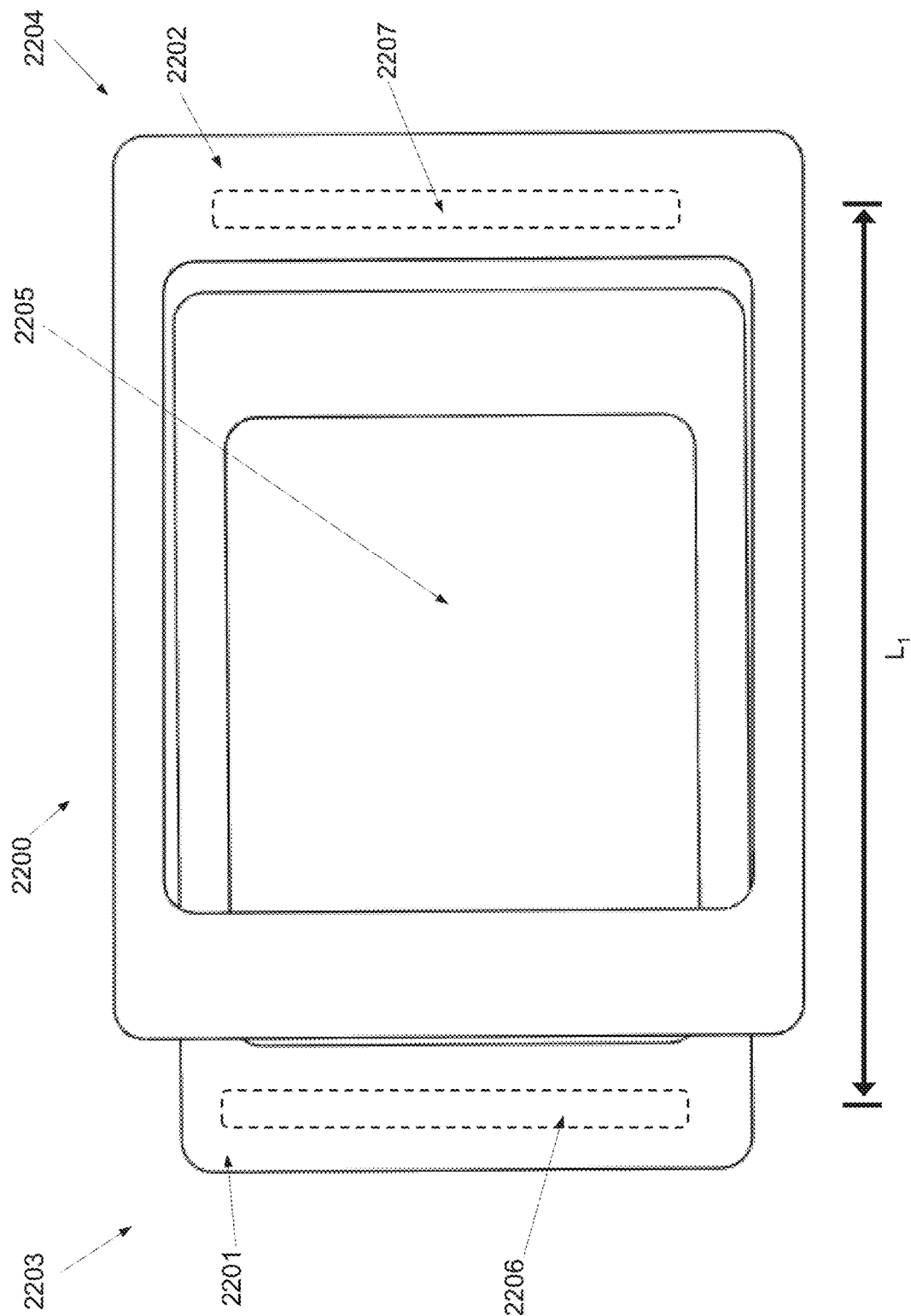
FIG. 66A is a superior view of a skin treatment device in a first position.
Figure 66B:
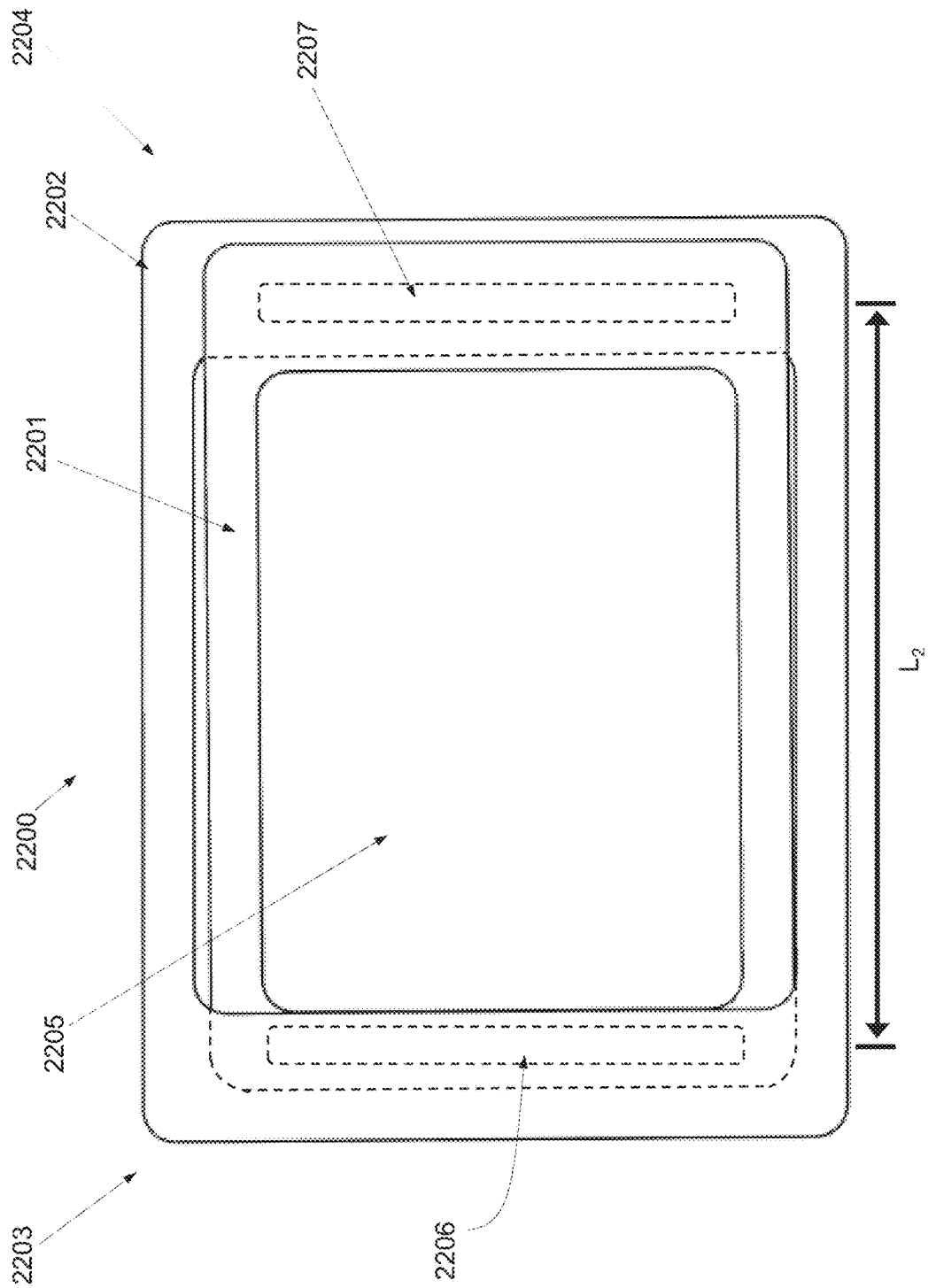
FIG. 66B is a superior view of the skin treatment device of FIG. 66A in a second position.

FIGS. 66A to 66B illustrate a skin frame 2200 configured to pre-strain skin prior to application of a skin treatment device to the skin that will hold the skin in a strained configuration. The frame 2200 comprises an inner sliding frame 2201 and an outer sliding frame 2202. Attachment structure 2206 is attached to the bottom of inner sliding frame 2201 on a first side 2203 of the skin frame 2200. Attachment structure 2207 is attached to the bottom of the outer sliding frame 2202 on a second side 2204 of the skin frame 2200. The attachment structures 2206, 2207 are configured to attach to skin, for example by way of adhesive, friction pads, microneedles and the like. The friction pads may comprise a silicone, a viscoelastic polymer such as styrenic block polymers, and the like. In use, the attachment structures 2206, 2207 are attached to skin when the skin frame is in the first position as shown in FIG. 66A. In the first position the distance between the attachment structures is L1. As shown in FIG. 66B, the sides 2203, 2204 of the skin frame are slid together by sliding inner frame 2201 and outer frame 2202 with respect to each other. Thus the distance between the attachment structures is L2 where L2 is less than L, thus straining the skin to which the attachment structures 2206, 2207 are attached. A skin treatment device may then be placed through opening 2205 of the skin frame. The skin treatment device is configured to hold the skin in place. The skin treatment structure may be an unstrained or a strained treatment structure. For example such as the dressings, wound treatment device or skin treatment devices described herein or use with an applicator.

While the particular examples illustrated and described herein include specific combinations of the variety of features described herein, one of skill in the art will understand that other combinations of features described herein are contemplated. For example, Applicators 100, 200, 220, 240, 260, 280, 300, 320, 714, 730, 70, 900, 1000, 1100, 1200, 1250, 1300, 1400, 1500, 1600, 1650, 1700 and 1750 are each depicted with a particular attachment mechanism but may also be designed with other attachment mechanisms (e.g. those shown in skin treatment devices 2, 600, 630, 650, 660, 670, 680, 700, or attachment mechanisms depicted in FIGS. 64C to 64M). Likewise, applicators comprising a stamper may also be configured without a stamper and provided with an access opening to permit direct pressing of a skin treatment device by the user.

In another variation, the device may be applied without an applicator by grasping the flap regions and manually stretching the device. The stretched device may then be applied to the skin and allowed to recover. In still another variation, instead of pre-stretching the device, the underlying skin may be pre-compressed while an unstrained device is adhered or attached to the compressed skin. Once attached, the compressive force acting on the skin may be removed to permit transfer and equilibration of the skin compression to tensile strain acting on the device.

To facilitate removal of the device, an outer edge of the device may be lifted and slowly peeled off, working toward the midline or incision site. In some examples, water, isopropyl alcohol or other adhesive removal agent may be administered to the device/skin interface to facilitate removal. The same agent may also be used to remove any remaining adhesive found on the skin after complete removal of the device. If another device is to be applied to the same site, the skin may be dried before the replacement device is applied.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed as new and desired to be protected by Letters Patent of the United States is:

1. A tissue treatment device, comprising:
   an adjustable frame, the frame comprising:
      first and second movable supports that are located on opposite ends of the frame and configured to displace from a retracted configuration to an extended configuration;
      first and second pivoting supports that are located on opposite sides of the frame and configured to pivot from a retracted configuration to an extended configuration by a first middle hinge in each pivoting support; and
      first and second dressing attachment structures located on the first and second movable supports.

2. The tissue treatment device of claim 1, further comprising a dressing configured for attachment to the adjustable frame.

3. The tissue treatment device of claim 2, wherein the dressing is configured for attachment to the first and second dressing attachment structures.

4. The tissue treatment device of claim 1, wherein the first and second dressing attachment structures comprise a clamp.

5. The tissue treatment device of claim 1, wherein the adjustable frame comprises at least one lock to maintain at least one of the first and second pivoting supports in the extended configuration.

6. The tissue treatment device of claim 1, wherein the first middle hinges of the first and second pivoting supports are located between the first and second movable supports when the first and second pivoting supports are in the retracted configuration.

7. The tissue treatment device of claim 1, wherein the first and second pivoting supports are folded inward between the first and second movable supports when the first and second pivoting supports are in the retracted configuration.

8. The tissue treatment device of claim 1, wherein each of the first and second pivoting supports comprise a pull interface configured to move the first and second pivoting supports from the retracted to the extended configuration.

9. The tissue treatment device of claim 8, wherein the pull interface is a pull handle.

10. The tissue treatment device of claim 1, wherein the first middle hinges of the first and second pivoting supports are not located between the first and second movable supports when the first and second pivoting supports are in the retracted configuration.

11. The tissue treatment device of claim 10, wherein the first and second pivoting supports each further comprise a second middle hinge and a push rod located between the first and second middle hinges.

12. The tissue treatment device of claim 1, further comprising a stamper configured to apply force through a lower face of the adjustable frame.

13. The tissue treatment device of claim 12, wherein the stamper comprises:
   a stamper handle;
   a stamper body, wherein the stamper body is configured to extend out through the lower face of the adjustable frame; and
   a first stamper rod, located between the stamper handle and the stamper body.

14. The tissue treatment device of claim 13, wherein the stamper further comprise a first spring located around the first stamper rod.

15. The tissue treatment device of claim 14, wherein the stamper further comprise a second spring located between the stamper handle and the stamper body, and a second spring located around the second stamper rod.

16. The tissue treatment device of claim 1, wherein the frame further comprises an access opening.

17. A method for tensioning a dressing, comprising:
   straightening two opposing hinged supports to separate two movable supports attached to a dressing to generate a predetermined strain to the dressing.

18. The method of claim 17, wherein straightening two opposing hinged supports comprises pulling two opposing hinged supports away from each other.

19. The method of claim 17, wherein straightening two opposing hinged supports comprises pushing two opposing hinged supports toward each other.

20. The method of claim 17, further comprising actuating a stamper to apply a force to the dressing.

21. The method of claim 17, further comprising: attaching a dressing to the two movable supports before straightening the two opposing hinged supports.

* * * * *